(12) United States Patent
Yohannes et al.

(10) Patent No.: US 6,653,471 B2
(45) Date of Patent: Nov. 25, 2003

(54) HETEROCYCLIC COMPOUNDS AS LIGANDS OF THE $GABA_A$ RECEPTOR

(75) Inventors: Daniel Yohannes, New London, CT (US); George Maynard, Clinton, CT (US); Jun Yuan, Guilford, CT (US); Linghong Xie, Guilford, CT (US); Kyungae Lee, Guilford, CT (US); Manuka Ghosh, Branford, CT (US); George Luke, Clinton, CT (US); Xiaojun Liu, New London, CT (US); Arthur Nagal, Gales Ferry, CT (US); Lawrence Vincent, Moosup, CT (US); Kevin Currie, North Branford, CT (US); Zhe-Quing Wang, East Haven, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/924,174

(22) Filed: Aug. 6, 2001

(65) Prior Publication Data

US 2003/0105081 A1 Jun. 5, 2003

Related U.S. Application Data

(60) Provisional application No. 60/223,669, filed on Aug. 7, 2000.

(51) Int. Cl.[7] ............................................ C07D 487/00
(52) U.S. Cl. ....................................................... 540/578
(58) Field of Search ......................................... 540/578

(56) References Cited

U.S. PATENT DOCUMENTS

| | | | |
|---|---|---|---|
| 5,344,826 A | 9/1994 | Covey et al. | 514/249 |
| 5,723,462 A | 3/1998 | Albaugh et al. | 514/167 |

FOREIGN PATENT DOCUMENTS

| | | |
|---|---|---|
| WO | WO 98/50384 | 11/1998 |
| WO | WO 98/50385 | 11/1998 |
| WO | WO 99/00391 | 1/1999 |
| WO | WO 99/29319 | 6/1999 |
| WO | WO 99/43681 | 9/1999 |
| WO | WO 99/43682 | 9/1999 |

OTHER PUBLICATIONS

Leusink, et al., (1992), *J. Chem. Soc., Chem. Commun.*, pp. 1401–1402.

*Primary Examiner*—Mark L. Berch
*Assistant Examiner*—Kahsay Habte
(74) *Attorney, Agent, or Firm*—McDonnell Boehnen Hulbert & Berghoff

(57) ABSTRACT

Disclosed are heterocyclic compounds of the formula

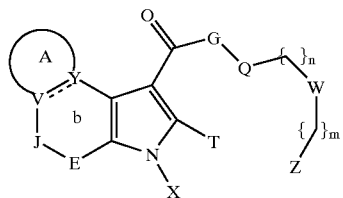

and the pharmaceutically acceptable salts thereof wherein the variables A, V, Y, J, E, X, T, G, Q, W, Z, b, n and m are defined herein. These compounds are highly selective agonists, antagonists or inverse agonists for $GABA_A$ brain receptors or prodrugs of agonists, antagonists or inverse agonists for $GABA_A$ brain receptor.

27 Claims, No Drawings

HETEROCYCLIC COMPOUNDS AS LIGANDS OF THE GABA$_A$ RECEPTOR

BACKGROUND OF THE INVENTION

This application claims priority from U.S. Provisional Application Ser. No. 60/223,669, filed Aug. 7, 2000.

FIELD OF THE INVENTION

This invention relates to heterocyclic compounds, and more specifically to such compounds that bind with high selectivity and high affinity to the benzodiazepine site of GABA$_A$ receptors. This invention also relates to pharmaceutical compositions comprising such compounds and to the use of such compounds in treatment of certain central nervous system (CNS) diseases.

DESCRIPTION OF THE RELATED ART

The GABA$_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the GABA$_A$ receptor, which causes alteration in chloride conductance and membrane polarization.

A number of cDNAs for GABA$_A$ receptor subunits have been characterized. To date at least 6α, 3β, 3γ, 1ε, 1δ and 2ρ subunits have been identified. It is generally accepted that native GABA$_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $α_1β_2γ_2$, $α_2β_3γ_2$, $α_3β_3γ_2$, and $α_5β_3γ_2$(Mohler et. al. Neuroch. Res. 1995; 20(5): 631–636).

Benzodiazepines exert their pharmacological actions by interacting with the benzodiazepine binding sites associated with the GABA$_A$ receptor. In addition to the benzodiazepine site, the GABA$_A$ receptor contains sites of interaction for several other classes of drugs. These include a steroid binding site, a picrotoxin site, and the barbiturate site. The benzodiazepine site of the GABA$_A$ receptor is a distinct site on the receptor complex that does not overlap with the site of interaction for GABA or for other classes of drugs that bind to the receptor (see, e.g., Cooper, et al., The Biochemical Basis of Neuropharmacology, 6$^{th}$ ed., 1991, pp. 145–148, Oxford University Press, New York). Early electrophysiological studies indicated that a major action of the benzodiazepines is enhancement of GABAergic inhibition. Compounds that selectively bind to the benzodiazepine site and enhance the ability of GABA to open GABA$_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of GABA$_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

GABA$_A$ selective ligands may also act to potentiate the effects of certain other CNS active compounds. For example, there is evidence that selective serotonin reuptake inhibitors (SSRIs) may show greater antidepressant activity when used in combination with GABA$_A$ selective ligands than when used alone.

SUMMARY OF THE INVENTION

This invention provides heterocyclic compounds, such as 5,6-Dihydro-4H-1,3a,6-triaza-as-indacenes and related compounds, that bind with high affinity and high selectivity to the benzodiazepine site of the GABA$_A$ receptor, including human GABA$_A$ receptors.

Thus, the invention provides novel compounds of Formula A (shown below), and pharmaceutical compositions comprising compounds of Formula A.

The invention further comprises methods of treating patients suffering from certain CNS disorders with an effective amount of a compound of the invention. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of GABA$_A$ receptors in tissue sections.

Accordingly, a broad aspect of the invention is directed to compounds of Formula A:

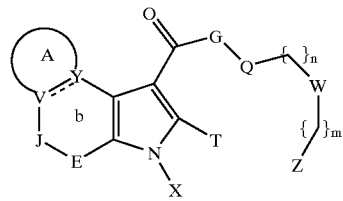

or a pharmaceutically acceptable salt thereof, wherein:
the b-ring is a 5–9 membered ring;
E represents $(CR^1R^2)_k$, —$CR^1$=$CR^2$—, —O—$(CR^1R^2)_k$—, —$(CR^1R^2)_k$—O—, —N=$CR^1$—, —$CR^1$=N—, —NR'—$(CR^1R^2)_k$—, or —$(CR^1R^2)_k$—NR'—, wherein
$R^1$ and $R^2$ independently represent
hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, or mono- or di($C_1$–$C_6$)alkylamino($C_1$–$C_6$)alkyl, or
phenyl, pyridyl, phenyl($C_1$–$C_6$)alkyl, or pyridyl ($C_1$–$C_6$)alkyl, where each phenyl or pyridyl is optionally substituted with $C_1$–$C_6$ alkyl, $C_1$–$C_6$ alkoxy, halogen, hydroxy, cyano, nitro, amino, and mono- or di($C_1$–$C_6$)alkylamino;

k is 0, 1, 2, or 3;

R' represents
hydrogen, $C_1$–$C_6$ alkyl, $C_2$–$C_7$ alkanoyl, $C_1$–$C_6$ alkoxy ($C_1$–$C_6$)alkyl, $C_2$–$C_6$ alkenyl, $C_2$–$C_6$ alkynyl, $C_1$–$C_6$ haloalkyl, amino($C_1$–$C_6$)alkyl, or mono- or di($C_1$–$C_6$)alkylamino($C_3$–$C_6$)alkyl, or aryl, heteroaryl, aryl($C_1$–$C_6$)alkyl, or heteroaryl ($C_1$–$C_6$)alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$)alkylamino;

G is oxygen or NH;

J represents $(CR^5R^6)_d$ where
d is 0 or 1; and $R^5$ and $R^6$ together form a carbonyl group; or $R^5$ and $R^6$ are independently hydrogen or $R_{100}$,
where each $R_{100}$ is independently selected from halogen, hydroxy, nitro, cyano, $R_{10}$, amino, —NH($R_{10}$), —N($R_{10}$)($R_{10}$), —COOH, —O($R_{10}$), —SO$_2$NH$_2$, —SO$_2$NH($R_{10}$), —SO$_2$N($R_{10}$)($R_{10}$) —NHCO($R_{10}$), —N($R_{10}$)CO($R_{10}$), —NHCO$_2$($R_{10}$), —N($R_{10}$)CO$_2$ ($R_{10}$), —NHSO$_2$($R_{10}$), —N($R_{10}$)SO$_2$($R_{10}$), —SO$_2$NHCO($R_{10}$), —SO$_2$N($R_{10}$)CO($R_{10}$) —CONHSO$_2$($R_{10}$), —CON($R_{10}$)SO$_2$($R_{10}$), —CONH$_2$, —CONH($R_{10}$), —CON($R_{10}$)($R_{10}$), —CO$_2$($R_{10}$), —CO ($R_{10}$), —SR$_{10}$, SO($R_{10}$), —SO2 ($R_{10}$), aryl having from 1 to 3 rings, and heteroaryl, said heteroaryl having from 1 to 3 rings, 5 to 7 ring members in each ring, and in at least one of said rings from 1 to about 3 heteroatoms selected from nitrogen, oxygen and sulfur, and where each aryl and heteroaryl is optionally substituted with 1, 2, or 3 groups independently selected from $C_1$–$C_6$ alkyl, $C_1$–$C_6$ alkoxy, halogen, hydroxy, cyano, nitro, amino, and mono- or di($C_1$–$C_6$)alkylamino;

each $R_{10}$ is independently a straight, branched, or cyclic alkyl group having up to 8 carbon atoms, contains zero or one or more double or triple bonds, and is optionally substituted with one or more substituents independently selected from hydroxy, oxo, halogen, amino, mono- or di-($C_1$–$C_6$)alkylamino, cyano, nitro, $C_1$–$C_6$alkoxy, —COOH, —SO$_2$NH$_2$, —SO$_2$NH ($C_1$–$C_6$alkyl), —SO$_2$N($C_1$–$C_6$alkyl)($C_1$–$C_6$alkyl), —NHCO($C_1$–$C_6$alkyl) —N($C_1$–$C_6$alkyl)CO ($C_1$–$C_6$alkyl), NHCO$_2$($C_1$–$C_6$alkyl), —N($C_1$–$C_6$alkyl) CO$_2$($C_1$–$C_6$alkyl), —NHSO$_2$($C_1$–$C_6$alkyl), —N($C_1$–$C_6$alkyl)SO$_2$($C_1$–$C_6$alkyl), —SO$_2$N ($C_1$–$C_6$alkyl)CO($C_1$–$C_6$alkyl), —SO$_2$NHCO ($C_1$–$C_6$alkyl), —CON($C_1$–$C_6$alkyl)SO$_2$($C_1$–$C_6$alkyl), —CONHSO$_2$($C_1$–$C_6$alkyl), —CONH$_2$, —CONH (alkyl), —CON(alkyl)(alkyl), —CO$_2$(alkyl), —CO (alkyl), —SO$_{0-2}$($C_1$–$C_6$alkyl), and $C_3$–$C_7$cycloalkyl;

the group

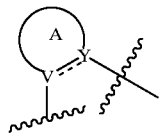

is the A ring and represents an optionally substituted saturated, partially unsaturated, or aromatic heterocyclic ring containing at least one nitrogen, oxygen, or sulfur atom, where the A ring is optionally substituted with up to three groups independently selected from $R_{100}$;

V is nitrogen, carbon, or CH;

Y is carbon or CH;

X is hydrogen, hydroxy, amino, mono- or di($C_1$–$C_6$) alkylamino, $C_1$–$C_6$ alkyl, or $C_1$–$C_6$ alkoxy;

T is hydrogen, halogen, hydroxy, amino, mono- or di($C_1$–$C_6$) alkylamino, $C_1$–$C_6$ alkyl, or $C_1$–$C_6$ alkoxy;

Q is a saturated carbocyclic or heterocyclic group, partially unsaturated carbocyclic or heterocyclic group, an aryl group, or heteroaryl group, where each group has from 1 to 3 rings where each ring contains from 3 to 8 ring members, and where each heterocyclic and heteroaryl group contains at least one ring having from 1 to 3 heteroatoms selected from nitrogen, oxygen and sulfur; and where each carbocyclic, heterocyclic, aryl, or heteroaryl group is optionally substituted with 1, 2, or 3 groups independently selected from $C_1$–$C_6$ alkyl, $C_1$–$C_6$ alkoxy, halogen, hydroxy, oxo, cyano, nitro, amino, $C_1$–$C_6$ haloalkyl, $C_1$–$C_6$ haloalkoxy, and mono- or di($C_1$–$C_6$)alkylamino;

W is a bond, oxygen, NH, sulfur, —CH=CH—, —C≡C—, or CR$^7$R$^8$ where R$^7$ and R$^8$ are the same or different and represent hydrogen, $C_1$–$C_6$ alkyl, halo ($C_1$–$C_6$)alkyl, amino($C_1$–$C_6$)alkyl, hydroxy($C_1$–$C_6$)alkyl, or $C_1$–$C_6$ alkoxy($C_1$–$C_6$)alkyl, or CR$^7$R$^8$ represents $C_3$–$C_7$ cycloalkyl;

Z is hydrogen, hydroxy, hydroxy($C_1$–$C_6$)alkyl, $C_1$–$C_6$ alkoxy, —CO($C_1$–$C_6$)alkyl, $C_3$–$C_7$ cycloalkyl, $C_3$–$C_7$ cycloalkyl($C_1$–$C_6$)alkyl, $C_3$–$C_7$ cycloalkyl($C_1$–$C_4$) alkoxy, amino, mono- or di($C_1$–$C_6$)alkylamino, or NR$_{11}$COR$_{12}$ where R$_{11}$ and R$_{12}$ are the same or different and represent hydrogen or $C_1$–$C_6$ alkyl, or NCOR$_{11}$R$_{12}$ represents a heterocycloalkanone ring, or Z is a saturated carbocyclic or heterocyclic group, a partially unsaturated carbocyclic or heterocyclic group, an aryl group, or a heteroaryl group, where each group has from 1 to 3 rings where each saturated ring contains from 3 to 8 ring members and each aromatic or partially unsaturated ring contains from 5–8 ring members, and where each heterocyclic and heteroaryl group contains at least one ring having from 1 to 3 heteroatoms selected from nitrogen, oxygen and sulfur; and where each carbocyclic, heterocyclic, aryl, and heteroaryl group is optionally substituted with 1, 2, or 3 groups independently selected from $C_1$–$C_6$ alkyl, $C_1$–$C_6$ alkoxy, halogen, hydroxy, cyano, nitro, amino, $C_1$–$C_6$ haloalkyl, $C_1$–$C_6$ haloalkoxy, and mono- or di($C_1$–$C_6$)alkylamino;

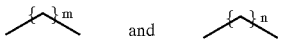

independently represent saturated carbon chains optionally substituted with one or more substituents independently selected from halogen, cyano, nitro, amino, mono- or di($C_1$–$C_6$)alkylamino, $C_2$–$C_6$ alkenyl, $C_2$–$C_6$ alkynyl, $C_1$–$C_6$ alkoxy, $C_1$–$C_6$ haloalkyl, $C_1$–$C_6$ haloalkoxy, $C_1$–$C_6$ alkyl, and $C_3$–$C_7$ cycloalkyl;

m is 0, 1, 2, or 3; and n is 0, 1, 2, or 3.

The invention also provides intermediates and methods useful for preparing the compounds of Formula A.

DETAILED DESCRIPTION OF THE INVENTION

Preferred compounds of Formula A include those where G is a nitrogen atom carrying $C_1$–$C_6$ alkyl or, preferably, hydrogen.

Other preferred compounds of Formula A are those where the group

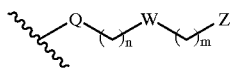

(hereinafter "Ar") represents
phenyl, pyridyl, pyrimidinyl, triazolyl, thiazolyl, thiadiazolyl, quinolinyl, pyrazolyl, isoxazolyl, pyrazinyl, triazolyl($C_1$–$C_6$)alkyl, pyridazinyl, 2-oxo-3-hydropyridyl, oxazole, oxadiazolyl, benzimidazol-5-yl, each of which is optionally substituted with 1, 2 or 3 groups independently selected from
halogen, $C_1$–$C_6$ alkoxy, $C_1$–$C_6$ alkyl, $C_3$–$C_7$ cycloalkyl, $C_3$–$C_7$ cycloalkyl($C_1$–$C_3$)alkyl, $C_1$–$C_6$ alkylthio, $C_1$–$C_6$ alkylamino, $C_3$–$C_7$ cycloalkylamino, $C_3$–$C_7$ cycloalkyl($C_1$–$C_3$)alkylamino, $C_1$–$C_6$ alkoxycarbonylamino($C_1$–$C_6$)alkyl), $C_1$–$C_6$ alkoxycarbonyl(($C_1$–$C_6$)alkyl)amino($C_1$–$C_6$)alkyl), $C_1$–$C_6$ alkylamino($C_1$–$C_6$)alkoxy, furanyl, (4-benzylpiperidinyl)($C_1$–$C_6$)alkoxy, (4-benzylpiperazinyl)($C_1$–$C_6$)alkoxy, $C_1$–$C_6$ alkoxy($C_1$–$C_6$)alkyl, $C_1$–$C_6$ alkoxy($C_1$–$C_6$)alkoxy, $C_1$–$C_6$ alkoxy($C_1$–$C_6$)alkylamino, morpholinyl($C_1$–$C_6$)alkoxy, trifluoromethyl, $C_1$–$C_6$ haloalkoxy, 1,3-dioxolanyl, ethyl-methanesulfonylamino($C_1$–$C_6$)alkoxy, 1,4-dioxepinyl, 1,4-dioxanyl, phenyoxy, pyrrolidinyl($C_1$–$C_6$)alkoxy, hydroxy($C_1$–$C_6$)alkyl, hydroxy($C_1$–$C_6$)alkoxy, $C_1$–$C_4$ alkylamino($C_1$–$C_4$)alkyl, imidazolyl, imidazolyl($C_1$–$C_6$)alkyl, imidazolyl($C_1$–$C_6$)alkoxy, triazolyl($C_1$–$C_6$)alkyl, benzyloxy($C_1$–$C_6$)alkoxy, piperidinyl($C_1$–$C_6$)alkyl, piperazinyl($C_1$–$C_6$)alkyl, morpholinyl($C_1$–$C_6$)alkyl, pyrrolidinyl($C_1$–$C_6$)alkyl, azetidinyl($C_1$–$C_6$)alkoxy, azetidinyl($C_1$–$C_6$)alkyl, $C_1$–$C_4$ alkoxy($C_1$–$C_4$)alkylamino($C_1$–$C_4$)alkyl, $C_1$–$C_6$ alkanoyl($C_1$–$C_6$)alkoxy, $C_1$–$C_6$ alkoxyphenoxy, phenoxy substituted with halo($C_1$–$C_6$)alkyl, tetrahydrofuranyloxy, oxetanyl($C_1$–$C_6$)alkoxy, oxetanyl($C_1$–$C_6$)alkyl, and 1-benzylimidazolyl($C_1$–$C_6$)alkoxy.

More preferred Ar groups include
phenyl, pyridyl, pyrimidinyl, 2-oxo-3-hydropyridyl, isoxazolyl, and oxazolyl, each of which is optionally substituted with 1 or 2 groups independently selected from
halogen, $C_1$–$C_6$ alkoxy, $C_1$–$C_6$ alkyl, $C_3$–$C_7$ cycloalkyl, $C_3$–$C_7$ cycloalkyl($C_1$–$C_3$)alkyl, $C_1$–$C_6$ alkylthio, $C_1$–$C_6$ alkylamino, $C_3$–$C_7$ cycloalkylamino, $C_3$–$C_7$ cycloalkyl($C_1$–$C_3$)alkylamino, $C_1$–$C_6$ alkoxycarbonylamino($C_1$–$C_6$)alkyl), $C_1$–$C_6$ alkoxycarbonyl(($C_1$–$C_6$)alkyl)amino($C_1$–$C_6$)alkyl), $C_1$–$C_6$ alkylamino($C_1$–$C_6$)alkoxy, furanyl, (4-benzylpiperidinyl)($C_1$–$C_6$)alkoxy, (4-benzylpiperazinyl)($C_1$–$C_6$)alkoxy, $C_1$–$C_6$ alkoxy($C_1$–$C_6$)alkyl, $C_1$–$C_6$ alkoxy($C_1$–$C_6$)alkoxy, $C_1$–$C_6$ alkoxy($C_1$–$C_6$)alkylamino, morpholinyl($C_1$–$C_6$)alkoxy, trifluoromethyl, $C_1$–$C_6$ haloalkoxy, 1,3-dioxolanyl, ethyl-methanesulfonylamino($C_1$–$C_6$)alkoxy, 1,4-dioxepinyl, 1,4-dioxanyl, phenyoxy, pyrrolidinyl($C_1$–$C_6$)alkoxy, hydroxy($C_1$–$C_6$)alkyl, hydroxy($C_1$–$C_6$)alkoxy, $C_1$–$C_4$ alkylamino($C_1$–$C_4$)alkyl, imidazolyl, imidazolyl($C_1$–$C_6$)alkyl, imidazolyl($C_1$–$C_6$)alkoxy, triazolyl($C_1$–$C_6$)alkyl, benzyloxy($C_1$–$C_6$)alkoxy, piperidinyl($C_1$–$C_6$)alkyl, piperazinyl($C_1$–$C_6$)alkyl, morpholinyl($C_1$–$C_6$)alkyl, pyrrolidinyl($C_1$–$C_6$)alkyl, azetidinyl($C_1$–$C_6$)alkoxy, azetidinyl($C_1$–$C_6$)alkyl, $C_1$–$C_4$ alkoxy($C_1$–$C_4$)alkylamino($C_1$–$C_4$)alkyl, $C_1$–$C_6$ alkanoyl($C_1$–$C_6$)alkoxy, $C_1$–$C_6$ alkoxyphenoxy, phenoxy substituted with halo($C_1$–$C_6$)alkyl, tetrahydrofuranyloxy, oxetanyl($C_1$–$C_6$)alkoxy, oxetanyl($C_1$–$C_6$)alkyl, and 1-benzylimidazolyl($C_1$–$C_6$)alkoxy.

Particularly preferred Ar groups include
phenyl, pyridyl, pyrimidinyl, and 2-oxo-3-hydropyridyl, each of which is optionally substituted with 1 or 2 groups independently selected from
halogen, $C_1$–$C_6$ alkoxy, $C_1$–$C_6$ alkyl, $C_3$–$C_7$ cycloalkyl, $C_3$–$C_7$ cycloalkyl($C_1$–$C_3$)alkyl, $C_1$–$C_6$ alkylthio, $C_1$–$C_6$ alkylamino, $C_3$–$C_7$ cycloalkylamino, $C_3$–$C_7$ cycloalkyl($C_1$–$C_3$)alkylamino, $C_1$–$C_6$ alkoxycarbonylamino($C_1$–$C_6$)alkyl), $C_1$–$C_6$ alkoxycarbonyl(($C_1$–$C_6$)alkyl)amino($C_1$–$C_6$)alkyl), $C_1$–$C_6$ alkylamino($C_1$–$C_6$)alkoxy, furanyl, (4-benzylpiperidinyl)($C_1$–$C_6$)alkoxy, (4-benzylpiperazinyl)($C_1$–$C_6$)alkoxy, $C_1$–$C_6$ alkoxy($C_1$–$C_6$)alkyl, $C_1$–$C_6$ alkoxy($C_1$–$C_6$)alkoxy, $C_1$–$C_6$ alkoxy($C_1$–$C_6$)alkylamino, morpholinyl($C_1$–$C_6$)alkoxy, trifluoromethyl, $C_1$–$C_6$ haloalkoxy, 1,3-dioxolanyl, ethyl-methanesulfonylamino($C_1$–$C_6$)alkoxy, 1,4-dioxepinyl, 1,4-dioxanyl, phenyoxy, pyrrolidinyl($C_1$–$C_6$)alkoxy, hydroxy($C_1$–$C_6$)alkyl, hydroxy($C_1$–$C_6$)alkoxy, $C_1$–$C_4$ alkylamino($C_1$–$C_4$)alkyl, imidazolyl, imidazolyl($C_1$–$C_6$)alkyl, imidazolyl($C_1$–$C_6$)alkoxy, triazolyl($C_1$–$C_6$)alkyl, benzyloxy($C_1$–$C_6$)alkoxy, piperidinyl($C_1$–$C_6$)alkyl, piperazinyl($C_1$–$C_6$)alkyl, morpholinyl($C_1$–$C_6$)alkyl, pyrrolidinyl($C_1$–$C_6$)alkyl, azetidinyl($C_1$–$C_6$)alkoxy, azetidinyl($C_1$–$C_6$)alkyl, $C_1$–$C_4$ alkoxy($C_1$–$C_4$)alkylamino($C_1$–$C_4$)alkyl, $C_1$–$C_6$ alkanoyl($C_1$–$C_6$)alkoxy, $C_1$–$C_6$ alkoxyphenoxy, phenoxy substituted with halo($C_1$–$C_6$)alkyl, tetrahydrofuranyloxy, oxetanyl($C_1$–$C_6$)alkoxy, oxetanyl($C_1$–$C_6$)alkyl, and 1-benzylimidazolyl($C_1$–$C_6$)alkoxy.

Highly preferred substituents on the Ar aryl and heteraryl groups include
halogen, $C_1$–$C_6$ alkoxy, $C_1$–$C_6$ alkyl, $C_3$–$C_7$ cycloalkyl, $C_3$–$C_7$ cycloalkyl($C_1$–$C_3$)alkyl, $C_1$–$C_6$ alkylamino, $C_3$–$C_7$ cycloalkylamino, $C_1$–$C_6$ alkoxycarbonylamino($C_1$–$C_6$)alkyl), $C_1$–$C_6$ alkoxycarbonyl(($C_1$–$C_6$)alkyl)amino($C_1$–$C_6$)alkyl), $C_1$–$C_6$ alkylamino($C_1$–$C_6$)alkoxy, $C_1$–$C_6$ alkoxy($C_1$–$C_6$)alkyl, $C_1$–$C_6$ alkoxy($C_1$–$C_6$)alkoxy, $C_1$–$C_6$ alkoxy($C_1$–$C_6$)alkylamino, morpholinyl($C_1$–$C_6$)alkoxy, pyrrolidinyl($C_1$–$C_6$)alkoxy, $C_1$–$C_4$ alkylamino($C_1$–$C_4$)alkyl, piperidinyl($C_1$–$C_6$)alkyl, piperazinyl($C_1$–$C_6$)alkyl, morpholinyl($C_1$–$C_6$)alkyl, pyrrolidinyl($C_1$–$C_6$)alkyl, and $C_1$–$C_4$ alkoxy($C_1$–$C_4$)alkylamino($C_1$–$C_4$)alkyl.

In addition to compounds of Formula A, the invention also provides compounds of Formula I

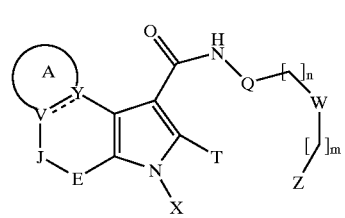

Formula I and the pharmaceutically acceptable salts thereof, wherein:
J is defined as above with respect to Formula I;
E is defined as above with respect to Formula I and preferably represents —$(CR^1R^2)_k$— where $R^1$ and $R^2$ are independently chosen at each occurrence from hydrogen, halogen, hydroxy, cyano, nitro, amino, haloalkyl, mono or diamino($C_{1-6}$)alkyl, $C_{1-6}$ alkyl, $C_{2-6}$alkenyl, $C_{2-6}$alkynyl and $C_{1-6}$ alkoxy, and k is 0, 1, 2, or 3;

the group

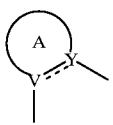

is a group of the formula:

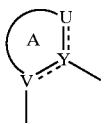

represents a saturated, unsaturated or aromatic heterocyclic ring containing at least one nitrogen, oxygen or sulfur atom, wherein the U===Y and V===Y bonds may be single, double or aromatic bonds, U is nitrogen, $NR^A$, S, or O;
V is nitrogen, carbon or CH;
Y is carbon, or CH;
and said saturated, unsaturated or aromatic heterocyclic ring is chosen from:
thienyl, thiazolyl, pyridyl, pyrimidinyl, imidazolyl, pyrazolyl, pyrazinyl, pyridizinyl, piperidinyl, oxazolyl, isoxazolyl, symmetrical and unsymmetrical triazolyl, pyrrolyl, furanyl, diazenyl, triazenyl, 1,2,4-triazolone, 4,5-dihydroimidazolyl, and 1,4,5,6-tetrahydropyrimidinyl,
each of which is optionally substituted at any available nitrogen by $R^A$ and optionally substituted at any available carbon by $R^3$ and $R^4$, wherein:
$R^A$ is selected from $(C_1-C_6)$alkyl, $C_1-C_6$ haloalkyl, amino$(C_1-C_6)$alkyl, or mono- or di$(C_1-C_6)$alkylamino$(C_1-C_6)$alkyl, hydroxy$(C_1-C_6)$alkyl, $C_1-C_6$ alkoxy$(C_1-C_6)$alkyl, aryl, heteroaryl, aryl$(C_1-C_6)$alkyl, or heteroaryl$(C_1-C_6)$alkyl, where each aryl and heteroaryl is optionally substituted with up to 3 groups independently selected from $C_1-C_6$ alkyl, $C_1-C_6$ alkoxy, halogen, hydroxy, cyano, nitro, amino, and mono- and di$(C_1-C_6)$alkylamino;
$R^5$ and $R^6$ are independently chosen from hydrogen, aryl, heteroaryl, halogen, hydroxy, nitro, cyano, $C_{1-6}$alkyl$_1$, amino, —COOH, —O($C_{1-6}$alkyl$_1$), —NH($C_{1-6}$alkyl$_1$), —N($C_{1-6}$alkyl$_1$)($C_{1-6}$alkyl$_1$), —SO$_2$NH$_2$, —SO$_2$NH($C_{1-6}$alkyl$_1$), —SO$_2$N($C_{1-6}$alkyl$_1$)($C_{1-6}$alkyl$_1$), —N($C_{1-6}$alkyl$_1$)CO($C_{1-6}$alkyl$_1$), N($C_{1-6}$alkyl$_1$)CO$_2$($C_{1-6}$alkyl$_1$), —NHSO$_2$($C_{1-6}$alkyl$_1$), —N($C_{1-6}$alkyl$_1$)SO$_2$($C_{1-6}$alkyl$_1$), —SO$_2$NHCO($C_{1-6}$alkyl$_1$), —CONHSO$_2$($C_{1-6}$alkyl$_1$), —CONH($C_{1-6}$alkyl$_1$), —CON($C_{1-6}$alkyl$_1$)($C_{1-6}$alkyl$_1$), —CO$_2$($C_{1-6}$alkyl$_1$), —CO($C_{1-6}$alkyl$_1$) and —SO$_{0-2}$($C_{1-6}$alkyl$_1$),
wherein $C_{1-6}$alkyl$_1$ is independently chosen at each occurrence and is straight branched or cyclic, may contain one or two double or triple bonds, and is unsubstituted or substituted with one or more substituents selected from: hydroxy, oxo, halogen, amino, cyano, nitro, alkoxy, carbocylic or heterocyclic group, —COOH, —SO$_2$NH$_2$, —SO$_2$NH(C$_{1-4}$alkyl), —SO$_2$N(C$_{1-4}$alkyl)(C$_{1-4}$alkyl), —N(C$_{1-4}$alkyl)CO(C$_{1-4}$alkyl), N(C$_{1-4}$alkyl)CO$_2$(C$_{1-4}$alkyl), —NHSO$_2$(alkyl), —N(C$_{1-4}$alkyl)SO$_2$(C$_{1-4}$alkyl), —SO$_2$NHCO(C$_{1-4}$alkyl), —CONHSO$_2$(C$_{1-4}$alkyl), —CONH(C$_{1-4}$alkyl), —CON(C$_{1-4}$alkyl)(C$_{1-4}$alkyl), —CO$_2$(C$_{1-4}$alkyl), —CO(C$_{1-4}$alkyl), and -SO$_{02}$(C$_{1-4}$alkyl);

$R^3$ and $R^4$ are independently chosen at each occurrence, and are defined the same as $R^5$ and $R^6$;

X is chosen from hydrogen, hydroxy, amino, $C_{1-6}$ alkyl, and $C_{1-6}$alkoxy;

T is chosen from hydrogen, halogen, hydroxy, amino, $C_{1-6}$ alkyl, and $C_{1-6}$ alkoxy;

Q is a phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrazolyl, furanyl, diazenyl, triazenyl, or triazolopyrazinyl group;
each of which may be unsubstituted or substituted with up to three substituents independently selected from i) and ii) wherein
i) represents hydroxy, cyano, halogen, nitro, amino, mono or di(C$_{1-6}$)alkylamino, C$_{2-6}$alkenyl, C$_{2-6}$alkynyl, C$_{1-6}$alkoxy, trifluoromethyl, or trifluoromethoxy;
ii) represents straight or branched chain C$_{1-6}$alkyl optionally containing heteroatoms and optionally substituted with one or more carbocyclic or heterocyclic group;

W is hydrogen, oxygen, nitrogen, sulfur, or $CR^7R^8$ where $R^7$ and $R^8$ are the same or different and represent hydrogen, straight or branched chain C$_{1-6}$alkyl, or $R^7$ and $R^8$ may be taken together to represent a cyclic moiety having 3–7 carbon atoms;

Z is hydrogen, hydroxy, straight or branched chain C$_{1-6}$alkoxy, C$_{3-7}$cycloalkyl, C$_{3-7}$cycloalkyl(C$_{1-3}$alkoxy), amino, mono or di C$_{1-6}$alkylamino, a carbocyclic or heterocylic group, or $NR^9COR_{10}$ where $R^9$ and $R_{10}$ are the same or different and represent hydrogen or straight or branched chain C$_{1-6}$alkyl, or $R^9$ and $R_{10}$ may be joined to from a C$_{3-7}$ cycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, triazenyl, 1,2,4-triazolone, 4,5-dihydroimidazolyl, or 1,4,5,6-tetrahydropyrimidinyl group;

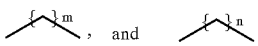

represent a carbon chain optionally substituted with hydrogen, halogen, cyano, nitro, amino, mono or di C$_{1-6}$alkylamino, C$_{2-6}$alkenyl, C$_{2-6}$alkynyl, C$_{1-6}$alkoxy, trifluoromethyl, trifluoromethoxy, straight or branched chain C$_{1-6}$alkyl, or C$_{3-7}$cycloalkyl, and
m is 0, 1, 2, or 3; and
n is 0, 1, 2, or 3.

In preferred embodiments of Formula I,
$R^5$ and $R^6$ are independently chosen from hydrogen, aryl where aryl is defined as above with respect to Formula A, heteroaryl where heteroaryl is defined as above with respect to Formula A, halogen, hydroxy, nitro, cyano, C$_{1-6}$alkyl$_1$, amino, —COOH, —O(C$_{1-6}$alkyl$_1$), —NH(C$_{1-6}$ alkyl$_1$), —N(C$_{1-6}$alkyl$_1$)(C$_{1-6}$alkyl$_1$), —SO$_2$NH$_2$, —SO$_2$NH(C$_{1-6}$alkyl$_1$), —SO$_2$N(C$_{1-6}$alkyl$_1$)(C$_{1-6}$alkyl$_1$), —N(C$_{1-6}$alkyl$_1$)CO(C$_{1-6}$alkyl$_1$), N(C$_{1-6}$alkyl$_1$)CO$_2$(C$_{1-6}$alkyl$_1$), —NHSO$_2$(C$_{1-6}$alkyl$_1$), —N(C$_{1-6}$alkyl$_1$) SO$_2$(C$_{1-6}$alkyl$_1$), —SO$_2$NHCO(C$_{1-6}$alkyl$_1$), —CONHSO$_2$(C$_{1-6}$ alkyl$_1$), —CONH(C$_{1-6}$alkyl$_1$), —CON(C$_{1-6}$alkyl$_1$)(C$_{1-6}$alkyl$_1$), —CO$_2$(C$_{1-6}$alkyl$_1$), —CO(C$_{1-6}$alkyl$_1$) and —SO$_{0-2}$(C$_{1-6}$alkyl$_1$), wherein C$_{1-6}$alkyl$_1$ is independently chosen at each occurrence and is straight branched or cyclic, may contain one or two double or triple bonds, and is unsubstituted or substituted with one or more substituents selected from: hydroxy, oxo, halogen, amino, cyano, nitro, alkoxy, carbocylic or heterocyclic group, —COOH, —SO$_2$NH$_2$, —SO$_2$NH(C$_{1-4}$alkyl), —SO$_2$N(C$_{1-4}$alkyl)(C$_{1-4}$alkyl), —N(C$_{1-4}$alkyl)CO(C$_{1-4}$alkyl), N(C$_{1-4}$alkyl)CO$_2$(C$_{1-4}$alkyl), —NHSO$_2$(alkyl), —N(C$_{1-4}$alkyl)SO$_2$(C$_{1-4}$alkyl), —SO$_2$NHCO(C$_{1-4}$alkyl), —CONHSO$_2$(C$_{1-4}$alkyl), —CONH(C$_{1-4}$alkyl), —CON(C$_{1-4}$alkyl)(C$_{1-4}$alkyl), —CO$_2$(C$_{1-4}$alkyl), —CO(C$_{1-4}$alkyl), and —SO$_{0-2}$(C$_{1-4}$alkyl);

R$^3$ and R$^4$ are independently selected at each occurrence, and are defined the same as R$^5$ and R$^6$.

Preferably R$^3$, R$^4$, R$^5$, and R$^6$ are independently hydrogen, halogen, hydroxy, nitro, cyano, C$_{1-6}$alkyl$_1$, amino, —COOH, —O(C$_{1-6}$alkyl), —NH(C$_{1-6}$alkyl), —N(C$_{1-6}$alkyl)(C$_{1-6}$alkyl), —SO$_2$NH$_2$, —SO$_2$NH(C$_{1-6}$alkyl), —SO$_2$N(C$_{1-6}$alkyl)(C$_{1-6}$alkyl), —N(C$_{1-6}$alkyl)CO(C$_{1-6}$alkyl), N(C$_{1-6}$alkyl)CO$_2$(C$_{1-6}$alkyl), —NHSO$_2$(C$_{1-6}$alkyl), —N(C$_{1-6}$alkyl) SO$_2$(C$_{1-6}$alkyl), —SO$_2$NHCO(C$_{1-6}$alkyl), —CONHSO$_2$(C$_{1-6}$alkyl), —CONH(C$_{1-6}$alkyl), —CON(C$_{1-6}$alkyl)(C$_{1-6}$alkyl), —CO2(C$_{1-6}$alkyl), —CO(C$_{1-6}$alkyl) and —SO$_{02}$(C$_{1-6}$alkyl), wherein each C$_{1-6}$alkyl is independently unsubstituted or substituted with one or more substituents selected from hydroxy, oxo, halogen, amino, cyano, nitro, alkoxy, carbocylic or heterocyclic group, —COOH, —SO$_2$NH$_2$, —SO$_2$NH(C$_{1-4}$alkyl), —SO$_2$N(C$_{1-4}$alkyl)(C$_{1-4}$alkyl), —N(C$_{1-4}$alkyl)CO(C$_{1-4}$alkyl), N(C$_{1-4}$alkyl)CO$_2$(C$_{1-4}$alkyl), —NHSO$_2$(alkyl), —N(C$_{1-4}$alkyl) SO$_2$(C$_{1-4}$alkyl), —SO$_2$NHCO(C$_{1-4}$alkyl), —CONHSO$_2$(C$_{1-4}$alkyl), —CONH(C$_{1-4}$alkyl), —CON(C$_{1-4}$ alkyl)(C$_{1-4}$alkyl), —CO2(C$_{1-4}$alkyl), —CO(C$_{1-4}$alkyl), and —SO$_{0-2}$(C$_{1-4}$alkyl).

More preferably, R$^3$, R$^4$, R$^5$, and R$^6$ are independently hydrogen, halogen, hydroxy, nitro, cyano, C$_1$–C$_6$ alkyl, amino, C$_1$–C$_6$ alkoxy, mono- or di(C$_1$–C$_6$)alkylamino, hydroxy(C$_1$–C$_6$)alkyl, amino(C$_1$–C$_6$)alkyl or halo(C$_1$–C$_6$) alkyl.

In one embodiment, W is a bond, m is 0, and Z is hydrogen, i.e.,

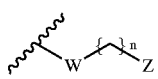

represents hydrogen. Alternatively, this may be viewed as compounds where W is hydrogen, m is 0, and Z is absent. Thus, in this embodiment, Q is optionally substituted as defined above and also optionally carries an optionally substituted carbon chain as defined above.

More preferred Ar groups include phenyl, 2-pyridyl, 2-pyrazinyl, and 3- or 4-pyrazolyl, each of which is optionally mono- or disubstituted with C$_1$–C$_6$ alkyl, C$_1$–C$_6$ alkoxy, halogen, hydroxy, halo(C$_1$–C$_6$)alkyl, hydroxy(C$_1$–C$_6$)alkyl, amino, or amino(C$_1$–C$_6$)alkyl. Particularly preferred are Ar groups that are unsubstituted or monosubstituted with C$_1$–C$_4$ alkyl, preferably methyl or ethyl. Specific Ar preferred Ar groups include phenyl substituted at the 2-position (ortho to the point of attachment) with C$_1$–C$_4$ alkyl, preferably methyl or ethyl and 4-pyrazolyl substituted in the 1-position with C$_1$–C$_6$ alkyl, preferably methyl, ethyl, or propyl.

Further provided are compounds of Formula II

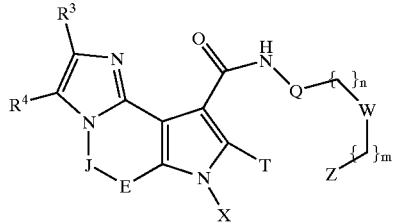

Formula II and the pharmaceutically acceptable salts thereof,
wherein the variables E, J, R$^1$, R$^2$, R$^3$, R$^4$, R$^5$, R$^6$, k, n, m, T, X, Q, W, and Z are as defined for Formula I.

Compounds of Formula II include compounds where
J is CR$^5$R$^6$;
E is —(CR$^1$CR$^2$)$_k$— where —R$^1$ and R$^2$ are hydrogen; k is 1 or 2;
R$^3$, R$^4$, R$^5$, and R$^6$, are independently chosen from hydrogen, halogen, amino, hydroxy, methyl, ethyl, methoxy, and ethoxy; and
X and T are both hydrogen (hereinafter compounds of Formula IIa).

Other compounds of Formula II are those where J is CR$^5$R$^6$, E is —CR$^1$CR$^2$— and R$^1$, R$^2$, R$^3$, R$^4$, R$^5$, and R$^6$ are hydrogen, and k is 1 (compounds of Formula IIb).

Particularly preferred compounds of Formula II are compounds of Formula IIc

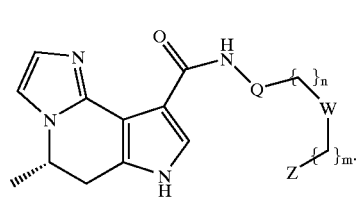

Formula IIc

In Formula IIc (above) the conformation of the methyl group at the 4-position of the indacene ring structure denotes (S) stereochemistry.

Other particularly preferred compounds of Formula II are compounds of Formula IId

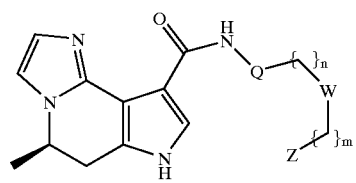

Formula IId

In Formula IId, the conformation of the methyl group at the 4-position of the indacene ring structure denotes (R) stereochemistry.

Preferred compounds of Formulas IIc and IId are those where

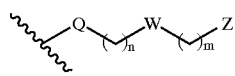

represents phenyl optionally substituted with R$_p$ where R$_p$ is C$_1$–C$_6$ alkyl, C$_1$–C$_6$ alkoxy, halogen, hydroxy, halo(C$_1$–C$_6$) alkyl, hydroxy(C$_1$–C$_6$)alkyl, amino, or amino(C$_1$–C$_6$)alkyl.

In another embodiment the invention includes compounds of Formula III

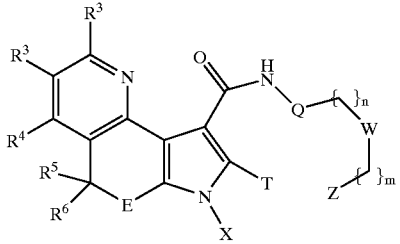

Formula III and the pharmaceutically acceptable salts thereof, wherein the variables E, $R^1$, $R^2$, $R^3$, $R^4$, $R^5$, $R^6$, k, n, m, T, X, Q, W, and Z are as defined for Formula I.

The definition of the variable $R^3$ at the 2-position of the pyridyl ring is independent of it definition at the 3-position.

Specific compounds of Formula III are those where E is —$(CR^1CR^2)_k$—; k is 2 and $R^1$ and $R^2$ are hydrogen (compounds of Formula IIIa). Other compounds of Formula III are compounds where E is —$(CR^1CR^2)_k$—; k is 2; $R^1$ and $R^2$ are hydrogen; $R^3$, $R^4$, $R^5$, and $R^5$ are independently chosen at each occurrence from hydrogen, halogen, amino, hydroxy, methyl, ethyl, methoxy, and ethoxy; and X and T are both hydrogen (compounds of Formula IIIb). Also particularly included as compounds of Formula III are compounds of Formula IIIc and Formula IIId

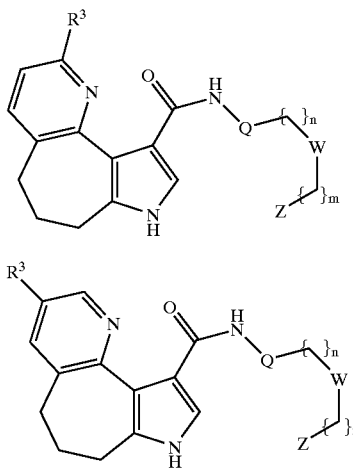

Formula IIIc

Formula IIId wherein each $R^3$ is independently hydrogen or methyl.

Preferred compounds of Formulas IIIc and IIId are those where

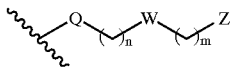

("Ar") represents phenyl or pyridyl optionally substituted with $R_p$ where $R_p$ is $C_1$–$C_6$ alkyl, $C_1$–$C_6$ alkoxy, halogen, hydroxy, halo($C_1$–$C_6$)alkyl, hydroxy($C_1$–$C_6$)alkyl, amino, or amino($C_1$–$C_6$)alkyl. Preferably, Ar in IIIc and IIId represents phenyl or 2- or 3-pyridyl each of which is optionally substituted with $C_1$–$C_6$ alkyl, or more preferably unsubstituted or substituted with methyl or ethyl.

The invention also includes compounds of Formula IV

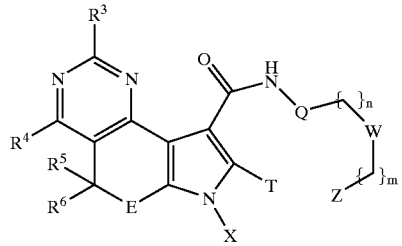

Formula IV and the pharmaceutically acceptable salts thereof, wherein the variables E, $R^1$, $R^2$, $R^3$, $R^4$, $R^5$, $R^6$, k, n, m, T, X, Q, W, and Z are as defined for Formula I. Particular compounds of Formula IV are those compounds where E is —$(CR^1CR^2)_k$—, k is 2 and $R^1$ and $R^2$ are hydrogen (compounds of Formula IVa). Other compounds of Formula IV are those compounds were E is —$(CR^1CR^2)_k$—, k is 2; $R^1$ and $R^2$ are hydrogen; $R^3$, $R^4$, $R^5$, and $R^6$, are independently chosen at each occurrence from hydrogen, halogen, amino, hydroxy, methyl, ethyl, methoxy, and ethoxy; and X and T are both hydrogen (compounds of Formula IVb). Compounds of Formula IV particularly include compounds where E is —$(CR^1CR^2)_k$—, k is 2 and $R^1$, $R^2$, $R^3$, $R^4$, $R^5$, and $R^6$ are all hydrogen (compounds of Formula IVc).

Preferred compounds of Formulas IV, and of IVa-IVc, are those where

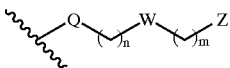

("Ar") represents phenyl, 2-pyrazinyl, or 2-pyridyl optionally substituted with $R_p$ where $R_p$ is $C_1$–$C_6$ alkyl, $C_1$–$C_6$ alkoxy, halogen, hydroxy, halo($C_1$–$C_6$)alkyl, hydroxy ($C_1$–$C_6$)alkyl, amino, or amino($C_1$–$C_6$)alkyl. Preferably, Ar in Formula IV is phenyl, 2-pyridyl, or 2-pyrazinyl, each of which is optionally substituted with $C_1$–$C_6$ alkyl, or more preferably unsubstituted or substituted with methyl or ethyl. Still other preferred Ar groups in Formula IV are 3- and 4-pyrazolyl groups substituted in the 1-position with $C_1$–$C_4$ alkyl group, preferably methyl or ethyl.

In another embodiment the invention includes compounds of Formula V

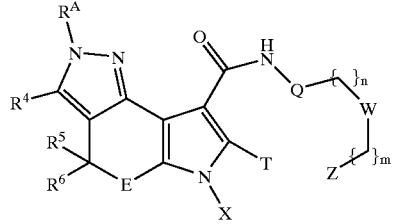

Formula V and the pharmaceutically acceptable salts thereof wherein the variables E, $R^1$, $R^2$, $R^3$, $R^4$, $R^5$, $R^6$, k, n, m, T, X, Q, W, and Z are as for Formula I. In a more specific embodiment, the invention includes compounds of Formula V where E is —$(CR^1CR^2)_k$—, k is 2 and $R^1$ and $R^2$ are hydrogen (compounds of Formula Va). Still other compounds of Formula V are those compounds where E is —$(CR^1CR^2)_k$—, k is 2; $R^1$ and $R^2$ are hydrogen; $R^A$ is $C_{1-6}$alkyl, $C_1$–$C_6$ haloalkyl, amino($C_1$–$C_6$)alkyl, or mono- or di($C_1$–$C_6$)alkylamino($C_1$–$C_6$)alkyl, hydroxy($C_1$–$C_6$)alkyl, $C_1$–$C_6$ alkoxy($C_1$–$C_6$)alkyl, phenyl, thienyl, pyridyl, pyrimidinyl, or pyrrolyl; $R^3$, $R^4$, $R^5$, and $R^6$, are independently chosen from hydrogen, halogen, amino, hydroxy, methyl, ethyl, methoxy, and ethoxy; and X and T are both hydrogen (compounds of Formula Vb). In a still more specific embodiment the invention includes compounds of Formula V where E is —($CR^1CR^2$)$_k$—, k is 2, $R^1$, $R^2$, $R^3$, $R^4$, $R^5$, and $R^6$ are all hydrogen; and $R^A$ is methyl, ethyl, or pyridyl.

Yet another embodiment of the invention includes compounds of Formula VI

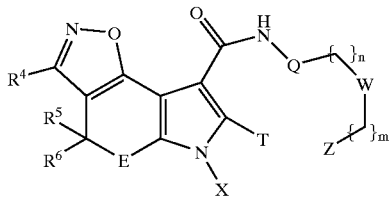

Formula VI and the pharmaceutically acceptable salts thereof, wherein the variables E, $R^1$, $R^2$, $R^4$, $R^5$, $R^6$, k, n, m, T, X, Q, W, and Z are as defined for Formula I. Particular compounds of Formula VI are compounds where E is —($CR^1CR^2$)$_k$—, k is 2 and $R^1$ and $R^2$ are both hydrogen (compounds of Formula VIa). Other compounds of Formula VI are compounds where E is —($CR^1CR^2$)$_k$—, k is 2; and $R^1$ and $R^2$ are both hydrogen; $R^4$, $R^5$, and $R^6$, are independently chosen from hydrogen, halogen, amino, hydroxy, methyl, ethyl, methoxy, and ethoxy; and X and T are both hydrogen (compounds of Formula VIb). A particular embodiment of the invention includes compounds of Formula VI where E is —($CR^1CR^2$)$_k$—, k is 2; and $R^1$, $R^2$, $R^5$, $R^6$, X and T are all hydrogen; and $R^4$ is methyl (compounds of Formula VIc).

In still another embodiment, the invention provides compounds of Formula VII

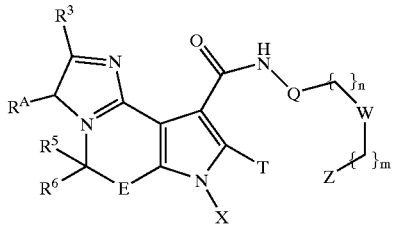

Formula VII and the pharmaceutically acceptable salts thereof, wherein the variables E, $R^1$, $R^2$, $R^A$, $R^4$, $R^5$, $R^6$, k, n, m, T, X, Q, W, and Z are as defined for Formula I. Included as compounds of Formula VII are compounds where k is 2 and $R^1$ and $R^2$ are hydrogen (compounds of Formula VIIa). More particularly, the invention includes compounds of Formula VII where E is —($CR^1CR^2$)$_k$—, k is 2; $R^1$ and $R^2$ are hydrogen; $R^A$ is methyl, ethyl, or pyridyl; $R^4$, $R^5$, and $R^6$, are independently chosen from hydrogen, halogen, amino, hydroxy, methyl, ethyl, methoxy, and ethoxy; and X and T are both hydrogen (compounds of Formula VIIb). The invention also particularly includes compounds of Formula VII where E is —($CR^1CR^2$)$_k$—, k is 2; $R^1$, $R^2$, $R^4$, $R^5$, $R^6$, X and T are all hydrogen; and $R^A$ is methyl (compounds of Formula VIIc).

Further included as compounds of the invention are compounds of Formula VIII

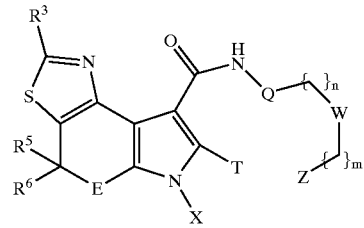

Formula VIII and the pharmaceutically acceptable salts thereof wherein the variables E, $R^1$, $R^2$, $R^4$, $R^5$, $R^6$, k, n, m, T, X, Q, W, and Z are as defined as for Formula I. Such compounds of Formula VIII include compounds where E is —($CR^1CR^2$)$_k$—, k is 2 and $R^1$ and $R^2$ are both hydrogen (compounds of Formula VIIIa). In yet another embodiment the invention provides compounds of Formula VIII where k is 2; $R^1$ and $R^2$ are both hydrogen; $R^4$, $R^5$, and $R^6$, are independently chosen from hydrogen, halogen, amino, hydroxy, methyl, ethyl, methoxy, and ethoxy; and X and T are both hydrogen (compounds of Formula VIIIb). More particularly, the invention provides compounds of Formula VIII where E is —($CR^1CR^2$)$_k$—, k is 2; $R^1$, $R^2$, $R^5$, $R^6$, X, and T are all hydrogen; and $R^4$ is methyl (compounds of Formula VIIIc).

For each of Formula IIa, IIb, IIc, IIIa, IIIb, IIIc, IIId, IVa, IVb, IVc, Va, Vb, Vc, VIa, VIb, VIc, VIIa, VIIb, VIIc, VIIIa, VIIIb, and VIIIc the variables n, m, Q, W, and Z are as defined for Formula I.

Alternate embodiments of the invention include compounds of Formula IX, Formula X, Formula XI, and Formula XII (shown below) and the pharmaceutically acceptable salts thereof wherein variables $R^1$, $R^2$, $R^3$, $R^4$, $R^5$, $R^6$, k, n, m, T, X, Q, W, and Z are as defined for Formula I.

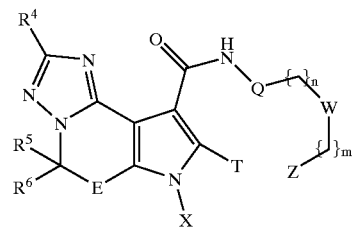

Formula IX

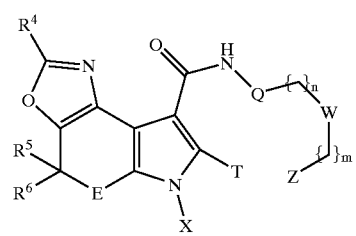

Formula X

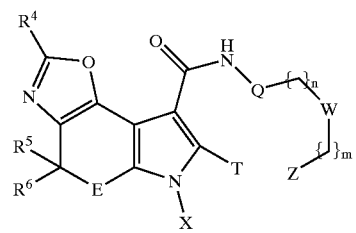

Formula XI

Formula XII

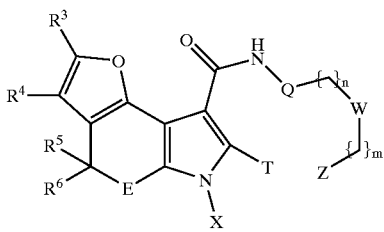

Other compounds provided by the invention, but outside the definition of general Formula I, are compounds of the formula

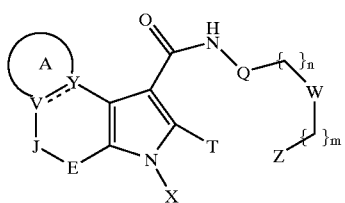

where Y is nitrogen, and all other variables are as defined for Formula I.

The invention also provides compounds of the formula B-1:

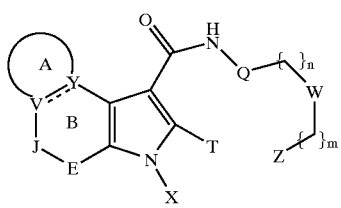

B-1 where the "B-ring" is a 5–9 membered ring containing up to 4 hetero atoms selected from nitrogen, $NR^A$, S, and oxygen. The B-ring is saturated, unsaturated or aromatic. All other variables are as defined for Formula I.

Preferred compounds of B-1 are those where the b-ring has the formula:

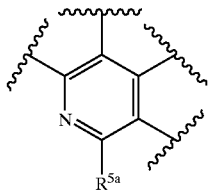

wherein $R^{5a}$ is hydrogen, hydroxy, halogen, cyano, nitro, $C_1$–$C_6$ alkyl, $C_1$–$C_6$ alkoxy, amino, mono- or di($C_1$–$C_6$) alkylamino, or phenyl optionally substituted with $C_1$–$C_6$ alkyl, $C_1$–$C_6$ alkoxy, halogen, hydroxy, cyano, nitro, amino, and mono- or di($C_1$–$C_6$)alkylamino.

Other preferred compounds of B-1 are those where the b-ring has the formula

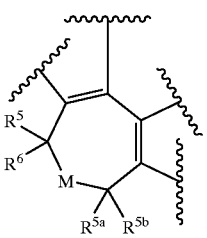

wherein $R^5$ and $R^6$ carry the definitions given above with respect to Formula A or Formula I;

M is NR' or oxygen; and $R^{5a}$ and $R^{5b}$ are independently hydrogen, hydroxy, halogen, cyano, nitro, $C_1$–$C_6$ alkyl, $C_1$–$C_6$ alkoxy, amino, or mono- or di($C_1$–$C_6$) alkylamino, or phenyl, pyridyl, phenyl($C_1$–$C_6$)alkyl, or pyridyl($C_1$–$C_6$) alkyl, where each phenyl and pyridyl is optionally substituted with $C_1$–$C_6$ alkyl, $C_1$–$C_6$ alkoxy, halogen, hydroxy, cyano, nitro, amino, and mono- or di($C_1$–$C_6$) alkylamino; and R' is hydrogen, $C_1$–$C_6$ alkyl, $C_1$–$C_6$ alkoxy($C_1$–$C_6$)alkyl, $C_2$–$C_6$ alkenyl, $C_2$–$C_6$ alkynyl, $C_1$–$C_6$ haloalkyl, amino ($C_1$–$C_6$)alkyl, or mono- or di($C_1$–$C_6$)alkylamino($C_3$–$C_6$) alkyl, or aryl, heteroaryl, aryl($C_1$–$C_6$)alkyl, or heteroaryl($C_1$–$C_6$) alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$) alkylamino.

More preferred compounds of this group are those where $R^5$ and $R^6$ are independently hydrogen or $C_1$–$C_6$ alkyl;

M is NR' where R' is hydrogen, $C_1$–$C_6$ alkyl, , $C_1$–$C_6$ alkoxy($C_1$–$C_6$)alkyl, $C_2$–$C_6$ alkenyl, $C_2$–$C_6$ alkynyl, $C_1$–$C_6$ haloalkyl, amino ($C_1$–$C_6$)alkyl, or mono- or di($C_1$–$C_6$)alkylamino ($C_1$–$C_6$)alkyl, or aryl, heteroaryl, aryl($C_1$–$C_6$)alkyl, or heteroaryl($C_1$–$C_6$) alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$) alkylamino; and $R^{5a}$ and $R^{5b}$ are hydrogen.

Still other more preferred compounds of this group are those where

X and T are hydrogen; and $R^{3a}$ and each $R^3$ independently represent hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, hydroxy($C_1$–$C_6$)alkyl, halo ($C_1$–$C_6$)alkyl, or phenyl, pyridyl, pyrimidinyl, imidazolyl, or $C_1$–$C_6$ alkyl substituted with phenyl, pyridyl, or pyrimidinyl, or imidazolyl, where each phenyl, pyridyl, pyrimidinyl, and imidazolyl is optionally substituted with one or two groups independently selected from $C_1$–$C_6$ alkyl, $C_1$–$C_6$ alkoxy, halogen, hydroxy, and amino.

Yet other more preferred compounds of this group are those where R' is hydrogen, $C_1$–$C_6$ alkyl, or $C_1$–$C_6$ alkyl substituted with phenyl or pyridyl, where each phenyl or pyridyl is optionally substituted with halogen, hydroxy, amino, $C_1$–$C_6$ alkyl or $C_1$–$C_6$ alkoxy.

Particularly preferred compounds of this group are those where $R^5$ and $R^6$ are independently hydrogen or $C_1$–$C_6$ alkyl;

M is oxygen; and $R^{5a}$ and $R^{5b}$ are hydrogen.

Also within formula B-1, there are included Formulas XIII and XIV.

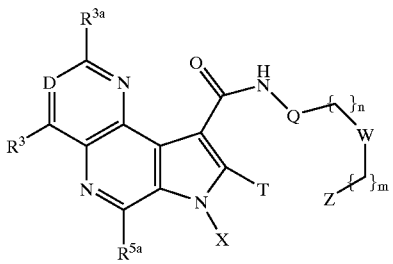

Formula XIII wherein

X, T, Q, n, W, m, and Z are as defined above with respect to Formula A or Formula I;

D is nitrogen or $CR^3$ where $R^{3a}$ and each $R^3$ independently represents hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, mono- or di($C_1$–$C_6$)alkylamino ($C_1$–$C_6$)alkyl, aryl, heteroaryl, hydroxy($C_1$–$C_6$)alkyl, halo($C_1$–$C_6$)alkyl, cyano($C_1$–$C_6$)alkyl, nitro($C_1$–$C_6$) alkyl, or $C_1$–$C_6$ alkyl substituted with aryl or heteroaryl; and $R^{5a}$ is hydrogen, hydroxy, halogen, cyano, nitro, $C_1$–$C_6$ alkyl, $C_1$–$C_6$ alkoxy, amino, mono- or di($C_1$–$C_6$) alkylamino, or phenyl optionally substituted with $C_1$–$C_6$ alkyl, $C_1$–$C_6$ alkoxy, halogen, hydroxy, cyano, nitro, amino, and mono- or di($C_1$–$C_6$)alkylamino.

In a specific aspect of Formula XIII, D is $CR^3$ (hereinafter Formula XIII-a). Preferred compounds of XIII-a include those where each $R^3$ is hydrogen, $R^{5a}$ and T are hydrogen, X is hydrogen or $C_1$–$C_6$ alkyl, preferably hydrogen or methyl, and $R^{3a}$ is $C_1$–$C_6$ alkyl, $C_1$–$C_6$ alkoxy, halogen, hydroxy, halo($C_1$–$C_6$)alkyl, or hydroxy($C_1$–$C_6$)alkyl. Particularly preferred $R^{3a}$ groups in Formula XIII-a are hydroxy, and more preferably, $C_1$–$C_3$ alkoxy.

In another specific aspect of Formula XIII, D is nitrogen (hereinafter Formula XIII-b). Preferred compounds of XIII-b include those where $R^3$ is hydrogen, $R^{5a}$ and T are hydrogen, X is hydrogen or $C_1$–$C_6$ alkyl, preferably hydrogen or methyl, and $R^{3a}$ is $C_1$–$C_6$ alkyl, $C_1$–$C_6$ alkoxy, halogen, halo($C_1$–$C_6$)alkyl, or hydroxy($C_1$–$C_6$) alkyl.

Preferred compounds of Formulas XIII-a and XIII-b are those where

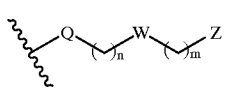

("Ar") represents phenyl, pyrazolyl, or pyridyl, each of which is optionally substituted with $R_p$ where $R_p$ is $C_1$–$C_6$ alkyl, $C_1$–$C_6$ alkoxy, halogen, hydroxy, halo($C_1$–$C_6$)alkyl, hydroxy($C_1$–$C_6$)alkyl, amino, or amino($C_1$–$C_6$)alkyl. More preferably, Ar is 3- or 4-pyrazolyl or 2- or 3-pyridyl, each of which is preferably substituted with $C_1$–$C_6$ alkyl, preferably methyl or ethyl, or more preferably unsubstituted. Particularly preferred Ar groups are 3-pyrazolyl and 2-pyridyl.

Preferred compounds of Formulas XIII-a and XIII-b are those where $R^{5a}$ is hydrogen.

Other preferred compounds of Formulas XIII-a and XIII-b are those where $R^{5a}$ is hydrogen;

X and T are hydrogen; and $R^{3a}$ and each $R^3$ independently represents hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, hydroxy($C_1$–$C_6$)alkyl, halo ($C_1$–$C_6$)alkyl, cyano($C_1$–$C_6$)alkyl, or nitro($C_1$–$C_6$) alkyl, or phenyl, pyridyl, pyrimidinyl, imidazolyl, or $C_1$–$C_6$ alkyl substituted with phenyl, pyridyl, or pyrimidinyl, or imidazolyl, where each phenyl, pyridyl, pyrimidinyl, and imidazolyl is optionally substituted with one or two groups independently selected from $C_1$–$C_6$ alkyl, $C_1$–$C_6$ alkoxy, halogen, hydroxy, and amino.

Still other preferred compounds of Formulas XIII-a and XIII-b are those where $R^{5a}$ is hydrogen;

$R^3$ is hydrogen and $R^{3a}$ is hydrogen, $C_1$–$C_6$ alkyl, halogen, hydroxy, $C_1$–$C_6$ alkoxy, amino or mono- or di($C_1$–$C_6$) alkylamino.

Yet other preferred compounds of Formulas XIII-a and XIII-b are those where $R^{5a}$ is hydrogen; and R is hydrogen, $C_1$–$C_6$ alkoxy, hydroxy, or $C_1$–$C_6$ alkoxy.

As noted above, within formula B-1, there is included Formula XIV.

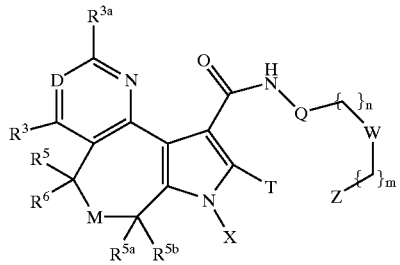

Formula XIV wherein

X, T, Q, n, W, m, and Z are as defined above with respect to Formula A or Formula I;

M is NR' or oxygen;

D is nitrogen or $CR^3$ where $R^{3a}$ and each $R^3$ independently represents hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, mono- or di($C_1$–$C_6$)alkylamino ($C_1$–$C_6$)alkyl, aryl, heteroaryl, hydroxy($C_1$–$C_6$)alkyl, halo($C_1$–$C_6$)alkyl, cyano($C_1$–$C_6$)alkyl, nitro($C_1$–$C_6$) alkyl, or $C_1$–$C_6$ alkyl substituted with aryl or heteroaryl;

$R^{5a}$ and $R^{5b}$ are independently hydrogen, hydroxy, halogen, cyano, nitro, $C_1$–$C_6$ alkyl, $C_1$–$C_6$ alkoxy, amino, or mono- or di($C_1$–$C_6$) alkylamino, or phenyl, pyridyl, phenyl($C_1$–$C_6$)alkyl, or pyridyl($C_1$–$C_6$) alkyl, where each phenyl and pyridyl is optionally substituted with $C_1$–$C_6$ alkyl, $C_1$–$C_6$ alkoxy, halogen, hydroxy, cyano, nitro, amino, and mono- or di($C_1$–$C_6$) alkylamino; and.

R' is hydrogen, $C_1$–$C_6$ alkyl, $C_1$–$C_6$ alkoxy($C_1$–$C_6$)alkyl, $C_2$–$C_6$ alkenyl, $C_2$–$C_6$ alkynyl, $C_1$–$C_6$ haloalkyl, amino ($C_1$–$C_6$)alkyl, or mono- or di($C_1$–$C_6$)alkylamino ($C_1$–$C_6$)alkyl, or aryl, heteroaryl, aryl($C_1$–$C_6$)alkyl, or heteroaryl($C_1$–$C_6$) alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$) alkylamino.

In a specific aspect of Formula XIV, D is $CR^3$ (hereinafter Formula XIV-a).

In another specific aspect of Formula XIV, D is nitrogen (hereinafter Formula XIV-b).

Preferred compounds of this group are those where
$R^5$ and $R^6$ are independently hydrogen or $C_1$–$C_6$ alkyl;
M is NR' where R' is hydrogen, $C_1$–$C_6$ alkyl, $C_2$–$C_7$ alkanoyl, $C_1$–$C_6$ alkoxy ($C_1$–$C_6$)alkyl, $C_2$–$C_6$ alkenyl, $C_2$–$C_6$ alkynyl, $C_1$–$C_6$ haloalkyl, amino($C_1$–$C_6$)alkyl, or mono- or di($C_1$–$C_6$) alkylamino($C_1$–$C_6$)alkyl, or aryl, heteroaryl, aryl($C_1$–$C_6$)alkyl, or heteroaryl($C_1$–$C_6$) alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$) alkylamino; and $R^{5a}$ and $R^{5b}$ are hydrogen.

Still other preferred compounds of this group of Formulas XIV-a and XIV-b are those where
X and T are hydrogen; and
$R^{3a}$ and each $R^3$ independently represent hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, hydroxy($C_1$–$C_6$)alkyl, halo ($C_1$–$C_6$)alkyl, or phenyl, pyridyl, pyrimidinyl, imidazolyl, or $C_1$–$C_6$ alkyl substituted with phenyl, pyridyl, or pyrimidinyl, or imidazolyl, where each phenyl, pyridyl, pyrimidinyl, and imidazolyl is optionally substituted with one or two groups independently selected from $C_1$–$C_6$ alkyl, $C_1$–$C_6$ alkoxy, halogen, hydroxy, and amino.

Yet other preferred compounds of this group are those where each $R^3$ is hydrogen and $R^{3a}$ is hydrogen, $C_1$–$C_6$ alkyl, halogen, hydroxy, $C_1$–$C_6$ alkoxy, amino or mono- or di($C_1$–$C_6$)alkylamino.

Still other preferred compounds within this group are those where $R^{3a}$ is hydrogen, $C_1$–$C_6$ alkoxy, hydroxy, or $C_1$–$C_6$ alkoxy.

Other preferred compounds within this group are those where $R^{5a}$ and $R^{5b}$ are hydrogen, $C_1$–$C_6$ alkyl, or $C_1$–$C_6$ alkyl substituted with phenyl or pyridyl, where each phenyl or pyridyl is optionally substituted with halogen, hydroxy, amino, $C_1$–$C_6$ alkyl or $C_1$–$C_6$ alkoxy.

Still other preferred compounds within this group are those where
$R^5$ and $R^6$ are independently hydrogen or $C_1$–$C_6$ alkyl;
M is oxygen; and
$R^{5b}$ and $R^{5b}$ are hydrogen.

Yet preferred compounds within this group are those wherein
X and T are hydrogen; and
$R^{3a}$ and each $R^3$ independently represent hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, hydroxy($C_1$–$C_6$)alkyl, halo ($C_1$–$C_6$)alkyl, cyano($C_1$–$C_6$)alkyl, or nitro($C_1$–$C_6$) alkyl, or phenyl, pyridyl, pyrimidinyl, imidazolyl, or $C_1$–$C_6$ alkyl substituted with phenyl, pyridyl, or pyrimidinyl, or imidazolyl, where each phenyl, pyridyl, pyrimidinyl, and imidazolyl is optionally substituted with one or two groups independently selected from $C_1$–$C_6$ alkyl, $C_1$–$C_6$ alkoxy, halogen, hydroxy, and amino.

Still other preferred compounds within this group are those wherein each each $R^3$ is hydrogen and $R^{3a}$ is hydrogen, $C_1$–$C_6$ alkyl, halogen, hydroxy, $C_1$–$C_6$ alkoxy, amino or mono- or di($C_1$–$C_6$)alkylamino.

Still other preferred compounds within this group are those where $R^{3a}$ is hydrogen, $C_1$–$C_6$ alkoxy, hydroxy, or $C_1$–$C_6$ alkoxy.

Preferred compounds of XIV-a (D is $CR^3$) include those where M is NR' where R' is hydrogen, $C_1$–$C_6$ alkyl, preferably $C_1$–$C_3$ alkyl, each $R^3$ is hydrogen, $R^{5a}$ $R^{5b}$, and T are hydrogen, X is hydrogen or $C_1$–$C_6$ alkyl, preferably hydrogen or methyl, $R^5$ and $R^6$ are independently hydrogen or $C_1$–$C_2$ alkyl, more preferably hydrogen or methyl, and $R^{3a}$ is $C_1$–$C_6$ alkyl, $C_1$–$C_6$ alkoxy, halogen, hydroxy, halo ($C_1$–$C_6$)alkyl, or hydroxy($C_1$–$C_6$)alkyl. Preferred $R^3$a groups in Formula XIV-a are hydroxy and $C_1$–$C_3$ alkoxy. Particularly preferred R' groups are Other preferred compounds of XIV-b (D is nitrogen) include those where M is NR' where R' is hydrogen or acetyl, $R^3$ is hydrogen, $R^{5a}$, $R^{5b}$, and T are hydrogen, X is hydrogen or $C_1$–$C_6$ alkyl, preferably hydrogen or methyl, and $R^{3a}$ is $C_1$–$C_6$ alkyl, $C_1$–$C_6$ alkoxy, halogen, hydroxy, halo($C_1$–$C_6$)alkyl, or hydroxy($C_1$–$C_6$)alkyl.

Preferred compounds of Formulas XIV-a and XIV-b are those where

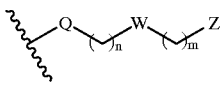

("Ar") represents phenyl, pyrazolyl, or pyridyl, each of which is optionally substituted with $R_p$ where $R_p$ is $C_1$–$C_6$ alkyl, $C_1$–$C_6$ alkoxy, halogen, hydroxy, halo($C_1$–$C_6$)alkyl, hydroxy($C_1$–$C_6$)alkyl, amino, or amino($C_1$–$C_6$)alkyl. More preferably, Ar is 3- or 4-pyrazolyl or 2- or 3-pyridyl, each of which is preferably substituted with $C_1$–$C_6$ alkyl, preferably methyl or ethyl, or more preferably unsubstituted. Particularly preferred Ar groups are 3-pyrazolyl and 2-pyridyl.

Further provided by the invention are intermediates useful in synthesizing compounds of the invention. Thus, the invention encompasses compounds of the following formulas Formula XV

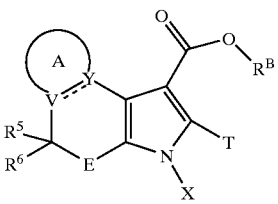

wherein
the A-ring, Y, V, E, R5, $R^6$, X and T carry the definitions assigned with respect to Formula A; and
$R^B$ is a group forming an ester, e.g., $C_1$–$C_6$ alkyl, aryl ($C_1$–$C_6$)alkyl, halo($C_1$–$C_6$)alkyl, hydroxy($C_1$–$C_6$)alkyl, $C_1$–$C_6$ alkoxy($C_1$–$C_6$)alkyl, and the like.

Preferred $R^B$ groups are hydrogen, methyl, ethyl and benzyl.

Specific compounds of Formula XV include those where U is nitrogen, $NR^A$, S, or O; V is nitrogen, carbon or CH; and Y is carbon, or CH;

Preferred compounds of Formula XV are those where the A-ring represents

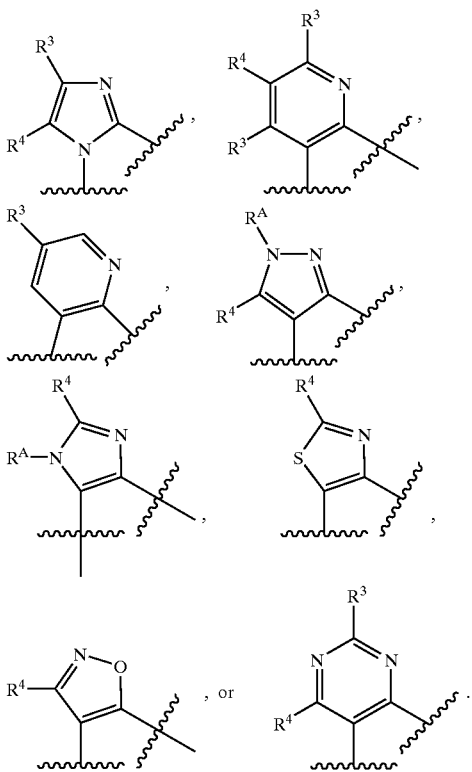

Preferred $R^A$, $R^3$, and $R^4$ groups on compounds of Formula XV are hydrogen, halogen, amino, hydroxy, methyl, ethyl, methoxy, and ethoxy.

Preferred compounds of XV include those of Formulas XVI and XVII.

Formula XVI

wherein:

$R^4$ is chosen from hydrogen, halogen, amino, hydroxy, methyl, ethyl, methoxy, and ethoxy.

Formula XVII

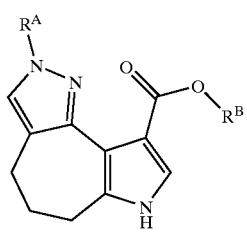

wherein:

$R^A$ is chosen from hydrogen, methyl, ethyl, and phenyl; and

Formula XVIII

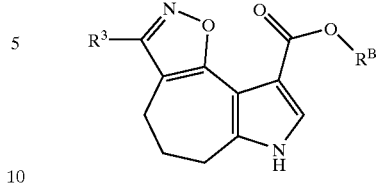

wherein:

$R^3$ is hydrogen, halogen, amino, hydroxy, methyl, ethyl, methoxy, or ethoxy.

The invention encompasses compounds of Formulas I-1, I-2, I-3, I-4, and I-5.

Formula I-1

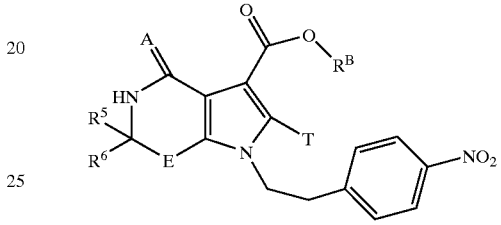

wherein:

A is oxygen or sulfur;

E, $R^5$, $R^6$, and T carry the definition assigned with respect to Formula I and Formula A; and $R^B$ is a group forming an ester, e.g., $C_1$–$C_6$ alkyl, aryl ($C_1$–$C_6$)alkyl, halo($C_1$–$C_6$)alkyl, hydroxy($C_1$–$C_6$)alkyl, $C_1$–$C_6$ alkoxy($C_1$–$C_6$)alkyl, and the like.

Preferred $R^B$ groups are hydrogen, methyl, ethyl and benzyl.

Formula I-2

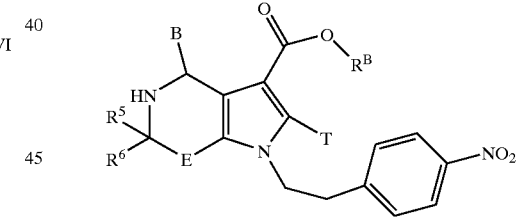

wherein

B is —$SCH_3$ or —$NH(CH_2)CH(OCH_3)_2$; and $R^B$ is chosen from hydrogen, methyl, ethyl and benzyl.

Formula I-3

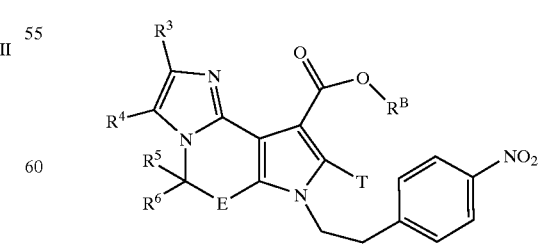

wherein

E, $R^5$, $R^6$, and T carry the definition assigned with respect to Formula I and Formula A; and $R^3$ and $R^4$ independently carry the same definitions as $R^5$ and $R^6$; and $R^B$ is chosen from hydrogen, methyl, ethyl and benzyl.

Formula I-4

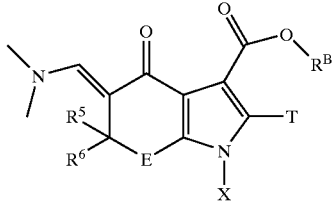

wherein:

E, X, $R^5$, $R^6$, and T carry the definition assigned with respect to Formula I and Formula A; and $R^B$ is chosen from hydrogen, methyl, ethyl and benzyl.

Formula I-5

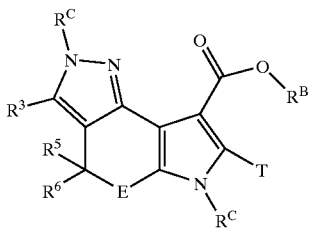

wherein:

E, $R^5$, $R^6$, and T carry the definition assigned with respect to Formula I and Formula A; and $R^3$ is defined the same as $R^5$ and $R^6$; and $R^B$ is chosen from hydrogen, methyl, ethyl and benzyl;

$R^C$ is independently chosen at each occurrence from t-butoxycarbonyl, phenyl, phenylsulfonyl, $C_1$–$C_6$ alkylsulfonyl, and ethylcarbamoyl.

Each of the synthetic schemes provided in the "Preparation of Compounds" section (below) involves the reaction of a ester compound to form an amide. For example, see step 11 of Scheme 1. Thus, the invention provides ester intermediates of Formula XX Formula XX

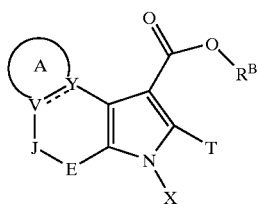

wherein

E and J carry the definitions assigned with respect to Formula A and Formula I;

$R^1$ and $R^2$ are independently chosen at each occurrence from hydrogen, halogen, hydroxy, cyano, nitro, amino, alkyl, alkenyl, alkynyl, haloalkyl, and mono or dialkylamino, mono or dialkylaminoalkyl, alkoxy, and k is 0, 1, 2, or 3;

the group

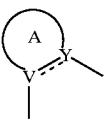

referred to as the "A-ring" represents an optionally substituted saturated, unsaturated or aromatic heterocyclic ring containing at least one nitrogen, oxygen or sulfur atom, wherein the V═Y bond is a single, double, or aromatic bond;

V is nitrogen, carbon, or CH;

Y is carbon, or CH;

$R^5$ and $R^6$ may be taken together to form a carbonyl group; or $R^5$ and $R^6$ are independently chosen from hydrogen, halogen, hydroxy, nitro, cyano, $alkyl_1$, amino, —COOH, —O($alkyl_1$), —SO$_2$NH$_2$, —SO$_2$NH($alkyl_1$), —SO$_2$N($alkyl_1$)($alkyl_1$), —N($alkyl_1$)CO($alkyl_1$), N($alkyl_1$)CO$_2$($alkyl_1$), —NHSO$_2$($alkyl_1$), —N($alkyl_1$)SO$_2$($alkyl_1$), —SO$_2$NHCO($alkyl_1$), —CONHSO$_2$($alkyl_1$), —CONH($alkyl_1$), —CON($alkyl_1$)($alkyl_1$), —CO$_2$($alkyl_1$), —CO($alkyl_1$), —SO$_{0-2}$($alkyl_1$), optionally substituted carbocyclic aryl and optionally substituted heteroaryl groups having from 1 to 3 rings, 3 to 8 members in each ring and from 1 to 3 heteroatoms;

wherein $alkyl_1$ is independently chosen at each occurrence and is straight branched or cyclic, may contain one or two double or triple bonds, and is unsubstituted or substituted with one or more substituents selected from: hydroxy, oxo, halogen, amino, cyano, nitro, alkoxy, —COOH, —SO$_2$NH$_2$, —SO$_2$NH(alkyl), —SO$_2$N(alkyl)(alkyl), —N(alkyl)CO(alkyl), N(alkyl)CO$_2$(alkyl), —NHSO$_2$(alkyl), —N(alkyl)SO$_2$(alkyl), —SO$_2$NHCO(alkyl), —CONHSO$_2$(alkyl), —CONH(alkyl), —CON(alkyl)(alkyl), —CO$_2$(alkyl), —CO(alkyl) —SO$_{0-2}$(alkyl)

X is chosen from hydrogen, hydroxy, amino, alkyl, and alkoxy;

T is chosen from hydrogen, halogen, hydroxy, amino, alkyl, and alkoxy; and $R^B$ is chosen from hydrogen, methyl, ethyl and benzyl.

Preferred compounds of Formula XX include compounds wherein E is —(CR$^1$R$^2$)$_k$—, —CR$^1$═CR$^2$—, —N═CR$^1$—, or —NR'—(CR$^1$R$^2$)$_k$—. Particularly preferred are —(CR$^1$R$^2$)$_k$—, —N═CR$^1$—, and —NR'—(CR$^1$R$^2$)$_k$—.

Other preferred compounds of Formula XX are those where J is —(CR$^5$R$^6$)$_d$— where d is 1.

Still other preferred compounds of Formula XX are those where E is —N═CR$^1$— and d is 0, or —NR'—(CR$^1$R$^2$)$_k$— where d is 0 and k is 1.

Preferred compounds of Formula XX include compounds wherein

E and J carry the definitions given with respect to Formulas A and I;

$R^1$ and $R^2$ are independently chosen at each occurrence from hydrogen, halogen, hydroxy, cyano, nitro, amino, haloalkyl, mono or diamino($C_{1-6}$)alkyl, $C_{1-6}$ alkyl, $C_{2-6}$alkenyl, $C_{2-6}$alkynyl and $C_{1-6}$ alkoxy, and k is 0, 1, 2, or 3;

the group

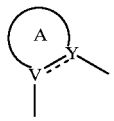

or the "A-ring" is a group of the formula:

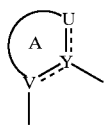

which is a saturated, unsaturated or aromatic heterocyclic ring containing at least one nitrogen, oxygen or sulfur atom, wherein the U===Y and V===Y bonds may be single, double or aromatic bonds,
U is nitrogen, $NR^A$, S, or O;
V is nitrogen, carbon or CH;
Y is carbon, or CH;
and said saturated, unsaturated or aromatic heterocyclic ring is chosen from:
  thienyl, thiazolyl, pyridyl, pyrimidinyl, imidazolyl, pyrazolyl, pyrazinyl, pyridizinyl, piperidinyl, oxazolyl, isoxazolyl, symmetrical and unsymmetrical triazolyl, pyrrolyl, furanyl, diazenyl, triazenyl, 1,2,4-triazolone, 4,5-dihydroimidazolyl, and 1,4,5,6-tetrahydropyrimidinyl,
  each of which is optionally substituted at any available nitrogen by $R^A$ and optionally substituted at any available carbon by $R^3$ and $R^4$, wherein:
$R^A$ is chosen from hydrogen, $C_{1-6}alkyl_1$, optionally substituted carbocyclic aryl and optionally substituted heteroaryl groups having from 1 to 3 rings, 3 to 8 members in each ring and from 1 to 3 heteroatoms;
$R^5$ and $R^6$ are independently chosen from hydrogen, halogen, hydroxy, nitro, cyano, $C_{1-6}alkyl_1$, amino, —COOH, —O($C_{1-6}alkyl_1$), —NH($C_{1-6}alkyl_1$), —N($C_{1-6}alkyl_1$)($C_{1-6}alkyl_1$), —SO$_2$NH$_2$, —SO$_2$NH($C_{1-6}alkyl_1$), —SO$_2$N($C_{1-6}alkyl_1$)($C_{1-6}alkyl_1$), —N($C_{1-6}alkyl_1$)CO($C_{1-6}$ alkyl$_1$)N($C_{1-6}alkyl_1$)CO$_2$($C_{1-6}alkyl_1$) NHSO$_2$($C_{1-6}$ alkyl$_1$), —N($C_{1-6}alkyl_1$) SO$_2$($C_{1-6}alkyl_1$), —SO2NHCO ($C_{1-6}alkyl_1$), —CONHSO$_2$($C_{1-6}alkyl_1$), —CONH($C_{1-6}$ alkyl$_1$), —CON($C_{1-6}alkyl_1$)($C_{1-6}alkyl_1$), —CO$_2$ ($C_6alkyl_1$), —CO($C_{1-6}alkyl_1$) and —SO$_{0-2}$($C_{1-6}alkyl_1$),
  wherein $C_{1-6}alkyl_1$ is independently chosen at each occurrence and is straight branched or cyclic, may contain one or two double or triple bonds, and is unsubstituted or substituted with one or more substituents selected from: hydroxy, oxo, halogen, amino, cyano, nitro, alkoxy, carbocylic or heterocyclic group, —COOH, —SO$_2$NH$_2$, —SO$_2$NH($C_{1-4}$alkyl), —SO$_2$N($C_{1-4}$alkyl) ($C_{1-4}$alkyl), —N($C_{1-4}$alkyl)CO($C_{1-4}$alkyl), N($C_{1-4}$ alkyl)CO$_2$($C_{1-4}$alkyl), —NHSO$_2$(alkyl), —N($C_{1-4}$ alkyl) SO$_2$($C_{1-4}$alkyl), —SO$_2$NHCO($C_{1-4}$alkyl), —CONHSO$_2$($C_{1-4}$alkyl), —CONH($C_{1-4}$alkyl), —CON($C_{1-4}$alkyl)($C_{1-4}$alkyl) —CO$_2$($C_{1-4}$alkyl), —CO($C_{1-4}$alkyl), and —SO$_{0-2}$($C_{1-4}$alkyl);
$R^3$ and $R^4$ are independently chosen at each occurrence, and are defined the same as $R^5$ and $R^6$;
X is chosen from hydrogen, hydroxy, amino, $C_{1-6}$ alkyl, and $C_{1-6}$alkoxy;
T is chosen from hydrogen, halogen, hydroxy, amino, $C_{1-6}$ alkyl, and $C_{1-6}$ alkoxy; and $R^B$ is chosen from hydrogen, methyl, ethyl and benzyl.

Such compounds will be referred to as compounds of Formula XXa.

The ester intermediates of this invention differ primarily in the type of "A-ring" present although other differences may be present. one class of intermediates provided by this invention is represented by Formula XXI

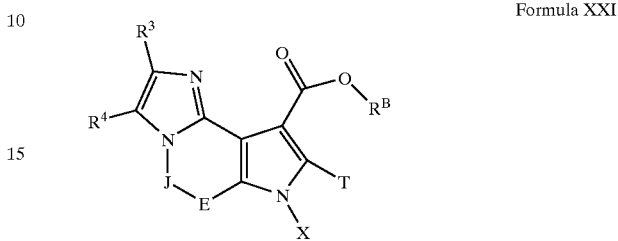

Formula XXI wherein J, E, $R^1$, $R^2$, $R^3$, $R^4$, $R^5$, $R^6$, J, E, k, X, T, and $R^B$ are as defined for Formula XXa. Preferred intermediates of Formula XXI are those compounds wherein $R^B$ is defined as for Formula XXa; E is —$(CR^1R^2)_k$—, k is 1 or 2; $R^1$ and $R^2$ are both hydrogen; and $R^3$, $R^4$, $R^5$, and $R^6$, are independently chosen from hydrogen, halogen, amino, hydroxy, methyl, ethyl, methoxy, and ethoxy (hereinafter compounds of Formula XXIa).

The invention further provides ester intermediates having a pyridyl "A-ring" such as compounds of Formula XXII

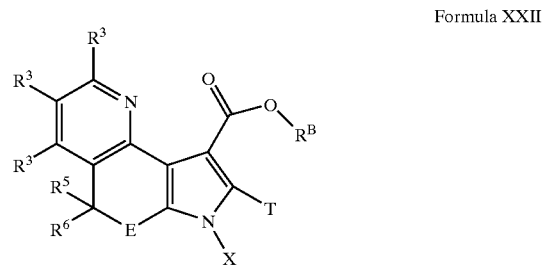

Formula XXII wherein $R^3$ is independently selected at each occurrence and is as defined as for Formula XXa and $R^1$, $R^2$, $R^3$, $R^4$, $R^5$, E, J, k, X, T, and $R^B$ are also defined as for Formula XXa.

Particularly, the invention provides as compounds of Formula XXII, compounds where $R^B$ is defined as for Formula XXa; E is —$(CR^1R^2)_k$—; $R^1$, $R^2$, $R^3$, $R^5$, $R^6$, X, and T are all hydrogen; $R^3$ is hydrogen at the 3- and 4-positions of the "A-ring" pyridyl group, and is chosen from hydrogen, halogen, amino, hydroxy, methyl, ethyl, methoxy, and ethoxy at the 2-position of this "A-ring" pyridyl group (hereinafter compounds of Formula XXIIa).

Also provided as compounds of Formula XXII, are compounds where E is —$(CR^1R^2)_k$—; $R^B$ is defined as for Formula XXa; $R^1$, $R^2$, $R^3$, $R^5$, $R^6$, X, and T are all hydrogen; $R^3$ is hydrogen at the 2- and 4-positions of the "A-ring" pyridyl group, and is chosen from hydrogen, halogen, amino, hydroxy, methyl, ethyl, methoxy, and ethoxy at the 3-position of this "A-ring" pyridyl group (hereinafter compounds of Formula XXIIb).

The invention provides intermediates of Formula XXIII having a pyrimidinyl "A-ring"

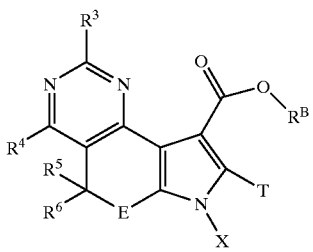

Formula XXIII wherein $R^1$, $R^2$, $R^3$, $R^4$, $R^5$, $R^6$, E, k, X, T, and R are as defined in claim XXa. Preferred compounds of Formula XXIII include compounds where E is —$(CR^1R^2)_k$—; k is 2; $R^1$, $R^2$, $R^3$, $R^5$, $R^6$, X, and T are all hydrogen; $R^B$ is defined as for Formula XXa; and $R^4$ is chosen from hydrogen, halogen, amino, hydroxy, methyl, ethyl, methoxy, and ethoxy (hereinafter compounds of Formula XXIIIa).

In one embodiment the invention provides compounds of Formula XXIV where the "A-ring" is a pyrrole

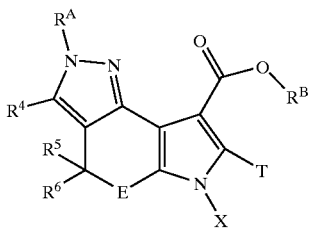

Formula XXIV wherein $R^A$, $R^1$, $R^2$, $R^4$, $R^5$, $R^6$, E, k, X, T, and $R^B$ are as defined in Formula XXa. Preferred compounds of Formula XXIV include compounds where E is —$(CR^1R^2)_k$—; k is 2; $R^A$ is chosen from hydrogen, methyl, ethyl, and phenyl; $R^B$ is as defined in Formula XXa; and $R^1$, $R^2$, $R^4$, $R^5$, $R^6$, X, and T are all hydrogen (hereinafter compounds of Formula XXIVa).

The invention further includes compounds of Formula XXV

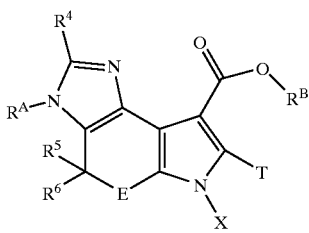

Formula XXV wherein $R^A$, $R^1$, $R^2$, $R^3$, $R^4$, $R^5$, $R^6$, E, k, X, T, and $R^B$ are as defined for Formula XXa. Also included as compounds of Formula XXV are compounds wherein E is —$(CR^1R^2)_k$—; k is 2; $R^A$, $R^1$, $R^2$, $R^4$, $R^5$, $R^6$, k, X, and T are all hydrogen; $R^B$ is as defined for Formula XXa; and $R^4$ is from chosen from hydrogen, halogen, amino, hydroxy, methyl, ethyl, methoxy, and ethoxy (hereinafter compounds of Formula XXVa).

In yet another embodiment the invention provides ester intermediates of Formula XXVI having thiazole "A-rings"

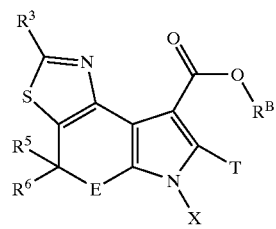

Formula XXVI wherein $R^1$, $R^2$, $R^3$, $R^5$, $R^6$, E, k, X, T, and $R^B$ are as defined for Formula XXa. Preferably compounds of this class are those compounds where E is —$(CR^1R^2)_k$—; k is 2; $R^1$, $R^2$, $R^5$, $R^6$, X, and T are hydrogen; $R^B$ is as defined for Formula XXa; and $R^3$ is chosen from $R^3$ is chosen from hydrogen, halogen, amino, hydroxy, methyl, ethyl, methoxy, and ethoxy (hereinafter compounds of Formula XXVIa).

Another class of intermediates of the invention is represented by compounds of Formula XXVII having and isoxazole "A-ring"

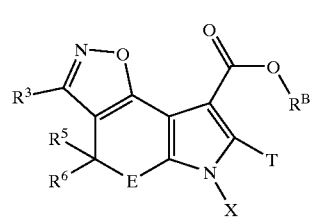

Formula XXVII wherein $R^1$, $R^2$, $R^3$, $R^5$, $R^6$, E, k, X, T, and $R^B$ are as defined in for Formula XXa. Preferably compounds of this class are those compounds where E is —$(CR^1R^2)_k$—; k is 2; $R^1$, $R^2$, $R^5$, $R^6$, X, and T are hydrogen; $R^3$ is as defined for Formula XXa; and $R^3$ is chosen from $R^3$ is chosen from hydrogen, halogen, amino, hydroxy, methyl, ethyl, methoxy, and ethoxy (hereinafter compounds of Formula XXVIIa).

In a number of the synthetic steps used to generate compounds of the invention novel protected intermediates are used. Such protected intermediates include compounds of Formula XXX useful in the synthesis of compounds of the invention having an imidazole "A-ring"

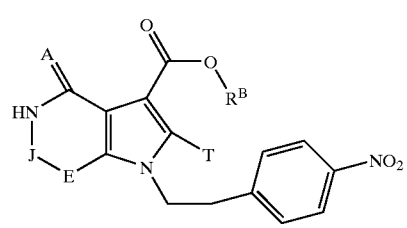

Formula XXX wherein A is oxygen or sulfur; J, E, k, $R^1$, $R^2$, $R^5$, $R^6$, $R^B$ and T are as defined for Formula XXa. Preferably, E is —$(CR^1R^2)_k$—; and d is 1 or 2, more preferably 1.

Another class of protected intermediates useful in the synthesis of compounds of the invention having an imidazole "A-ring" are compounds of Formula XXXI Formula XXXI

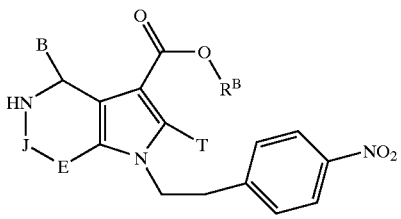

wherein B is —SCH₃ or —NH(CH₂)CH(OCH₃)₂ and J, E, k, $R^1$, $R^2$, $R^5$, $R^6$, $R^B$ and T are as defined for Formula XXa. Preferably, E is —$(CR^1R^2)_k$—; and d is 1 or 2, more preferably 1.

Also provided are compounds of Formula XXXII

Formula XXXII

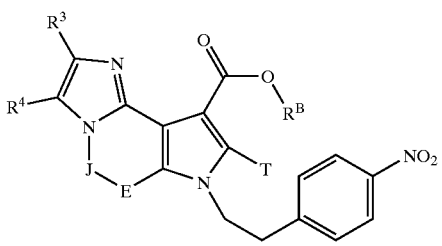

wherein all variables present in compounds of Formula XXXII are defined as for compounds of Formula XXa. Preferably, E is —$(CR^1R^2)_k$—; and d is 1 or 2, more preferably 1.

Other classes of novel intermediates provided by the invention are intermediates have BOC and TMS protecting groups (or analogues of such groups) such as compounds of Formula XXXIII Formula XXXIII

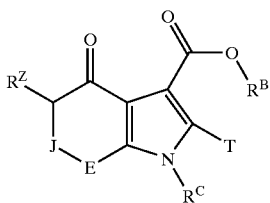

wherein $R^C$ is chosen from t-butoxycarbonyl, phenyl, alkylsulfonyl, and ethylcarbamoyl; $R^Z$ is hydrogen or bromo; and J, E, k, $R^B$, $R^1$, $R^2$, $R^5$, $R^6$, and T are defined as for compounds of Formula XXa.

Preferably, E is —$(CR^1R^2)_k$—; and d is 1 or 2, more preferably 1.

Further provided are compounds of Formula XXXIV

Formula XXXIV

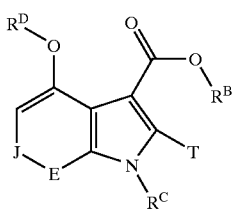

$R^C$ is chosen from t-butoxycarbonyl, phenyl, phenylsulfonyl, alkylsulfonyl, and ethylcarbamoyl;

$R^D$ is chosen from trimethylsilyl and t-butyldimethylsilyl; and

J, E, k, $R^B$, $R^1$, $R^2$, $R^5$, $R^6$, and T are defined as for Formula XXa.

Preferably, E is —$(CR^1R^2)_k$—; and d is 1 or 2, more preferably 1.

Further, the invention provides as intermediates compounds of Formula XXXV

Formula XXXV

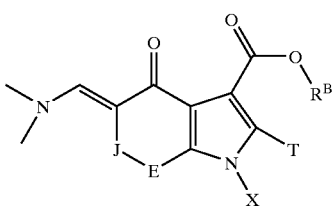

wherein E, J, k, $R^B$, $R^1$, $R^2$, $R^5$, $R^6$, X and T are as defined for Formula XXa. In compounds of XXXV, E is preferably —$(CR^1R^2)_k$— and d is 1 or 2, more preferably 1.

Finally, the invention provides compounds of Formula XXXVI as intermediates

Formula XXXVI

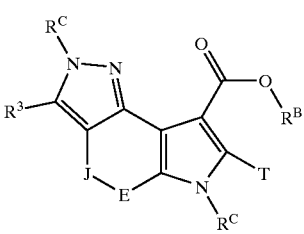

$R^C$ is independently chosen at each occurrence from t-butoxycarbonyl, phenyl, phenylsulfonyl, alkylsulfonyl, and ethylcarbamoyl and all other variables are as defined for compounds of Formula XXa.

In preferred compounds of XXXVI, Preferably, E is preferably —$(CR^1R^2)_k$— and d is 1 or 2, more preferably 1.

This invention relates to heterocyclic compounds, such as 5,6-Dihydro-4H-1,3a,6-triaza-as-indacenes,3-thia-1,7-diaza-cyclopenta[e]azulene-9-carboxylic acids, 4,5,6,7-tetrahydro-1-oxa-2,7-diaza-cyclopenta[e]azulene-9-carboxylic acids, 3,8,10-triaza-benzo[e]azulene-1-carboxylic acids, 1-oxa-2,7-diaza-cyclopenta[e]azulene-9-carboxylic acids, 1,3,7-triaza-cyclopenta[e]azulene-9-carboxylic acid phenyl amide and related compounds, that bind with high affinity to the benzodiazepine site of GABA$_A$ receptors, including human GABA$_A$ receptors. This invention also includes such compounds that bind with high selectivity to the benzodiazepine site of GABA$_A$ receptors, including human GABA$_A$ receptors. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/- agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. Attention Deficit Disorder (ADD), Attention Deficit Hyperactivity Disorder (ADHD)

The invention also provides pharmaceutical compositions comprising one or more compounds of the invention together with at least one pharmaceutically acceptable carrier. Pharmaceutical compositions include packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl) methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula A or Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via a $GABA_A$ receptor binding assay, such as the assay described in Example 24. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula A or Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 25.

The $GABA_A$ receptor ligands provided by this invention and labeled derivatives thereof are also useful as standards and reagents in determining the ability of a potential pharmaceutical to bind to the $GABA_A$ receptor.

Labeled derivatives the $GABA_A$ receptor ligands provided by this invention are also useful as radiotracers for positron emission tomography (PET) imaging or for single photon emission computerized tomography (SPECT).

Definitions

For compounds of the present invention that have The compounds of the invention may have asymmetric centers;

this invention includes all of the stereoisomers and optical isomers as well as mixtures thereof.

In addition, compounds with carbon-carbon double bonds may occur in Z— and E— forms; all such isomeric forms of the compounds are included in the invention.

When any variable (e.g. $C_{1-6}$ alkyl, $R^1$, $R^2$, $R^5$, and $R^6$) occurs more than one time in any formula herein, its definition on each occurrence is independent of its definition at every other occurrence.

As used herein, the terms "alkyl" and "$C_{y-x}$ alkyl" in the present invention is meant straight or branched chain alkyl groups of generally up to 6 or 8 carbon atoms, or for $C_{y-x}$ alkyl the number of carbon atoms specified, for example, $C_{1-6}$ alkyl indicates straight or branched chain alkyl groups having from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_{1-8}$ alkyl groups are methyl, ethyl, propyl, butyl, pentyl and cyclopentyl.

As used herein, "alkanoyl" refers to an alkyl group as defined above attached through a carbonyl bridge. Examples include acetyl, propionyl, and butyryl.

The term "alkoxy" represents an alkyl group, as described above, attached through an oxygen bridge, such as methoxy, ethoxy, propoxy and isopropoxy.

The term "alkenyl" is intended to include hydrocarbon chains of either a straight or branched configuration comprising one or more unsaturated carbon-carbon bonds which may occur in any stable point along the chain, such as ethenyl and propenyl.

The term "alkynyl" is intended to include hydrocarbon chains of either a straight or branched configuration comprising one or more triple carbon-carbon bonds which may occur in any stable point along the chain, such as ethynyl and propynyl.

As used herein, "carbocyclic group" refers to aromatic carbocyclic ring systems and to cycloalkyl ring systems that have one or more double or triple bonds.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,4-tetrahydronaphthalene, indanyl, and biphenyl. Preferred examples of aryl groups include phenyl and naphthyl. The aryl groups herein are unsubstituted or, as specified, substituted in one or more substitutable positions with various groups. Thus, such aryl groups are optionally substituted with, for example, $C_1-C_6$ alkyl, $C_1-C_6$ alkoxy, halogen, hydroxy, cyano, nitro, amino, mono- or di-($C_1-C_6$) alkylamino, $C_2-C_6$alkenyl, $C_2-C_6$alkynyl, $C_1-C_6$ haloalkyl, $C_1-C_6$ haloalkoxy, amino($C_1-C_6$)alkyl, mono- or di(($C_1-C_6$) alkylamino($C_1-C_6$)alkyl,.

The term "cycloalkyl" as used herein refers to saturated ring groups, having the specified number of carbon atoms, e.g., $C_3-C_7$ cycloalkyl, such as cyclopropyl, cyclobutyl, cyclopentyl, or cyclohexyl. In certain situations, the cycloalkyl group will contain one or more double or triple bonds and may be substituted with one or more substituents such as $C_1-C_6$ alkyl, $C_1-C_6$ alkoxy, halogen, hydroxy, cyano, nitro, amino, mono- or di-($C_1-C_6$)alkylamino, $C_2-C_6$alkenyl, $C_2-C_6$alkynyl, $C_1-C_6$ haloalkyl, $C_1-C_6$ haloalkoxy, amino($C_1-C_6$)alkyl, mono- or di($C_1-C_6$) alkylamino($C_1-C_6$)alkyl, aryl and heteroaryl. Cycloalkyl groups herein that lack any unsaturation are referred to as saturated cycloalkyl groups while cycloalkyl groups that contain at least one double or triple bond but are not aromatic are referred to as either unsaturated or partially unsaturated.

The term "cycloalkylalkyl" refers to cycloalkyl groups as defined above attached to an alkyl group. Generally, the cycloalkyl group will contain from 3–7 carbon atoms and the alkyl portion will contain from 1–8, more preferably, 1–6, carbon atoms. These cycloalkylalkyl groups are identified herein as $C_3-C_7$ cycloalkyl($C_1-C_6$)alkyl groups. Examples of such groups are cyclopropylmethyl, cyclohexylmethyl, and cyclohexylmethyl.

The term "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Preferred haloalkyl groups are halo($C_1-C_6$)alkyl groups; particularly preferred are trifluoromethyl, perfluoropropyl, and difluoromethyl.

By "haloalkoxy" as used herein is meant represents a haloalkyl group, as defined above, attached through an oxygen bridge to a parent group. Preferred haloalkoxy groups are halo($C_1-C_6$)alkoxy groups. Examples of haloalkoxy groups are trifluoromethoxy, 2,2-difluoroethoxy, 2,2,3-trifluoropropoxy and perfluoroisopropoxy.

As used herein, the group "V═══Y" represents V and Y connected by a single or double bond. Similarly, the groups "U═══Y" and "V═══Y" represent single or double bonds connecting U and Y and V and Y respectively. In specific embodiments, where these groups are double bonds, they give rise to aromatic groups.

The term "heterocycloalkanone" refers to 4-, 5-, 6- and 7-membered ring systems having at least one hetero atom selected from oxygen, nitrogen, and sulfur and also having at least one oxo group, i.e., the ring contains a carbonyl group. Such heterocycloalkanone groups are optionally substituted with $C_1-C_6$ alkyl, $C_1-C_6$ alkoxy, hydroxy, halogen, amino, mono- or di($C_1-C_6$)alkylamino, and the like. Examples include

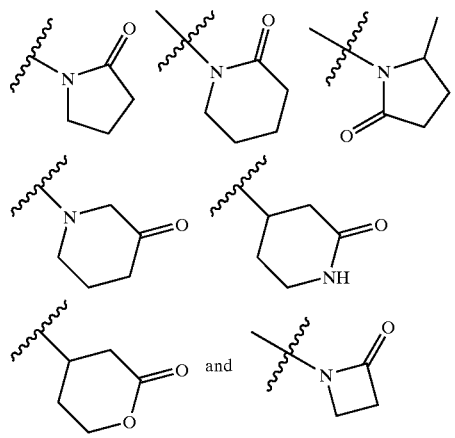

As used herein, the terms "heterocyclic group" or "heterocycloalkyl" are intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 hetero atoms independently selected from N, O and S and including any bicyclic group in which any of the above-defined heterocyclic rings is fused to a benzene ring. The nitrogen and sulfur hetero atoms may optionally be oxidized. The term "heteroaryl" is used to specifically indicate aromatic heterocyclic groups.

The heterocyclic ring may be attached to its pendant group at any hetero atom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these hetero atoms are not adjacent to one another. It is preferred that the total number of S and O atoms in the heterocycle is not more than 1. As used herein, the term "aromatic heterocyclic system" is intended to mean a stable 5-to 7-membered monocyclic or bicyclic or 7- to 10-membered bicyclic heterocyclic aromatic ring which consists of carbon atoms and from 1 to 4 hetero atoms independently selected from N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzothiazolyl, benzotriazolyl, benoztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;-1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Where an aryl, cycloalkyl, heterocycloalkyl, or heteroaryl is substituted with oxo, the resulting groups will have an oxygen atom connected to a ring within the system by a double bond. Examples of such oxo substiuted systems include 2-oxo-1,2-dihydro-pyridin-3-yl and 2-oxo-1,2-dihydro-pyridin-4-yl groups. Such groups have the formulas

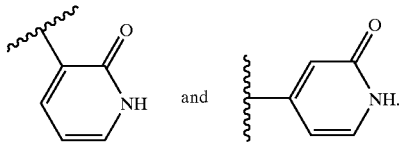

These groups may be substituted on any of the ring carbon atoms or the ring nitrogen, with various substituents as specified herein.

The term "halogen" indicates fluorine, chlorine, bromine, and iodine.

Non-toxic "pharmaceutically acceptable salts" include, but are not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, salicylate and stearate. Similarly, pharmaceutically acceptable cations include, but are not limited to sodium, potassium, calcium, aluminum, lithium and ammonium. The present invention also encompasses the prodrugs of the compounds of Formula I.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate;

granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

Preparation of Compounds

A general illustration of the preparation of compounds of Formula I in the present invention is given in Schemes 1–12. In the reaction schemes and discussions that follow, unless otherwise indicated, k, $R^A$, $R^1$, $R^2$, $R^3$, $R^4$, $R^5$, $R^6$ are as defined above. Within the schemes and tables that follow, Ar is intended to represent Q—$(CH_2)_n$—W—$(CH_2)_m$—Z as defined in Formula I or a suitably protected form thereof. When a protecting group is required, an optional deprotection step may be employed. Suitable protecting groups and methodology for protection and deprotection such as those described in *Protecting Groups in Organic Synthesis* by T. Greene are well known and appreciated in the art. Compounds and intermediates requiring protection/deprotection will be readily apparent to those skilled in the art.

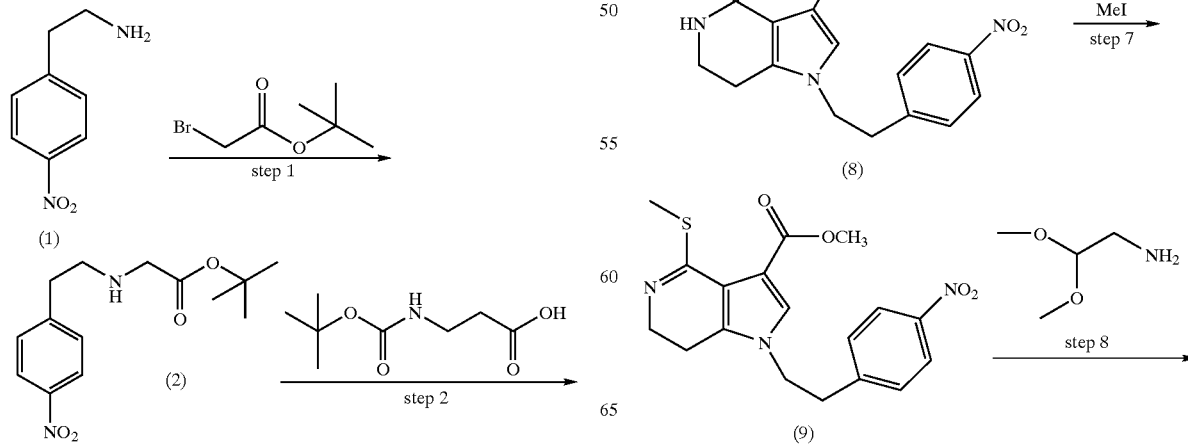

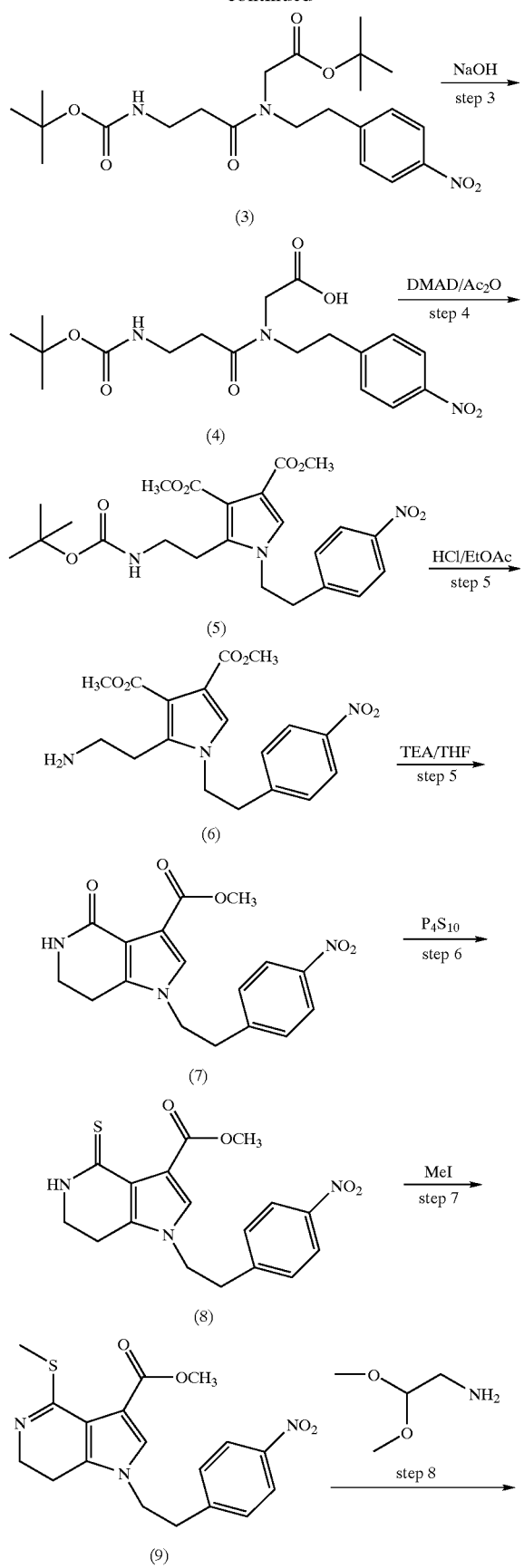

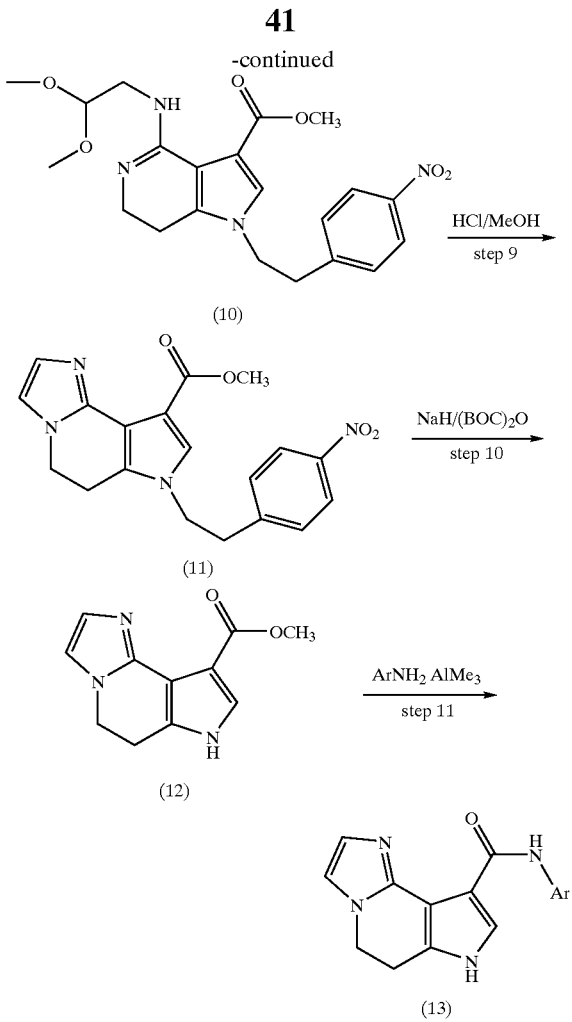

In Scheme 1 step 1, p-nitrophenethylamine is alkylated with tert-butyl bromo acetate to form compound (2). In general, excess p-nitrophenethylamine is used in this reaction to minimize bis-alkylation. In step 2, the secondary amine in compound (2) is coupled with BOC-protected 3-aminopropanoic acid to form compound (3). This coupling may be efficiently accomplished by treating a mixture of compound (2) in pyridine with N-Boc 3-aminopropanoic with a coupling agent such as EDCI with stirring at ambient temperature. In step 3, the tert-butyl ester in compound (3) is cleaved under basic conditions to form the carboxylic acid (4). Compound (4) is reacted with dimethyl acetylene dicarboxylate in the presence of acetic anhydride in step 4 to form the pyrrole (5). Pyrrole (5) is sequentually deprotected using hydrogen chloride in step 5 to expose the primary amine in compound (6) and cyclized in the presence of base to form lactam (7). In step 6, lactam (7) is converted to the thiolactam (8) by reaction under appropriate sulfur transfer conditions such as heating with $P_4S_{10}$ in pyridine. In steps 7 and 8, thiolactam (8) is alkylated with methyl iodide in acetone to form the methylsulfanyl compound (9) which is reacted with aminoacetaldehyde dimethyl acetal in methanol to form compound (10). Cyclization of the dimethyl acetal derivative (10) is accomplished in step 9 by heating (10) with concentrated hydrochloric acid in methanol to form compound (11). Removal of the p-nitrophenethyl protecting group is accomplished in step 10 by treatment of (11) with sodium hydride in the presence of di-tert-butyl dicarbonate in dimethylformamide. Quenching of excess sodium hydride with acetic acid followed by hydrolysis of the BOC group from the pyrrole nitrogen using aqueous potassium bicarbonate provides the desired deprotected material (12). As indicated by step 11 in Scheme 1, ester (12) serves as a versatile acylating agent for a variety of aluminum complexes of aryl and heteroaryl amines to form the corresponding amides (13).

Another procedure for forming amide derivatives (13) is provided in Example 2a and involves hydrolysis of ester (12) by heating in the presence of 48% hydrobromic acid. The resulting carboxylic acid is then reacted with various aryl amines in the presence of an appropriate coupling reagent such as O-(1H-benzotriazol-1-yl)-N,N,N',N'-tetramethyluronium hexafluorophosphate. Alternatively, the carboxylic acid may be converted to the mixed anhydride by reaction with ethyl or isobutyl chloroformate in the presence of triethylamine. The resulting mixed anhydride is then reacted with aryl amines.

Compounds of Formula II where $R^5$ or $R^6$ is methyl are formed as illustrated in Scheme 1 by reaction of compound (2) with 3-aminobutyric acid in step 2. Optically pure or optically enriched material is obtained by separation of advanced intermediates on a suitable chiral HPLC column such as Chiralpak AD. For material resolved by this method, the absolute stereochemistry is correlated to a X-ray crystal structure of a chiral amide derivative. Alternatively, optically pure 3-aminobutyric acid may be employed in step 2. Compounds of Formula II wherein both $R^5$ and $R^6$ are methyl are obtained as illustrated in Scheme 1 by use of 3-amino-3-methylbutyric acid in step 2.

Compounds of Formula II wherein $R^3$ is methyl may be formed as illustrated by Scheme 1 by employing 2-aminopropionaldehyde dimethyl acetal in step 8.

Those skilled in the art will realize that the synthetic transformations described by Scheme 1 may be accomplished using a variety of alternate reagents and reaction conditions. Further, it is readily apparent that additional compounds within the scope of Formula II but not specifically described within the experimental section may be prepared in analogous fashion.

Scheme 2

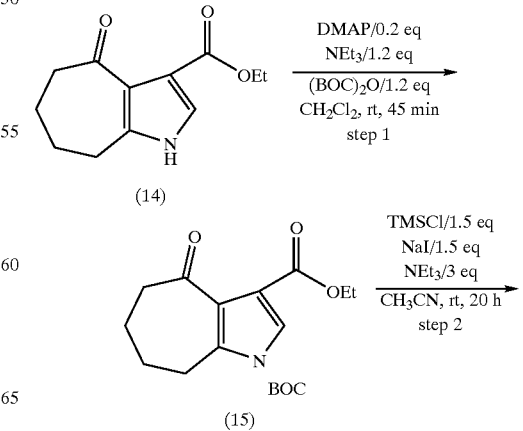

43

-continued

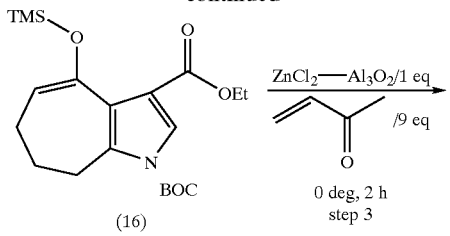

(16)

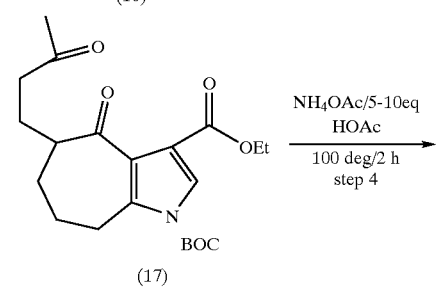

(17)

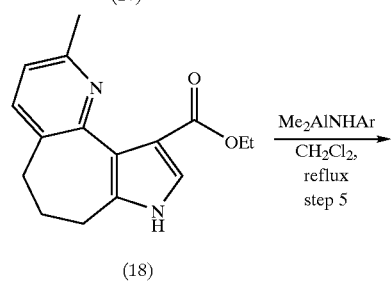

(18)

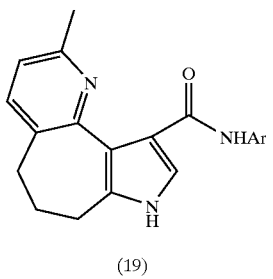

(19)

Scheme 2 reveals a method for converting known ketone (14) (U.S. Pat. No. 5,723,462, col.23–31 is hereby incorporated by reference for its teachings regarding the synthesis of such ketones) to compounds of Formula III with $R^3$ as methyl. Step 1 describes formation of the BOC-protected derivative (15). Typically this transformation is carried out by treating pyrrole (14) with di-tert-butyl dicarbonate in a suitable solvent such as dichloromethane or 1,4-dioxane at temperatures ranging from 0° C. to ambient temperature in the presence of an organic base such as triethylamine. Additives such as 4-N,N-dimethylaminopyridine may be used to facilitate this transformation. In step 2, the BOC-protected material (15) is efficiently converted to silyl enol ether (16) by treatment with a mixture of trimethylsilyl chloride, sodium iodide and triethylamine at ambient temperature. Lewis acid-facilitated 1,4-addition is accomplished in step 3 by treatment with excess methyl vinyl ketone at 0° C. in the presence of zinc chloride-alumina to yield the diketone (17). Treatment of the diketone (17) with ammonium acetate at elevated temperature in step 4 provides the desired methyl-substituted pyridyl derivative (18) which is aminated in step 5 using amination conditions previously described for Scheme 1.

44

Scheme 3

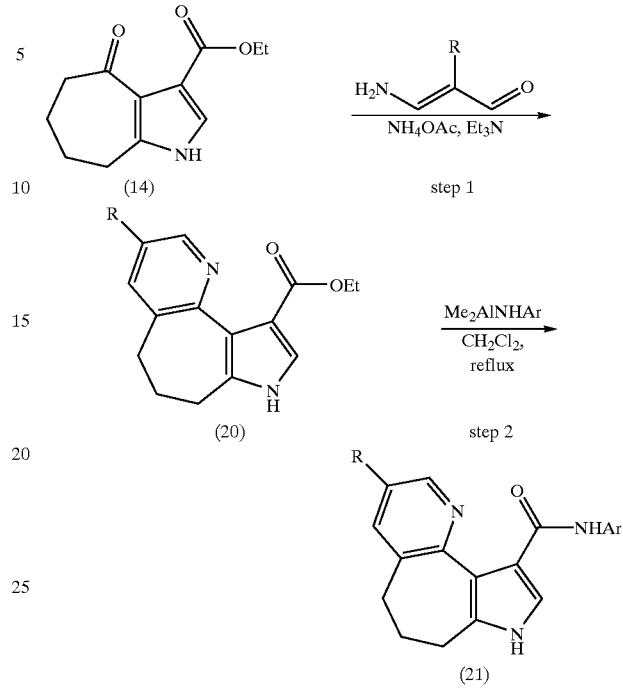

Scheme 3 shows a method for converting known ketone (14) [U.S. Pat. No. 5,723,462] to compounds of Formula III with $R^3$ as hydrogen. In step 1, pyridine ring formation is accomplished by treatment of ketone (14) with 3-aminoacrolein (R=H) and catalytic ammonium acetate in triethylamine at elevated temperature. Conversion of (14) to (20) can also be accomplished by heating (14) in triethylamine with 3-dimethylaminoacrolein in the presence of excess ammonium acetate. If 3-amino-2-methylacrolein (R=CH$_3$) is used in step 1, a 3-methylpyridine ring is formed. Amination is accomplished in step 2 as previously described.

Those skilled in the art will recognize that the reactions described in Scheme 3 may also be applied to synthesize compounds of Formula III wherein k=1 by starting with the appropriate known ketone.

Scheme 4

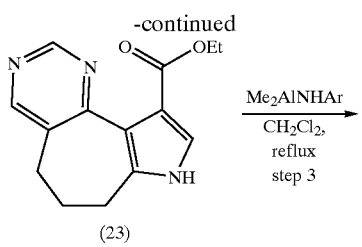

(23)

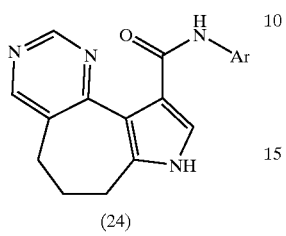

(24)

Scheme 4 outlines conditions for conversion of ketone (15) to compounds of Formula IV. In step 1, ketone (15) is reacted with tris(dimethylamino)methane with heating in a sealed tube to afford compound (22). In step 2, compound (22) undergoes reaction with formamidine acetate in ethanol at 120° C. to yield the pyrimidine derivative (23). As shown in step 3, compound (23) serves as a versatile intermediate for reaction with aluminum complexes of a variety of aryl amines under conditions previously described.

Scheme 5 describes a method for producing compounds of Formula IV wherein $R^4$ is methyl. Reaction of compound (16) from Scheme 2 with acetyl chloride in the presence of catalytic sodium iodide and a suitable Lewis acid such as bismuth trichloride gives diketone (25). Subsequent reaction with formamidine acetate as per Scheme 4, provides methyl pyrimidine (26) which is aminated in step 3 as previously described.

Scheme 5

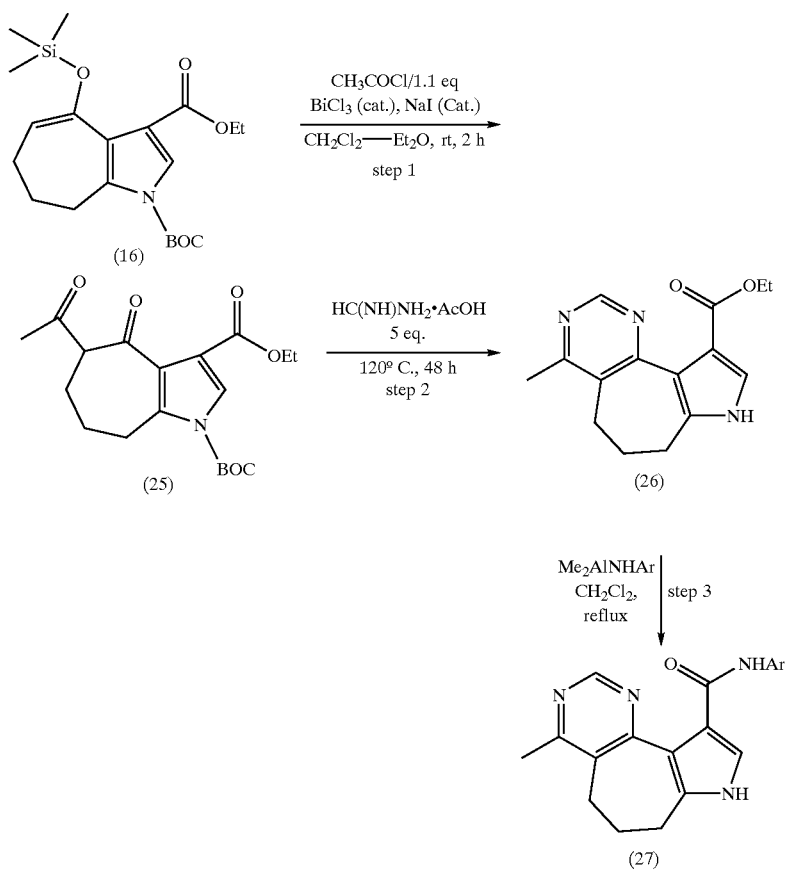

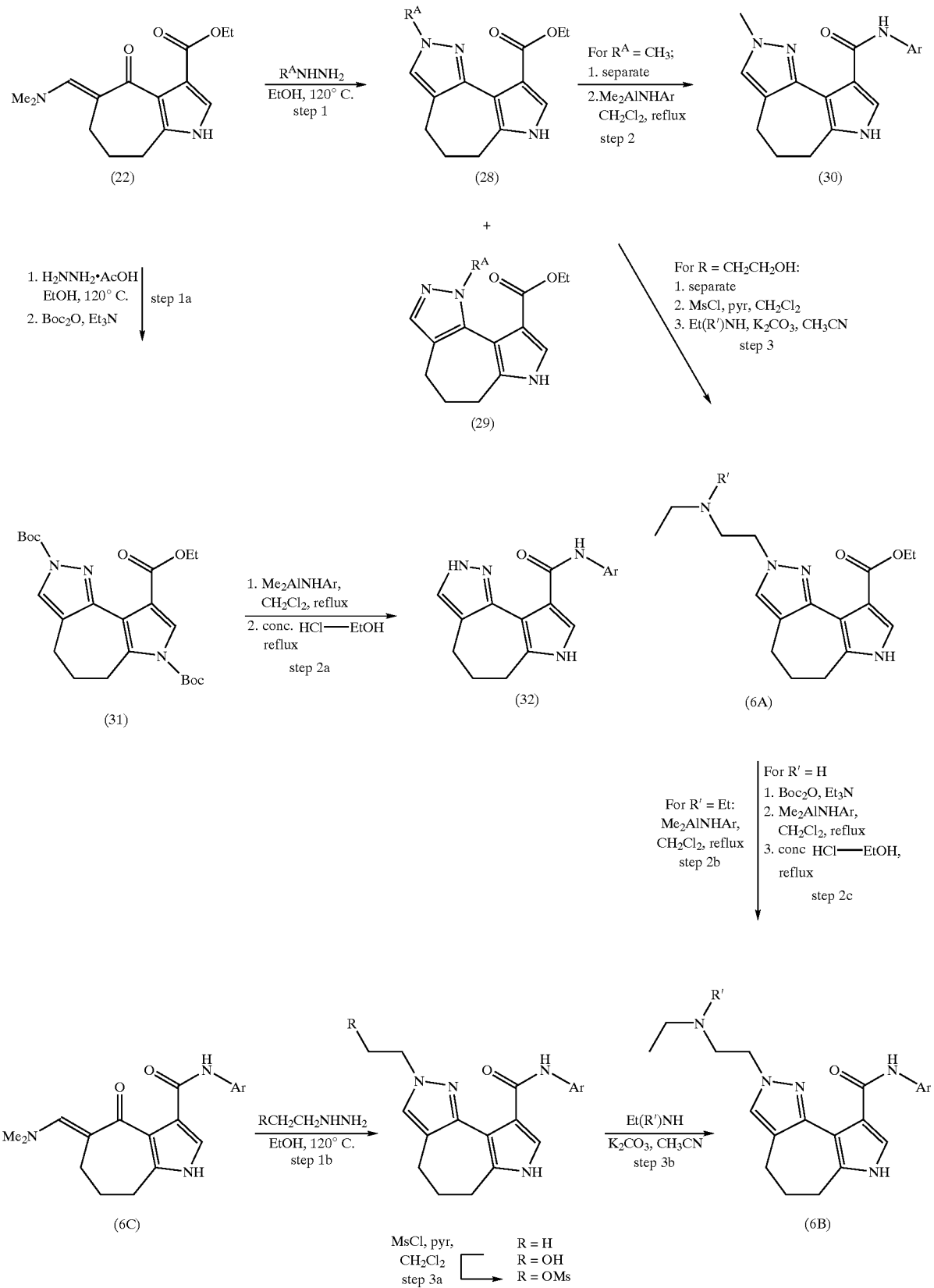

Scheme 6 provides a means of obtaining compounds of Formula V. In step 1, compound (22) from Scheme 4 is reacted with methylhydrazine ($R^A$=$CH_3$) in ethanol at 120° C. to obtain approximately a 3:1 mixture of compounds (28) and (29). The structure of compound (28) is assigned based on X-ray crystal analysis. After separation by chromatography on silica gel, compound (28) is converted to amide derivatives in step 2 as previously described. Compound (29) may likewise be reacted. Reaction of (22) with hydrazine acetate as shown in step 1a provides a pyrazole ring with a free NH. To improve the handling characteristics of this material, it is BOC-protected by means of reaction with di-tert-butyl dicarbonate in the presence of triethylamine to give compound (31). Compound (31) can be converted to amide derivatives (32) as shown in step 2a using previously described conditions.

Compounds of Formula V, wherein $R^A$ is a substituted aminoethyl substituent, may be prepared as shown in step 3. Compound (28) ($R^A$=$CH_2CH_2OH$), which is prepared as shown in step 1 by the reaction of (22) with 2-hydroxyethylhydrazine, is converted to the corresponding mesylate using standard conditions, such as methanesulfonyl chloride in the presence of pyridine. The mesylate is then displaced with various amines in the presence of $K_2CO_3$ and $CH_3CN$ at elevated temperature to produce compounds (6A). Amide derivatives (6B) are prepared as shown in steps 2b and 2c using previously described conditions.

Compounds of Formula V may also be prepared by first introducing the amide functionality. Thus, compound (14) is first aminated as previously described [U.S. Pat. No. 5,723, 462] and the amide derivatives converted to enaminone derivatives (6C) using conditions analogous to those for the preparation of (22) (Scheme 4). Compound (6C) is converted to various ethyl pyrazole derivatives as shown in steps 1b, 3a, and 3b using previously described methods. Those skilled in the art will recognize that compounds of Formula V containing a variety of $R^A$ groups, such as alkyl, alkoxy ethyl, and variously substituted aminoethyl groups, may be prepared using methods analogous to those depicted in Scheme 6.

Those skilled in the art will also recognize that compounds of Formula V, wherein $R^A$=$CH_3$, may be prepared from compound (25) (Scheme 5) using conditions analogous to those shown in Scheme 6.

Scheme 7

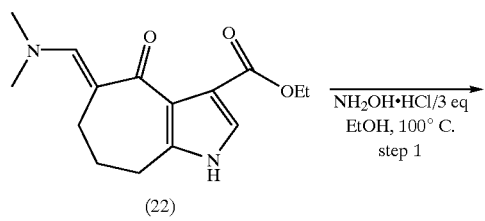

(22)

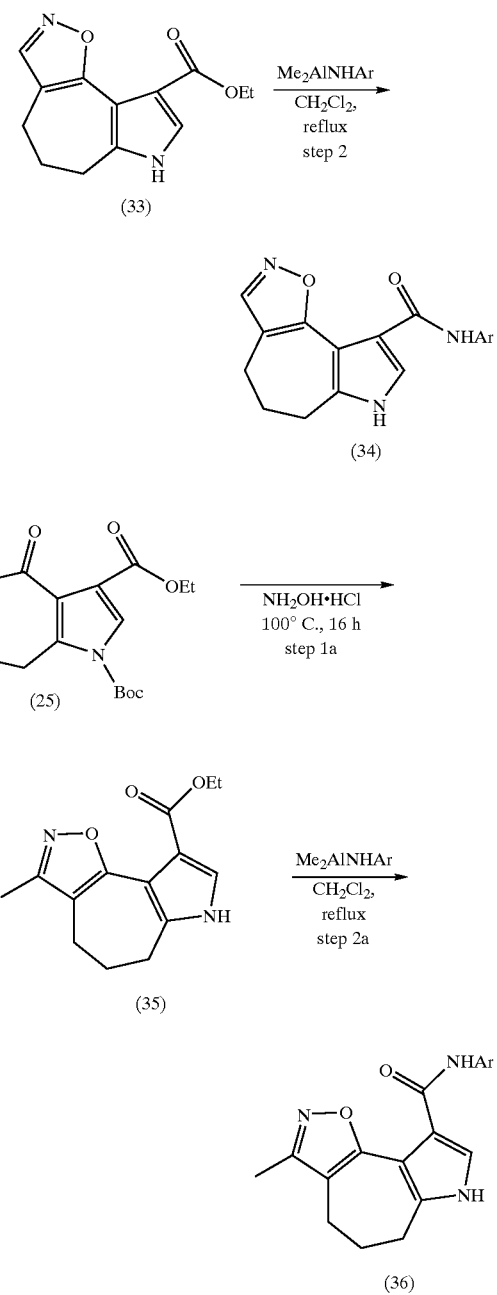

Scheme 7 illustrates the synthesis of isoxazole derivatives of Formula VI. In step 1, compound (22) from Scheme 4 is reacted with hydroxylamine hydrochloride in ethanol at 100° C. to provide isoxazole (33). Analogous reaction of diketone (25) with hydroxylamine hydrochloride affords the methyl isoxazole (35). Amination of (33) and (35) is accomplished in steps 2 and 2a using previously described

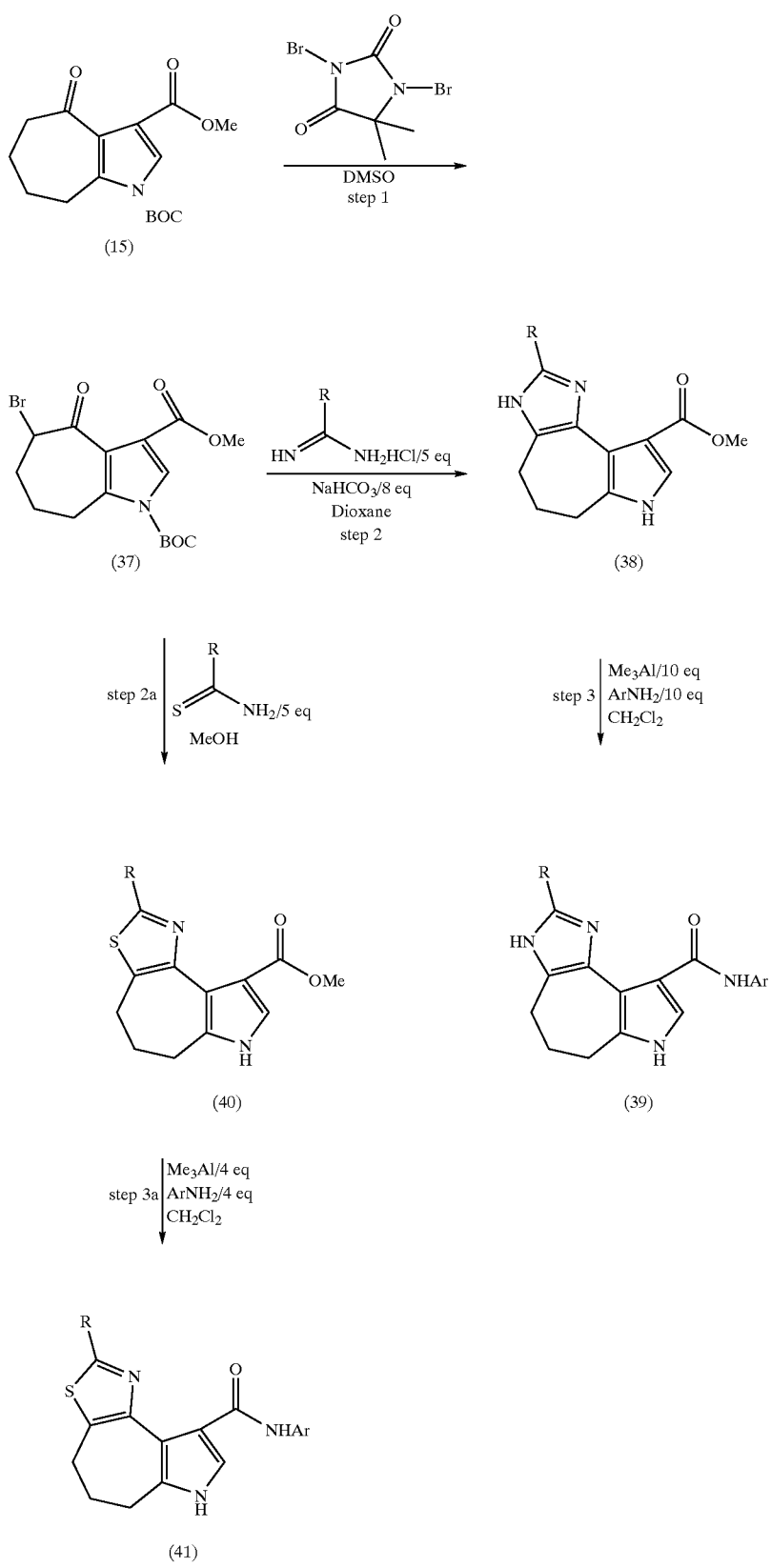

The synthesis of compounds of Formula VII and Formula VIII is outlined in Scheme 8. In Scheme 8 step 1, ketone (15) from Scheme 2 is brominated with a suitable brominating agent such as 1,3-dibromo-4,4-dimethylhydantoin. The resulting bromoketone (37) is reacted with various amidines in step 2 to give the corresponding imidazoles (38). Typically, the amidine hydrochloride is used in the presence of excess base in 1,4-dioxane as solvent. Alternatively, bromoketone (37) can be reacted with thioamides to form thiazole derivatives (40). The esters (38) and (40) react to form amides as in steps 3 and 3a as previously described. Examples in the present invention of Formula VII and VIII with k=1 are formed using entirely analogous procedures.

Scheme 9

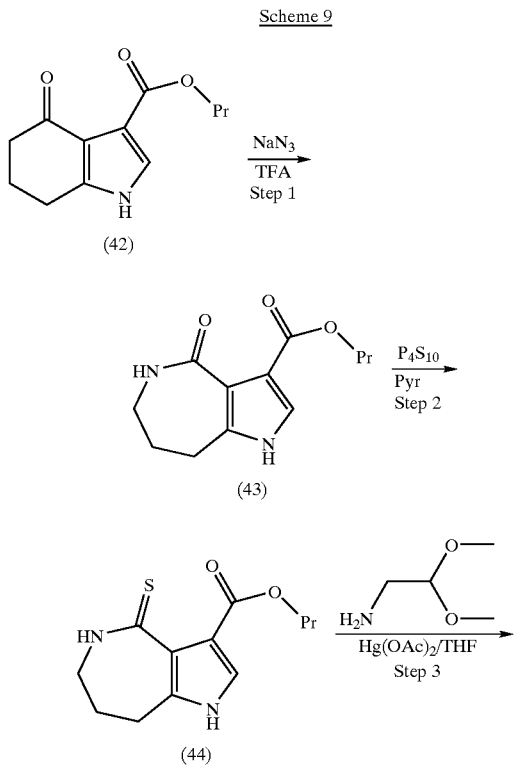

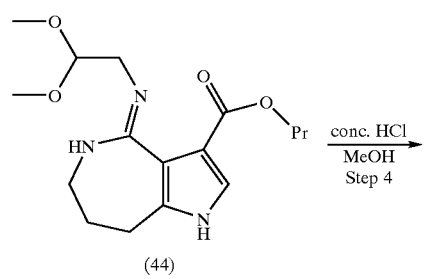

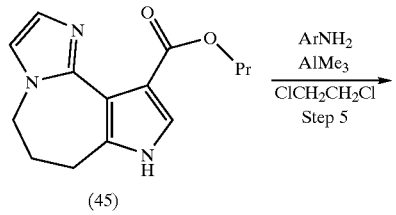

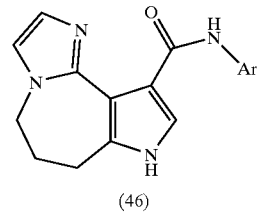

Scheme 9 illustrates the synthesis of fused imidazo derivatives (46). Step 1 involves a regioselective Schmidt type rearrangement of the ketone (42). The resulting amide (43) is converted to the thioamide (44) in Step 2. Thioamide (44) is efficiently converted to amidine (44) in the presence of mercury (II) acetate. Treatment of (44) with concentrated hydrochloric acid in Step 4 followed by amination of the ester in Step 5 provides the desired amide (46).

Scheme 10

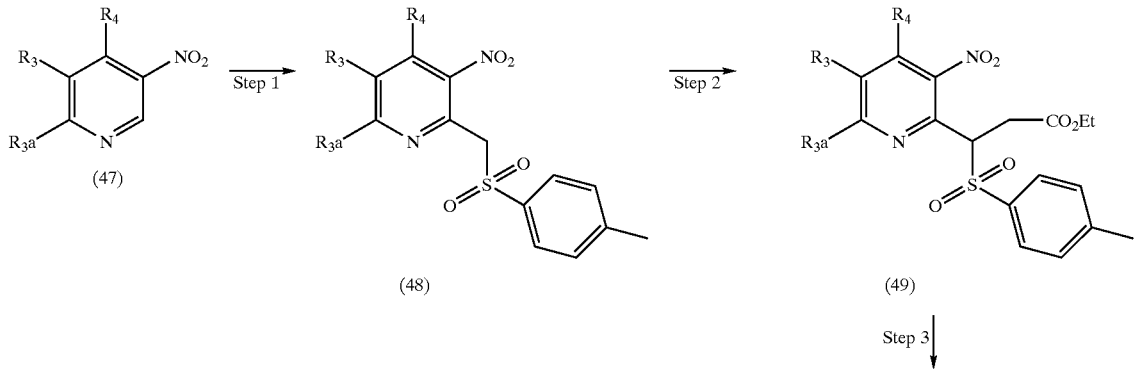

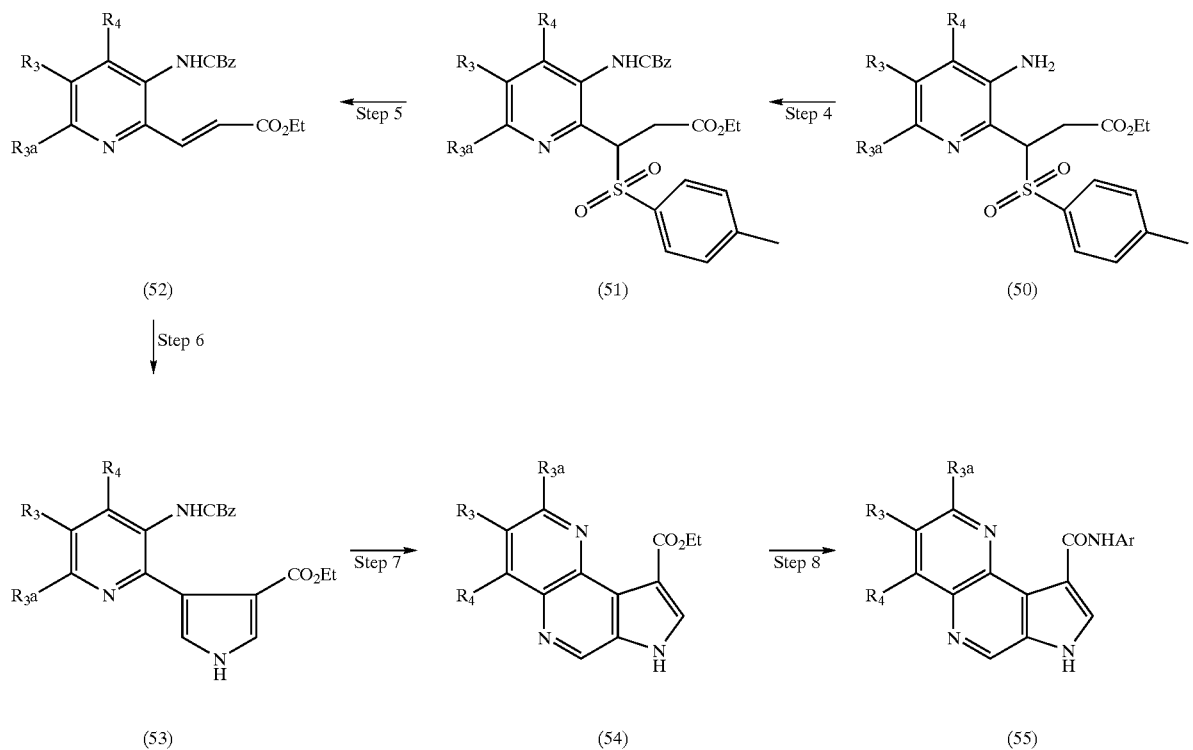
(52) (51) (50)
(53) (54) (55)
Scheme 11
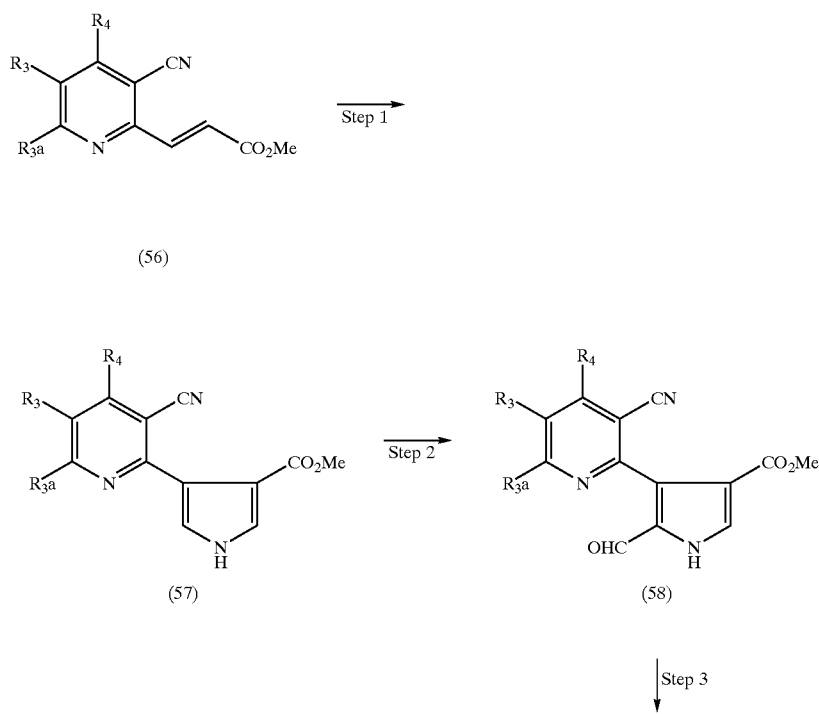
(56)
(57) (58)

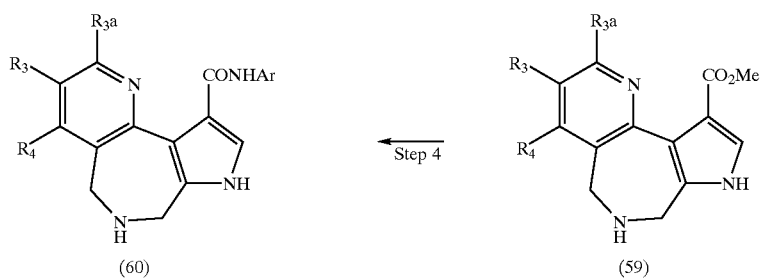
(60)  (59)
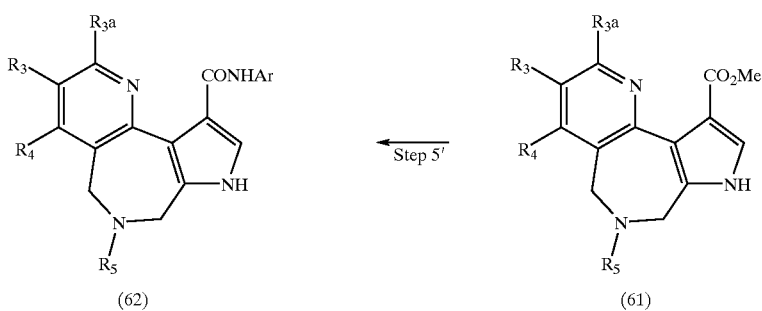
(62)  (61)
Scheme 12
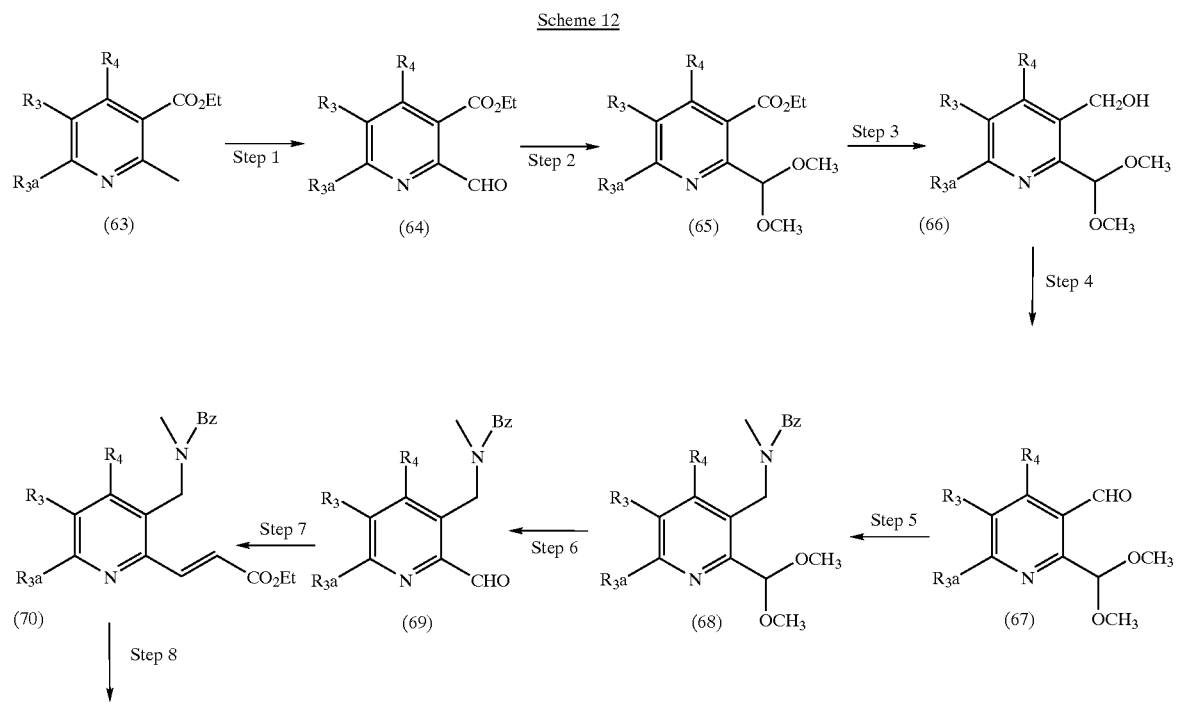

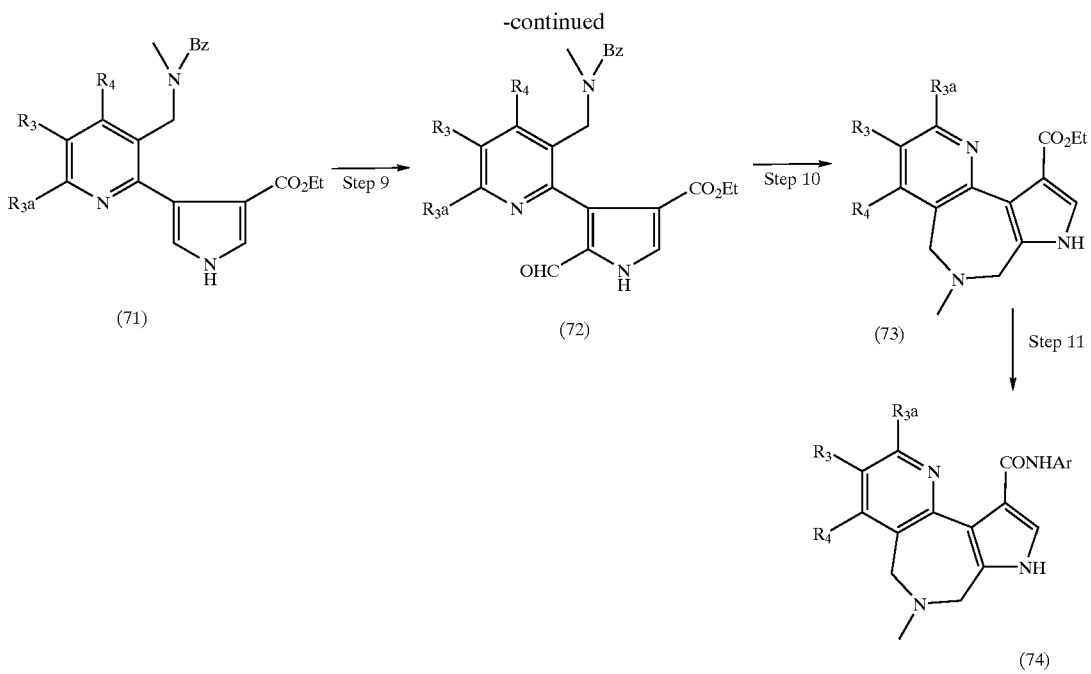

Scheme 10 illustrates the synthesis of 7H-pyrrolo [2,3c] [1,5] naphthyridine derivatives (55). Step 1 involves reaction of nitropyridine derivative (47) with 1-chloromethanesulfonyl-4-methyl-benzene in the presence of strong base. In Step 2, (48) is alkylated with ethyl bromoacetate in the presence of base. Catalytic hydrogenation of (49) in Step 3 efficiently provides 3-aminopyridine derivative (50) which is subsequently protected in Step 4 using carbobenzyloxy chloride to provide (51). Heating (51) with strong base in Step 5 yields the acrylic acid derivative (52). Intermediate (52) is converted the pyrrole (53) in Step 6 using tosylmethyl isocyamide and base. Reaction of (53) with phosphorous oxychloride in the presence of DMF provides cyclized produce (54). In Step 8, ester derivative (54) is conveniently converted to amide (55) by reaction with aryl and heteroaryl amines in the presence of trimethyl aluminum. Preparation of 7H-pyrrolo [2,3c][1,5] naphthyridine derivatives according to Scheme 10 is further illustrated by Example 21b.

Scheme 11 illustrates the synthesis of 3,4,5,6-tetrahydro-3,5,10-triaza-benzo(e)azulene derivatives (62). In Step 1, acrylic acid derivative (56) is converted the pyrrole (57) in using tosylmethyl isocyamide and base. Step 2 involves reaction of pyrrole (57) with phosphorous oxychloride in the presence of DMF to obtain the aldehyde (58). Catalytic hydrogenation of nitrile (58) results in cyclized product (59) which is converted in Step 4 to amide (60) using trimethyl aluminum in the presence of an appropriate aryl or heteroaryl amine. In optional Steps 4' and 5', (59) is converted to N-alkylated product (61) via reductive amination and subsequently reacted to form amide (62). Preparation of 3,4,5,6-tetrahydro-3,5,10-triaza-benzo(e)azulene derivatives according to Scheme 11 is further illustrated by Examples 21d and 21e.

Scheme 12 illustrates the synthesis of 5-methyl-3,4,5,6-tetrahydro-3,5,10-triaza-benzo(e)azulene derivatives (74). In Step 1, 2-methylpyridine (63) is oxidized to aldehyde (64) in the presence of selenium dioxide. The aldehyde group in (64) is protected as the dimethyl ketal (65) in Step 2. Reduction of (64) in Step 3 using lithium aluminum hydride followed by oxidation to aldehyde in Step 4 using manganese dioxide provides aldehyde (67). Reductive amination of (67) in Step 5 with N-benzyl methyl amine provides (68) which is deprotected under acidic conditions in Step 6 to aldehyde (69). In Step 7, aldehyde (69) is reacted with triethylphosphoro-acetate and potassium bis(trimethylsilyl) amide to form acrylic acid derivative (70). In Step 8, reaction of (70) with tosylmethyl isocyamide and base provides pyrrole (71). Reaction of (71) with phosphorous oxychloride and DMF in Step 9 provides aldehyde (72) which is subsequently hydrogenated in Step 10 to provide cyclized product (73). Ester (73) is conveniently converted to amide (74) in the presence of trimethyl aluminum and an appropriate aryl or heteroaryl amine. Preparation of 5-methyl-3,4,5,6-tetrahydro-3,5,10-triaza-benzo(e)azulene derivatives according to Scheme 12 is further illustrated by Example 21f.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples, which are not to be construed as limiting the invention in scope or spirit to the specific procedures described in them.

EXAMPLES

Example 1

Preparation of 5,6-dihydro-4H-1,3a,6-triaza-as-indacene-8-carboxylic acid methyl ester Step 1:

To a solution of p-nitro phenethylamine (45.3 mmol) in 75 mL water is added enough 30% NaOH in water to achieve a pH of 12. The water layer is extracted with dichloromethane. The organic layers are collected, dried over Na$_2$SO$_4$, and evaporated in vacuo yielding 7.4 g yellow brown oil (98%). To a partialy dissolved mixture of free base (44.58 mmol) in ether bromoacetic acid t-butyl ester (22.29 mmol) is slowly added over 15 min. Using an overhead stirring apparatus, the resulting mixture is stirred for 3½ days under a nitrogen atmosphere. Water is added to the reaction mixture, and the ether layer is washed 3 times with water and once with brine. The water layers are collected and back-extracted with a 50/50 ether/ethyl acetate mix. All the organic layers are collected, dried over Na$_2$SO$_4$, and evaporated in vacuo. The dark orange solid is chromatographed using hexane 3:ethyl acetate 1 as mobile phase to yield 3.48 g yellow solid (56%): $^1$H NMR (CDCl$_3$) 1.42 (s, 9H), 2.90 (s, 4H), 3.29 (s, 2H), 7.35 (d, 2H), 8.13 (d, 2H); LRMS calcd 280.33, found [M+H] 281.1.

Step 2:

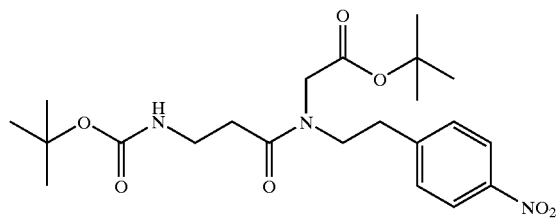

To a mixture of 2-(4-Nitro-phenyl)-ethylamino-acetic acid tert-butyl ester in 1 mL pyridine is added N-BOC β-alanine (0.178 mmol), and EDCI (0.214 mmol). After stirring at room temperature for 3½ hours, the pyridine is evaporated at reduced pressure. The remaining oil is taken up in ethyl acetate and washed with dilute hydrochloric acid. The organic layers are combined, dried over Na$_2$SO$_4$, and evaporated in vacuo yielding (3-tert-Butoxycarbonylamino-propionyl)-[2-(4-nitro-phenyl)-ethyl]-α-amino-acetic acid tert-butyl ester, 78 mg yellow oil: $^1$H NMR (CD$_3$OD) 1.45 (d, 9H), 1.50 (d, 9 h), 2.46–2.48 (m, 2H), 2.98–3.08 (m, 2H), 3.27–3.35 (m, 2H), 3.62–3.75 (m, 2H), [4.03, 4.11](s, 2H), 7.56–7.59 (m, 2H), 8.20–8.23 (m, 2H); LRMS calcd 451.52, found [M] 451.2.

Step 3:

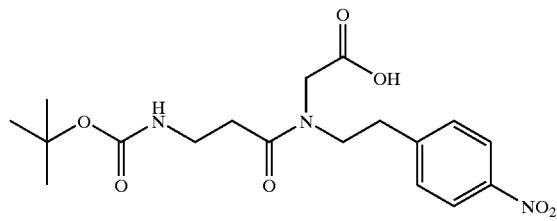

To a mixture of {(3-tert-Butoxycarbonylamino-propionyl)-[2-(4-nitro-phenyl)-ethyl]-amino}-acetic acid tert-butyl ester (2.5 mmol) in 11 mL THF is 22 mL water added, followed by NaOH (17.5 mmol). After heating at 60° C. for 5½ hours it is quenched with acetic acid (20 mmol). It is placed in the refrigerator for 2% days. The THF is evaporated off, and the remaining water is extracted several times with EtOAc. The organic layers are combined, dried over Na$_2$SO$_4$ and evaporated in vacuo yielding {(3-tert-Butoxycarbonylamino-propionyl)-[2-(4-nitro-phenyl)-ethyl]-amino}-acetic acid, 983 mg, as a dark yellow/brown oil/foam (99%): $^1$H NMR (CD$_3$OD) 1.40 (d, 9H), 2.44–2.45 (m, 2H), [2.98, 3.03](t, 2H), 3.22–3.30 (m, 2H), [3.60, 3.65](t, 2H), 4.06 (s, 2H), [7.52, 7.54](d, 2h), 8.16 (t, 2H); LRMS calcd 395.42, found [M–H] 394.0.

Step 4:

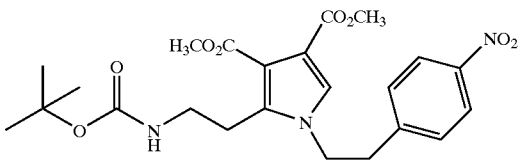

To a mixture of {(3-tert-Butoxycarbonylamino-propionyl)-[2-(4-nitro-phenyl)-ethyl]-amino}-acetic acid (0.253 mmol) in 1 ml acetic anhydride is dimethyl acetylene dicarboxylate (0.278 mmol) added. After stirring at 85° C. for 4½ hours the solvent is evaporated in vacuo. The dark brown oil is chromatographed using ethyl acetate 2:Hexane 3 as a mobile phase to yield 2-(2-tert-Butoxycarbonylamino-ethyl)-1-[2-(4-nitro-phenyl)-ethyl]-1H-pyrrole-3,4-dicarboxylic acid dimethyl ester, 79 mg, as a yellow oil (66%): $^1$H NMR (CD$_3$OD) 1.50 (s, 9H), 2.84 (t, 2H), 3.14–3.34 (m, 4H), 3.77 (s, 3H), 3.82 (s, 3H), 4.33 (t, 2H), 6.74 (t, 1H), 7.29 (s, 1H), 7.44 (d, 2H), 8.16 (d, 2H) LRMS calcd 475.50, found [M] 475.1.

Step 5:

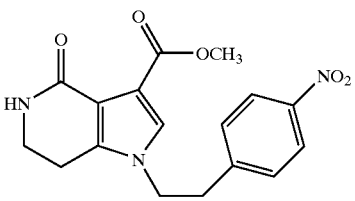

A solution of 2-(2-tert-Butoxycarbonylamino-ethyl)-1-[2-(4-nitro-phenyl)-ethyl]-1H-pyrrole-3,4-dicarboxylic acid dimethyl ester (0.292 mmol) in 10 HCl/ethyl acetate is stirred at RT for ½ hour. The solvent is evaporated in vacuo and placed on the high vacuum pump for several hours yielding 139 mg white solid $^1$H NMR (CD$_3$OD) 2.92–2.94 (m, 2H), 2.97–2.99 (m, 2H), 3.20 (t, 3H), 3.75 (s, 3H), 3.79 (s, 3H), 4.26 (t, 2H), 7.33 (d, 3H), 8.15 (d, 2H). LRMS calcd 375.38, found [M+H] 376.2) which is stirred in 7 mL THF with triethylamine (1.168 mmol) at 60° C. for 16 hours. The solvent is evaporated in vacuo and chromatographed using ethyl acetate 9:MeOH 1 as mobile phase to yield 1-[2-(4-Nitro-phenyl)-ethyl]-4-oxo-4,5,6,7-tetrahydro-1H-pyrrolo[3,2-C]pyridine-3-carboxylic acid methyl ester, 73 mg, as a white solid (73%): $^1$H NMR (CD$_3$OD) 2.47 (t, 2H), 3.16 (t, 2H), 3.23–3.33 (m, 2H), 3.74 (s, 3H), 4.23 (t, 2H), 7.30 (t, 3H), 8.11 (d, 2H); LRMS calcd 343.33, found [M+H] 344.2.

Step 6:

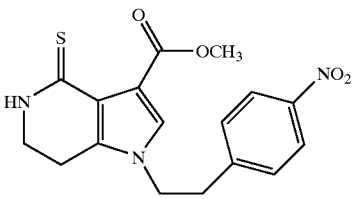

In a round bottom flask under N₂ atm. are the 1-[2-(4-Nitro-phenyl)-ethyl]-4-oxo-4,5,6,7-tetrahydro-1H-pyrrolo[3,2-c]pyridine-3-carboxylic acid methyl ester (48.64 mmol), $P_4S_{10}$ (24.32 mmol) and 240 mL pyridine combined and heated at 65° C. for 8 hours. After cooling to RT it is poured over ~600 mL ice and stirred for 2 hours. The yellow solid is filtered off, washed (2×) with water and dried on the high vacuum for 18 h to yield 1-[2-(4-Nitro-phenyl)-ethyl]-4-thioxo-4,5,6,7-tetrahydro-1H-pyrrolo[3,2-C]pyridine-3-carboxylic acid methyl ester, 10.24 g, as a yellow solid (65%): ¹H NMR (CD₃OD) 2.43 (t, 2H), 3.16 (t, 2H), 3.28–3.33 (m, 2H), 3.75 (s, 3H), 4.21 (t, 2H), 7.16 (s, 1H), 7.30 (d, 2H), 8.13 (d, 2H); LRMS calcd 359.41, found [M+H] 360.2.

Step 7:

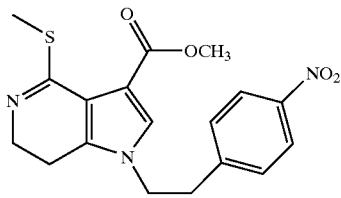

To a solution of 1-[2-(4-Nitro-phenyl)-ethyl]-4-thioxo-4,5,6,7-tetrahydro-1H-pyrrolo[3,2c]pyridine-3-carboxylic acid methyl ester (28.16 mmol) in 130 mL acetone is MeI (56.32 mmol) and $K_2CO_3$ (84.48 mmol) added. The reaction mixture is stirred at RT for 2½ hours whereby the acetone is evaporated in vacuo. The remaining oil is taken up in Dichloromethane and washed two times with water. The organic solvents are collected, dried over $Na_2SO_4$ and evaporated in vacuo to yield 4-Methylsulfanyl-1-[2-(4-nitro-phenyl)-ethyl]-6,7-dihydro-1H-pyrrolo[3,2-c]pyridine-3-carboxylic acid methyl ester, 9.46 g, as a yellow foam (90%); ¹H NMR (CD₃OD) 2.34–2.39 (m, 5H), 3.21 (t, 2H), 3.56 (t, 2H), 3.80 (s, 3H), 4.29 (t, 2H), 7.32–7.38 (m, 3H), 8.17 (d, 2H); LRMS calcd 373.43, found [M+H] 374.2.

Step 8:

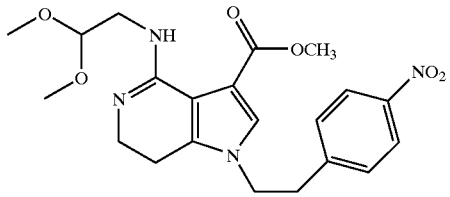

In a round bottom flask are 4-Methylsulfanyl-1-[2-(4-nitro-phenyl)-ethyl]-6,7-dihydro-1H-pyrrolo[3,2-C]pyridine-3-carboxylic acid methyl ester (25.33 mmol), amino acetaldhyde dimethyl acetal (63.32 mmol) and 125 mL MeOH combined (a part "oiled-out" that later went into solution) and stirred at RT for 20 hours. The solvent is evaporated in vacuo yielding 4-(2,2-Dimethoxy-ethylamino)-1-[2-(4-nitro-phenyl)-ethyl]-6,7-dihydro-1H-pyrrolo[3,2-c]pyridine-3-carboxylic acid methyl ester, 11.56 g, as a yellow oil/solid that is used without purification.

Step 9:

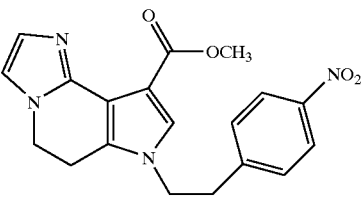

To a solution of 4-(2,2-Dimethoxy-ethylamino)-1-[2-(4-nitro-phenyl)-ethyl]-6,7-dihydro-1H-pyrrolo[3,2-c]pyridine-3-carboxylic acid methyl ester (25.33 mmol) in 125 mL MeOH is 10 mL HCl conc. added. It is heated at 63° C. for 15 hours. Since the reaction is not complete another 5 mL HCl conc. is added, and it is heated again at 63° C. for 10 hours. The solvent is evaporated in vacuo, and the remaining oil is dissolved in MeOH whereby $K_2CO_3$ (1.2 eq.) is added. After stirred at RT for 1 h the solid is filtered off, washed with MeOH and the filtrate is evaporated in vacuo yielding a yellow solid that is protonated. The protonated product is stirred in Dichloromethane and saturated $NaCO_3$ sol. until everything dissolved. The two layers are separated and the water layer is extracted two times with dichloromethane. The organic layers are collected, dried and evaporated in vacuo yielding a free base which is triturated in ethyl acetate yielding 6-[2-(4-Nitro-phenyl)-ethyl]-5,6-dihydro-4H-1,3a,6-triaza-as-indacene-8-carboxylic acid methyl ester, 9.11 g, as a yellow solid (77%): ¹H NMR (CD₃OD) 2.76 (t, 2H), 3.18 (t, 2H), 3.78 (s, 3H), 4.07 (t, 2H), 4.28 (t, 2H), 6.94 (s, 1H), 7.01 (s, 1H), 7.31 (d, 3H), 8.10 (d, 2H); LRMS calcd 366.38, found [M+H] 367.2.

Step 10:

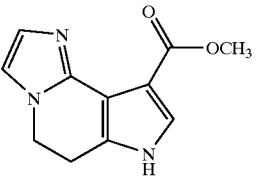

To a solution of 6-[2-(4-Nitro-phenyl)-ethyl]-5,6-dihydro-4H-1,3a,6-triaza-as-indacene-8-carboxylic acid methyl ester (19.67 mmol) in 100 mL DMF is treated with sodium hydride (60%, 1.97 g, 49.18 mmol) portion wise. The reaction is complete in about 2 h at 20° C. Chloroform is added and the reaction mixture is cooled to 5° C. before the dropwise addition of acetic acid (3.15 mL, 55.08 mmol) until pH of 1–3. A saturated solution of aqueous KHCO3 (150 mL) is added, stirred and separated. The separated organic phase is washed with water twice. The filtrate is concentrated directly. Most of the DMF is removed by high vacuum to give a brown wet solid. The wet solid is cooled to room temp. Ether is added, stirred, and filtered to give a brown solid which is dried in air overnight to give 5,6-dihydro-4H-1,3a,6-triaza-as-indacene-8-carboxylic acid methyl ester, 9.11 g, (77%): ¹H NMR (CD₃OD) 3.05 (t, 2H), 3.86 (s, 3H), 4.25 (t, 2H), 6.97 (s, 1H), 7.05 (s, 1H), 7.40 (s, 1H); LRMS calcd 217.23, found [M–H] 216.1.

Example 2

Preparation of 5,6-Dihydro-4H-1,3a,6-triaza-as-indacene-8-carboxylic acid (2-fluoro-phenyl)-amide

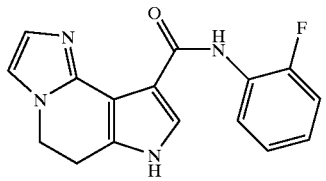

To a solution of 2-fluoroaniline (84 uL, 0.829 mmol) in 2 mL dichloromethane at room temperature is added a 2M solution of trimethylaluminum in toluene (414 uL, 0.829 mmol) and the reaction is stirred at room temperature for 0.5 h. This solution is then syringed into the neat give 5,6-dihydro-4H-1,3a,6-triaza-as-indacene-8-carboxylic acid methyl ester (90 mg, 0.415 mmol) and stirred at reflux for 10 h. The reaction mixture is diluted with dichloromethane and poured onto water (30 mL). The whole mixture is filtered through celite and then separated. The aqueous phase is washed with dichloromethane and the combined organics are dried (Na2SO4) and concentrated in vacuo. The residue is purified by Flash-40 chromatography (EtOAc) to afford the product, 5,6-Dihydro-4H-1,3a,6-triaza-as-indacene-8-carboxylic acid (2-fluoro-phenyl)-amide, 63 mg, as an glassy oil (48%): $^1$H NMR (DMSO) 3.25 (t, 2H), 4.44 (t, 2H), 7.23–7.42 (m, 4H), 7.57–7.63 (m, 2H), 7.96 (s, 1H); LRMS calcd 296.30, found (M–H) 295.0.

Example 2a 5,6-Dihydro-4H-1,3a,6-triaza-as-indacene-8-carboxylic acid hydrobromide A solution of 5,6-dihydro-4H-1,3a,6-triaza-as-indacene-8-carboxylic acid methyl ester (516 mg) and 48% hydrobromic acid (5 mL) is heated at 600 for 60 hours. The mixture is cooled to room temperature and concentrated in vacuo. The residue is slurried with diethyl ether and the ether is decanted off. This is repeated until no more color is visible in the ether layer. The remaining solid is dried in vacuo to give 5,6-dihydro-4H-1,3a,6-triaza-as-indacene-8-carboxylic acid hydrobromide, 350 mg, brown solid: $^1$H NMR(DMSO-d$_6$) 3.17 (2H, t), 4.40 (2H, t), 7.35 (1H, d), 7.57 (1H, d), 7.63 (1H, s) 12.34 (1H, s), 12.45 (1H, s).

Example 2b 5,6-Dihydro-4H-1,3a,6-triaza-as-indacene-8-carboxylic acid (4-fluorophenyl)amide A mixture of 5,6-dihydro-4H-1,3a,6-triaza-as-indacene-8-carboxylic acid hydrobromide (58 mg), O-(1H-benzotriazol-1-yl)-N,N,N',N'-tetramethyluronium hexafluorophosphate (181 mg), triethylamine (0.07 mL), 4-fluoroaniline (30 mg), and N,N-dimethylformamide (4 mL) is heated at 400 for 18 hours. The mixture is cooled to room temperature, treated with water (15 mL), and extracted with ethyl acetate (3×50 mL). The combined organic layers are washed with water (2×15 mL) and brine (1×15 mL), dried over magnesium sulfate, and concentrated in vacuo. The residue is purified by preparative thin layer chromatography on silica gel, eluting with 5% methanol in dichloromethane, to give 5,6-dihydro-4H-1,3a,6-triaza-as-indacene-8-carboxylic acid (4-fluorophenyl)amide, pale brown solid, 18 mg: LRMS calcd 296.30, found [M+H] 297.2.

Example 2c

4-Methyl-5,6-dihydro-4H-1,3a,6-triaza-as-indacene-8-carboxylic methyl ester

The title compound is prepared following the procedure outlined in Example 1 starting with 3-aminobutyric acid: Electrospray MS m/z 232 [M+1]; $^1$H NMR (DMSO-d6, 300 MHz) δ11.62 (s, 1H) 7 .38 (s, 1H), 7.08 (s, 1H), 6.81 (s, 1H), 4.43 (m, 1H), 3.68 (s, 3H), 3.05 (dd, 1H), 2.67 (dd, 1H), 1.38 (d, 3H).

Example 2d 4,4-Dimethyl-5,6-dihydro-4H-1,3a,6-triaza-as-indacene-8-carboxylic methyl ester The title compound is prepared following the procedure outlined in Example 1 starting with 3-amino-3-methylbutyric acid: Electrospray MS m/z 246 [M+1]; $^1$H NMR (DMSO-d6, 300 MHz) δ11.70 (s, 1H), 7.39 (s, 1H), 7.18 (s, 1H), 6.82 (s, 1H), 3.68 (s, 3H), 2.85 (s, 2H), 1.40 (s, 6H)

Example 2e

4-Methyl-5,6-dihydro-4H-1,3a,6-triaza-as-indacene-8-carboxylic acid phenyl amide

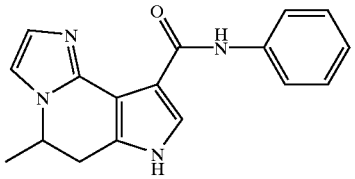

A mixture of 4-methyl-5,6-dihydro-4H-1,3a,6-triaza-as-indacene-8-carboxylic acid hydrobromide (25 mg), aniline (12 mg), 1-[3-(dimethylamino)propyl]-3-ethylcarbodiimide hydrochloride (23 mg), 1,4-dioxane (1.5 mL), and water (1.5 mL) is stirred at room temperature for 4 days. 0.5N sodium hydroxide solution (3 mL) is added and the mixture is extracted with dichloromethane (3×50 mL). The combined organic layers are washed with brine (1×10 mL), dried over magnesium sulfate and concentrated in vacuo. The residue is purified by preparative thin layer chromatography on silica gel, eluting with 5% methanol in dichloromethane, to give 4-methyl-5,6-dihydro-4H-1,3a,6-triaza-as-indacene-8-carboxylic acid phenyl amide, cream solid, 7 mg: LRMS calcd 292.34, found [M+H] 293.2.

Example 3

4-Methyl-5,6-dihydro-4H-1,3a,6-triaza-as-indacene-8-carboxylic acid (2-fluoro-4-isopropoxyphenyl) amide

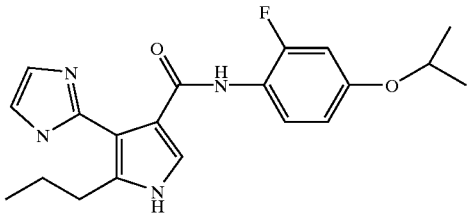

Ethyl chloroformate (66 μL) is added dropwise to an ice-cold mixture of 4-methyl-5,6-dihydro-4H-1,3a,6-triaza-as-indacene-8-carboxylic acid hydrobromide (192 mg), triethylamine (0.33 mL), and N,N-dimethylformamide (5 mL). The mixture is stirred at 0° for 1 hour then at room temperature for 30 minutes. 2-Fluoro-4-isopropoxyaniline (66 mg) is added and the mixture is stirred at room temperature for 18 hours. The mixture is diluted with ethyl acetate (50 mL) then treated with water (25 mL), and extracted with ethyl acetate (3×50 mL). The combined organic layers are washed with water (2×20 mL) and brine (1×20 mL), dried over magnesium sulfate, and concentrated in vacuo. The residue is purified by preparative thin layer chromatography on silica gel, eluting with diethyl ether, to give a brown solid. This is treated with ethanol (2 mL) and saturated aqueous potassium carbonate solution (1 mL) and the mixture is heated at 600 for 30 minutes. The mixture is cooled to room temperature and diluted with water (3 mL) and extracted with ethyl acetate (3×30 mL). The combined organic layers are washed with brine (1×10 mL), dried over magnesium sulfate, and concentrated in vacuo. The oily residue is purified by preparative thin layer chromatography on silica gel, eluting with 10% methanol in dichloromethane, to give 4-methyl-5,6-dihydro-4H-1,3a,6-triaza-as-indacene-8-carboxylic acid (2-fluoro-4-isopropoxyphenyl)amide, pale yellow solid, 10 mg: LRMS calcd 368.40, found [M+H] 369.2.

Example 4

Using methods as generally shown in Scheme 1 and further illustrated in Examples 1, 2–2e, and 3 the compounds shown in Table 1 were synthesized.

The column headings used to indicate substituents groups in Table 1–Table 8, e.g. R1, R2, Ar, are intended for use only in the Table in which they appear.

TABLE 1

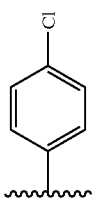

| Cpd # | Name | R3 | R4 | R5 | R6 | k | Ar | Spectral Data |
|---|---|---|---|---|---|---|---|---|
| 1. | 5,6-Dihydro-4H-1,3a,6-triaza-as-indacene-8-carboxylic acid (4-chloro-phenyl)-amide | H | H | H | H | 1 | 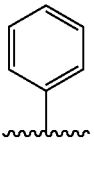 | ¹H NMR (DMSO) 3.24 (t, 2H), 4.44 (t, 2H), 7.37 (s, 1H), 7.45 (d, 2H), 7.65 (s, 1H), 7.82 (d, 2H), 8.01 (m, 1H) LRMS calcd 312.76 found (M-H) 311.0 |
| 2. | 5,6-Dihydro-4H-1,3a,6-triaza-as-indacene-8-carboxylic acid phenylamide | H | H | H | H | 1 | 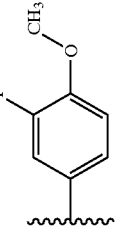 | ¹H NMR (DMSO) 3.24 (t, 2H), 4.44 (t, 2H), 7.14 (t, 1H), 7.37–7.42 (m, 3H), 7.65 (s, 1H), 7.77 (d, 2H), 8.00 (s, 1H) LRMS calcd 278.31 found (M-H) 277.0 |
| 3. | 5,6-Dihydro-4H-1,3a,6-triaza-as-indacene-8-carboxylic acid (3-fluoro-4-methoxy-phenyl)-amide | H | H | H | H | 1 | 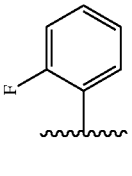 | ¹H NMR (DMSO) 3.23 (t, 2H), 3.84 (s, 3H), 4.44 (t, 2H), 7.19 (t, 1H), 7.37–7.44 (m, 2H), 7.64 (s, 1H), 7.79 (d, 1H), 7.95 (s, 1H) LRMS calcd 326.33 found (M-H) 325.2 |
| 4. | 5,6-Dihydro-4H-1,3a,6-triaza-as-indacene-8-carboxylic acid 2-fluoro-benzylamide | H | H | H | H | 1 |  | ¹H NMR (DMSO) 3.21 (t, 2H), 4.41 (t, 2H), [4.52, 4.58] (d, 2H), 7.17–7.24 (m, 2H), 7.31–7.41 (m, 3H), 7.60 (s, 1H), 7.78 (s, 1H) LRMS calcd 310.33 found [M−H] 309.0 |

TABLE 1-continued

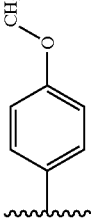

| Cpd # | Name | R3 | R4 | R5 | R6 | k | Ar | Spectral Data |
|---|---|---|---|---|---|---|---|---|
| 5. | 5,6-Dihydro-4H-1,3a,6-triaza-as-indacene-8-carboxylic acid (4-methoxy-phenyl)-amide | H | H | H | H | 1 | 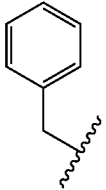 | ¹H NMR (DMSO) 3.19 (t, 2H), 3.72 (s, 3H), 4.39 (t, 2H), 6.92 (d, 2H), 7.31 (s, 1H), 7.60 (d, 3H), 7.92 (s, 1H) LRMS calcd 308.34 found [M+H] 309.0 |
| 6. | 5,6-Dihydro-4H-1,3a,6-triaza-as-indacene-8-carboxylic acid benzylamide | H | H | H | H | 1 | 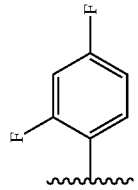 | ¹H NMR (DMSO) 3.18 (t, 2H), 4.37 (t, 2H), 4.49 (d, 2H), 7.22–7.24 (m, 1H), 7.27–7.33 (m, 5H), 7.56 (s, 1H), 7.72 (s, 1H), 9.03 (m, 1H) LRMS calcd 292.34 found [M+H] 293.4 |
| 7. | 5,6-Dihydro-4H-1,3a,6-triaza-as-indacene-8-carboxylic acid (2,4-difluoro-phenyl)-amide | H | H | H | H | 1 | 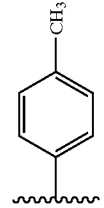 | ¹H NMR (CD3OD) 3.28–3.31 (m, 2H), 4.7 (t, 2H), 6.95–7.04 (m, 1H), 7.05–7.09 (m, 1H), 7.31 (s, 1H), 7.43 (s, 1H), 7.69–7.74 (m, 1H), 7.79 (s, 1H), 9.80 (s, 1H) LRMS calcd found [M+ ] |
| 8. | 5,6-Dihydro-4H-1,3a,6-triaza-as-indacene-8-carboxylic acid p-tolylamide | H | H | H | H | 1 | 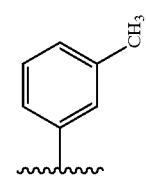 | ¹H NMR (CD3OD) 2.30 (s, 3H), 3.10 (t, 2H), 4.24 (t, 2H), 7.03–7.04 (m, 2H), 7.14 (d, 2H), 7.42 (s, 1H), 7.69 (d, 2H) LRMS calcd 292.34 found [M+H] 293.3 |
| 9. | 5,6-Dihydro-4H-1,3a,6-triaza-as-indacene-8-carboxylic acid m-tolylamide | H | H | H | H | 1 |  | ¹H NMR (CD3OD) 2.34 (s, 3H), 3.11 (t, 2H), 4.24 (t, 2H), 6.89 (d, 1H), 7.04 (s, 2H), 7.20 (t, 1H), 7.42 (s, 1H), 7.60 (d, 1H), 7.65 (s, 1H) LRMS calcd 292.34 found [M+H] 293.2 |

TABLE 1-continued

| Cpd # | Name | R3 | R4 | R5 | R6 | k | Ar | Spectral Data |
|---|---|---|---|---|---|---|---|---|
| 10. | 5,6-Dihydro-4H-1,3a,6-triaza-as-indacene-8-carboxylic acid (4-ethoxy-phenyl)-amide | H | H | H | H | 1 | 4-ethoxyphenyl | $^1$H NMR (CD3OD) 1.37 (t, 3H), 3.10 (t, 2H), 4.01 (q, 2H), 4.23 (t, 2H), 6.90 (d, 2H), 7.02 (d, 2H), 7.41 (s, 1H), 7.69 (d, 2H) LRMS calcd 322.37 found [M+H] 323.3 |
| 11. | 5,6-Dihydro-4H-1,3a,6-triaza-as-indacene-8-carboxylic acid o-tolylamide | H | H | H | H | 1 | 2-methylphenyl | $^1$H NMR (CD3OD) 2.37 (s, 3H), 3.12 (t, 2H), 4.24 (t, 2H), 6.91 (s, 1H), 7.01 (s, 1H), 7.09 (t, 1H), 7.18 (t, 1H), 7.24 (d, 1H), 7.44 (s, 1H), 7.50 (d, 1H) LRMS calcd 292.34 found [M+H] 293.3 |
| 12. | 5,6-Dihydro-4H-1,3a,6-triaza-as-indacene-8-carboxylic acid (3-methoxy-phenyl)-amide | H | H | H | H | 1 | 3-methoxyphenyl | $^1$H NMR (CD3OD) 3.11 (t, 2H), 3.80 (s, 3H), 4.24 (t, 2H), 6.64 (d, 1H), 7.04 (s, 2H), 7.23 (t, 1H), 7.31 (d, 1H), 7.43 (s, 1H), 7.57 (s, 1H) LRMS calcd 308.33 found [M+H] 309.2 |
| 13. | {4-[(5,6-Dihydro-4H-1,3a,6-triaza-as-indacene-8-carbonyl)-amino]-benzyl}-methyl-carbamic acid tert-butyl ester | H | H | H | H | 1 | 4-(N-Boc-N-methylaminomethyl)phenyl | |

TABLE 1-continued

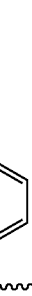

| Cpd # | Name | R3 | R4 | R5 | R6 | k | Ar | Spectral Data |
|---|---|---|---|---|---|---|---|---|
| 14. | 5,6-Dihydro-4H-1,3a,6-triaza-as-indacene-8-carboxylic acid (4-methylaminomethyl-phenyl)-amide | H | H | H | H | 1 |  | $^1$H NMR (CD3OD) 2.70 (s, 1H), 3.28–3.31 (m, 2H), 4.15 (s, 2H), 4.46 (t, 2H), 7.35 (s, 1H), 7.45–7.49 (m, 3H), 7.81 (s, 1H), 7.87–7.90 (m, 2H) LRMS calcd 321.38 found [M+H] 322.3 |
| 15. | 5,6-Dihydro-4H-1,3a,6-triaza-as-indacene-8-carboxylic acid (4-fluoro-phenyl)-amide | H | H | H | H | 1 |  | |
| 16. | 5,6-Dihydro-4H-1,3a,6-triaza-as-indacene-8-carboxylic acid (3-fluoro-phenyl)-amide | H | H | H | H | 1 |  | |
| 17. | 4-Methyl-5,6-dihydro-4H-1,3a,6-triaza-as-indacene-8-carboxylic acid [4-(2-propylamino-ethoxy)-phenyl]-amide | H | H | H | CH3 | 1 |  | |
| 18. | 4-Methyl-5,6-dihydro-4H-1,3a,6-triaza-as-indacene-8-carboxylic acid (2-fluoro-phenyl)-amide | H | H | H | CH3 | 1 |  | LRMS calcd 310.33, found [M+H] 311.1 |

TABLE 1-continued

| Cpd # | Name | R3 | R4 | R5 | R6 | k | Ar | Spectral Data |
|---|---|---|---|---|---|---|---|---|
| 19. | 5,6-Dihydro-4H-1,3a,6-triaza-as-indacene-8-carboxylic acid [4-(2-propylamino-ethoxy)-phenyl]-amide | H | H | H | H | 1 | 4-(2-propylaminoethoxy)phenyl | LRMS calcd 379.46, found [M+H] 380.3 |
| 20. | 5,6-Dihydro-4H-1,3a,6-triaza-as-indacene-8-carboxylic acid (3,4-difluoro-phenyl)-amide | H | H | H | H | 1 | 3,4-difluorophenyl | $^1$H NMR (CD3OD) 3.16 (t, 2H), 4.30 (t, 2H), 7.10 (s, 2H), 7.21–7.29 (m, 1H), 7.49–7.55 (m, 2H), 7.93–8.02 (m, 1H) LRMS calcd 314.29 found [M+H] 315.1 |
| 21. | 5,6-Dihydro-4H-1,3a,6-triaza-as-indacene-8-carboxylic acid (4-trifluoromethyl-phenyl)-amide | H | H | H | H | 1 | 4-(trifluoromethyl)phenyl | $^1$H NMR (CD3OD) 3.12 (t, 2H), 4.25 (t, 2H), 7.06–7.07 (m, 2H), 7.46 (s, 1H), 7.62 (d, 2H), 8.04 (d, 2H) LRMS calcd 346.31 found [M+H] 347.1 |

TABLE 1-continued

| Cpd # | Name | R3 | R4 | R5 | R6 | k | Ar | Spectral Data |
|---|---|---|---|---|---|---|---|---|
| 22. | 5,6-Dihydro-4H-1,3a,6-triaza-as-indacene-8-carboxylic acid {4-[2-(4-benzyl-piperidin-1-yl)-ethoxy]-3-fluoro-phenyl}-amide | H | H | H | H | 1 |  | LRMS calcd 513.61, found [M+H] 514.4 |
| 23. | 5,6-Dihydro-4H-1,3a,6-triaza-as-indacene-8-carboxylic acid (6-methoxy-2-methyl-pyridin-3-yl)-amide | H | H | H | H | 1 | 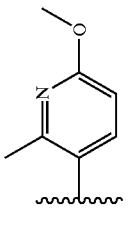 | MS found [M+H] 324.0 |
| 24. | 5,6-Dihydro-4H-1,3a,6-triaza-as-indacene-8-carboxylic acid (2-methoxymethyl-pyrimidin-4-yl)-amide | H | H | H | H | 1 | 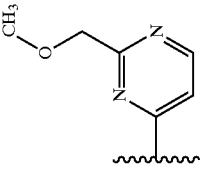 | MS found [M+H] 325.0 |

TABLE 1-continued

| Cpd # | Name | R3 | R4 | R5 | R6 | k | Ar | Spectral Data |
|---|---|---|---|---|---|---|---|---|
| 25. | 5,6-Dihydro-4H-1,3a,6-triaza-as-indacene-8-carboxylic acid (6-methoxy-pyridin-3-yl)-amide | H | H | H | H | 1 | 6-methoxy-pyridin-3-yl | ¹H NMR [DMSO-d6] 3.1 (t, 1H), 3.9 (s, 3H), 4.3 (t, 2H), 6.9 (d, 1H), 7.0 (s, 1H), 7.2 (s, 1H), 7.5 (s, 2H), 8.2 (d, 1H), 8.6 (s, 1H), 11.8 (s, 1H), 13.2 (s, 1H) |
| 26. | 5,6-Dihydro-4H-1,3a,6-triaza-as-indacene-8-carboxylic acid (6-methoxy-pyrazin-2-yl)-amide | H | H | H | H | 1 | 6-methoxy-pyrazin-2-yl | MS found [M+H] 310.9 |
| 27. | 5,6-Dihydro-4H-1,3a,6-triaza-as-indacene-8-carboxylic acid (5-tert-butyl-isoxazol-3-yl)-amide | H | H | H | H | 1 | 5-tert-butyl-isoxazol-3-yl | MS found [M+H] 326.0 |
| 28. | 5,6-Dihydro-4H-1,3a,6-triaza-as-indacene-8-carboxylic acid (1-methyl-5-methylsulfanyl-1H-[1,2,4]triazol-3-yl)-amide | H | H | H | H | 1 | 1-methyl-5-methylsulfanyl-triazol-3-yl | MS found [M+H] 329.9 |
| 29. | 5,6-Dihydro-4H-1,3a,6-triaza-as-indacene-8-carboxylic acid (3-methyl-[1,2,4]thiadiazol-5-yl)-amide | H | H | H | H | 1 | 3-methyl-[1,2,4]thiadiazol-5-yl | MS found [M+H] 300.9 |

TABLE 1-continued

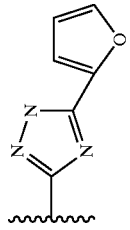

| Cpd # | Name | R3 | R4 | R5 | R6 | k | Ar | Spectral Data |
|---|---|---|---|---|---|---|---|---|
| 30. | 5,6-Dihydro-4H-1,3a,6-triaza-as-indacene-8-carboxylic acid thiazol-2-ylamide | H | H | H | H | 1 | 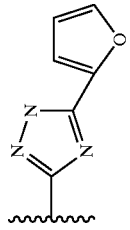 | $^1$H NMR [DMSO-d6] 3.1 (t, 1H), 4.3 (t, 2H), 7.0 (s, 1H), 7.2 (s, 1H), 7.3 (s, 1H), 7.5 (s, 2H), 7.6 (s, 1H), 12.0 (br s, 1H), >15 (s, 1H) |
| 31. | 5,6-Dihydro-4H-1,3a,6-triaza-as-indacene-8-carboxylic acid (5-furan-2-yl-1H-pyrazol-3-yl)-amide | H | H | H | H | 1 | 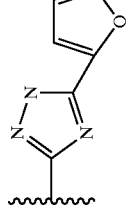 | MS found [M+H] 334.9 |
| 32. | 5,6-Dihydro-4H-1,3a,6-triaza-as-indacene-8-carboxylic acid (5-methyl-pyridin-2-yl)-amide | H | H | H | H | 1 | 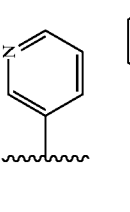 | MS found [M+H] 293.9 |
| 33. | 5,6-Dihydro-4H-1,3a,6-triaza-as-indacene-8-carboxylic acid pyridin-3-ylamide | H | H | H | H | 1 | 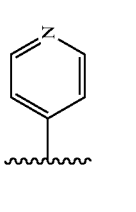 | MS found [M+H] 279.9 |
| 34. | 5,6-Dihydro-4H-1,3a,6-triaza-as-indacene-8-carboxylic acid quinolin-3-ylamide | H | H | H | H | 1 | 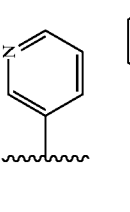 | MS found [M+H] 329.9 |
| 35. | 5,6-Dihydro-4H-1,3a,6-triaza-as-indacene-8-carboxylic acid pyridin-4-ylamide | H | H | H | H | 1 | 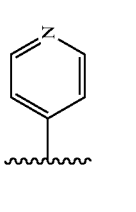 | MS found [M+H] 279.9 |

TABLE 1-continued

| Cpd # | Name | R3 | R4 | R5 | R6 | k | Ar | Spectral Data |
|---|---|---|---|---|---|---|---|---|
| 36. | 5,6-Dihydro-4H-1,3a,6-triaza-as-indacene-8-carboxylic acid pyrimidin-2-ylamide | H | H | H | H | 1 | 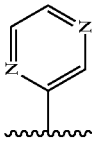 | MS found [M+H] 280.9 |
| 37. | 5,6-Dihydro-4H-1,3a,6-triaza-as-indacene-8-carboxylic acid pyrazin-2-ylamide | H | H | H | H | 1 | 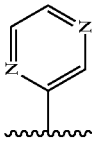 | MS found [M+H] 280.9 |
| 38. | 5,6-Dihydro-4H-1,3a,6-triaza-as-indacene-8-carboxylic acid pyridin-2-ylamide | H | H | H | H | 1 | 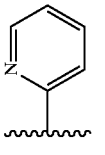 | ¹H NMR [DMSO-d6] 3.1 (t, 1H), 4.3 (t, 2H), 7.0 (s, 1H), 7.1 (t, 1H), 7.2 (s, 1H), 7.5 (s, 2H), 7.8 (t, 1H), 8.3 (d, 1H), 8.4 (s, 1H), 11.8 (s, 1H), 13.3 (s, 1H) |
| 39. | 5,6-Dihydro-4H-1,3a,6-triaza-as-indacene-8-carboxylic acid (5-methyl-[1,3,4]thiadiazol-2-yl)-amide | H | H | H | H | 1 | 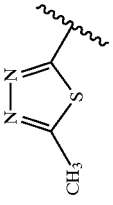 | MS found [M+H] 300.9 |
| 40. | 5,6-Dihydro-4H-1,3a,6-triaza-as-indacene-8-carboxylic acid (1H-pyrazol-3-yl)-amide | H | H | H | H | 1 | 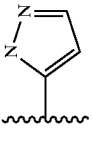 | MS found [M+H] 269.0 |

TABLE 1-continued

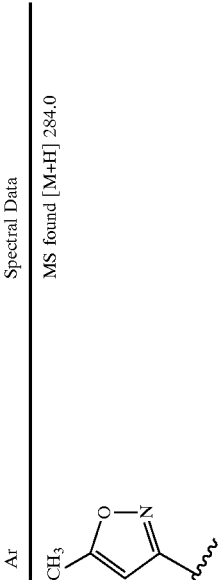

| Cpd # | Name | R3 | R4 | R5 | R6 | k | Ar | Spectral Data |
|---|---|---|---|---|---|---|---|---|
| 41. | 5,6-Dihydro-4H-1,3a,6-triaza-as-indacene-8-carboxylic acid (5-methyl-isoxazol-3-yl)-amide | H | H | H | H | 1 | 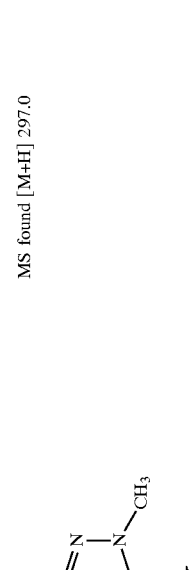 | MS found [M+H] 284.0 |
| 42. | 5,6-Dihydro-4H-1,3a,6-triaza-as-indacene-8-carboxylic acid (2,5-dimethyl-2H-pyrazol-3-yl)-amide | H | H | H | H | 1 | 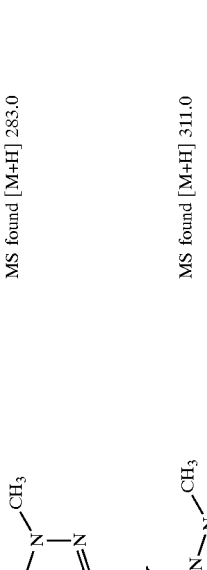 | MS found [M+H] 297.0 |
| 43. | 5,6-Dihydro-4H-1,3a,6-triaza-as-indacene-8-carboxylic acid (1-methyl-1H-pyrazol-3-yl)-amide | H | H | H | H | 1 |  | MS found [M+H] 283.0 |
| 44. | 5,6-Dihydro-4H-1,3a,6-triaza-as-indacene-8-carboxylic acid (1,3,5-trimethyl-1H-pyrazol-4-yl)-amide | H | H | H | H | 1 | | MS found [M+H] 311.0 |

TABLE 1-continued

| Cpd # | Name | R3 | R4 | R5 | R6 | k | Ar | Spectral Data |
|---|---|---|---|---|---|---|---|---|
| 45. | 5,6-Dihydro-4H-1,3a,6-triaza-as-indacene-8-carboxylic acid (6-chloro-pyrazin-2-yl)-amide | H | H | H | H | 1 | 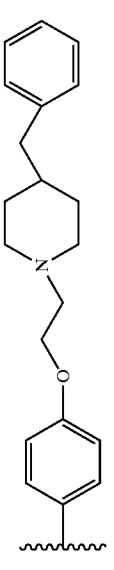 | |
| 46. | 4-Methyl-5,6-dihydro-4H-1,3a,6-triaza-as-indacene-8-carboxylic acid {4-[2-(4-benzyl-piperidin-1-yl)-ethoxy]-phenyl}-amide | H | H | H | CH3 | 1 |  | |
| 47. | (R)-4-Methyl-5,6-dihydro-4H-1,3a,6-triaza-as-indacene-8-carboxylic acid (2-fluoro-phenyl)-amide | H | H | H | CH3 | 1 | 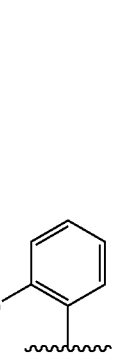 | |
| 48. | (S)-4-Methyl-5,6-dihydro-4H-1,3a,6-triaza-as-indacene-8-carboxylic acid (2-fluoro-phenyl)-amide | H | H | H | CH3 | 1 | 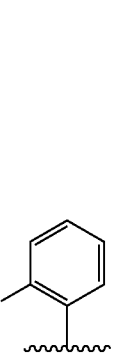 | |
| 49. | 3-Dimethylamino-methyl-5,6-dihydro-4H-1,3a,6-triaza-as-indacene-8-carboxylic acid (2-fluoro-phenyl)-amide | CH2N(CH3)2 | H | H | H | 1 | | |

TABLE 1-continued

![structure: R3, R4, R5, R6, k, Ar amide of pyrrole-fused triazaindacene]

| Cpd # | Name | R3 | R4 | R5 | R6 | k | Ar | Spectral Data |
|---|---|---|---|---|---|---|---|---|
| 50. | 4-Methyl-5,6-dihydro-4H-1,3a,6-triaza-as-indacene-8-carboxylic acid (4-ethoxy-phenyl)-amide | H | H | H | CH3 | 1 | 4-ethoxyphenyl | |
| 51. | 3-Diethylaminomethyl-5,6-dihydro-4H-1,3a,6-triaza-as-indacene-8-carboxylic acid (2-fluoro-phenyl)-amide | CH$_2$N(Et)$_2$ | H | H | H | 1 | 2-fluorophenyl | |
| 52. | (R)-4-Methyl-5,6-dihydro-4H-1,3a,6-triaza-as-indacene-8-carboxylic acid (6-methoxy-pyrazin-2-yl)-amide | H | H | CH$_3$ | H | 1 | 6-methoxypyrazin-2-yl | MS found [M+H] 325.1 |
| 53. | (R)-4-Methyl-5,6-dihydro-4H-1,3a,6-triaza-as-indacene-8-carboxylic acid (6-methoxy-pyridin-3-yl)-amide | H | H | CH$_3$ | H | 1 | 6-methoxypyridin-3-yl | MS found [M+H] 323.9 |
| 54. | (R)-4-Methyl-5,6-dihydro-4H-1,3a,6-triaza-as-indacene-8-carboxylic acid (6-methoxy-2-methyl-pyridin-3-yl)-amide | H | H | CH$_3$ | H | 1 | 6-methoxy-2-methylpyridin-3-yl | MS found [M+H] 338.0 |

TABLE 1-continued

| Cpd # | Name | R3 | R4 | R5 | R6 | k | Ar | Spectral Data |
|---|---|---|---|---|---|---|---|---|
| 55. | (R)-4-Methyl-5,6-dihydro-4H-1,3a,6-triaza-as-indacene-8-carboxylic acid p-tolylamide | H | H | CH₃ | H | 1 | 4-methylphenyl | MS found [M+H] 307.0 |
| 56. | (R)-4-Methyl-5,6-dihydro-4H-1,3a,6-triaza-as-indacene-8-carboxylic acid (2-methoxymethyl-pyrimidin-4-yl)-amide | H | H | CH₃ | H | 1 | 2-(methoxymethyl)pyrimidin-4-yl | MS found [M+H] 338.9 |
| 57. | (R)-4-Methyl-5,6-dihydro-4H-1,3a,6-triaza-as-indacene-8-carboxylic acid (3-fluoro-phenyl)-amide | H | H | CH₃ | H | 1 | 3-fluorophenyl | MS found [M+H] 310.9 |
| 58. | (R)-4-Methyl-5,6-dihydro-4H-1,3a,6-triaza-as-indacene-8-carboxylic acid (5-methyl-[1,2,4]thiadiazol-2-yl)-amide | H | H | CH₃ | H | 1 | 3-methyl-1,2,4-thiadiazol-5-yl | MS found [M+H] 314.9 |
| 59. | (R)-4-Methyl-5,6-dihydro-4H-1,3a,6-triaza-as-indacene-8-carboxylic acid (2,4-difluoro-phenyl)-amide | H | H | CH₃ | H | 1 | 2,4-difluorophenyl | MS found [M+H] 328.9 |

TABLE 1-continued

| Cpd # | Name | R3 | R4 | R5 | R6 | k | Ar | Spectral Data |
|---|---|---|---|---|---|---|---|---|
| 60. | (R)-4-Methyl-5,6-dihydro-4H-1,3a,6-triaza-as-indacene-8-carboxylic acid (3-fluoro-4-methoxy-phenyl)-amide | H | H | CH₃ | H | 1 | 3-fluoro-4-methoxyphenyl | MS found [M+H] 341.0 |
| 61. | (R)-4-Methyl-5,6-dihydro-4H-1,3a,6-triaza-as-indacene-8-carboxylic acid (3-methoxy-phenyl)-amide | H | H | CH₃ | H | 1 | 3-methoxyphenyl | MS found [M+H] 322.9 |
| 62. | (R)-4-Methyl-5,6-dihydro-4H-1,3a,6-triaza-as-indacene-8-carboxylic acid (4-fluoro-phenyl)-amide | H | H | CH₃ | H | 1 | 4-fluorophenyl | MS found [M+H] 310.9 |
| 63. | (R)-4-Methyl-5,6-dihydro-4H-1,3a,6-triaza-as-indacene-8-carboxylic acid pyridin-2-ylamide | H | H | CH₃ | H | 1 | pyridin-2-yl | MS found [M+H] 293.9 |
| 64. | (R)-4-Methyl-5,6-dihydro-4H-1,3a,6-triaza-as-indacene-8-carboxylic acid quinolin-3-ylamide | H | H | CH₃ | H | 1 | quinolin-3-yl | MS found [M+H] 343.9 |

TABLE 1-continued

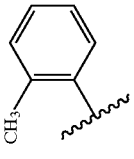

| Cpd # | Name | R3 | R4 | R5 | R6 | k | Ar | Spectral Data |
|---|---|---|---|---|---|---|---|---|
| 65. | (R)-4-Methyl-5,6-dihydro-4H-1,3a,6-triaza-as-indacene-8-carboxylic acid (2-methyl-phenyl)-amide | H | H | CH$_3$ | H | 1 | 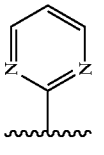 | MS found [M+H] 307.0 |
| 66. | (R)-4-Methyl-5,6-dihydro-4H-1,3a,6-triaza-as-indacene-8-carboxylic acid pyrimidin-2-ylamide | H | H | CH$_3$ | H | 1 | 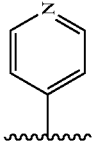 | MS found [M+H] 294.9 |
| 67. | (R)-4-Methyl-5,6-dihydro-4H-1,3a,6-triaza-as-indacene-8-carboxylic acid pyridin-4-ylamide | H | H | CH$_3$ | H | 1 | 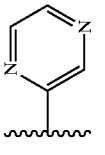 | MS found [M+H] 293.9 |
| 68. | (R)-4-Methyl-5,6-dihydro-4H-1,3a,6-triaza-as-indacene-8-carboxylic acid pyrazin-2-ylamide | H | H | CH$_3$ | H | 1 | 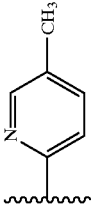 | MS found [M+H] 294.9 |
| 69. | (R)-4-Methyl-5,6-dihydro-4H-1,3a,6-triaza-as-indacene-8-carboxylic acid (5-methyl-pyridin-2-yl)-amide | H | H | CH$_3$ | H | 1 |  | MS found [M+H] 307.9 |

TABLE 1-continued

| Cpd # | Name | R3 | R4 | R5 | R6 | k | Ar | Spectral Data |
|---|---|---|---|---|---|---|---|---|
| 70. | (R)-4-Methyl-5,6-dihydro-4H-1,3a,6-triaza-as-indacene-8-carboxylic acid pyridin-3-ylamide | H | H | CH$_3$ | H | 1 | pyridin-3-yl | MS found [M+H] 293.9 |
| 71. | (R)-4-Methyl-5,6-dihydro-4H-1,3a,6-triaza-as-indacene-8-carboxylic acid (5-methyl-isoxazol-3-yl)-amide | H | H | CH$_3$ | H | 1 | 5-methyl-isoxazol-3-yl | MS found [M+H] 297.9 |
| 72. | (S)-4-Methyl-5,6-dihydro-4H-1,3a,6-triaza-as-indacene-8-carboxylic acid (6-methoxy-pyridin-3-yl)-amide | H | H | H | CH$_3$ | 1 | 6-methoxy-pyridin-3-yl | MS found [M+H] 323.9 |
| 73. | (S)-4-Methyl-5,6-dihydro-4H-1,3a,6-triaza-as-indacene-8-carboxylic acid (6-methoxy-2-methyl-pyridin-3-yl)-amide | H | H | H | CH$_3$ | 1 | 6-methoxy-2-methyl-pyridin-3-yl | MS found [M+H] 337.9 |
| 74. | (S)-4-Methyl-5,6-dihydro-4H-1,3a,6-triaza-as-indacene-8-carboxylic acid p-tolylamide | H | H | H | CH$_3$ | 1 | p-tolyl | MS found [M+H] 306.9 |

TABLE 1-continued

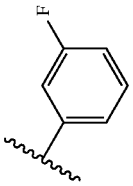

| Cpd # | Name | R3 | R4 | R5 | R6 | k | Ar | Spectral Data |
|---|---|---|---|---|---|---|---|---|
| 75. | (S)-4-Methyl-5,6-dihydro-4H-1,3a,6-triaza-as-indacene-8-carboxylic acid (3-fluoro-phenyl)-amide | H | H | H | CH₃ | 1 | 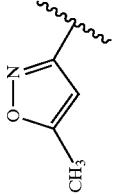 | MS found [M+H] 311.1 |
| 76. | (S)-4-Methyl-5,6-dihydro-4H-1,3a,6-triaza-as-indacene-8-carboxylic acid (5-methyl-isoxazol-3-yl)-amide | H | H | H | CH₃ | 1 | 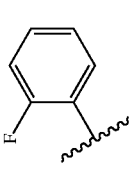 | MS found [M+H] 297.9 |
| 77. | (S)-4-Methyl-5,6-dihydro-4H-1,3a,6-triaza-as-indacene-8-carboxylic acid (2-fluoro-phenyl)-amide | H | H | CH₃ | CH₃ | 1 | 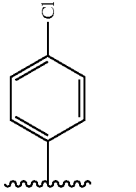 | |
| 78. | (S)-4-Methyl-5,6-dihydro-4H-1,3a,6-triaza-as-indacene-8-carboxylic acid (4-chloro-phenyl)-amide | H | H | H | CH₃ | 1 | 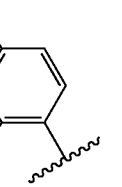 | MS found [M+H] 326.9 |
| 79. | (S)-4-Methyl-5,6-dihydro-4H-1,3a,6-triaza-as-indacene-8-carboxylic acid (2,4-difluoro-phenyl)-amide | H | H | H | CH₃ | 1 |  | MS found [M+H] 328.9 |

TABLE 1-continued

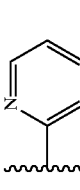

| Cpd # | Name | R3 | R4 | R5 | R6 | k | Ar | Spectral Data |
|---|---|---|---|---|---|---|---|---|
| 80. | (S)-4-Methyl-5,6-dihydro-4H-1,3a,6-triaza-as-indacene-8-carboxylic acid 4-fluoro-phenyl)-amide | H | H | H | CH₃ | 1 | 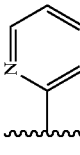 | MS found [M+H] 310.9 |
| 81. | (S)-4-Methyl-5,6-dihydro-4H-1,3a,6-triaza-as-indacene-8-carboxylic acid (4-fluoro-phenyl)-amide | H | H | CH₃ | H | 1 | 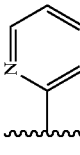 | MS found [M+H] 293.9 |
| 82. | (S)-4-Methyl-5,6-dihydro-4H-1,3a,6-triaza-as-indacene-8-carboxylic acid pyridin-4-ylamide | H | H | H | CH₃ | 1 | 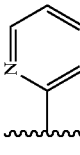 | MS found [M+H] 293.9 |
| 83. | (S)-4-Methyl-5,6-dihydro-4H-1,3a,6-triaza-as-indacene-8-carboxylic acid pyrazin-2-ylamide | H | H | H | CH₃ | 1 | 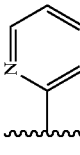 | MS found [M+H] 294.9 |
| 84. | (S)-4-Methyl-5,6-dihydro-4H-1,3a,6-triaza-as-indacene-8-carboxylic acid pyridin-3-ylamide | H | H | H | CH₃ | 1 |  | MS found [M+H] 293.9 |

TABLE 1-continued

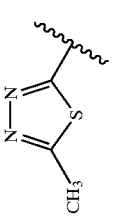

| Cpd # | Name | R3 | R4 | R5 | R6 | k | Ar | Spectral Data |
|---|---|---|---|---|---|---|---|---|
| 85. | (S)-4-Methyl-5,6-dihydro-4H-1,3a,6-triaza-as-indacene-8-carboxylic acid (5-methyl-[1,3,4]thiadiazol-2-yl)-amide | H | H | H | CH₃ | 1 | 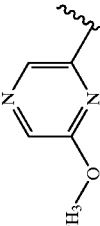 | MS found [M+H] 314.9 |
| 86. | (S)-4-Methyl-5,6-dihydro-4H-1,3a,6-triaza-as-indacene-8-carboxylic acid (6-methoxy-pyrazin-2-yl)-amide | H | H | H | CH₃ | 1 | 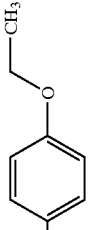 | MS found [M+H] 324.9 |
| 87. | (S)-4-Methyl-5,6-dihydro-4H-1,3a,6-triaza-as-indacene-8-carboxylic acid (4-ethoxy-phenyl)-amide | H | H | H | CH₃ | 1 | 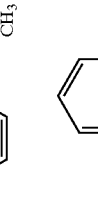 | MS found [M+H] 337.0 |
| 88. | (S)-4-Methyl-5,6-dihydro-4H-1,3a,6-triaza-as-indacene-8-carboxylic acid (3-fluoro-4-methoxy-phenyl)-amide | H | H | H | CH₃ | 1 | 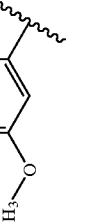 | |
| 89. | (S)-4-Methyl-5,6-dihydro-4H-1,3a,6-triaza-as-indacene-8-carboxylic acid (3-methoxy-phenyl)-amide | H | H | H | CH₃ | 1 | | |

TABLE 1-continued

| Cpd # | Name | R3 | R4 | R5 | R6 | k | Ar | Spectral Data |
|---|---|---|---|---|---|---|---|---|
| 90. | (S)-4-Methyl-5,6-dihydro-4H-1,3a,6-triaza-as-indacene-8-carboxylic acid quinolin-3-ylamide | H | H | H | CH₃ | 1 | 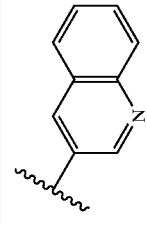 | |
| 91. | (S)-4-Methyl-5,6-dihydro-4H-1,3a,6-triaza-as-indacene-8-carboxylic acid (2-methyl-phenyl)-amide | H | H | H | CH₃ | 1 | 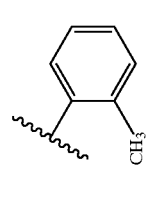 | |
| 92. | (S)-4-Methyl-5,6-dihydro-4H-1,3a,6-triaza-as-indacene-8-carboxylic acid (5-methyl-pyridin-2-yl)-amide | H | H | H | CH₃ | 1 | 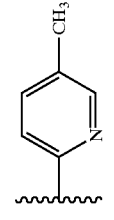 | |
| 93. | (S)-4-Methyl-5,6-dihydro-4H-1,3a,6-triaza-as-indacene-8-carboxylic acid (1-methyl-1H-pyrazol-3-yl)-amide | H | H | H | CH₃ | 1 | 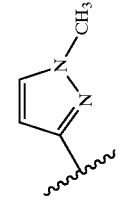 | |
| 94. | 4,4-Dimethyl-5,6-dihydro-4H-1,3a,6-triaza-as-indacene-8-carboxylic acid (1-methyl-1H-pyrazol-3-yl)-amide | H | H | CH₃ | CH₃ | 1 | 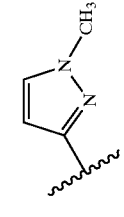 | |

TABLE 1-continued

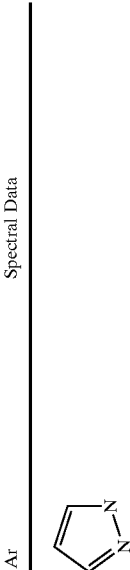

| Cpd # | Name | R3 | R4 | R5 | R6 | k | Ar | Spectral Data |
|---|---|---|---|---|---|---|---|---|
| 95. | 4,4-Dimethyl-5,6-dihydro-4H-1,3a,6-triaza-as-indacene-8-carboxylic acid (1H-pyrazol-3-yl)-amide | H | H | CH₃ | CH₃ | 1 | 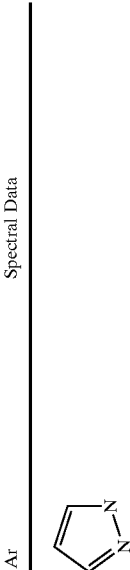 | |
| 96. | 2-Methyl-5,6-dihydro-4H-1,3a,6-triaza-as-indacene-8-carboxylic acid (2-fluoro-phenyl)-amide | CH₃ | H | H | H | 1 | 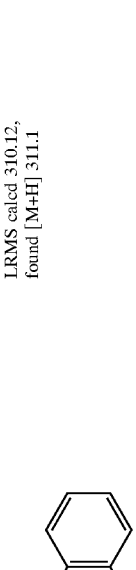 | LRMS calcd 310.12, found [M+H] 311.1 |
| 97. | 4,4-Dimethyl-5,6-dihydro-4H-1,3a,6-triaza-as-indacene-8-carboxylic acid (3-methoxy-phenyl)-amide | H | H | CH₃ | CH₃ | 1 |  | MS found [M+H] 337.1 |
| 98. | 4,4-Dimethyl-5,6-dihydro-4H-1,3a,6-triaza-as-indacene-8-carboxylic acid (5-methyl-pyridin-2-yl)-amide | H | H | CH₃ | CH₃ | 1 |  | MS found [M+H] 322.1 |

TABLE 1-continued

| Cpd # | Name | R3 | R4 | R5 | R6 | k | Ar | Spectral Data |
|---|---|---|---|---|---|---|---|---|
| 99. | 4,4-Dimethyl-5,6-dihydro-4H-1,3a,6-triaza-as-indacene-8-carboxylic acid (2,4-difluoro-phenyl)-amide | H | H | CH₃ | CH₃ | 1 | 2,4-difluorophenyl | MS found [M+H] 343.1 |
| 100. | 4,4-Dimethyl-5,6-dihydro-4H-1,3a,6-triaza-as-indacene-8-carboxylic acid (4-fluoro-phenyl)-amide | H | H | CH₃ | CH₃ | 1 | 4-fluorophenyl | MS found [M+H] 325.1 |
| 101. | 4,4-Dimethyl-5,6-dihydro-4H-1,3a,6-triaza-as-indacene-8-carboxylic acid (6-methoxy-pyridin-3-yl)-amide | H | H | CH₃ | CH₃ | 1 | 6-methoxypyridin-3-yl | MS found [M+H] 338.1 |
| 102. | 4,4-Dimethyl-5,6-dihydro-4H-1,3a,6-triaza-as-indacene-8-carboxylic acid (2-methoxymethyl-pyrimidin-4-yl)-amide | H | H | CH₃ | CH₃ | 1 | 2-methoxymethylpyrimidin-4-yl | MS found [M+H] 353.1 |
| 103. | 4,4-Dimethyl-5,6-dihydro-4H-1,3a,6-triaza-as-indacene-8-carboxylic acid (5-bromo-pyridin-3-yl)-amide | H | H | CH₃ | CH₃ | 1 | 5-bromopyridin-3-yl | MS found [M+H] 386.0 |

TABLE 1-continued

| Cpd # | Name | R3 | R4 | R5 | R6 | k | Ar | Spectral Data |
|---|---|---|---|---|---|---|---|---|
| 104. | 4,4-Dimethyl-5,6-dihydro-4H-1,3a,6-triaza-as-indacene-8-carboxylic acid (3-fluoro-phenyl)-amide | H | H | CH₃ | CH₃ | 1 | 3-fluorophenyl | MS found [M+H] 325.1 |
| 105. | 4,4-Dimethyl-5,6-dihydro-4H-1,3a,6-triaza-as-indacene-8-carboxylic acid (6-methoxy-2-methyl-pyridin-3-yl)-amide | H | H | CH₃ | CH₃ | 1 | 6-methoxy-2-methyl-pyridin-3-yl | MS found [M+H] 352.1 |
| 106. | 4,4-Dimethyl-5,6-dihydro-4H-1,3a,6-triaza-as-indacene-8-carboxylic acid (6-chloro-5-methyl-pyridin-3-yl)-amide | H | H | CH₃ | CH₃ | 1 | 6-chloro-5-methyl-pyridin-3-yl | MS found [M+H] 356.1 |
| 107. | 4,4-Dimethyl-5,6-dihydro-4H-1,3a,6-triaza-as-indacene-8-carboxylic acid [6-(3-isopropoxy-propylamino)-pyridin-3-yl]-amide | H | H | CH₃ | CH₃ | 1 | 6-(3-isopropoxypropylamino)-pyridin-3-yl | MS found [M+H] 423.2 |
| 108. | 4,4-Dimethyl-5,6-dihydro-4H-1,3a,6-triaza-as-indacene-8-carboxylic acid (6-methoxy-pyrazin-2-yl)-amide | H | H | CH₃ | CH₃ |  | 6-methoxy-pyrazin-2-yl | MS found [M+H] 339.1 |

TABLE 1-continued

| Cpd # | Name | R3 | R4 | R5 | R6 | k | Ar | Spectral Data |
|---|---|---|---|---|---|---|---|---|
| 109. | 4,4-Dimethyl-5,6-dihydro-4H-1,3a,6-triaza-as-indacene-8-carboxylic acid (5-methyl-isoxazol-3-yl)-amide | H | H | CH₃ | CH₃ | 1 | 5-methyl-isoxazol-3-yl | MS found [M+H] 312.1 |
| 110. | 4,4-Dimethyl-5,6-dihydro-4H-1,3a,6-triaza-as-indacene-8-carboxylic acid pyrimidin-2-ylamide | H | H | CH₃ | CH₃ | 1 | pyrimidin-2-yl | MS found [M+H] 309.1 |
| 111. | 4,4-Dimethyl-5,6-dihydro-4H-1,3a,6-triaza-as-indacene-8-carboxylic acid pyrazin-2-ylamide | H | H | CH₃ | CH₃ | 1 | pyrazin-2-yl | MS found [M+H] 309.1 |
| 112. | 4,4-Dimethyl-5,6-dihydro-4H-1,3a,6-triaza-as-indacene-8-carboxylic acid (6-chloro-pyridin-3-yl)-amide | H | H | CH₃ | CH₃ | 1 | 6-chloro-pyridin-3-yl | MS found [M+H] 342.0 |
| 113. | 4,4-Dimethyl-5,6-dihydro-4H-1,3a,6-triaza-as-indacene-8-carboxylic acid [6-(2-morpholin-4-yl-ethoxy)-pyridin-3-yl]-amide | H | H | CH₃ | CH₃ | 1 | 6-(2-morpholin-4-yl-ethoxy)-pyridin-3-yl | MS found [M+H] 437.2 |

TABLE 1-continued

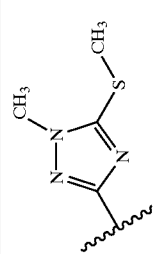

| Cpd # | Name | R3 | R4 | R5 | R6 | k | Ar | Spectral Data |
|---|---|---|---|---|---|---|---|---|
| 114. | 4,4-Dimethyl-5,6-dihydro-4H-1,3a,6-triaza-as-indacene-8-carboxylic acid (1-methyl-5-methylsulfanyl-1H-[1,2,4]triazol-3-yl)-amide | H | H | CH₃ | CH₃ | 1 | 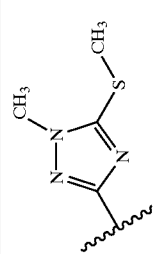 | MS found [M+H] 358.1 |
| 115. | 4,4-Dimethyl-5,6-dihydro-4H-1,3a,6-triaza-as-indacene-8-carboxylic acid (3-methyl-[1,2,4]thiadiazol-5-yl)-amide | H | H | CH₃ | CH₃ | 1 | 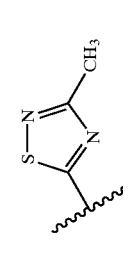 | MS found [M+H] 329.0 |
| 116. | 4,4-Dimethyl-5,6-dihydro-4H-1,3a,6-triaza-as-indacene-8-carboxylic acid (6-methyl-pyridin-3-yl)-amide | H | H | CH₃ | CH₃ | 1 | 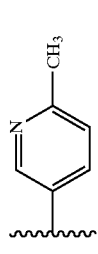 | MS found [M+H] 322.1 |
| 117. | 4,4-Dimethyl-5,6-dihydro-4H-1,3a,6-triaza-as-indacene-8-carboxylic acid (5-chloro-pyridin-2-yl)-amide | H | H | CH₃ | CH₃ | 1 | 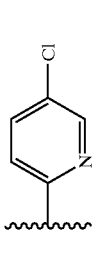 | MS found [M+H] 342.0 |
| 118. | 4,4-Dimethyl-5,6-dihydro-4H-1,3a,6-triaza-as-indacene-8-carboxylic acid (5-methyl-[1,3,4]thiadiazol-2-yl)-amide | H | H | CH₃ | CH₃ | 1 | 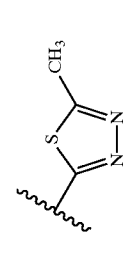 | MS found [M+H] 329.0 |

TABLE 1-continued

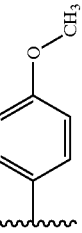

| Cpd # | Name | R3 | R4 | R5 | R6 | k | Ar | Spectral Data |
|---|---|---|---|---|---|---|---|---|
| 119. | 4,4-Dimethyl-5,6-dihydro-4H-1,3a,6-triaza-as-indacene-8-carboxylic acid (3-fluoro-4-methoxy-phenyl)-amide | H | H | CH₃ | CH₃ | 1 | 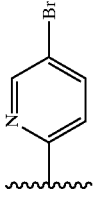 | MS found [M+H] 355.1 |
| 120. | 4,4-Dimethyl-5,6-dihydro-4H-1,3a,6-triaza-as-indacene-8-carboxylic acid (5-bromo-pyridin-2-yl)-amide | H | H | CH₃ | CH₃ | 1 | 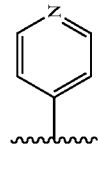 | MS found [M+H] 386.0 |
| 121. | 4,4-Dimethyl-5,6-dihydro-4H-1,3a,6-triaza-as-indacene-8-carboxylic acid pyridin-4-ylamide | H | H | CH₃ | CH₃ | 1 | 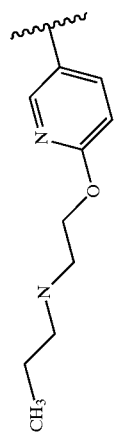 | MS found [M+H] 308.1 |
| 122. | 4,4-Dimethyl-5,6-dihydro-4H-1,3a,6-triaza-as-indacene-8-carboxylic acid [6-(2-propylamino-ethoxy)-pyridin-3-yl]-amide | H | H | CH₃ | CH₃ | 1 | 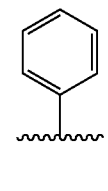 | |
| 123. | 4,4-Dimethyl-5,6-dihydro-4H-1,3a,6-triaza-as-indacene-8-carboxylic acid phenylamide | H | H | CH₃ | CH₃ | 1 |  | MS found [M+H] 307.1 |

TABLE 1-continued

| Cpd # | Name | R3 | R4 | R5 | R6 | k | Ar | Spectral Data |
|---|---|---|---|---|---|---|---|---|
| 124. | 4,4-Dimethyl-5,6-dihydro-4H-1,3a,6-triaza-as-indacene-8-carboxylic acid pyridin-3-ylamide | H | H | CH₃ | CH₃ | 1 | 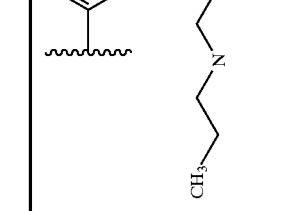 | LRMS calcd 393.48, found [M+H] 394.4 |
| 125. | 4-Methyl-5,6-dihydro-4H-1,3a,6-triaza-as-indacene-8-carboxylic acid [4-(2-propylaminoethoxy)phenyl]amide | H | H | H | CH₃ | 1 | 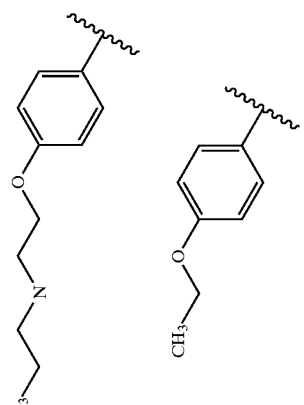 | |
| 126. | 4-Methyl-5,6-dihydro-4H-1,3a,6-triaza-as-indacene-8-carboxylic acid (4-ethoxyphenyl)amide | H | H | H | CH₃ | 1 | 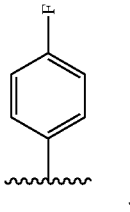 | LRMS calcd 336.39, found [M+H] 337.2 |
| 127. | 5,6-dihydro-4H-1,3a,6-triaza-as-indacene-8-carboxylic acid (4-fluorophenyl)amide | H | H | H | H | 1 | 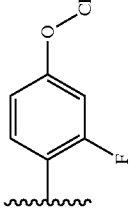 | LRMS calcd 296.30, found [M+H] 297.2 |
| 128. | 5,6-dihydro-4H-1,3a,6-triaza-as-indacene-8-carboxylic acid (2-fluoro-4-methoxyphenyl)amide | H | H | H | H | 1 |  | LRMS calcd 326.33, found [M+H] 327.2 |

TABLE 1-continued

| Cpd # | Name | R3 | R4 | R5 | R6 | k | Ar | Spectral Data |
|---|---|---|---|---|---|---|---|---|
| 129. | 4-Methyl-5,6-dihydro-4H-1,3a,6-triaza-as-indacene-8-carboxylic acid (2-fluoro-4-isopropoxy-phenyl)amide | H | H | H | CH3 | 1 | 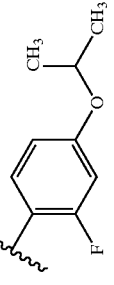 | LRMS calcd 368.40, found [M+H] 369.2 |
| 130. | 5,6-dihydro-4H-1,3a,6-triaza-as-indacene-8-carboxylic acid (2-fluoro-4-isopropoxy-phenyl)amide | H | H | H | H | 1 | 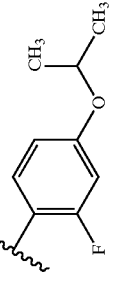 | LRMS calcd 354.38, found [M+H] 355.2 |
| 131. | 4-Methyl-5,6-dihydro-4H-1,3a,6-triaza-as-indacene-8-carboxylic acid [4-(2-propylamino-ethoxy)phenyl]amide | H | H | H | CH3 | 1 | 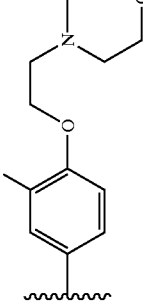 | LRMS calcd 393.48, found [M+H] 394.4 |
| 132. | 4-methyl-5,6-dihydro-4H-1,3a,6-triaza-as-indacene-8-carboxylic acid {4-[2-(4-benzyl-piperidinyl)ethoxy]phenyl}amide | H | H | H | CH3 | 1 | 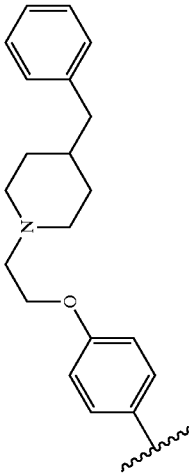 | LRMS calcd 509.64, found [M+H] 510.5 |

TABLE 1-continued

| Cpd # | Name | R3 | R4 | R5 | R6 | k | Ar | Spectral Data |
|---|---|---|---|---|---|---|---|---|
| 133. | 2,3-Bis-dimethylaminomethyl-5,6-dihydro-4H-1,3a,6-triaza-as-indacene-8-carboxylic acid (2-fluoro-phenyl)-amide | CH$_2$N(CH$_3$)$_2$ | CH$_2$N(CH$_3$)$_2$ | H | H | 1 | 2-fluorophenyl | LRMS calcd 324 found [M+1] 325 |
| 134. | 4,4-Dimethyl-5,6-dihydro-4H-1,3a,6-triaza-as-indacene-8-carboxylic acid (2-fluoro-phenyl)-amide | H | H | CH3 | CH3 | 1 | 2-fluorophenyl | LRMS calcd 350 found [M+1] 351 |
| 135. | 4,4-Dimethyl-5,6-dihydro-4H-1,3a,6-triaza-as-indacene-8-carboxylic acid (4-ethoxy-phenyl)-amide | H | H | CH3 | CH3 | 1 | 4-ethoxyphenyl | LRMS calcd 350 found [M+1] 351 |
| 136. | 4,4-Dimethyl-5,6-dihydro-4H-1,3a,6-triaza-as-indacene-8-carboxylic acid pyridin-2-ylamide | H | H | CH3 | CH3 | 1 | pyridin-2-yl | LRMS calcd 307 found [M+1] 308 |
| 137. | 4,4-Dimethyl-5,6-dihydro-4H-1,3a,6-triaza-as-indacene-8-carboxylic acid (4-[1,2,4]triazol-1-ylmethyl-phenyl)-amide | H | H | CH3 | CH3 | 1 | 4-(1,2,4-triazol-1-ylmethyl)phenyl | LRMS calcd 387 found [M+1] 388 |

TABLE 1-continued

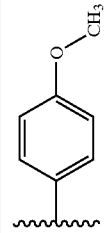

| Cpd # | Name | R3 | R4 | R5 | R6 | k | Ar | Spectral Data |
|---|---|---|---|---|---|---|---|---|
| 138. | 4,4-Dimethyl-5,6-dihydro-4H-1,3a,6-triaza-as-indacene-8-carboxylic acid (4-methoxy-phenyl)-amide | H | H | CH3 | CH3 | 1 | 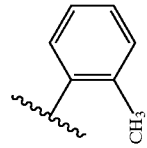 | LRMS calcd 336 found [M+1] 337 |
| 139. | 4,4-Dimethyl-5,6-dihydro-4H-1,3a,6-triaza-as-indacene-8-carboxylic acid o-tolylamide | H | H | CH3 | CH3 | 1 | 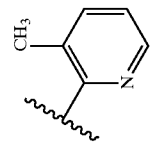 | LRMS calcd 320 found [M+1] 321 |
| 140. | 4,4-Dimethyl-5,6-dihydro-4H-1,3a,6-triaza-as-indacene-8-carboxylic acid (3-methyl-pyridin-2-yl)-amide | H | H | CH3 | CH3 | 1 | 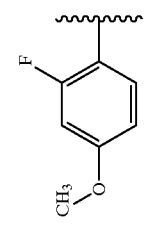 | LRMS calcd 321 found [M+1] 322 |
| 141. | 4,4-Dimethyl-5,6-dihydro-4H-1,3a,6-triaza-as-indacene-8-carboxylic acid (2-fluoro-4-methoxy-phenyl)-amide | H | H | CH3 | CH3 | 1 | 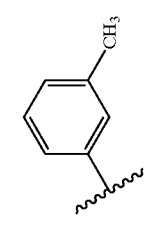 | LRMS calcd 354 found [M+1] |
| 142. | (R)-4-Methyl-5,6-dihydro-4H-1,3a,6-triaza-as-indacene-8-carboxylic acid m-tolylamide | H | H | CH3 | H | 1 |  | MS m/z 307 |

TABLE 1-continued

| Cpd # | Name | R3 | R4 | R5 | R6 | k | Ar | Spectral Data |
|---|---|---|---|---|---|---|---|---|
| 143. | (R)-4-Methyl-5,6-dihydro-4H-1,3a,6-triaza-as-indacene-8-carboxylic acid (3,4-dimethyl-phenyl)-amide | H | H | CH3 | H | 1 | 3,4-dimethylphenyl | MS m/z 321 |
| 144. | (R)-4-Methyl-5,6-dihydro-4H-1,3a,6-triaza-as-indacene-8-carboxylic acid (3-fluoro-4-methyl-phenyl)-amide | H | H | CH3 | H | 1 | 3-fluoro-4-methylphenyl | MS m/z 325 |
| 145. | (R)-4-Methyl-5,6-dihydro-4H-1,3a,6-triaza-as-indacene-8-carboxylic acid (3-chloro-phenyl)-amide | H | H | CH3 | H | 1 | 3-chlorophenyl | MS m/z 327 |
| 146. | (R)-4-Methyl-5,6-dihydro-4H-1,3a,6-triaza-as-indacene-8-carboxylic acid (3,4-difluoro-phenyl)-amide | H | H | CH3 | H | 1 | 3,4-difluorophenyl | MS m/z 329 |
| 147. | (R)-4-Methyl-5,6-dihydro-4H-1,3a,6-triaza-as-indacene-8-carboxylic acid (4-ethyl-phenyl)-amide | H | H | CH3 | H | 1 | 4-ethylphenyl | MS m/z 321 |

TABLE 1-continued

| Cpd # | Name | R3 | R4 | R5 | R6 | k | Ar | Spectral Data |
|---|---|---|---|---|---|---|---|---|
| 148. | (R)-4-Methyl-5,6-dihydro-4H-1,3a,6-triaza-as-indacene-8-carboxylic acid (4-propyl-phenyl)-amide | H | H | CH3 | H | 1 | 4-propylphenyl | MS m/z 321 |
| 149. | (R)-4-Methyl-5,6-dihydro-4H-1,3a,6-triaza-as-indacene-8-carboxylic acid (2,5-dimethyl-phenyl)-amide | H | H | CH3 | H | 1 | 2,5-dimethylphenyl | ¹H NMR [CDCl3] 1.5 (d, 3H), 2.8 (dd, 1H), 3.1 (dd, 1H), 4.3 (q, 1H), 6.9 (app s, 2H), 7.0 (app s, 2H), 7.5 (s, 1H), 8.0 (d, 1H), 11.8 (s, 1H), 13.1 (s, 1H) |
| 150. | (R)-4-Methyl-5,6-dihydro-4H-1,3a,6-triaza-as-indacene-8-carboxylic acid (2-fluoro-5-methyl-phenyl)-amide | H | H | CH3 | H | 1 | 2-fluoro-5-methylphenyl | ¹H NMR [CDCl3] 1.5 (d, 3H), 2.8 (dd, 1H), 3.1 (dd, 1H), 4.3 (q, 1H), 6.9 (s, 1H), 6.95 (m, 2H), 7.0 (s, 1H), 7.5 (s, 1H), 8.0 (t, 1H), 10.8 (s, 1H), 13.1 (s, 1H) |
| 151. | (R)-4-Methyl-5,6-dihydro-4H-1,3a,6-triaza-as-indacene-8-carboxylic acid (2-fluoro-4-methyl-phenyl)-amide | H | H | CH3 | H | 1 | 2-fluoro-4-methylphenyl | |
| 152. | (R)-4-Methyl-5,6-dihydro-4H-1,3a,6-triaza-as-indacene-8-carboxylic acid (5-fluoro-2-methyl-phenyl)-amide | H | H | CH3 | H | 1 | 5-fluoro-2-methylphenyl | ¹H NMR [CD3OD] 1.2 (d, 3H), 2.1 (s, 3H), 2.55 (dd, 1H), 2.95 (q, 1H), 4.2 (q, 1H), 6.5 (t, 1H), 6.6 (s, 1H), 6.8 (s, 1H), 6.9 (t, 1H), 7.2 (m, 2H) |

TABLE 1-continued

| Cpd # | Name | R3 | R4 | R5 | R6 | k | Ar | Spectral Data |
|---|---|---|---|---|---|---|---|---|
| 153. | (R)-4-Methyl-5,6-dihydro-4H-1,3a,6-triaza-as-indacene-8-carboxylic acid (2,5-difluoro-phenyl)-amide | H | H | CH3 | H | 1 | 2,5-difluorophenyl | ¹H NMR [CD3OD] 1.2 (d, 3H), 2.55 (dd, 1H), 2.95 (dd, 1H), 4.2 (q, 1H), 6.55 (m, 1H), 6.6 (s, 1H), 6.8 (s, 1H), 6.85 (m, 1H), 7.2 (s, 1H), 7.8 (m, 1H) |
| 154. | (R)-4-Methyl-5,6-dihydro-4H-1,3a,6-triaza-as-indacene-8-carboxylic acid (6-ethyl-pyridin-2-yl)-amide | H | H | CH3 | H | 1 | 6-ethyl-pyridin-2-yl | ¹H NMR [CD3OD] 1.0 (t, 3H), 1.2 (d, 3H), 2.45 (q, 2H), 2.5 (dd, 1H), 2.9 (dd, 1H), 4.2 (q, 1H), 6.65 (d, 1H), 6.7 (s, 1H), 6.8 (s, 1H), 7.2 (s, 1H), 7.4 (t, 1H), 7.8 (d, 1H) |
| 155. | (R)-4-Methyl-5,6-dihydro-4H-1,3a,6-triaza-as-indacene-8-carboxylic acid (6-chloro-pyridin-3-yl)-amide | H | H | CH3 | H | 1 | 6-chloro-pyridin-3-yl | ¹H NMR [CD3OD] 1.2 (d, 3H), 2.55 (dd, 1H), 2.95 (dd, 1H), 3.0 (s, 3H), 4.2 (q, 1H), 6.6 (s, 1H), , 6.8 (s, 1H), 7.1 (d, 1H), 7.2 (s, 1H), 8.0 (d, 1H), 8.6 (s, 1H) |
| 156. | (R)-4-Methyl-5,6-dihydro-4H-1,3a,6-triaza-as-indacene-8-carboxylic acid (3-methyl-pyridin-2-yl)-amide | H | H | CH3 | H | 1 | 3-methyl-pyridin-2-yl | ¹H NMR [CD3OD] 1.2 (d, 3H), 2.1 (s, 3H), 2.55 (dd, 1H), 2.95 (dd, 1H), 4.2 (q, 1H), 6.6 (s, 1H), 6.8 (s, 1H), 6.95 (d, 1H), 7.2 (s, 1H), 7.45 (d, 1H), 8.0 (d, 1H) |
| 157. | (R)-4-Methyl-5,6-dihydro-4H-1,3a,6-triaza-as-indacene-8-carboxylic acid (6-propyl-pyridin-2-yl)-amide | H | H | CH3 | H | 1 | 6-propyl-pyridin-2-yl | ¹H NMR [CD3OD] 0.7 (t, 3H), 1.2 (d, 3H), 1.6 (sextet, 2H), 2.4 (t, 2H), 2.5 (dd, 1H), 2.9 (dd, 1H), 4.2 (q, 1H), 6.6 (d, 1H), 6.7 (s, 1H), 6.8 (s, 1H), 7.2 (s, 1H), 7.4 (t, 1H), 7.7 (d, 1H) |

TABLE 1-continued

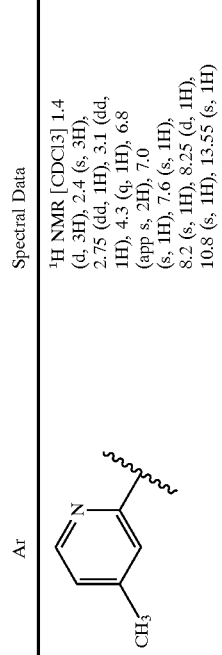

| Cpd # | Name | R3 | R4 | R5 | R6 | k | Ar | Spectral Data |
|---|---|---|---|---|---|---|---|---|
| 158. | (R)-4-Methyl-5,6-dihydro-4H-1,3a,6-triaza-as-indacene-8-carboxylic acid (4-methyl-pyridin-2-yl)-amide | H | H | CH3 | H | 1 | 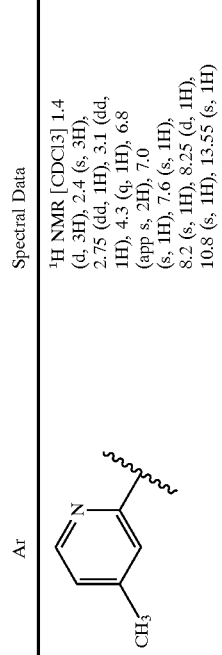 | ¹H NMR [CDCl3] 1.4 (d, 3H), 2.4 (s, 3H), 2.75 (dd, 1H), 3.1 (dd, 1H), 4.3 (q, 1H), 6.8 (app s, 2H), 7.0 (s, 1H), 7.6 (s, 1H), 8.2 (s, 1H), 8.25 (d, 1H), 10.8 (s, 1H), 13.55 (s, 1H) |
| 159. | (R)-4-Methyl-5,6-dihydro-4H-1,3a,6-triaza-as-indacene-8-carboxylic acid (6-methyl-pyridin-2-yl)-amide | H | H | CH3 | H | 1 |  | ¹H NMR [CDCl3] 1.4 (d, 3H), 2.6 (s, 3H), 2.75 (dd, 1H), 3.1 (dd, 1H), 4.3 (q, 1H), 6.9 (m, 2H), 7.1 (s, 1H), 7.55 (s, 1H), 7.6 (t, 1H), 8.2 (d, 1H), 10.7 (s, 1H), 13.6 (s, 1H) |
| 160. | (R)-4-Methyl-5,6-dihydro-4H-1,3a,6-triaza-as-indacene-8-carboxylic acid (4-ethyl-pyridin-2-yl)-amide | H | H | CH3 | H | 1 |  | ¹H NMR [CDCl3] 1.3 (t, 3H), 1.4 (d, 3H), 2.7 (q, 2H), 2.75 (dd, 1H), 3.1 (dd, 1H), 4.3 (q, 1H), 6.8 (s, 1H), 6.85 (d, 1H), 7.0 (s, 1H), 7.6 (s, 1H), 8.3 (m, 2H), 10.8 (s, 1H), 13.55 (s, 1H) |
| 161. | (R)-4-Methyl-5,6-dihydro-4H-1,3a,6-triaza-as-indacene-8-carboxylic acid (5-chloro-pyridin-2-yl)-amide | H | H | CH3 | H | 1 |  | ¹H NMR [DMSO-d6] 1.5 (d, 3H), 2.8 (dd, 1H), 3.2 (dd, 1H), 4.5 (q, 1H), 7.0 (s, 1H), 7.3 (s, 1H), 7.6 (s, 1H), 7.9 (d, 1H), 8.4 (d, 1H), 8.5 (s, 1H) |

TABLE 1-continued

| Cpd # | Name | R3 | R4 | R5 | R6 | k | Ar | Spectral Data |
|---|---|---|---|---|---|---|---|---|
| 162. | (R)-4-Methyl-5,6-dihydro-4H-1,3a,6-triaza-as-indacene-8-carboxylic acid (5-trifluoromethyl-pyridin-2-yl)-amide | H | H | CH3 | H | 1 |  | ¹H NMR [DMSO-d6] 1.5 (d, 3H), 2.8 (dd, 1H), 3.2 (dd, 1H), 4.5 (q, 1H), 7.0 (s, 1H), 7.3 (s, 1H), 7.6 (s, 1H), 8.2 (d, 1H), 8.6 (d, 1H), 8.8 (s, 1H) |
| 163. | (R)-4-Methyl-5,6-dihydro-4H-1,3a,6-triaza-as-indacene-8-carboxylic acid (5-bromo-pyridin-2-yl)-amide | H | H | CH3 | H | 1 |  | ¹H NMR [DMSO-d6] 1.5 (d, 3H), 2.8 (dd, 1H), 3.2 (dd, 1H), 4.5 (q, 1H), 7.0 (s, 1H), 7.3 (s, 1H), 7.6 (s, 1H), 8.0 (d, 1H), 8.4 (d, 1H), 8.5 (s, 1H) |
| 164. | (R)-4-Methyl-5,6-dihydro-4H-1,3a,6-triaza-as-indacene-8-carboxylic acid (1-methyl-1H-pyridin-3-yl)-amide | H | H | CH3 | H | 1 | 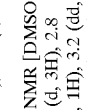 | ¹H NMR [DMSO-d6] 1.5 (d, 3H), 2.8 (dd, 1H), 3.2 (dd, 1H), 3.8 (s, 3H), 4.5 (t, 1H), 6.6 (s, 1H), 7.0 (s, 1H), 7.3 (s, 1H), 7.4 (s, 1H), 7.6 (s, 1H), 11.8 (s, 1H), 13.1 (s, 1H) |
| 165. | (R)-4-Methyl-5,6-dihydro-4H-1,3a,6-triaza-as-indacene-8-carboxylic acid (2,5-dimethyl-2H-pyrazol-3-yl)-amide | H | H | CH3 | H | 1 | 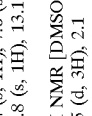 | ¹H NMR [DMSO-d6] 1.5 (d, 3H), 2.1 (s, 3H), 2.8 (dd, 1H), 3.2 (dd, 1H), 3.8 (s, 3H), 4.5 (q, 1H), 6.5 (s, 1H), 7.0 (s, 1H), 7.3 (s, 1H), 7.5 (s, 1H), 11.8 (s, 1H), 13.2 (s, 1H) |

TABLE 1-continued

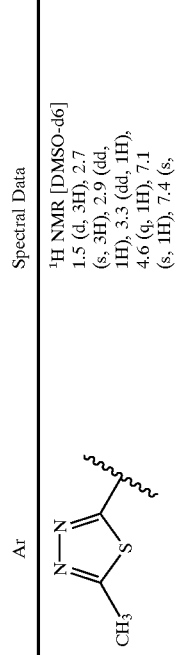

| Cpd # | Name | R3 | R4 | R5 | R6 | k | Ar | Spectral Data |
|---|---|---|---|---|---|---|---|---|
| 166. | (R)-4-Methyl-5,6-dihydro-4H-1,3a,6-triaza-as-indacene-8-carboxylic acid (5-methyl-[1,3,4]thiadiazol-2-yl)-amide | H | H | CH3 | H | 1 |  | $^1$H NMR [DMSO-d6] 1.5 (d, 3H), 2.7 (s, 3H), 2.9 (dd, 1H), 3.3 (dd, 1H), 4.6 (q, 1H), 7.1 (s, 1H), 7.4 (s, 1H), 7.6 (s, 1H), 12.0 (s, 1H), >14 (s, 1H) |
| 167. | (R)-4-Methyl-5,6-dihydro-4H-1,3a,6-triaza-as-indacene-8-carboxylic acid (5-ethyl-[1,3,4]thiadiazol-2-yl)-amide | H | H | CH3 | H | 1 |  | $^1$H NMR [DMSO-d6] 1.3 (t, 3H), 1.5 (d, 3H), 2.9 (dd, 1H), 3.0 (q, 2H), 3.3 (dd, 1H), 4.6 (q, 1H), 7.1 (s, 1H), 7.4 (s, 1H), 7.6 (s, 1H), 12.0 (s, 1H), >14 (s, 1H) |
| 168. | (R)-4-Methyl-5,6-dihydro-4H-1,3a,6-triaza-as-indacene-8-carboxylic acid (3-methyl-isoxazol-5-yl)-amide | H | H | CH3 | H | 1 |  | MS m/z 298 |
| 169. | (R)-4-Methyl-5,6-dihydro-4H-1,3a,6-triaza-as-indacene-8-carboxylic acid (3,4-dimethyl-isoxazol-5-yl)-amide | H | H | CH3 | H | 1 | | MS m/z 312 |

TABLE 1-continued

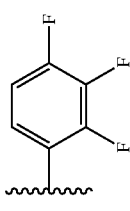

| Cpd # | Name | R3 | R4 | R5 | R6 | k | Ar | Spectral Data |
|---|---|---|---|---|---|---|---|---|
| 170. | (R)-4-Methyl-5,6-dihydro-4H-1,3a,6-triaza-as-indacene-8-carboxylic acid (2,3,4-trifluoro-phenyl)-amide | H | H | CH3 | H | 1 | 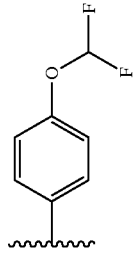 | MS m/z 347 |
| 171. | (R)-4-Methyl-5,6-dihydro-4H-1,3a,6-triaza-as-indacene-8-carboxylic acid (4-difluoromethoxy-phenyl)-amide | H | H | CH3 | H | 1 | 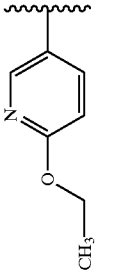 | MS m/z 359 |
| 172. | (R)-4-Methyl-5,6-dihydro-4H-1,3a,6-triaza-as-indacene-8-carboxylic acid (6-ethoxy-pyridin-3-yl)-amide | H | H | H | CH3 | 1 | 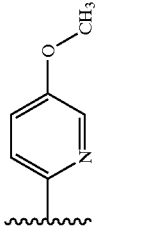 | LRMS 337.38 found (M+1) 338.2 |
| 173. | (S)-4-Methyl-5,6-dihydro-4H-1,3a,6-triaza-as-indacene-8-carboxylic acid (5-methoxy-pyridin-2-yl)-amide | H | H | H | CH3 | 1 | 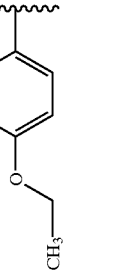 | LRMS calcd 323 found [M+1] 324 |
| 174. | (S)-4-Methyl-5,6-dihydro-4H-1,3a,6-triaza-as-indacene-8-carboxylic acid (5-ethoxy-pyridin-2-yl)-amide | H | H | H | CH3 | 1 |  | LRMS calcd 337 found [M+1] 338 |

TABLE 1-continued

| Cpd # | Name | R3 | R4 | R5 | R6 | k | Ar | Spectral Data |
|---|---|---|---|---|---|---|---|---|
| 175. | (R)-4-Methyl-5,6-dihydro-4H-1,3a,6-triaza-as-indacene-8-carboxylic acid benzo[1,3]dioxol-5-ylamide | H | H | CH3 | H | 1 | benzo[1,3]dioxol-5-yl | MS m/z 337 |
| 176. | (R)-4-Methyl-5,6-dihydro-4H-1,3a,6-triaza-as-indacene-8-carboxylic acid (6-chloro-pyridazin-3-yl)-amide | H | H | CH3 | H | 1 | 6-chloropyridazin-3-yl | MS m/z 329 |
| 177. | (R)-4-Methyl-5,6-dihydro-4H-1,3a,6-triaza-as-indacene-8-carboxylic acid (5-cyclopropyl-2-methyl-2H-pyrazol-3-yl)-amide | H | H | CH3 | H | 1 | 5-cyclopropyl-2-methyl-2H-pyrazol-3-yl | MS m/z 337 |
| 178. | (R)-4-Methyl-5,6-dihydro-4H-1,3a,6-triaza-as-indacene-8-carboxylic acid (5-cyclopropyl-[1,3,4]thiadiazol-2-yl)-amide | H | H | CH3 | H | 1 | 5-cyclopropyl-[1,3,4]thiadiazol-2-yl | MS m/z 341 |

TABLE 1-continued

| Cpd # | Name | R3 | R4 | R5 | R6 | k | Ar | Spectral Data |
|---|---|---|---|---|---|---|---|---|
| 179. | (R)-4-Methyl-5,6-dihydro-4H-1,3a,6-triaza-as-indacene-8-carboxylic acid (5-trifluoromethyl-[1,3,4]thiadiazol-2-yl)-amide | H | H | CH3 | H | 1 | 5-trifluoromethyl-1,3,4-thiadiazol-2-yl | MS m/z 369 |
| 180. | (R)-4-Methyl-5,6-dihydro-4H-1,3a,6-triaza-as-indacene-8-carboxylic acid (3,4-dimethoxy-phenyl)-amide | H | H | CH3 | H | 1 | 3,4-dimethoxyphenyl | MS m/z 353 |
| 181. | (R)-4-Methyl-5,6-dihydro-4H-1,3a,6-triaza-as-indacene-8-carboxylic acid (2-methyl-quinolin-6-yl)-amide | H | H | CH3 | H | 1 | 2-methylquinolin-6-yl | MS m/z 358 |
| 182. | 5,6-Dihydro-4H-1,3a,6-triaza-as-indacene-8-carboxylic acid (2-chloro-pyridin-4-yl)-amide | H | H | H | H | 1 | 2-chloropyridin-4-yl | MS m/z 314 |
| 183. | (R)-4-Methyl-5,6-dihydro-4H-1,3a,6-triaza-as-indacene-8-carboxylic acid (2-chloro-pyridin-4-yl)-amide | H | H | CH3 | H | 1 | 2-chloropyridin-4-yl | MS m/z 328 |

TABLE 1-continued

| Cpd # | Name | R3 | R4 | R5 | R6 | k | Ar | Spectral Data |
|---|---|---|---|---|---|---|---|---|
| 184. | (S)-4-Methyl-5,6-dihydro-4H-1,3a,6-triaza-as-indacene-8-carboxylic acid (2-ethyl-2H-pyrazol-3-yl)-amide | H | H | H | CH3 | 1 | 2-ethyl-2H-pyrazol-3-yl | LCMS found (M+H) 312 |
| 185. | (R)-4-Methyl-5,6-dihydro-4H-1,3a,6-triaza-as-indacene-8-carboxylic acid (2-ethyl-2H-pyrazol-3-yl)-amide | H | H | CH3 | H | 1 | 2-ethyl-2H-pyrazol-3-yl | LCMS found (M+H) 312 |
| 186. | 4,4-Dimethyl-5,6-dihydro-4H-1,3a,6-triaza-as-indacene-8-carboxylic acid (2-ethyl-2H-pyrazol-3-yl)-amide | H | H | CH3 | CH3 | 1 | 2-ethyl-2H-pyrazol-3-yl | LCMS found (M+H) 326 |
| 187. | 4,4-Dimethyl-5,6-dihydro-4H-1,3a,6-triaza-as-indacene-8-carboxylic acid (5-fluoro-pyridin-2-yl)-amide | H | H | CH3 | CH3 | 1 | 5-fluoro-pyridin-2-yl | LCMS found (M+H) 326 |
| 188. | (R)-4-Methyl-5,6-dihydro-4H-1,3a,6-triaza-as-indacene-8-carboxylic acid (5-fluoro-pyridin-2-yl)-amide | H | H | CH3 | H | 1 | 5-fluoro-pyridin-2-yl | LCMS found (M+H) 312 |

TABLE 1-continued

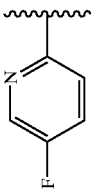

| Cpd # | Name | R3 | R4 | R5 | R6 | k | Ar | Spectral Data |
|---|---|---|---|---|---|---|---|---|
| 189. | 5,6-Dihydro-4H-1,3a,6-triaza-as-indacene-8-carboxylic acid (5-fluoro-pyridin-2-yl)-amide | H | H | H | H | 1 | 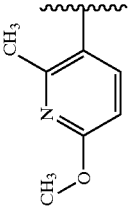 | LCMS found (M+H) 297 |
| 190. | (S)-4-Methyl-5,6-dihydro-4H-1,3a,6-triaza-as-indacene-8-carboxylic acid (6-methoxy-2-methyl-pyridin-3-yl)-amide | H | H | H | CH3 | 1 | 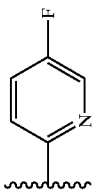 | LRMS 337.38 found (M+1) 338.2 |
| 191. | (S)-4-Methyl-5,6-dihydro-4H-1,3a,6-triaza-as-indacene-8-carboxylic acid (5-fluoro-pyridin-2-yl)-amide | H | H | H | CH3 | 1 | 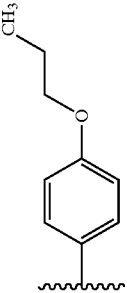 | LRMS 311.11 found (M+1) 312.2 |
| 192. | (S)-4-Methyl-5,6-dihydro-4H-1,3a,6-triaza-as-indacene-8-carboxylic acid (4-propoxy-phenyl)-amide | H | H | H | CH3 | 1 | 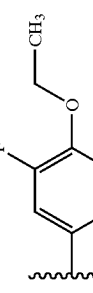 | LRMS 350.42 found (M-1) 349.2 |
| 193. | (S)-4-Methyl-5,6-dihydro-4H-1,3a,6-triaza-as-indacene-8-carboxylic acid (4-ethoxy-3-fluoro-phenyl)-amide | H | H | H | CH3 | 1 |  | LRMS 354.38 found (M-1) 353.2 |

TABLE 1-continued

| Cpd # | Name | R3 | R4 | R5 | R6 | k | Ar | Spectral Data |
|---|---|---|---|---|---|---|---|---|
| 194. | (R)-4-Methyl-5,6-dihydro-4H-1,3a,6-triaza-as-indacene-8-carboxylic acid (3-propyl-[1,2,4]thiadiazol-5-yl)-amide | H | H | CH3 | H | 1 |  | LCMS found (M+H) 343 |
| 195. | (R)-3,4,5,6-Tetrahydro-3,8,10-triaza-benzo[e]azulene-1-carboxylic acid (1-ethyl-1H-pyrazol-3-yl)-amide | H | H | CH3 | H | 1 |  | LCMS found (M+H) 311 |
| 196. | (R)-3,4,5,6-Tetrahydro-3,8,10-triaza-benzo[e]azulene-1-carboxylic acid (1-propyl-1H-pyrazol-3-yl)-amide | H | H | CH3 | H | 1 |  | LCMS found (M+H) 337 |
| 197. | (S)-4-Methyl-5,6-dihydro-4H-1,3a,6-triaza-as-indacene-8-carboxylic acid (5-propoxy-pyridin-2-yl)-amide | H | H | H | CH3 | 1 |  | LRMS calcd [M+H] 352 |

Example 5a

Preparation of 2-Methyl-5,7-dihydro-6H-pyrrolo[2,3-h]quinoline-9-carboxylic acid ethyl ester Step 1:

Di-tert-butyl dicarbonate (1.09 g, 5.02 mmol) is slowly added to the solution of triethylamine (0.697 mL, 5.02 mmol), 4-dimethylaminopyridine (51 mg, 0.42 mmol) and 4-oxo-4,5,6,7-tetrahydro-1H-indole-3-carboxylic acid methyl ester (0.81 g, 4.18 mmol) in dichloromethane (15 mL). The reaction mixture is stirred at room temperature for 2 h, 8 mL sat. NaHCO$_3$ solution is added, the layers are separated, and the aqueous phase is extracted with dichloromethane (3×10 mL). The combined organic layers are dried (Na$_2$SO$_4$) and evaporated. Flash chromatography on silica gel, eluting with hexanes: ethyl acetate (5:1), provides 4-oxo-4,5,6,7-tetrahydro-indole-1,3-dicarboxylic acid 1-tert-butyl ester 3-methyl ester (1.10 g, 89%) as a colorless solid. $^1$H NMR (400 MHz, CDCl$_3$) δ1.605 (9H, s), 2.126 (2H, m), 2.510 (2H, t), 3.133 (2H, t), 3.844 (3H, s), 7.701 (1H, s). MS (ES$^+$) 294 (M+1)

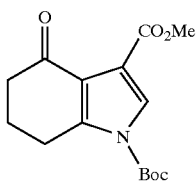

Step 2:

To a solution of 4-oxo-4,5,6,7-tetrahydro-indole-1,3-dicarboxylic acid 1-tert-butyl ester 3-methyl ester (1.10 g, 3.74 mmol), NaI (841 mg, 5.61 mmol) and triethylamine (1.56 mL, 11.22 mmol) in CH$_3$CN (15 mL), is added trimethylsilyl chloride (0.707 mL, 5.61 mmol) via syringe. The reaction mixture is stirred at room temperature for 15 h., 30 mL of ethyl acetate/hexanes (1:1 with a few drops of triethylamine) is added to dilute the solution. Saturated sodium bicarbonate solution (20 mL) is added. The layers are separated and the aqueous phase is extracted with ethyl acetate/hexanes (1:1) (3×10 mL). The combined organic layers are dried (Na$_2$SO$_4$) and evaporated to provide 4-trimethylsilanyloxy-6,7-dihydro-indole-1,3-dicarboxylic acid 1-tert-butyl ester 3-methyl ester (1.3 g, 100%) as a viscous red oil. $^1$H NMR (400 MHz, CDCl$_3$) δ0.180 (9H, s), 1.576 (9H, s), 2.343 (2H, m), 2.930 (2H, t), 3.781 (3H, s), 4.826 (1H, t), 7.580 (1H, s). MS (ES$^+$) 366 (M+1)

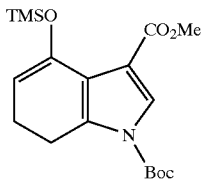

Step 3:

a): Alumina (3 g, neutral) is activated at 200° C. for 4 h. It is cooled to room temperature under nitrogen. ZnCl$_2$(1M in ether, 3.7 mL) is added and the solution is stirred at room temperature for another 30 min, after which the solvent is removed by rotary evaporator and pump. The fresh prepared Al$_2$O$_3$—ZnCl$_2$ powder is slowly added to the mixture of 4-trimethylsilanyloxy-6,7-dihydro-indole-1,3-dicarboxylic acid 1-tert-butyl ester 3-methyl ester (1.3 g, 3.7 mmol) and methyl vinyl ketone (1.54 mL, 18.5 mmol) at 0° C. The reaction mixture is stirred at 0° C. for 3 h and then diluted with 30 mL of dichloromethane. Solid residue is filtered off. Several drops of water are added to the solution and it is heated to a boil for one minute. The solution is dried over Na$_2$SO$_4$ and organic solvents are removed by rotary evaporator. Flash chromatography on silica gel, eluting with hexanes:ethyl acetate (6:1 to 1:1), provides a mixture (1.06 g, diketone product and starting material) as intermediate.

b): A solution of the mixture (760 mg) from the last step and ammonium acetate (804 mg, 10.45 mmol) in acetic acid (15 mL) is placed in a round bottom flask equipped with an open-to-the-air condenser. The solution is heated at 100° C. for 4 h. Acetic acid is removed by rotary evaporator. Solid residue is dissolved in dichloromethane (20 mL) and sat. NaHCO$_3$ (20 mL) The layers are separated and the aqueous phase is extracted with dichloromethane: 2-propanol (4:1) (4×15 mL). The combined organic solvents are dried (Na$_2$SO$_4$) and evaporated. Flash chromatography on silica gel, eluting with 5% MeOH/CH$_3$CN, provides 2-methyl-5,7-dihydro-6H-pyrrolo[2,3-h]quinoline-9-carboxylic acid methyl ester (178 mg, 27% for two steps) as an off-white solid. $^1$H NMR (400 MHz, CD$_3$OD) δ2.453 (3H, s), 2.704 (2H, t), 2.887 (2H, s), 3.791 (3H, s), 6.878 (1H, d) 7.313 (1H, s), 7.426 (1H, d). MS (ES$^+$) 243 (M+1)

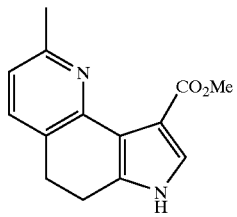

Example 5b

Preparation of 9-Methyl-3,4,5,6-tetrahydro-3,10-diaza-benzo[e]azulene-1-carboxylic acid ethyl ester Step 1:

Di-tert-butyl dicarbonate (4.46 g, 20 mmol) is slowly added to a solution of triethylamine (2.84 mL, 20 mmol), 4-dimethylaminopyridine (414 mg, 3.4 mmol) and 4-oxo-1,4,5,6,7,8-hexahydro-cyclohepta[b]pyrrole-3-carboxylic acid ethyl ester (3.8 g, 17.04 mmol) in dichloromethane (100 mL). The reaction mixture is stirred at room temperature for 45 min. Saturated sodium bicarbonate solution (30 mL) is added, the layers are separated, and the aqueous phase is extracted with dichloromethane (4×30 mL). The combined organic layers are dried (Na$_2$SO$_4$) and evaporated. Flash chromatography on silica gel, eluting with hexanes: ethyl acetate (5:1), provides 4-oxo-5,6,7,8-tetrahydro-4H-cyclohepta[b]pyrrole-1,3-dicarboxylic acid 1-tert-butyl ester 3-ethyl ester (4.6 g 83%) as light yellow solid. $^1$H NMR (400 MHz, CDCl$_3$) δ1.277 (3H, t), 1.568 (9H, s), 1.855 (4H, m), 2.744 (2H, m), 3.205 (2H, m), 4.229 (2H, q), 7.589 (1H, s). MS (ES$^+$) 322 (M+1).

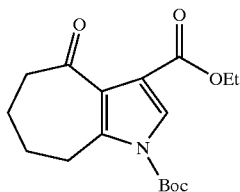

Step 2:

To a solution of 4-oxo-5,6,7,8-tetrahydro-4H-cyclohepta[b]pyrrole-1,3-dicarboxylic acid 1-tert-butyl ester 3-ethyl ester (2.17 g, 6.72 mmol), NaI (1.51 g, 10.07 mmol) and triethylamine (2.80 mL, 20.14 mmol) in $CH_3CN$ (30 mL), is added trimethylsilyl chloride (1.27 mL, 10.07 mmol) slowly via syringe. The reaction mixture is stirred at room temperature for 20 h. and then partitioned between 50 mL of ethyl acetate/hexanes (1:1 with a few drops of triethylamine) and 30 mL of sat. $NaHCO_3$ solution. The layers are separated and the aqueous phase is extracted with ethyl acetate/hexanes (1:1) (3×20 mL). The combined organic layers are washed with brine, dried ($Na_2SO_4$) and evaporated to provide 4-trimethylsilanyloxy-7,8-dihydro-6H-cyclohepta[b]pyrrole-1,3-dicarboxylic acid 1-tert-butyl ester 3-ethyl ester (2.56 g, 100%) as viscous red oil. $^1H$ NMR (400 MHz, $CDCl_3$) δ0.177 (9H, s), 1.308 (3H, t), 1.585 (9H, s), 1.906 (2H, m), 2.016 (2H, m), 2.974 (2H, t), 4.243 (2H, q), 5.353 (1H, t), 7.627 (1H, s). MS ($ES^+$) 395 (M+1).

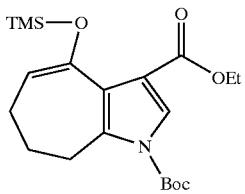

Step 3:

a): Alumina (5 g, neutral) is activated at 200° C. for 2 h. It is cooled to room temperature under nitrogen. $ZnCl_2$(1M in ether, 7.1 mL) is added and the solution is stirred at room temperature for another 30 min, after which the solvent is removed by rotary evaporator and pump. The freshly prepared $Al_2O_3$—$ZnCl_2$ powder is slowly added to a mixture of 4-trimethylsilanyloxy-7,8-dihydro-6H-cyclohepta[b]pyrrole-1,3-dicarboxylic acid 1-tert-butyl ester 3-ethyl ester (2.56 g, 6.51 mmol) and methyl vinyl ketone (5 mL, 60 mmol) at 0° C. The reaction mixture is stirred at 0° C. for 2 h and diluted with 30 mL dichloromethane. Solid residue is filtered off. Several drops of water are added to the solution and it is heated to boil for one minute. The solution is dried over $Na_2SO_4$ and organic solvents are removed by rotary evaporator. Flash chromatography on silic gel, eluting with hexanes:ethyl acetate (6:1 to 1:1), provides a mixture (1.15 g, diketone product and starting material) as intermediate.

b): A solution of the mixture (1.15 g ) from the last step and ammonium acetate (2.3 g, 30 mmol) in acetic acid (25 mL) is placed in a round-bottom flask equipped with an open-to-the-air condenser. The solution is heated at 100° C. for 2 h. Acetic acid is removed by rotary evaporator. Solid residue is dissolved in dichloromethane (30 mL) and sat. $NaHCO_3$ (30 mL). The layers are separated and the aqueous phase is extracted with dichloromethane: 2-propanol (4:1) (3×30 mL). The combined organic solvents are dried ($Na_2SO_4$) and evaporated. Flash chromatography on silica gel, eluting with 10% MeOH/$CH_2Cl_2$, provides 9-methyl-3,4,5,6-tetrahydro-3,10-diaza-benzo[e]azulene-1-carboxylic acid ethyl ester (347 mg, 18% for two steps) as an off-white solid. $^1H$ NMR (400 MHz, $CD_3OD$) δ1.192 (3H, t), 2.153 (2H, m), 2.472 (3H, s), 2.568 (4H, m), 4.145 (2H, q), 7.003 (1H, d), 7.355 (1H, s), 7.521 (1H, d) MS ($ES^+$) 271 (M+1)

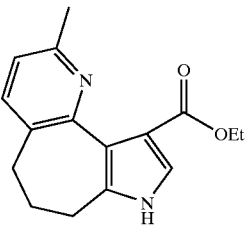

Example 5c

Preparation of 3,4,5,6-Tetrahydro-3,10-diaza-benzo[e]azulene-1-carboxylic acid ethyl ester Step 1:

A solution of isoxazole (18 g, 0.26 mol) and Raney Nickel (2 g) in 200 mL MeOH is hydrogenated at 50 psi for 20 h. The reaction mixture is filtered to remove the catalyst and the solvent is evaporated to give title compound (12 g, 67%) as a yellow solid. mp 96–98° C. $^1H$ NMR (400 MHz, $CD_3OD$) δ5.387 (1H, m), 7.395 (1H, d), 8.812 (1H, d).

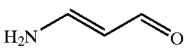

Step 2:

A mixture of 4-oxo-1,4,5,6,7,8-hexahydro-cyclohepta(b)pyrrole-3-carboxylic acid ethyl ester (7.0 g, 31.67 mmol), 3-amino-prop-2-enal (3.37 g, 47.5 mmol) and ammonium acetate (365 mg, 4.75 mmol) in triethylamine (7 mL) is heated at 110° C. for 4 h. It is cooled to room temperature and the solid residue is dissolved in 100 mL dichloromethane and 100 mL sat. $NaHCO_3$ solution. Layers are separated and the aqueous phase is extracted with 4:1 DCM/2-propanol (4×100 mL). Combined organic layers are dried ($Na_2SO_4$) and evaporated. Flash Chromatography on silica gel, eluting with EtOAc:triethylamine (20:1), provides 3,4,5,6-tetrahydro-3,10-diaza-benzo[e]azulene-1-carboxylic acid ethyl ester (1.6 g, 20%) as off-white solid. $^1H$ NMR (400 MHz, $CD_3OD$) δ1.247 (3H, t), 2.227 (2H, m), 2.631 (4H, m), 4.197 (2H, q), 7.170 (1H, m), 7.405 (1H, s), 7.686 (1H, d), 8.375 (1H, d). MS ($ES^+$) 257 (M+1)

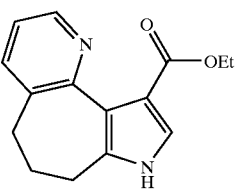

Example 5d

Preparation of 3,4,5,6-tetrahydro-3,10-diazabenzo[e]azulene-1-carboxylic acid [1-(2-ethylaminoethyl)-2-oxo-1,2-dihydropyridin-3-yl]amide The title compound is prepared by a slightly modified route involving a rearrangement reaction to form the pyridone.

Step 1:

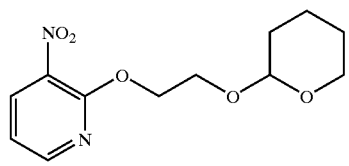

To a solution of 2-(tetrahydropyran-2-yloxy)ethanol (5.4 g, 36.6 mmol) and 2-chloro-3-nitropyridine (5.8 g, 36.6 mmol) in THF (50 mL) at 0° C. is added t-BuOK (1.0 M solution in t-BuOH, 44 mL). The mixture is then stirred at room temperature overnight. The solvent is removed and the residue is separated by column chromatography on silica gel (hexanes:ethyl acetate 4:1) to give 5.8 g of 3-nitro-2-[[2-(tetrahydro-pyran-2-yloxy)-ethoxy]pyridine as an oil.

Step 2:

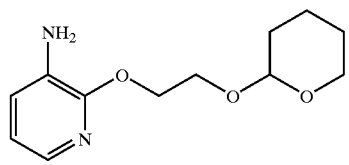

A mixture of 3-nitro-2-[2-(2-tetrahydro-pyran-2-yloxy)-ethoxy]pyridine (5.8 g) and 10% Pd/C (500 mg) in ethanol (30 mL) is placed in a Parr bottle and pressurized at 50–60 psi for 4 h. The resulting mixture is filtered through Celite and concentrated in vacuo to give 5.0 g of 5.8 g of 3-amino-2-[[2-(tetrahydro-pyran-2-yloxy)-ethoxy]pyridine.

Step 3:

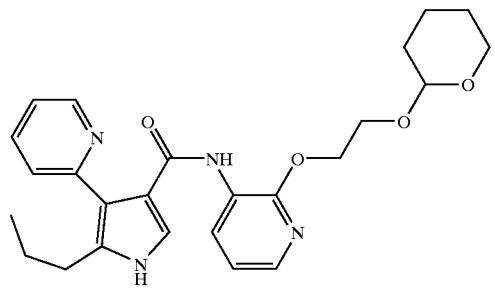

To a solution of 2-[2-(tetrahydropyran-2-yloxy)-ethoxy]pyridin-3-ylamine (2.3 g, 9.7 mmol) in DCM (8 mL) is added AlMe₃ (2M in toluene, 4.9 mL) at rt. After stirring at room temperature for 1 h, a solution of 3,4,5,6-tetrahydro-3,10-diazabenzo[e]azulene-1-carboxylic acid ethyl ester (500 mg, 1.95 mmol) in DCM (10 mL) is added. The mixture is refluxed overnight. On cooling, water (5 mL) is added, and the resulting mixture is extracted with DCM. The combined DCM extracts are dried and solvent removed. The residue is separated by column chromatography on silica gel (5% methanol in DCM) to give 850 mg of 3,4,5,6-tetrahydro-3,10-diaza-benzo[e]azulene-1-carboxylic acid {2-[2-(tetrahydropyran-2-yloxy)-ethoxy]-pyridin-3-yl}amide as an oil.

Step 4:

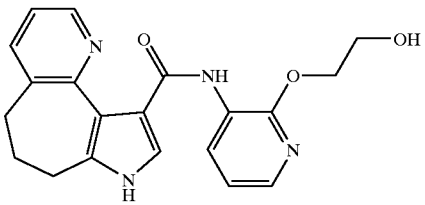

A solution of 3,4,5,6-tetrahydro-3,10-diaza-benzo[e]azulene-1-carboxylic acid {2-[2-(tetrahydropyran-2-yloxy)-ethoxy]-pyridin-3-yl}amide (850 mg) and p-toluenesulfonic acid monohydrate (700 mg) in methanol (30 mL) is refluxed for 1 h. The solvent is removed and the residue is extracted with DCM and washed with NaHCO₃ (aq.). The organic layer is dried and solvent removed to give 700 mg of 3,4,5,6-tetrahydro-3,10-diazabenzo[e]azulene-1-carboxylic acid [2-(2-hydroxy-ethoxy)pyridin-3-yl]amide.

Step 5:

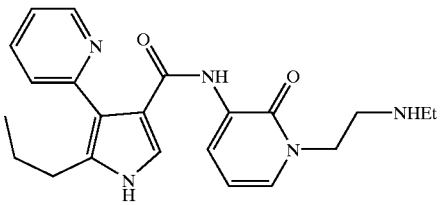

To a mixture of 3,4,5,6-tetrahydro-3,10-diazabenzo[e]azulene-1-carboxylic acid [2-(2-hydroxy-ethoxy)pyridin-3-yl]amide (150 mg, 0.41 mmol) and triethylamine (125 mg, 1.2 mmol) in DCM (10 mL) at 0° C. is added methanesulfonyl chloride (94 mg, 0.82 mmol) dropwise. The mixture is stirred at 0° C. for 15 min. The solvent is removed and the residue is dissolved in acetonitrile (10 mL) and transferred to a sealed tube. Ethylamine (1 mL) is added and the mixture is heated at 60° C. for 3 h. The solvent is removed and the residue is separated by preparative TLC to give 87 mg of 3,4,5,6-tetrahydro-3,10-diazabenzo[e]azulene-1-carboxylic acid [1-(2-ethylaminoethyl)-2-oxo-1,2-dihydro-pyridin-3-yl]amide. LRMS Calcd 391.5; found M−1 390.2.

Example 5e

Using the methods shown in Schemes 2 and 3 the compounds shown in Table 2 were prepared.

TABLE 2

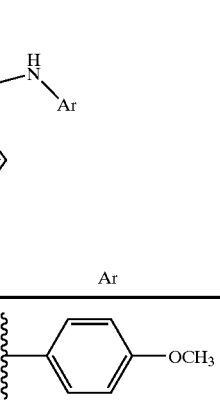

| Cmp. # | Name | R³ᵃ | R³ | R⁴ | R⁵ | R⁶ | k | Ar | Spectral Data |
|---|---|---|---|---|---|---|---|---|---|
| 1. | 9-Methyl-3,4,5,6-tetrahydro-3,10-diaza-benzo[e]azulene-1-carboxylic acid (4-methoxy-phenyl)-amide | CH₃ | H | H | H | H | 2 | 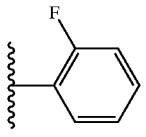 | |
| 2. | 9-Methyl-3,4,5,6-tetrahydro-3,10-diaza-benzo[e]azulene-1-carboxylic acid (2-fluoro-phenyl)-amide | CH₃ | H | H | H | H | 2 | 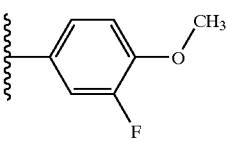 | |
| 3. | 9-Methyl-3,4,5,6-tetrahydro-3,10-diaza-benzo[e]azulene-1-carboxylic acid (3-fluoro-4-methoxy-phenyl)-amide | CH₃ | H | H | H | H | 2 |  | |
| 4. | 9-Methyl-3,4,5,6-tetrahydro-3,10-diaza-benzo[e]azulene-1-carboxylic acid (4-fluoro-phenyl)-amide | CH₃ | H | H | H | H | 2 | 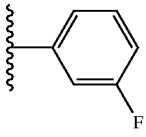 | |
| 5. | 9-Methyl-3,4,5,6-tetrahydro-3,10-diaza-benzo[e]azulene-1-carboxylic acid (3-fluoro-phenyl)-amide | CH3 | H | H | H | H | 2 | 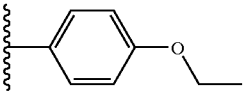 | |
| 6. | 9-Methyl-3,4,5,6-tetrahydro-3,10-diaza-benzo[e]azulene-1-carboxylic acid (4-ethoxy-phenyl)-amide | CH₃ | H | H | H | H | 2 | 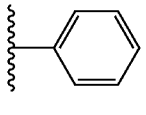 | |
| 7. | 9-Methyl-3,4,5,6-tetrahydro-3,10-diaza-benzo[e]azulene-1-carboxylic acid phenylamide | CH₃ | H | H | H | H | 2 | 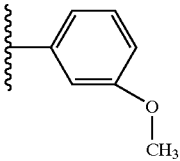 | |
| 8. | 9-Methyl-3,4,5,6-tetrahydro-3,10-diaza-benzo[e]azulene-1-carboxylic acid (3-methoxy-phenyl)-amide | CH₃ | H | H | H | H | 2 |  | |

TABLE 2-continued

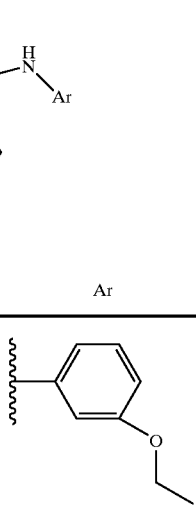

| Cmp. # | Name | R³ᵃ | R³ | R⁴ | R⁵ | R⁶ | k | Ar | Spectral Data |
|---|---|---|---|---|---|---|---|---|---|
| 9. | 9-Methyl-3,4,5,6-tetrahydro-3,10-diaza-benzo[e]azulene-1-carboxylic acid (3-ethoxy-phenyl)-amide | CH₃ | H | H | H | H | 2 | 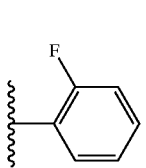 | |
| 10. | 3,4,5,6-Tetrahydro-3,10-diaza-benzo[e]azulene-1-carboxylic acid (2-fluoro-phenyl)-amide | H | H | H | H | H | 2 | 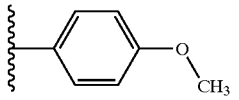 | |
| 11. | 3,4,5,6-Tetrahydro-3,10-diaza-benzo[e]azulene-1-carboxylic acid (4-methoxy-phenyl)-amide | H | H | H | H | H | 2 | 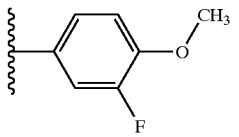 | |
| 12. | 3,4,5,6-Tetrahydro-3,10-diaza-benzo[e]azulene-1-carboxylic acid (3-fluoro-4-methoxy-phenyl)-amide | H | H | H | H | H | 2 | 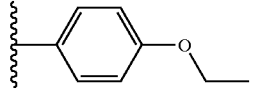 | MS found [M + H] 352.0 |
| 13. | 3,4,5,6-Tetrahydro-3,10-diaza-benzo[e]azulene-1-carboxylic acid (4-ethoxy-phenyl)-amide | H | H | H | H | H | 2 | 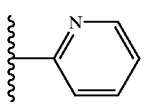 | MS found [M + H] 348.1 |
| 14. | 3,4,5,6-Tetrahydro-3,10-diaza-benzo[e]azulene-1-carboxylic acid pyridin-2-ylamide | H | H | H | H | H | 2 | 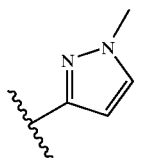 | MS found [M + H] 305.0 |
| 15. | 3,4,5,6-Tetrahydro-3,10-diaza-benzo[e]azulene-1-carboxylic acid (1-methyl-1H-pyrazol-3-yl)-amide | H | H | H | H | H | 2 | | MS found [M + H] 308.0 |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 16. | 3,4,5,6-Tetrahydro-3,10-diaza-benzo[e]azulene-1-carboxylic acid (5-methyl-[1,3,4]thiadiazol-2-yl)-amide | H | H | H | H | H | 2 | 5-methyl-1,3,4-thiadiazol-2-yl | MS found [M + H] 326.0 |
| 17. | 3,4,5,6-Tetrahydro-3,10-diaza-benzo[e]azulene-1-carboxylic acid (5-fluoro-pyridin-2-yl)-amide | H | H | H | H | H | 2 | 5-fluoro-pyridin-2-yl | |
| 18. | 3,4,5,6-Tetrahydro-3,10-diaza-benzo[e]azulene-1-carboxylic acid {4-[2-(ethyl-methanesulfonyl-amino)-ethoxy]-phenyl}-amide | H | H | H | H | H | 2 | 4-[2-(ethyl-methanesulfonyl-amino)-ethoxy]-phenyl | LRMS calcd 468 found [M + 1] 469 |
| 19. | 3,4,5,6-Tetrahydro-3,10-diaza-benzo[e]azulene-1-carboxylic acid [4-(2-ethylamino-ethoxy)-phenyl]-amide | H | H | H | H | H | 2 | 4-(2-ethylamino-ethoxy)-phenyl | LRMS calcd 390 found [M + 1] 391 |
| 20. | 8-Methyl-3,4,5,6-tetrahydro-3,10-diaza-benzo[e]azulene-1-carboxylic acid (4-ethoxy-phenyl)-amide | H | CH₃ | H | H | H | 2 | 4-ethoxy-phenyl | |
| 21. | 8-Methyl-3,4,5,6-tetrahydro-3,10-diaza-benzo[e]azulene-1-carboxylic acid pyridin-2-ylamide | H | CH₃ | H | H | H | 2 | pyridin-2-yl | |
| 22. | 3,4,5,6-Tetrahydro-3,10-diaza-benzo[e]azulene-1-carboxylic acid pyridin-3-ylamide | H | H | H | H | H | 2 | pyridin-3-yl | MS found [M + H] 304.9 |

TABLE 2-continued

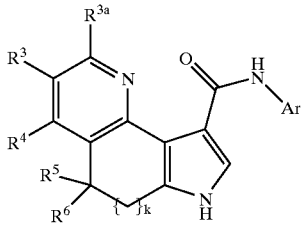

| Cmp. # | Name | R³ᵃ | R³ | R⁴ | R⁵ | R⁶ | k | Ar | Spectral Data |
|---|---|---|---|---|---|---|---|---|---|
| 23. | 3,4,5,6-Tetrahydro-3,10-diaza-benzo[e]azulene-1-carboxylic acid (3-methyl-[1,2,4]thiadiazol-5-yl)-amide | H | H | H | H | H | 2 | 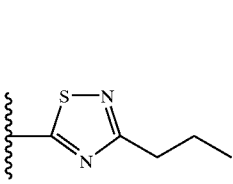 | MS found [M + H] 326.0 |
| 24. | 3,4,5,6-Tetrahydro-3,10-diaza-benzo[e]azulene-1-carboxylic acid (3-propyl-[1,2,4]thiadiazol-5-yl)-amide | H | H | H | H | H | 2 | 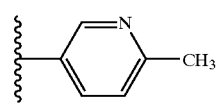 | LCMS found [M + H] 354 |
| 25. | 3,4,5,6-Tetrahydro-3,10-diaza-benzo[e]azulene-1-carboxylic acid (6-methyl-pyridin-3-yl)-amide | H | H | H | H | H | 2 | 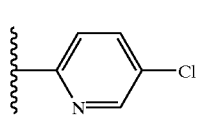 | MS found [M + H] 319.1 |
| 26. | 3,4,5,6-Tetrahydro-3,10-diaza-benzo[e]azulene-1-carboxylic acid (5-chloro-pyridin-2-yl)-amide | H | H | H | H | H | 2 | 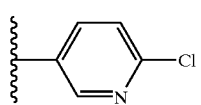 | MS found [M + H] 339.0 |
| 27. | 3,4,5,6-Tetrahydro-3,10-diaza-benzo[e]azulene-1-carboxylic acid (6-chloro-pyridin-3-yl)-amide | H | H | H | H | H | 2 | 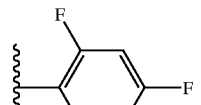 | MS found [M + H] 339.0 |
| 28. | 3,4,5,6-Tetrahydro-3,10-diaza-benzo[e]azulene-1-carboxylic acid (2,4-difluoro-phenyl)-amide | H | H | H | H | H | 2 | 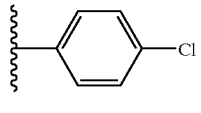 | MS found [M + H] 340.1 |
| 29. | 3,4,5,6-Tetrahydro-3,10-diaza-benzo[e]azulene-1-carboxylic acid (4-chloro-phenyl)-amide | H | H | H | H | H | 2 |  | MS found [M + H] 338.0 |

TABLE 2-continued

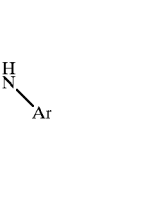

| Cmp. # | Name | R³ᵃ | R³ | R⁴ | R⁵ | R⁶ | k | Ar | Spectral Data |
|---|---|---|---|---|---|---|---|---|---|
| 30. | 3,4,5,6-Tetrahydro-3,10-diaza-benzo[e]azulene-1-carboxylic acid pyrimidin-2-ylamide | H | H | H | H | H | 2 | 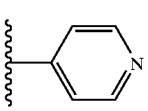 | MS found [M + H] 306.1 |
| 31. | 3,4,5,6-Tetrahydro-3,10-diaza-benzo[e]azulene-1-carboxylic acid pyridin-4-ylamide | H | H | H | H | H | 2 | 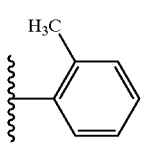 | MS found [M + H] 305.1 |
| 32. | 3,4,5,6-Tetrahydro-3,10-diaza-benzo[e]azulene-1-carboxylic acid o-tolyl-amide | H | H | H | H | H | 2 | 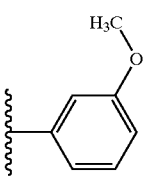 | MS found [M + H] 318.1 |
| 33. | 3,4,5,6-Tetrahydro-3,10-diaza-benzo[e]azulene-1-carboxylic acid (5-bromo-pyridin-2-yl)-amide | H | H | H | H | H | 2 | 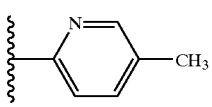 | MS found [M + H] 383.0 |
| 34. | 3,4,5,6-Tetrahydro-3,10-diaza-benzo[e]azulene-1-carboxylic acid (5-methyl-pyridin-2-yl)-amide | H | H | H | H | H | 2 | 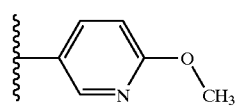 | MS found [M + H] 319.1 |
| 35. | 3,4,5,6-Tetrahydro-3,10-diaza-benzo[e]azulene-1-carboxylic acid (6-methoxy-pyridin-3-yl)-amide | H | H | H | H | H | 2 | 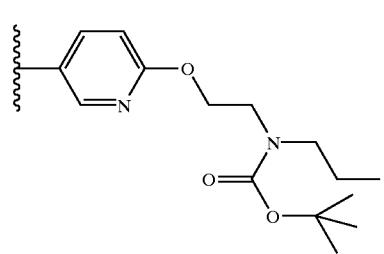 | MS found [M + H] 335.2 |
| 36. | Propyl-(2-{5-[(3,4,5,6-tetrahydro-3,10-diaza-benzo[e]azulene-1-carbonyl)-amino]-pyridin-2-yloxy}-ethyl)-carbamic acid tert-butyl ester | H | H | H | H | H | 2 | | MS found [M + H] 506.3 |

TABLE 2-continued

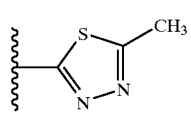

| Cmp. # | Name | R³ᵃ | R³ | R⁴ | R⁵ | R⁶ | k | Ar | Spectral Data |
|---|---|---|---|---|---|---|---|---|---|
| 37. | 8-Methyl-3,4,5,6-tetrahydro-3,10-diaza-benzo[e]azulene-1-carboxylic acid (5-methyl-[1,3,4]thiadiazol-2-yl)-amide | H | CH₃ | H | H | H | 2 | 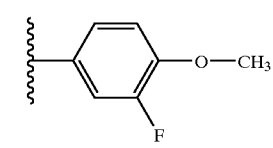 | |
| 38. | 8-Methyl-3,4,5,6-tetrahydro-3,10-diaza-benzo[e]azulene-1-carboxylic acid (3-fluoro-4-methoxy-phenyl)-amide | H | CH₃ | H | H | H | 2 | 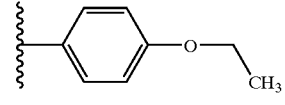 | |
| 39. | 3,4,5,6-Tetrahydro-3,10-diaza-benzo[e]azulene-1-carboxylic acid (4-ethoxy-phenyl)-amide | H | H | H | H | H | 2 | 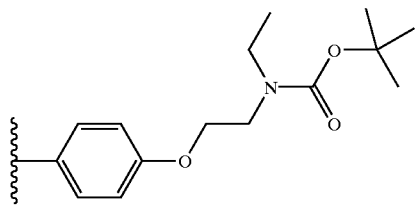 | MS found [M + H] 348.1 |
| 40. | Ethyl-(2-{4-[(3,4,5,6-tetrahydro-3,10-diaza-benzo[e]azulene-1-carbonyl)-amino]-phenoxy}-ethyl)-carbamic acid tert-butyl ester | H | H | H | H | H | 2 | 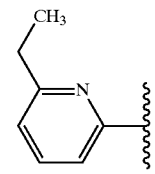 | |
| 41. | 3,4,5,6-Tetrahydro-3,10-diaza-benzo[e]azulene-1-carboxylic acid (6-ethyl-pyridin-2-yl)-amide | H | H | H | H | H | 2 | | ¹H NMR [CDCl3] 1.35(t, 3H), 2.3(quint, 2H), 2.6(t, 2H), 2.7(t, 2H), 2.8(q, 2H), 6.8(d, 1H), 7.2(dd, 1H), 7.55(t, 1H), 7.6(dd, 1H), 7.65(s, 1H), 8.2(d, 1H), 8.75(d, 1H), 9.2(br s, 1H) |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 42. | 3,4,5,6-Tetrahydro-3,10-diaza-benzo[e]azulene-1-carboxylic acid benzo[1,3]dioxol-5-ylamide | H | H | H | H | H | 2 | benzo[1,3]dioxol-5-yl | $^1$H NMR [CDCl3] 2.3(quint, 2H), 2.6(t, 2H), 2.7(t, 2H), 6.8(d, 1H), 7.1(d, 1H), 7.2(dd, 1H), 7.5(s, 1H), 7.6(s, 1H), 7.65(d, 1H), 8.6(d, 1H), 9.7(br s, 1H) |
| 43. | 3,4,5,6-Tetrahydro-3,10-diaza-benzo[e]azulene-1-carboxylic acid (2-chloro-pyridin-4-yl)-amide | H | H | H | H | H | 2 | 2-chloro-pyridin-4-yl | $^1$H NMR [CDCl3] 2.3(quint, 2H), 2.6(t, 2H), 2.7(t, 2H), 7.2(dd, 1H), 7.5(d, 1H), 7.6(s, 1H), 7.65(d, 1H), 7.8(s, 1H), 8.2(d, 1H), 8.6(d, 1H), 9.0(br s, 1H) |
| 44. | 3,4,5,6-Tetrahydro-3,10-diaza-benzo[e]azulene-1-carboxylic acid (3-methoxy-phenyl)-amide | H | H | H | H | H | 2 | 3-methoxy-phenyl | [CDCl3] 2.3(quint, 2H), 2.6(t, 2H), 2.7(t, 2H), 3.8(s, 3H), 6.6(app s, 1H), 7.2(dd, 1H), 7.25(app s, 2H), 7.6(m, 2H), 8.6(d, 1H), 9.9(br s, 1H) |
| 45. | 3,4,5,6-Tetrahydro-3,10-diaza-benzo[e]azulene-1-carboxylic acid (2,5-difluoro-phenyl)-amide | H | H | H | H | H | 2 | 2,5-difluoro-phenyl | $^1$H NMR [CDCl3] 2.3(quint, 2H), 2.6(t, 2H), 2.7(t, 2H), 6.7(m, 1H), 7.0(m, 1H), 7.2(dd, 1H), 7.6(dd, 1H), 7.65(s, 1H), 8.5(m, 1H), 8.6(d, 1H), 9.2(br s, 1H) |

TABLE 2-continued

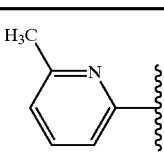

| Cmp. # | Name | R³ᵃ | R³ | R⁴ | R⁵ | R⁶ | k | Ar | Spectral Data |
|---|---|---|---|---|---|---|---|---|---|
| 46. | 3,4,5,6-Tetrahydro-3,10-diaza-benzo[e]azulene-1-carboxylic acid (6-methyl-pyridin-2-yl)-amide | H | H | H | H | H | 2 | 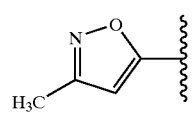 | ¹H NMR [CDCl3] 2.3(quint, 2H), 2.4(s, 3H), 2.6(t, 2H), 2.7(t, 2H), 6.8(d, 1H), 7.2(dd, 1H), 7.5(t, 1H), 7.6(dd, 1H), 7.65(s, 1H), 8.2(d, 1H), 8.7(d, 1H), 9.8(br s, 1H) |
| 47. | 3,4,5,6-Tetrahydro-3,10-diaza-benzo[e]azulene-1-carboxylic acid (3-methyl-isoxazol-5-yl)-amide | H | H | H | H | H | 2 | 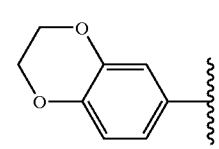 | ¹H NMR [CDCl3] 2.25(s, 3H), 2.3(quint, 2H), 2.6(t, 2H), 2.7(t, 2H), 6.3(s, 1H), 7.2(dd, 1H), 7.6(m, 2H), 8.6(d, 1H), 8.8(br s, 1H) |
| 48. | 3,4,5,6-Tetrahydro-3,10-diaza-benzo[e]azulene-1-carboxylic acid (2,3-dihydro-benzo[1,4]dioxin-6-yl)-amide | H | H | H | H | H | 2 | 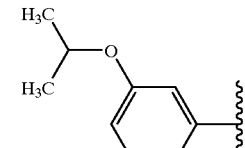 | LRMS m/z 362 |
| 49. | 3,4,5,6-Tetrahydro-3,10-diaza-benzo[e]azulene-1-carboxylic acid (3-isopropoxy-phenyl)-amide | H | H | H | H | H | 2 | 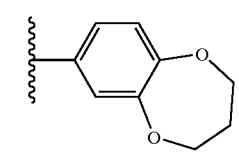 | LRMS m/z 362 |
| 50. | 3,4,5,6-Tetrahydro-3,10-diaza-benzo[e]azulene-1-carboxylic acid (3,4-dihydro-2H-benzo[b][1,4]dioxepin-7-yl)-amide | H | H | H | H | H | 2 | 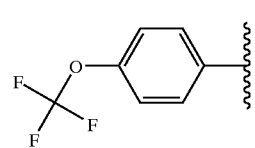 | LRMS m/z 376 |
| 51. | 3,4,5,6-Tetrahydro-3,10-diaza-benzo[e]azulene-1-carboxylic acid(4-trifluoromethoxy-phenyl)-amide | H | H | H | H | H | 2 |  | LRMS m/z 388 |

TABLE 2-continued

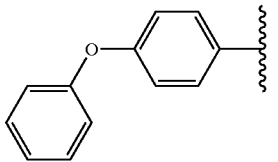

| Cmp. # | Name | R³ª | R³ | R⁴ | R⁵ | R⁶ | k | Ar | Spectral Data |
|---|---|---|---|---|---|---|---|---|---|
| 52. | 3,4,5,6-Tetrahydro-3,10-diaza-benzo[e]azulene-1-carboxylic acid (4-phenoxy-phenyl)-amide | H | H | H | H | H | 2 | 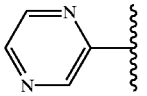 | LRMS m/z 396 |
| 53. | 3,4,5,6-Tetrahydro-3,10-diaza-benzo[e]azulene-1-carboxylic acid pyrazin-2-ylamide | H | H | H | H | H | 2 | 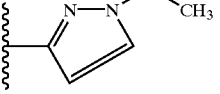 | LRMS m/z 306 |
| 54. | 3,4,5,6-Tetrahydro-3,10-diaza-benzo[e]azulene-1-carboxylic acid (1-ethyl-1H-pyrazol-3-yl)-amide | H | H | H | H | H | 2 | 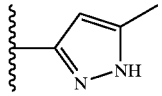 | LCMS found (M + H) 322 |
| 55. | 3,4,5,6-Tetrahydro-3,10-diaza-benzo[e]azulene-1-carboxylic acid (5-methyl-1H-pyrazol-3-yl)-amide | H | H | H | H | H | 2 | 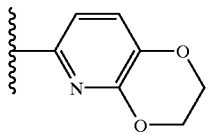 | LCMS found (M + H) 309 |
| 56. | 3,4,5,6-Tetrahydro-3,10-diaza-benzo[e]azulene-1-carboxylic acid (2,3-dihydro-[1,4]dioxino[2,3-b]pyridin-6-yl)-amide | H | H | H | H | H | 2 | 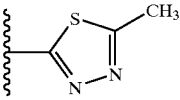 | LCMS found (M + H) 363 |
| 57. | 3,4,5,6-Tetrahydro-3,10-diaza-benzo[e]azulene-1-carboxylic acid (5-methyl-[1,3,4]thiadiazol-2-yl)-amide | H | H | H | H | H | 2 | 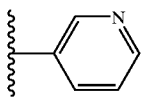 | |
| 58. | 3,4,5,6-Tetrahydro-3,10-diaza-benzo[e]azulene-1-carboxylic acid pyridin-3-ylamide | H | H | H | H | H | 2 |  | |

TABLE 2-continued

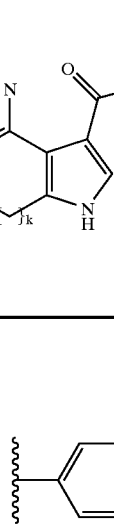

| Cmp. # | Name | R³ᵃ | R³ | R⁴ | R⁵ | R⁶ | k | Ar | Spectral Data |
|---|---|---|---|---|---|---|---|---|---|
| 59. | 3,4,5,6-Tetrahydro-3,10-diaza-benzo[e]azulene-1-carboxylic acid [6-(3-isopropoxy-propylamino)-pyridin-3-yl]-amide | H | H | H | H | H | 2 | 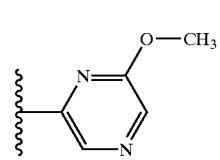 | MS found [M + H] 420.3 |
| 60. | 3,4,5,6-Tetrahydro-3,10-diaza-benzo[e]azulene-1-carboxylic acid (6-methoxy-pyrazin-2-yl)-amide | H | H | H | H | H | 2 | 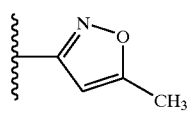 | MS found [M + H] 336.2 |
| 61. | 3,4,5,6-Tetrahydro-3,10-diaza-benzo[e]azulene-1-carboxylic acid (5-methyl-isoxazol-3-yl)-amide | H | H | H | H | H | 2 | 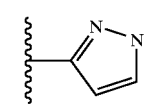 | MS found [M + H] 309.2 |
| 62. | 3,4,5,6-Tetrahydro-3,10-diaza-benzo[e]azulene-1-carboxylic acid (1H-pyrazol-3-yl)-amide | H | H | H | H | H | 2 | 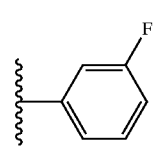 | MS found [M + H] 294.2 |
| 63. | 3,4,5,6-Tetrahydro-3,10-diaza-benzo[e]azulene-1-carboxylic acid (3-fluoro-phenyl)-amide | H | H | H | H | H | 2 | 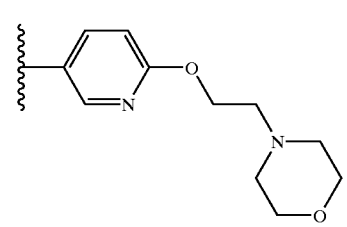 | MS found [M + H] 322.2 |
| 64. | 3,4,5,6-Tetrahydro-3,10-diaza-benzo[e]azulene-1-carboxylic acid [6-(2-morpholin-4-yl-ethoxy)-pyridin-3-yl]-amide | H | H | H | H | H | 2 | 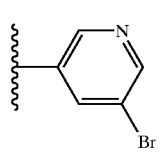 | MS found [M + H] 434.4 |
| 65. | 3,4,5,6-Tetrahydro-3,10-diaza-benzo[e]azulene-1-carboxylic acid (5-bromo-pyridin-3-yl)-amide | H | H | H | H | H | 2 | | MS found [M + H] 383.1 |

TABLE 2-continued

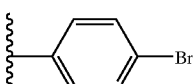

| Cmp. # | Name | R³ᵃ | R³ | R⁴ | R⁵ | R⁶ | k | Ar | Spectral Data |
|---|---|---|---|---|---|---|---|---|---|
| 66. | 3,4,5,6-Tetrahydro-3,10-diaza-benzo[e]azulene-1-carboxylic acid (6-bromo-pyridin-3-yl)-amide | H | H | H | H | H | 2 | 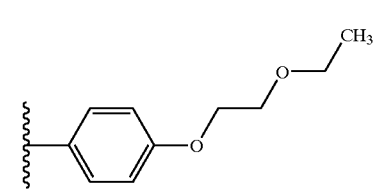 | MS found [M + H] 383.2 |
| 67. | 3,4,5,6-Tetrahydro-3,10-diaza-benzo[e]azulene-1-carboxylic acid [4-(2-ethoxy-ethoxy)-phenyl]-amide | H | H | H | H | H | 2 | 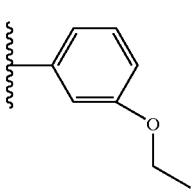 | ¹H NMR(DMSO) 1.11(t, 3H), 2.15(t, 2H), 2.49(t, 2H), 2.73(t, 2H), 3.46–3.49(m, 2H), 3.67(t, 2H), 4.0(t, 2H), 6.90–6.92(m, 2H), 7.58–8.41(m, 5H), 8.69(brs, 1H) LCMS found (M + H) 392.3 |
| 68. | 3,4,5,6-Tetrahydro-3,10-diaza-benzo[e]azulene-1-carboxylic acid (3-ethoxy-phenyl)-amide | H | H | H | H | H | 2 | 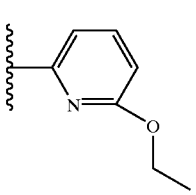 | LCMS found (M + H) 348 |
| 69. | 3,4,5,6-Tetrahydro-3,10-diaza-benzo[e]azulene-1-carboxylic acid (6-ethoxy-pyridin-2-yl)-amide | H | H | H | H | H | 2 | 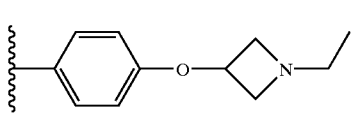 | LCMS found (M + H) 349 |
| 70. | 3,4,5,6-Tetrahydro-3,10-diaza-benzo[e]azulene-1-carboxylic acid [4-(1-ethyl-azetidin-3-yloxy)-phenyl]-amide | H | H | H | H | H | 2 | 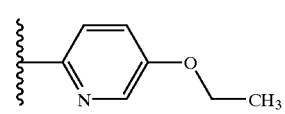 | Electrospray mass spectrum: m/z 401.4 [M − 1] |
| 71. | 3,4,5,6-tetrahydro-3,10-diaza-benzo[e]azulene-1-carboxylic acid (5-ethoxy-pyridin-2-yl)-amide | H | H | H | H | H | 2 |  | LRMS calcd 348 found [M + 1] 349 |

TABLE 2-continued

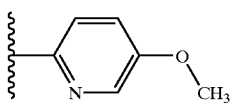

| Cmp. # | Name | R³ᵃ | R³ | R⁴ | R⁵ | R⁶ | k | Ar | Spectral Data |
|---|---|---|---|---|---|---|---|---|---|
| 72. | 8-Methyl-3,4,5,6-tetrahydro-3,10-diaza-benzo[e]azulene-1-carboxylic acid (5-methoxy-pyridin-2-yl)-amide | H | CH₃ | H | H | H | 2 | 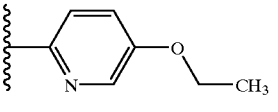 | LRMS calcd 348 found [M + 1] 349 |
| 73. | 8-Methyl-3,4,5,6-tetrahydro-3,10-diaza-benzo[e]azulene-1-carboxylic acid (5-ethoxy-pyridin-2-yl)-amide | H | CH₃ | H | H | H | 2 | 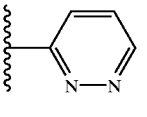 | LRMS calcd 362 found [M + 1] 363 |
| 74. | 8-Methyl-3,4,5,6-tetrahydro-3,10-diaza-benzo[e]azulene-1-carboxylic acid pyridazin-3-ylamide | H | CH₃ | H | H | H | 2 | 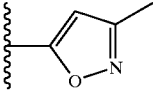 | ¹H NMR (CD3OD): 2.25(t, 2H), 2.35(s, 3H), 2.55–2.7(tt, 4H), 7.55–7.65(m, 3H), 8.58.6(m, 2H), 8.85(d, 1H); LRMS calcd 319 found [M + 1] 320 |
| 75. | 8-Methyl-3,4,5,6-tetrahydro-3,10-diaza-benzo[e]azulene-1-carboxylic acid (3-methyl-isoxazol-5-yl)-amide | H | CH₃ | H | H | H | 2 | 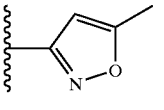 | ¹H NMR (CD3OD): 2.2–2.3(m, 5H), 2.40(s, 3H), 2.6–2.7(tt, 4H), 6.2(s, 1H), 7.55–7.6(ss, 2H), 8.45(s, 1H); LRMS calcd 322 found [M + 1] 323 |
| 76. | 8-Methyl-3,4,5,6-tetrahydro-3,10-diaza-benzo[e]azulene-1-carboxylic acid (5-methyl-isoxazol-3-yl)-amide | H | CH₃ | H | H | H | 2 | | ¹H NMR (CD3OD): 2.25(t, 2H), 2.35–2.40(ss, 6H), 2.55–2.7(tt, 4H), 6.7(s, 1H), 7.55–7.65(ss, 2H), 8.4(s, 1H); LRMS calcd 322 found [M + 1] 323 |

TABLE 2-continued

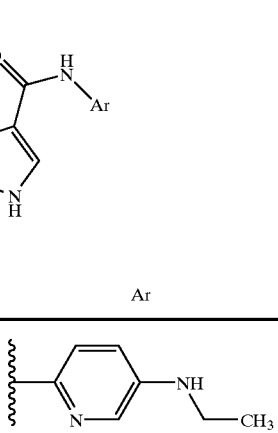

| Cmp. # | Name | R³ᵃ | R³ | R⁴ | R⁵ | R⁶ | k | Ar | Spectral Data |
|---|---|---|---|---|---|---|---|---|---|
| 77. | 3,4,5,6-Tetrahydro-3,10-diaza-benzo[e]azulene-1-carboxylic acid (6-ethylamino-pyridin-3-yl)-amide | H | H | H | H | H | 2 | 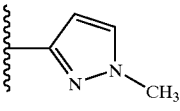 | LRMS calcd 347 found [M + 1] 323 |
| 78. | 3,4,5,6-Tetrahydro-3,10-diaza-benzo[e]azulene-1-carboxylic acid(1-methyl-1H-pyrazol-3-yl)-amide | H | CH₃ | H | H | H | 2 | 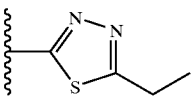 | LRMS 320 (M − 1) |
| 79. | 3,4,5,6-Tetrahydro-3,10-diaza-benzo[e]azulene-1-carboxylic acid(5-ethyl-1,3,4]thiadiazol-2-yl)amide | H | H | H | H | H | 2 | 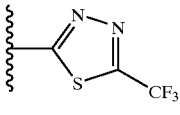 | LRMS calcd 339.4 found [M − 1] 338.2 |
| 80. | 3,4,5,6-Tetrahydro-3,10-diaza-benzo[e]azulene-1-carboxylic acid(5-trifluoromethyl-[1,3,4]thiadiazol-2-yl)amide | H | H | H | H | H | 2 | 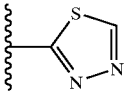 | LRMS calcd 379.4 found [M − 1] 378.2 |
| 81. | 3,4,5,6-Tetrahydro-3,10-diaza-benzo[e]azulene-1-carboxylic acid [1,3,4]thiadiazol-2-ylamide | H | H | H | H | H | 2 | 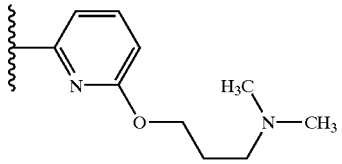 | LCMS found (M − H) 310 |
| 82. | 3,4,5,6-Tetrahydro-3,10-diaza-benzo[e]azulene-1-carboxylic acid[6-(2-dimethylamino-propoxy)-pyridin-2-yl]-amide | H | H | H | H | H | 2 | 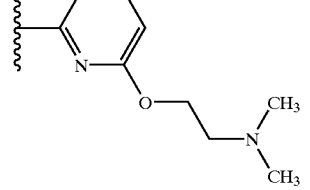 | LRMS: m/z 404.4 [M − 1] |
| 83. | 3,4,5,6-Tetrahydro-3,10-diaza-benzo[e]azulene-1-carboxylic acid[6-(2-dimethylamino-ethoxy)-pyridin-2-yl]-amide | H | H | H | H | H | 2 |  | LRMS: m/z 390.3 [M − 1] |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 84. | 3,4,5,6-Tetrahydro-3,10-diaza-benzo[e]azulene-1-carboxylic acid[6-(2-pyrrolidin-1-yl-ethoxy)-pyridin-2-yl]-amide | H | H | H | H | H | 2 | 6-(2-pyrrolidin-1-yl-ethoxy)-pyridin-2-yl | LRMS: m/z 416.3 [M − 1] |
| 85. | 3,4,5,6-Tetrahydro-3,10-diaza-benzo[e]azulene-1-carboxylic acid[1-(3-cyclobutylamino-propyl)-1H-pyrazol-3-yl]-amide | H | H | H | H | H | 2 | 1-(3-cyclobutylamino-propyl)-1H-pyrazol-3-yl | ¹H NMR [CDCl3] 1.65(m, 4H), 1.9–2.2(m, 6H), 2.4–2.7(m, 6H), 3.2(m, 1H), 4.05(t, 2H), 6.75(d, 1H), 7.05(m, 1H), 7.3(d, 1H), 7.6(m, 2H), 8.6(d, 1H), 10.5(br, 1H), 13.7(br, 1H) LRMS calcd 404 found [M + 1] 405 |
| 86. | Methyl-(2-{3-[(3,4,5,6-tetrahydro-3,10-diaza-benzo[e]azulene-1-carbonyl)-amino]-pyridin-2-yloxy}-ethyl)-carbamic acid tert-butyl ester | H | H | H | H | H | 2 | 2-{N-Boc-N-methylamino-ethoxy}-pyridin-3-yl | ¹H NMR(CDCl3) 1.39(s, 9H); 2.25(m, 2H); 2.62(m, 4H); 2.84(s, 3H); 3.62(t, 2H); 4.61(t, 2H); 6.88(m, 1H); 7.15(m, 1H); 7.60(m, 2H),; 7.80(m, 1H); 8.58(m, 1H); 8.68(d, 1H); 9.59(br s, 1H); 12.62(br s, 1H); LRMS calcd 477 found [M + 1] 478 |
| 87. | 3,4,5,6-Tetrahydro-3,10-diaza-benzo[e]azulene-1-carboxylic acid[2-(2-methylamino-ethoxy)-pyridin-3-yl]-amide | H | H | H | H | H | 2 | 2-(2-methylamino-ethoxy)-pyridin-3-yl | ¹H NMR(CDCl3) 2.22(m, 2H); 2.39(s, 3H); 2.60(m, 4H); 3.00(t, 2H); 4.61(t, 2H); 6.88 dd, 1H); 7.10(dd 1H); 7.60(m, 2H); 7.820(dd, 1H); 8.52(m, 2H); 10.1(br s, 1H) |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 88. | 3,4,5,6-Tetrahydro-3,10-diaza-benzo[e]azulene-1-carboxylic acid [1-(3-hydroxy-propyl)-1H-pyrazol-3-yl]-amide | H | H | H | H | H | 2 | pyrazole-N-CH₂CH₂CH₂OH | ¹H NMR [CDCl3] 2.0–2.3(m, 4H), 2.5–2.8(m, 4H), 3.7(m, 2H), 4.2(t, 2H), 6.75(d, 1H), 7.15(m, 1H), 7.3(d, 1H), 7.6(m, 2H), 8.6(d, 1H), 9.8(br, 1H); LRMS 350 (M + 1) |
| 89. | 3,4,5,6-Tetrahydro-3,10-diaza-benzo[e]azulene-1-carboxylic acid [1-(3-ethylamino-propyl)-1H-pyrazol-3-yl]-amide | H | H | H | H | H | 2 | pyrazole-N-CH₂CH₂CH₂NHEt | ¹H NMR [CDCl3] 1.05(t, 3H), 2.0–2.4(m, 4H), 2.5–2.7(m, 8H), 4.15(t, 2H), 6.75(d, 1H), 7.05(m, 1H), 7.3(d, 1H), 7.6(m, 2H), 8.6(d, 1H), 10.05(br, 1H); LRMS 377(M − 1) |
| 90. | 3,4,5,6-Tetrahydro-3,10-diaza-benzo[e]azulene-1-carboxylic acid [1-(3-imidazol-1-yl-propyl)-1H-pyrazol-3-yl]-amide | H | H | H | H | H | 2 | pyrazole-N-CH₂CH₂CH₂-imidazole | ¹H NMR [CDCl3] 2.2–2.7(m, 8H), 4.05(t, 4H), 6.8(d, 1H), 7.0–7.2(m, 3H), 7.25(d, 1H), 7.6(m, 3H), 8.6(d, 1H), 9.7(br, 1H); LR-MS 402 (M + 1) |
| 91. | 3,4,5,6-Tetrahydro-3,10-diaza-benzo[e]azulene-1-carboxylic acid [1-(3-propylamino-propyl)-1H-pyrazol-3-yl]-amide | H | H | H | H | H | 2 | pyrazole-N-CH₂CH₂CH₂NHPr | ¹H NMR(CDCl3): 0.9(t, 3H), 1.50(t, 2H), 1.90–2.30(m, 6H), 2.40–2.70(m, 6H), 4.05(t, 2H), 6.70(d, 1H), 7.10(m, 1H), 7.55(m, 2H), 8.60(d, 2H), 9.80(bs, 1H), 13.6(bs, 1H). |

TABLE 2-continued

| Cmp. # | Name | R3a | R3 | R4 | R5 | R6 | k | Ar | Spectral Data |
|---|---|---|---|---|---|---|---|---|---|
| 92. | 3,4,5,6-Tetrahydro-3,10-diaza-benzo[e]azulene-1-carboxylic acid{1-[3-(cyclopropylmethyl-amino)-propyl]-1H-pyrazol-3-yl}-amide | H | H | H | H | H | 2 | pyrazole with N-propyl-NH-CH2-cyclopropyl | 1H NMR [CDCl3] 0.5(d, 2H), 1.45(d, 2H), 0.95(m, 1H), 2.0–2.8(m, 12H), 4.05(t, 2H), 6.7(d, 1H), 7.1(m, 1H), 7.3(d, 1H), 7.6(m, 2H), 8.6(d, 1H), 9.4(br, 1H); LR-MS 405 (M + 1) |
| 93. | 3,4,5,6-Tetrahydro-3,10-diaza-benzo[e]azulene-1-carboxylic acid(3-methyl-isothiazol-5-yl)-amide | H | H | H | H | H | 2 | 3-methyl-isothiazol-5-yl | 1H NMR(CDCl3): 2.30(t, 2H), 2.40(s, 3H), 2.60(t, 2H), 2.80(t, 2H), 6.62(s, 1H), 7.20(m, 1H), 7.60–7.70(m, 2H), 8.55(dd, 1H), 10.7(bs, 1H). |
| 94. | 3,4,5,6-Tetrahydro-10-aza-benzo[e]azulene-1-carboxylic acid[6-(3-ethylamino-propoxy)-pyridin-2-yl]-amide | H | H | H | H | H | 2 | 6-(3-ethylamino-propoxy)-pyridin-2-yl | LRMS: m/z 404.4 [M − 1] |
| 95. | 3,4,5,6-Tetrahydro-10-aza-benzo[e]azulene-1-carboxylic acid[6-(3-propylamino-propoxy)-pyridin-2-yl]-amide | H | H | H | H | H | 2 | 6-(3-propylamino-propoxy)-pyridin-2-yl | LRMS: m/z 418.3 [M − 1] |
| 96. | 3,4,5,6-Tetrahydro-10-aza-benzo[e]azulene-1-carboxylic acid[6-(3-cyclobutylamino-propoxy)-pyridin-2-yl]-amide | H | H | H | H | H | 2 | 6-(3-cyclobutylamino-propoxy)-pyridin-2-yl | LRMS: m/z 430.4 [M − 1] |
| 97. | 3,4,5,6-Tetrahydro-3,10-diaza-benzo[e]azulene-1-carboxylic acid[6-(3-hydroxy-propoxy)-pyridin-2-yl]-amide | H | H | H | H | H | 2 | 6-(3-hydroxy-propoxy)-pyridin-2-yl | LRMS: m/z 377.3 [M − 1] |

TABLE 2-continued

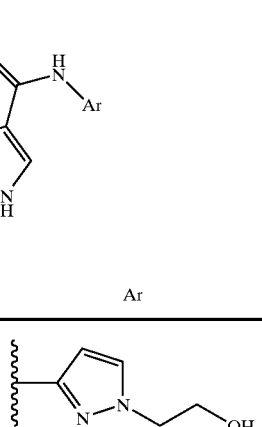

| Cmp. # | Name | R³ᵃ | R³ | R⁴ | R⁵ | R⁶ | k | Ar | Spectral Data |
|---|---|---|---|---|---|---|---|---|---|
| 98. | 3,4,5,6-Tetrahydro-3,10-diaza-benzo[e]azulene-1-carboxylic acid[1-(2-hydroxy-ethyl)-1H-pyrazol-3-yl]-amide | H | H | H | H | H | 2 | 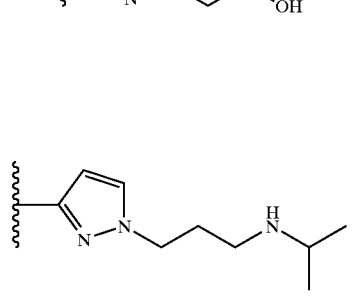 | $^1$H NMR(CDCl3): 2.20(t, 2H), 2.5–2.80(m, 6H), 6.80(s, 1H), 7.15(m, 1H), 7.30(s, 1H), 7.6(m, 2H), 8.55(m, 1H), 9.70(bs, 1H), 13.7(bs, 1H) |
| 99. | 3,4,5,6-Tetrahydro-3,10-diaza-benzo[e]azulene-1-carboxylic acid[1-(3-isopropylamino-propyl)-1H-pyrazol-3-yl]-amide | H | H | H | H | H | 2 | 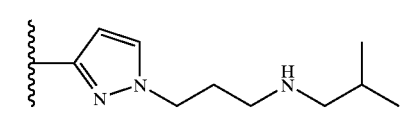 | LRMS calcd 392 found [M − 1] 391 |
| 100. | 3,4,5,6-Tetrahydro-3,10-diaza-benzo[e]azulene-1-carboxylic acid[1-(3-isobutylamino-propyl)-1H-pyrazol-3-yl]-amide | H | H | H | H | H | 2 | 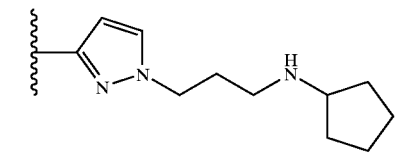 | $^1$H NMR [CDCl3] 0.9(d, 6H), 1.75(M. 1H), 2.0–2.4(M, 6H), 2.4–2.7(m, 6H), 4.05(t, 2H), 6.75(d, 1H), 7.05(m, 1H), 7.25(d, 1H), 7.55–7.6(m, 2H), 8.6(d, 1H), 10.2(br, 1H); LRMS calcd 406 found [M + 1] 407 |
| 101. | 3,4,5,6-Tetrahydro-3,8,10-triaza-benzo[e]azulene-1-carboxylic acid[1-(3-cyclopentylamino-propyl)-1H-pyrazol-3-yl]-amide | H | H | H | H | H | 2 | 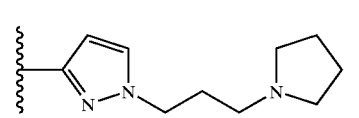 | LRMS calcd 418 found [M + 1] 419 |
| 102. | 3,4,5,6-Tetrahydro-3,8,10-triaza-benzo[e]azulene-1-carboxylic acid [1-(3-pyrrolidin-1-yl-propyl)-1H-pyrazol-3-yl]-amide | H | H | H | H | H | 2 | 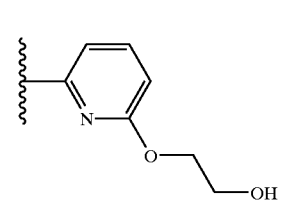 | LRMS calcd 404 found [M + 1] 405 |
| 103. | 3,4,5,6-Tetrahydro-3,10-diaza-benzo[e]azulene-1-carboxylic acid[6-(2-hydroxy-ethoxy)-pyridin-2-yl]-amide | H | H | H | H | H | 2 |  | LRMS: m/z 363.2 [M − 1] |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 104. | 3,4,5,6-Tetrahydro-3,10-diaza-benzo[e]azulene-1-carboxylic acid[6-(2-ethylamino-ethoxy)-pyridin-2-yl]-amide | H | H | H | H | H | 2 | | LRMS: m/z 390.2 [M − 1] |
| 105. | 3,4,5,6-Tetrahydro-3,10-diaza-benzo[e]azulene-1-carboxylic acid[1-(2-cyclobutylamino-ethyl)-6-oxo-1,6-dihydro-pyridin-2-yl]-amide | H | H | H | H | H | 2 | | LRMS: m/z 416.3 [M − 1] |
| 106. | 3,4,5,6-Tetrahydro-3,10-diaza-benzo[e]azulene-1-carboxylic acid[1-(2-ethylamino-ethyl)-1H-pyrazol-3-yl]-amide | H | H | H | H | H | 2 | | ¹H NMR(CDCl3): 1.10(t, 3H), 2.30(t, 2H), 2.50–2.80(m, 6H), 3.05(t, 2H), 4.05(t, 2H), 6.75(d, 1H), 7.10(m, 1H), 7.3(m, 2H), 8.60(d, 2H), 9.15(bs, 1H), 13.7(bs, 1H). |
| 107. | 3,4,5,6-Tetrahydro-3,10-diaza-benzo[e]azulene-1-carboxylic acid[1-(2-propylamino-ethyl)-1H-pyrazol-3-yl]-amide | H | H | H | H | H | 2 | | ¹H NMR(CDCl3): 0.9(t, 3H), 1.50(t, 2H), 2.20(t, 2H), 2.50–2.80(m, 6H), 3.05(t, 2H), 4.05(t, 2H), 6.80(d, 1H), 7.10(m, 1H), 7.30(d, 1H), 7.60(m, 2H), 8.60(d, 1H), 9.90(bs, 1H), 13.7(bs, 1H). |
| 108. | 3,4,5,6-Tetrahydro-3,10-diaza-benzo[e]azulene-1-carboxylic acid[1-(2-tert-butylamino-ethyl)-1H-pyrazol-3-yl]-amide | H | H | H | H | H | 2 | | ¹H NMR(CDCl3): 1.05(s, 9H), 2.25(t, 2H), 2.50–2.70(m, 6H), 3.05(t, 2H), 4.10(t, 2H), 6.75(d, 1H), 7.10(m, 1H), 7.30(d, 1H), 7.60(m, 2H), 8.60(d, 1H), 9.50(bs, 1H), 13.7(bs, 1H). |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 109. | 3,4,5,6-Tetrahydro-3,10-diaza-benzo[e]azulene-1-carboxylic acid[1-(2-pyrrolidin-1-yl-ethyl)-1H-pyrazol-3-yl]-amide | H | H | H | H | H | 2 | pyrazole with N-CH₂CH₂-pyrrolidine | ¹H NMR(CDCl3): 1.75(m, 4H), 2.25(t, 2H), 2.50–2.70(m, 6H), 2.95(t, 2H), 4.20(t, 2H), 6.75(d, 1H), 7.10(m, 1H), 7.30(d, 1H), 7.60(m, 2H), 8.60(d, 1H), 9.90(bs, 1H), 13.65(bs, 1H). |
| 110. | 3,4,5,6-Tetrahydro-3,10-diaza-benzo[e]azulene-1-carboxylic acid[2-(2-hydroxy-ethoxy)-pyridin-3-yl]-amide | H | H | H | H | H | 2 | 2-(2-hydroxyethoxy)pyridin-3-yl | LRMS calcd 364.4 found [M − 1] 363.0 |
| 111. | 3,4,5,6-Tetrahydro-3,10-diaza-benzo[e]azulene-1-carboxylic acid[1-(2-ethylamino-ethyl)-2-oxo-1,2-dihydro-pyridin-3-yl]-amide | H | H | H | H | H | 2 | 1-(2-ethylaminoethyl)-2-oxo-1,2-dihydropyridin-3-yl | LRMS calcd 391.5 found [M − 1] 390.2 |
| 112. | 3,4,5,6-Tetrahydro-3,10-diaza-benzo[e]azulene-1-carboxylic acid[1-(3-tert-butylamino-propyl)-1H-pyrazol-3-yl]-amide | H | H | H | H | H | 2 | pyrazole with N-CH₂CH₂CH₂-NH-tBu | ¹H NMR(CDCl3): 1.05(s, 9H), 2.25(t, 2H), 2.50–2.70(m, 6H), 3.05(t, 2H, 4.10(t, 2H), 6.75(d, 1H), 7.10(m, 1H), 7.30(d, 1H, 7.60(m, 2H), 8.60(d, 1H), 9.50(bs, 1H), 13.7(bs, 1H). |

TABLE 2-continued

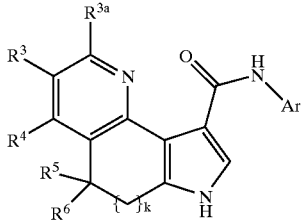

| Cmp. # | Name | R$^{3a}$ | R$^3$ | R$^4$ | R$^5$ | R$^6$ | k | Ar | Spectral Data |
|---|---|---|---|---|---|---|---|---|---|
| 113. | 3,4,5,6-Tetrahydro-3,10-diaza-benzo[e]azulene-1-carboxylic acid[1-(2-tert-butylamino-ethyl)-2-oxo-1,2-dihydro-pyridin-3-yl]-amide | H | H | H | H | H | 2 | 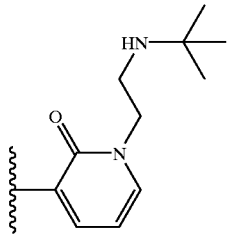 | $^1$H NMR(CDCl3) 1.39(s, 9H); 2.22(m, 2H); 2.59(t, 2H; 2.67(t, 2H); 3.42(t, 2H); 4.50(t, 2H); 6.11(t, 1H); 7.12(m, 2H); 7.58(dd, 1H); 7.70(d, 1H); 8.36(d, 1H); 8.80(dd, 1H); 9.42(br s, 1H |
| 114. | 3,4,5,6-Tetrahydro-3,10-diaza-benzo[e]azulene-1-carboxylic acid[2-oxo-1-(2-propylamino-ethyl)-1,2-dihydro-pyridin-3-yl]-amide | H | H | H | H | H | 2 | | $^1$H NMR(CDCl3) 0.91(t, 3H); 1.58(m, 2H); 2.22(m, 2H); 2.60(m, 6H; 3.10(t, 2H); 4.20(t, 2H); 6.18(t, 1H); 7.00(dd, 1H); 7.10(dd, 1H); 7.58(m, 2H); 8.59(d, 1H); 8.82(d, 1H); 9.20(br s, 1H); 13.28(br s, 1H); LRMS calcd 405.5 found [M − 1] 404.3 |
| 115. | 3,4,5,6-Tetrahydro-3,10-diaza-benzo[e]azulene-1-carboxylic acid[6-(3-butylamino-propoxy)-pyridin-2-yl]-amide | H | H | H | H | H | 2 | 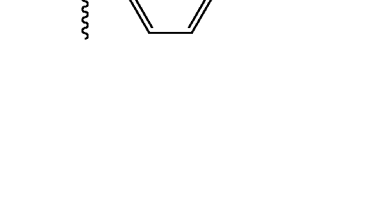 | $^1$H NMR [CDCl3] 0.85(t, 3H), 1.3(t, 2H), 1.47(t, 2H), 1.9(t, 2H), 2.2(t, 2H), 2.49–2.57(m, 2H), 2.6(t, 2H), 2.8(t, 2H), 3.0–3.5(m, 2H), 4.36(s, 2H), 6.4(d, 1H), 7.26(t, 1H), 7.5(s, 1H), 7.6(t, 1H), 7.8(d, 1H), 8.6(d, 1H); LRMS: m/z 432.5 [M − 1] |

TABLE 2-continued

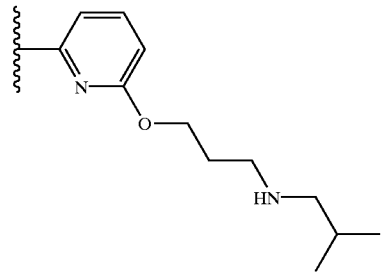

| Cmp. # | Name | $R^{3a}$ | $R^3$ | $R^4$ | $R^5$ | $R^6$ | k | Ar | Spectral Data |
|---|---|---|---|---|---|---|---|---|---|
| 116. | 3,4,5,6-Tetrahydro-3,10-diaza-benzo[e]azulene-1-carboxylic acid[6-(3-isobutylamino-propoxy)-pyridin-2-yl]-amide | H | H | H | H | H | 2 | 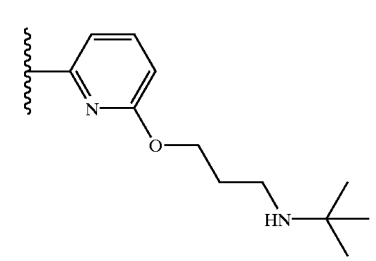 | LRMS: m/z 432.4 [M − 1] |
| 117. | 3,4,5,6-Tetrahydro-3,10-diaza-benzo[e]azulene-1-carboxylic acid[6-(3-tert-butylamino-propoxy)-pyridin-2-yl]-amide | H | H | H | H | H | 2 | 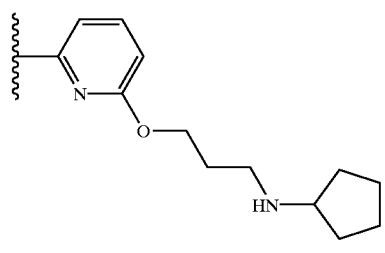 | LRMS: m/z 432.4 [M − 1] |
| 118. | 3,4,5,6-Tetrahydro-3,10-diaza-benzo[e]azulene-1-carboxylic acid[6-(3-cyclopentylamino-propoxy)-pyridin-2-yl]-amide | H | H | H | H | H | 2 | 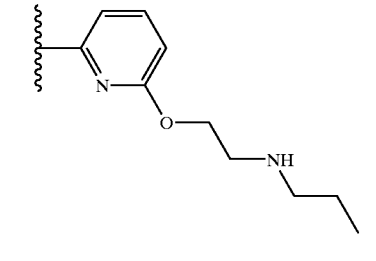 | LRMS: m/z 444.3 [M − 1] |
| 119. | 3,4,5,6-Tetrahydro-3,10-diaza-benzo[e]azulene-1-carboxylic acid[6-(2-propylamino-ethoxy)-pyridin-2-yl]-amide | H | H | H | H | H | 2 | 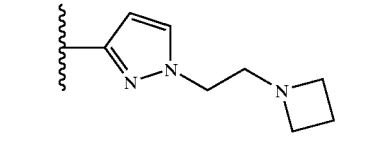 | LRMS: m/z 405.0 [M − 1] |
| 120. | 3,4,5,6-Tetrahydro-3,10-diaza-benzo[e]azulene-1-carboxylic acid[1-(2-azetidin-1-yl-ethyl)-1H-pyrazol-3-yl]-amide | H | H | H | H | H | 2 |  | $^1$H NMR(CDCl3): 2.0(t, 2H), 2.25(m, 2H), 2.6(tt, 4H), 2.9(t, 2H), 3.2(t, 4H), 4.05(t, 2H), 6.75(d, 1H), 7.10(m, 1H), 7.3(m, 2H), 8.60(d, 2H), 9.6(bs, 1H), 13.6(bs, 1H). |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 121. | 3,4,5,6-Tetrahydro-3,10-diaza-benzo[e]azulene-1-carboxylic acid[1-(2-diethylamino-ethyl)-1H-pyrazol-3-yl]-amide | H | H | H | H | H | 2 | pyrazole with N-CH₂CH₂-N(Et)₂ substituent | ¹NMR(CDCl3): 1.0(t, 6H), 2.20(t, 2H), 2.50–2.80(m, 6H), 2.9(t, 2H), 4.1(t, 2H), 6.75(d, 1H), 7.10(m, 1H), 7.3(m, 2H), 8.60(d, 2H), 9.6(bs, 1H), 13.6(bs, 1H). |
| 122. | 3,4,5,6-Tetrahydro-3,10-diaza-benzo[e]azulene-1-carboxylic acid(2-oxo-1,2-dihydro-pyridin-3-yl)-amide | H | H | H | H | H | 2 | 2-oxo-1,2-dihydropyridin-3-yl | ¹H NMR (CDCl3) 2.13(m, 2H); 2.46(m, 4H); 6.18(t, 1H); 6.84(dd, 1H); 6.98(dd, 1H); 7.40(s, 1H); 7.48(dd, 1H0; 8.49(dd, 1H); 8.60(dd, 1H) |
| 123. | 3,4,5,6-Tetrahydro-3,10-diaza-benzo[e]azulene-1-carboxylic acid[1-(2-cyclobutylamino-ethyl)-2-oxo-1,2-dihydro-pyridin-3-yl]-amide | H | H | H | H | H | 2 | 1-(2-cyclobutylaminoethyl)-2-oxo-1,2-dihydropyridin-3-yl | LRMS calcd 417.5 found [M − 1] 416.3 |
| 124. | 3,4,5,6-Tetrahydro-3,10-diaza-benzo[e]azulene-1-carboxylic acid[2-(3-benzyloxy-propoxy)-pyridin-3-yl]-amide | H | H | H | H | H | 2 | 2-(3-benzyloxypropoxy)pyridin-3-yl | ¹H NMR(CDCl3) 2.12(m, 2H); 2.22(m, 2H); 2.63(m, 4H); 3.58(t, 2H); 4.24(s, 2H); 4.62(t, 2H); 6.84(dd, 1H); 7.05(dd, 1H); 7.31(m, 5H); 7.59(dd, 1H); 7.62(d, 1H); 7.83(dd, 1H); 8.58(dd, 1H); 8.63(dd, 1H); 9.84(br s, 1H); LRMS calcd 468.6 found [M − 1] 467.4 |

TABLE 2-continued

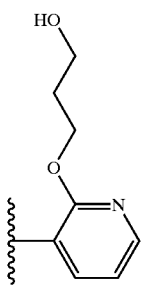

| Cmp. # | Name | R3a | R3 | R4 | R5 | R6 | k | Ar | Spectral Data |
|---|---|---|---|---|---|---|---|---|---|
| 125. | 3,4,5,6-Tetrahydro-3,10-diaza-benzo[e]azulene-1-carboxylic acid[2-(3-hydroxy-propoxy)-pyridin-3-yl]-amide | H | H | H | H | H | 2 | 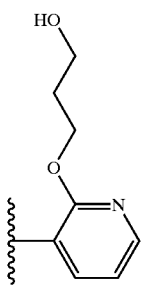 | 1H NMR(DMSO-d6) 1.85(m, 2H); 2.19(m, 2H); 2.57(m, 4H); 3.45(m, 2H); 4.48(m, 2H); 6.91(m, 1H); 7.22(m, 1H); 7.43(s, 1H); 7.78(m, 2H); 8.51(m, 2H); 11.60(br s, 1H); 12.42(br s, 1H) |
| 126. | 3,4,5,6-Tetrahydro-3,10-diaza-benzo[e]azulene-1-carboxylic acid[1-(3-diethylamino-propyl)-1H-pyrazol-3-yl]-amide | H | H | H | H | H | 2 | 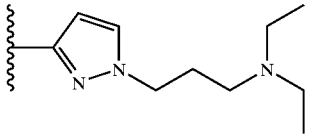 | 1H NMR (CDCl3): 1.05(t, 6H), 2.05(t, 2H), 2.25(t, 2H), 2.40–2.80(m, 8H), 4.10(t, 2H), 6.75(d, 1H), 7.10(m, 1H), 7.30(d, 1H), 7.60(m, 2H), 8.60(d, 1H), 9.30(bs, 1H), 13.55(bs, 1H). |
| 127. | 3,4,5,6-Tetrahydro-3,8,10-triaza-benzo[e]azulene-1-carboxylic acid[1-(3-piperidin-1-yl-propyl)-1H-pyrazol-3-yl]-amide | H | H | H | H | H | 2 | 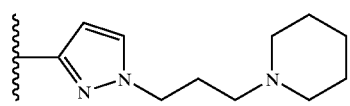 | 1H NMR [CDCl3] 1.45(m, 2H), 1.6(m, 4H), 2.0–2.7(m, 14H, 4.05(t, 2H), 6.75(d, 1H), 7.05(m, 1H), 7.3(d, 1H), 7.6(m, 2H), 8.6(d, 1H), 10.2(br, 1H); LRMS 417(M − 1) |
| 128. | 3,4,5,6-Tetrahydro-3,10-diaza-benzo[e]azulene-1-carboxylic acid[1-(3-diethylamino-propyl)-2-oxo-1,2-dihydro-pyridin-3-yl]-amide | H | H | H | H | H | 2 | 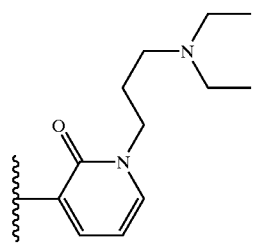 | LRMS calcd 433.6 found [M + 1] 434.1 |

TABLE 2-continued

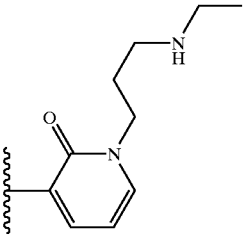

| Cmp. # | Name | R³ᵃ | R³ | R⁴ | R⁵ | R⁶ | k | Ar | Spectral Data |
|---|---|---|---|---|---|---|---|---|---|
| 129. | 3,4,5,6-Tetrahydro-3,10-diaza-benzo[e]azulene-1-carboxylic acid[1-(3-ethylamino-propyl)-2-oxo-1,2-dihydro-pyridin-3-yl]-amide | H | H | H | H | H | 2 | 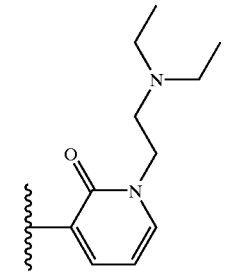 | ¹H NMR(CDCl3) 1.13(t, 3H); 2.00, m, 2H); 2.24(m, 2H); 2.62(M, 6H); 4.13(t, 2H); 6.20(t, 1H); 6.97(dd, 1H); 7.12(m, 1H); 7.58(d, 1H); 7.60(s, 1H); 8.62(d, 1H); 8.90(d, 1H); 13.26(br s, 1H) |
| 130. | 3,4,5,6-Tetrahydro-3,10-diaza-benzo[e]azulene-1-carboxylic acid[1-(2-diethylamino-ethyl)-2-oxo-1,2-dihydro-pyridin-3-yl]-amide | H | H | H | H | H | 2 | 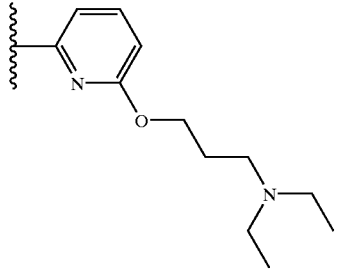 | ¹H NMR(CDCl3) 1.00(t, 6H); 2.18(m, 2H); 2.57(m, 8H); 2.79(m, 2H); 4.02(m, 2H); 6.17(t, 1H); 6.97(d, 1H0; 7.08(m, 1H); 7.57(m, 2H); 8.62(d, 1H); 8.87(d, 1H0; 9.73(br s, 1H0; 13.30(br s, 1H; |
| 131. | 3,4,5,6-Tetrahydro-10-aza-benzo[e]azulene-1-carboxylic acid[6-(3-diethylamino-propoxy)-pyridin-2-yl]-amide | H | H | H | H | H | 2 | 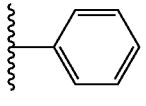 | LRMS: m/z 432.4 [M − 1] |
| 132. | 3,4,5,6-Tetrahydro-3,10-diaza-benzo[e]azulene-1-carboxylic acid phenylamide | H | H | H | H | H | 2 |  | ¹H NMR(CDCl3): 2.3(t, 2H), 2.6(m, 4H), 7.10(m, 1H), 7.0–7.2(m, 2H), 7.30(t, 2H), 7.60–7.8(m, 4H), 8.60(d, 1H), 8.8(bs, 1H), 13.9(bs, 1H); LCMS found (M + H) 304 |

TABLE 2-continued

| Cmp. # | Name | R³ᵃ | R³ | R⁴ | R⁵ | R⁶ | k | Ar | Spectral Data |
|---|---|---|---|---|---|---|---|---|---|
| 133. | 3,4,5,6-Tetrahydro-3,10-diaza-benzo[e]azulene-1-carboxylic acid[1-(3-azetidin-1-yl-propyl)-1H-pyrazol-3-yl]-amide | H | H | H | H | H | 2 | | ¹H NMR [CDCl3] 1.8–2.7(m, 14H), 3.05(m, 2H), 4.05(t, 2H), 6.75(d, 1H), 7.1–7.8(m, 4H), 8.6(M, 1H), 9.8(br, 1H); LRMS found [M + 1] 391 |
| 134. | 3,4,5,6-Tetrahydro-10-aza-benzo[e]azulene-1-carboxylic acid[6-(3-pyrrolidin-1-yl-propoxy)-pyridin-2-yl]-amide | H | H | H | H | H | 2 | | LRMS calcd 431.5 found [M − 1] 430.4 |
| 135. | 3,4,5,6-Tetrahydro-3,10-diaza-benzo[e]azulene-1-carboxylic acid [1-(2-morpholin-4-yl-ethyl)-2-oxo-1,2-dihydro-pyridin-3-yl]-amide | H | H | H | H | H | 2 | | LRMS calcd 433.5 found [M + 1] 434.5 |
| 136. | 3,4,5,6-Tetrahydro-3,10-diaza-benzo[e]azulene-1-carboxylic acid [1-(2-azetidin-1-yl-ethyl)-2-oxo-1,2-dihydro-pyridin-3-yl]-amide | H | H | H | H | H | 2 | | LRMS calcd 403.4 found [M + 1] 404.4 |

TABLE 2-continued

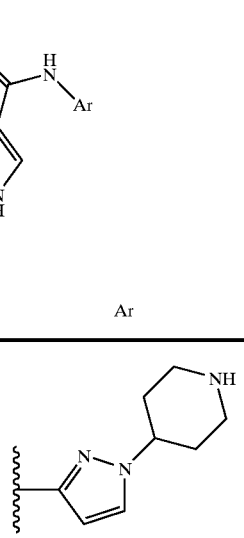

| Cmp. # | Name | R³ᵃ | R³ | R⁴ | R⁵ | R⁶ | k | Ar | Spectral Data |
|---|---|---|---|---|---|---|---|---|---|
| 137. | 3,4,5,6-Tetrahydro-3,10-diaza-benzo[e]azulene-1-carboxylic acid (1-piperidin-4-yl-1H-pyrazol-3-yl)-amide | H | H | H | H | H | 2 | 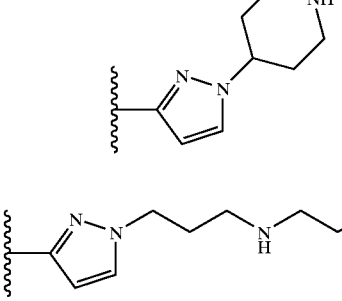 | MS m/z [M − 1] 375 |
| 138. | 3,4,5,6-Tetrahydro-3,10-diaza-benzo[e]azulene-1-carboxylic acid {1-[3-(2-methoxy-ethylamino)-propyl]-1H-pyrazol-3-yl}-amide | H | H | H | H | H | 2 | 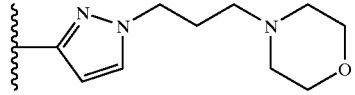 | ¹H NMR [CDCl3] 2.0–2.2(m, 4H), 2.5–2.8(m, 8H), 3.35(t, 2H), 3.5(t, 2H), 4.05(t, 2H), 6.75(d, 1H), 7.1(m, 1H), 7.25(d, 1H), 7.6(m, 2H), 8.6(d, 1H), 10.0(br, 1H) |
| 139. | 3,4,5,6-Tetrahydro-3,10-diaza-benzo[e]azulene-1-carboxylic acid [1-(3-morpholin-4-yl-propyl)-1H-pyrazol-3-yl]-amide | H | H | H | H | H | 2 | 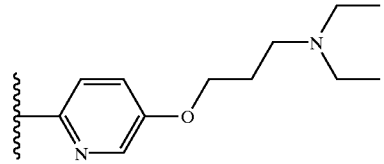 | ¹H NMR [CDCl3] 2.0–2.3(m, 6H), 2.4(m, 4H), 2.5–2.7(m, 4H), 3.7(m, 4H), 4.05(t, 2H), 6.75(d, 1H), 7.1(m, 1H), 7.25(d, 1H), 7.6(m, 2H), 8.6(d, 1H), 10.5(br, 1H) |
| 140. | 3,4,5,6-Tetrahydro-3,10-diaza-benzo[e]azulene-1-carboxylic acid [5-(3-diethylamino-propoxy)-pyridin-2-yl]-amide | H | H | H | H | H | 2 | 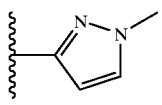 | |
| 141. | 8-Methyl-3,4,5,6-tetrahydro-3,10-diaza-benzo[e]azulene-1-carboxylic acid (1-methyl-1H-pyrazol-3-yl)-amide | H | CH₃ | H | H | H | 2 |  | |

Example 6

3-Methyl-3,4,5,6-tetrahydro-3,10-diaza-benzo[e]azulene-1-carboxylic acid ethyl ester

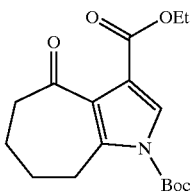

Step 1:

To a solution of 4-oxo-1,4,5,6,7,8-hexahydro-cyclohepta[b]pyrrole-3-carboxylic acid ethyl ester (4.80 g, 21.7 mmol) and Et$_3$N (3.93 mL, 28.2 mmol) in CH$_2$Cl$_2$(40 mL) at 0° C. is added Boc$_2$O (5.68 g, 26.0 mmol) in one portion. The reaction mixture is allowed to stir at 0° C. for 10 min. and then at room temperature for 18 h. The reaction mixture is then diluted with half saturated aq NH$_4$Cl (70 mL) and extracted with EtOAc. The organic layer is then washed with H$_2$O (50 mL) and brine (50 mL). The aqueous washes are reextracted once with EtOAc, and the combined extracts are dried over Na$_2$SO$_4$ and concentrated. The crude material is purified by flash chromatography on silica gel. Elution with 4:1 hexanes-ethyl acetate followed by 3:1 hexanes-ethyl acetate afforded 7.00 g (quant) of 4-oxo-5,6,7,8-tetrahydro-4H-cyclohepta[b]pyrrole-1,3-dicarboxylic acid 1-tert-butyl ester 3-ethyl ester as a light yellow solid. $^1$H NMR (CDCl$_3$, 300 MHz) δ7.62 (s, 1H), 4.27 (q, J=7.2 Hz, 2H), 3.22 (m, 2H), 2.78 (m, 2H), 1.86 (m, 4H), 1.60 (s, 9H), 1.31 (t, J=7.2 Hz)

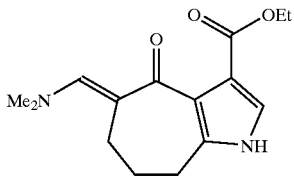

Step 2:

A mixture of 4-oxo-5,6,7,8-tetrahydro-4H-cyclohepta[b]pyrrole-1,3-dicarboxylic acid 1-tert-butyl ester 3-ethyl ester (1.13 g, 3.52 mmol) and tris(dimethylamino)methane (1.02 g, 7.04 mmol) is stirred at 60° C. in a sealed tube for 4.5 h. After cooling, the thick slurry is taken up in Et$_2$O and filtered. The solid is washed with Et$_2$O and dried, affording 847 mg (87%) of 5-dimethylaminomethylene-4-oxo-1,4,5,6,7,8-hexahydro-cyclohepta[b]pyrrole-3-carboxylic acid ethyl ester as a light yellow-orange solid. $^1$H NMR (CDCl$_3$, 300 MHz) δ9.93 (br s, 1H), 7.58 (s, 1H), 7.12 (d, J=2.7 Hz, 1H), 4.21 (q, J=7.2 Hz, 2H), 3.06 (s, 6H), 2.68 (m, 2H), 2.47 (m, 2H), 1.80 (m, 2H), 1.26 (t, J=7.2 Hz, 3H).

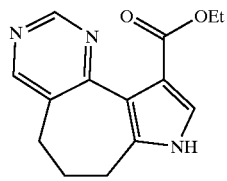

Step 3:

A mixture of 5-dimethylaminomethylene-4-oxo-1,4,5,6,7,8-hexahydro-cyclohepta [b]pyrrole-3-carboxylic acid ethyl ester (840 mg) and formamidine acetate (956 mg, 9.1 mmol) in EtOH (10 mL) is stirred at 120° C. for 4 h. After cooling, the reaction mixture is diluted with CH$_2$Cl$_2$ and washed with half saturated aq NaHCO$_3$ (25 mL), H$_2$O (25 mL), and brine (25 mL) The aqueous washes are reextracted once with CH$_2$Cl$_2$, and the combined extracts are dried over K$_2$CO$_3$ and concentrated. The crude material is purified by flash chromatography on silica gel. Elution with 30:1 CHCl$_3$-MeOH followed by 20:1 CHCl$_3$-MeOH and finally 15:1 CHCl$_3$-MeOH afforded 606 mg (77%) of 3,4,5,6-tetrahydro-3,8,10-triaza-benzo[e]azulene-1-carboxylic acid ethyl ester as a light yellow solid. $^1$H NMR (CDCl$_3$, 300 MHz) δ9.30 (br s, 1H), 9.02 (s, 1H), 8.43 (s, 1H), 7.24 (d, J=2.7 Hz, 1H), 4.26 (q, J=7.2 Hz, 2H), 2.78 (t, J=7.2 Hz, 2H) 2.70 (m, 2H), 2.12 (m, 2H), 1.26 (t, J=7.2 Hz, 3H).

Example 7

3,4,5,6-Tetrahydro-3,8,10-triaza-benzo[e]azulene-1-carboxylic acid 2-fluoro-phenyl-amide

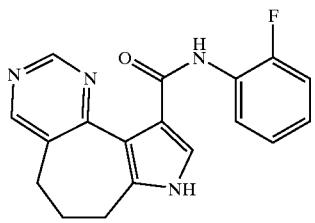

To a solution of 2-fluoroaniline (108 mg, 0.972 mmol, in CH$_2$Cl$_2$ (2.0 mL) at 0° C. under N is slowly added AlMe$_3$ (0.49 mL, 2.0 M in toulene). The resulting solution is stirred at room temperature for 1 h. Next 3,4,5,6-tetrahydro-3,8,10-triaza-benzo[e]azulene-1-carboxylic acid ethyl ester (50 mg, 0.194 mmol) is added in one portion. The resulting mixture is then stirred at reflux for 2 h. After cooling the reaction mixture is carefully diluted with saturated aq NH$_4$Cl (~5 mL and some H$_2$O. The mixture is stirred vigorously for 15 min. and then extracted three times with CH$_2$Cl$_2$. The combined extracts are dried over K$_2$CO$_3$ and concentrated. The crude material is purified by flash chromatography on silica gel. Elution with 40:1 CHCl$_3$—MeOH followed by 30:1 CHCl$_3$-MeOH and finally 20:1 CHCl$_3$—MeOH afforded 45 mg (72%) of 3,4,5,6-tetrahydro-3,8,10-triaza-benzo[e]azulene-1-carboxylic acid 2-fluoro-phenyl-amide as a light yellow solid. Electrospray mass spectrum: m/z 321 [M−1].

Example 7a

3-Methyl-4,5,6,7-tetrahydro-1-oxa-2,7-diaza-cyclopenta[e]azulene-9-carboxcylic acid ethyl ester

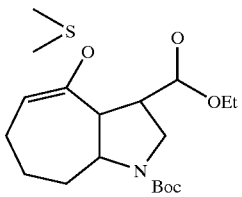

Step 1:

To a mixture of 4-oxo-5,6,7,8-tetrahydro-4H-cyclohepta[b]pyrrole-1,3-dicarboxylic acid 1-tert-butyl ester 3-ethyl ester (4.6 mmol), sodium iodide (9.3 mmol), and triethylamine (13.9 mmol) in 15 mL acetonitrile is added trimethylsilyl chloride (9.3 mmol). After stirring at RT for 2 hours it is quenched with 20 mL saturated NaHCO$_3$ solution and extracted several times with EtOAc. The combined organic layers are dried over Na$_2$SO$_4$ and evaporated in vacuo yielding 4-trimethylsilanyloxy-7,8-dihydro-6H-cyclohepta[b]pyrrole-1,3-dicarboxylic acid 1-tert-butyl ester 3-ethyl ester as a brown oil (95%). $^1$H NMR (CDCl$_3$) 0.15 (s, 9H), 1.32 (t, 3H), 1.60 (s, 9H), 1.83–1.97 (m, 2H), 1.99–2.06 (m, 2H), 3.00 (t, 2H), 4.33 (q, 2H), 5.40 (t, 1H), 7.62 (s, 1H)

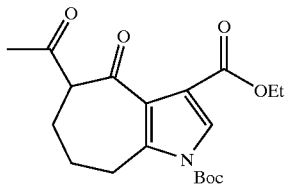

Step 2:

Bismuth (III) chloride (0.1 mmol) and sodium iodide (0.3 mmol) are transferred to a dried flask under nitrogen and 5 mL of a mixture of CH$_2$Cl$_2$/ether (9/1) is added by a syringe. This is followed by the addition of acetyl chloride (2.2 mmol) and the suspension is stirred for 5 min at RT. 4-trimethylsilanyloxy-7,8-dihydro-6H-cyclohepta[b]pyrrole-1,3-dicarboxylic acid 1-tert-butyl ester 3-ethyl ester (2 mmol) in 5 mL of the same solvent mixture is added. After 2 hours at RT, the mixture is quenched with 20 mL saturated NaHCO$_3$ solution and extracted several times with CH$_2$Cl$_2$. The organic layers are combined, dried over Na$_2$SO$_4$ and evaporated in vacuo yielding 5-acetyl-4-oxo-5,6,7,8-tetrahydro-4H-cyclohepta[b]pyrrole-1,3-dicarboxylic acid 1-tert-butyl ester 3-ethyl ester as an oil (86%). LRMS 363.4 found (M+1) 364.2

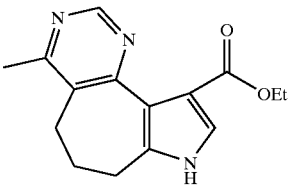

Step 3:

In a sealed tube are 5-acetyl-4-oxo-5,6,7,8-tetrahydro-4H-cyclohepta[b]pyrrole-1,3-dicarboxylic acid 1-tert-butyl ester 3-ethyl ester (1.1 mmol) and formamidine acetate (5.5 mmol) and 10 mL EtOH. The mixture is heated at 120° C. for 48 hours. The solvent is evaporated in vacuo and the residue is taken up in CH$_2$Cl$_2$ and washed two times with NaHCO$_3$ (aq). The organic layer is dried over Na$_2$SO$_4$ and evaporated in vacuo and the residue chromatographed using 10% MeOH in CH$_2$Cl$_2$ as mobile phase to yield 7-Methyl-3,4,5,6-tetrahydro-3,8,10-triaza-benzo[e]azulene-1-carboxylic acid ethyl ester (36%). LRMS 271.1 found (M+1) 272

Example 7b

Using the methods shown in Scheme 4 and further illustrated in Examples 6 and 7–7a the following compounds shown in Table 3 were synthesized.

TABLE 3

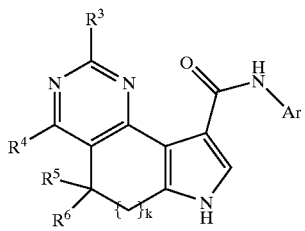

| Cmp # | Name | R$^3$ | R$^4$ | R$^5$ | R$^6$ | k | Ar | Spectral Data |
|---|---|---|---|---|---|---|---|---|
| 1 | 3,4,5,6-Tetrahydro-3,8,10-triaza-benzo[e]azulene-1-carboxylic acid (5-ethoxy-pyridin-2-yl)-amide | H | H | H | H | 2 | pyridine-O-CH$_3$ | Electrospray mass spectrum: m/z 348 [M − 1] |
| 2 | 3,4,5,6-Tetrahydro-3,8,10-triaza-benzo[e]azulene-1-carboxylic acid (5-n-propoxy-pyridin-2-yl)-amide | H | H | H | H | 2 | pyridine-O-CH$_2$CH$_3$ | LRMS calcd 363 found [M + 1] 364 |

TABLE 3-continued

| Cmp # | Name | R³ | R⁴ | R⁵ | R⁶ | k | Ar | Spectral Data |
|---|---|---|---|---|---|---|---|---|
| 3 | 3,4,5,6-Tetrahydro-3,8,10-triaza-benzo[e]azulene-1-carboxylic acid (4-ethoxy-phenyl)-amide | H | H | H | H | 2 | 4-ethoxyphenyl | Electrospray mass spectrum: m/z 347 [M − 1] |
| 4 | 3,4,5,6-Tetrahydro-3,8,10-triaza-benzo[e]azulene-1-carboxylic acid (4-fluoro-phenyl)-amide | H | H | H | H | 2 | 2-fluorophenyl | |
| 5 | 3,4,5,6-Tetrahydro-3,8,10-triaza-benzo[e]azulene-1-carboxylic acid [4-(2-propylamino-ethoxy)-phenyl]-amide | H | H | H | H | 2 | 4-(2-propylamino-ethoxy)-phenyl | LRMS calcd 405 found [M + 1] 406 |
| 6 | 3,4,5,6-Tetrahydro-3,8,10-triaza-benzo[e]azulene-1-carboxylic acid (5-methyl-oxazol-2-yl)-amide | H | H | H | H | 2 | 5-methyl-oxazol-2-yl | LCMS found (M + H) 336 |
| 7 | 3,4,5,6-Tetrahydro-3,8,10-triaza-benzo[e]azulene-1-carboxylic acid (3-ethoxy-phenyl)-amide | H | H | H | H | 2 | 3-ethoxyphenyl | LCMS found (M + H) 349 |
| 8 | 3,4,5,6-Tetrahydro-3,8,10-triaza-benzo[e]azulene-1-carboxylic acid (3-propyl-[1,2,4]thiadiazol-5-yl)-amide | H | H | H | H | 2 | 3-propyl-[1,2,4]thiadiazol-5-yl | LCMS found (M + H) 355 |

TABLE 3-continued

| Cmp # | Name | R³ | R⁴ | R⁵ | R⁶ | k | Ar | Spectral Data |
|---|---|---|---|---|---|---|---|---|
| 9 | 3,4,5,6-Tetrahydro-3,8,10-triaza-benzo[e]azulene-1-carboxylic acid (6-ethoxy-pyridin-3-yl)-amide | H | H | H | H | 2 | 6-ethoxy-pyridin-3-yl | LRMS 349.39 found (M + 1) 350.3 |
| 10 | 3,4,5,6-Tetrahydro-3,8,10-triaza-benzo[e]azulene-1-carboxylic acid (5-methyl-[1,3,4]thiadiazol-2-yl)-amide | H | H | H | H | 2 | 5-methyl-[1,3,4]thiadiazol-2-yl | Electrospray mass spectrum: m/z 325 [M − 1] |
| 11 | 3,4,5,6-Tetrahydro-3,8,10-triaza-benzo[e]azulene-1-carboxylic acid (6-ethylamino-pyridin-3-yl)-amide | H | H | H | H | 2 | 6-ethylamino-pyridin-3-yl | LRMS calcd 348 found [M + 1] 349 |
| 12 | 3,4,5,6-Tetrahydro-3,8,10-triaza-benzo[e]azulene-1-carboxylic acid (3-fluoro-phenyl)-amide | H | H | H | H | 2 | 3-fluoro-phenyl | ¹H NMR [CDCl3] 2.3(quint, 2H), 2.6(t, 2H), 2.8(t, 2H), 6.8(app s, 1H), 7.3(m, 2H), 7.7(s, 1H), 7.8(d, 1H), 8.6(s, 1H), 9.2(s, 1H), 10.4(br s, 1H), 13.0(s, 1H); LRMS calcd 322 found [M + 1] 323 |
| 13 | 3,4,5,6-Tetrahydro-3,8,10-triaza-benzo[e]azulene-1-carboxylic acid (3-methoxy-phenyl)-amide | H | H | H | H | 2 | 3-methoxy-phenyl | ¹H NMR [CDCl3] 2.3(quint, 2H), 2.6(t, 2H), 2.8(t, 2H), 3.8(s, 3H), 6.6(d, 1H), 7.2(m, 2H), 7.6(s, 1H), 7.7(s, 1H), 8.6(s, 1H), 9.2(s, 1H), 10.4(br s, 1H), 12.9(s, 1H) |
| 14 | 3,4,5,6-Tetrahydro-3,8,10-triaza-benzo[e]azulene-1-carboxylic acid o-tolyl-amide | H | H | H | H | 2 | o-tolyl | ¹H NMR [CDCl3] 2.3(quint, 2H), 2.4(s, 3H), 2.6(app t, 4H), 7.1(t, 1H), 7.2(m, 2H), 7.65(s, 1H), 7.75(s, 1H), 8.6(s, 1H), 9.0(s, 1H), 10.5(br s, 1H), 12.2(s, 1H); LRMS calcd 318 found [M + 1] 319 |

TABLE 3-continued

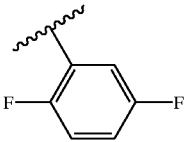

| Cmp # | Name | R³ | R⁴ | R⁵ | R⁶ | k | Ar | Spectral Data |
|---|---|---|---|---|---|---|---|---|
| 15 | 3,4,5,6-Tetrahydro-3,8,10-triaza-benzo[e]azulene-1-carboxylic acid (2,5-difluoro-phenyl)-amide | H | H | H | H | 2 | 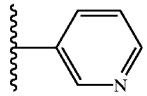 | ¹H NMR [CDCl3] 2.3(quint, 2H), 2.6(t, 2H), 2.8(t, 2H), 6.7(m, 1H), 7.05(m, 1H), 7.75(s, 1H), 8.45(m, 1H), 8.6(s, 1H), 9.2(s, 1H), 10.0(br s, 1H), 13.4(s, 1H); Electrospray mass spectrum: m/z 339 [M − 1] |
| 16 | 3,4,5,6-Tetrahydro-3,8,10-triaza-benzo[e]azulene-1-carboxylic acid pyridin-3-ylamide | H | H | H | H | 2 | 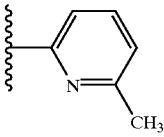 | ¹H NMR [CDCl3 + CD3OD] 2.3(quint, 2H), 2.6(t, 2H), 2.8(t, 2H), 7.3(m, 2H), 7.6(s, 1H), 8.3(m, 2H), 8.6(s, 1H), 8.8(s, 1H), 9.2(s, 1H) |
| 17 | 3,4,5,6-Tetrahydro-3,8,10-triaza-benzo[e]azulene-1-carboxylic acid (6-methyl-pyridin-2-yl)-amide | H | H | H | H | 2 | 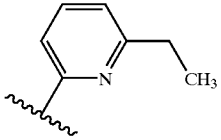 | ¹H NMR [CDCl3] 2.3(quint, 2H), 2.5(s, 3H), 2.6(t, 2H), 2.8(t, 2H), 6.85(d, 1H), 7.6(t, 1H), 7.7(s, 1H), 8.2(d, 1H), 8.6(s, 1H), 9.3(s, 1H), 9.6(br s, 1H) |
| 18 | 3,4,5,6-Tetrahydro-3,8,10-triaza-benzo[e]azulene-1-carboxylic acid (6-ethyl-pyridin-2-yl)-amide | H | H | H | H | 2 | 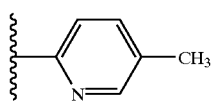 | ¹H NMR [CDCl3] 1.3(t, 3H), 2.3(quint, 2H), 2.6(t, 2H), 2.8(m, 4H), 6.8(d, 1H), 7.5(t, 1H), 7.6(s, 1H), 8.1(d, 1H), 8.5(s, 1H), 9.2(s, 1H) |
| 19 | 3,4,5,6-Tetrahydro-3,8,10-triaza-benzo[e]azulene-1-carboxylic acid (5-methyl-pyridin-2-yl)-amide | H | H | H | H | 2 | 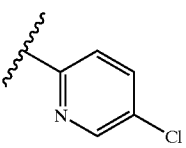 | ¹H NMR [CDCl3] 2.2(s, 3H), 2.3(quint, 2H), 2.6(t, 2H), 2.8(t, 2H), 7.4(d, 1H), 7.6(s, 1H), 8.1(s, 1H), 8.2(d, 1H), 8.5(s, 1H), 9.2(s, 1H) |
| 20 | 3,4,5,6-Tetrahydro-3,8,10-triaza-benzo[e]azulene-1-carboxylic acid (5-chloro-pyridin-2-yl)-amide | H | H | H | H | 2 | 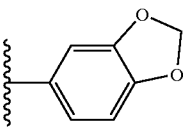 | ¹H NMR [CDCl3] 2.3(quint, 2H), 2.6(t, 2H), 2.8(t, 2H), 7.6(dd, 1H), 7.7(s, 1H), 8.3(d, 1H), 8.35(d, 1H), 8.6(s, 1H), 9.2(s, 1H), 9.7(br s, 1H) |
| 21 | 3,4,5,6-Tetrahydro-3,8,10-triaza-benzo[e]azulene-1-carboxylic acid benzo[1,3]dioxol-5-ylamide | H | H | H | H | 2 | | ¹H NMR [CDCl3 + CD3OD] 2.3(quint, 2H), 2.6(t, 2H), 2.8(t, 2H), 6.0(s, 2H), 6.8(d, 1H), 7.0(dd, 1H), 7.4(d, 1H), 7.6(s, 1H), 8.6(s, 1H), 9.1(s, 1H) |

TABLE 3-continued

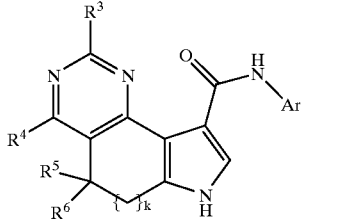

| Cmp # | Name | R³ | R⁴ | R⁵ | R⁶ | k | Ar | Spectral Data |
|---|---|---|---|---|---|---|---|---|
| 22 | 3,4,5,6-Tetrahydro-3,8,10-triaza-benzo[e]azulene-1-carboxylic acid (2,3-dihydro-benzo[1,4]dioxin-6-yl)-amide | H | H | H | H | 2 | 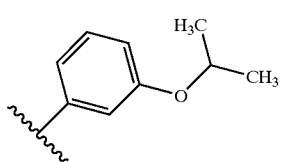 | Electrospray mass spectrum: m/z 363 [M − 1] |
| 23 | 3,4,5,6-Tetrahydro-3,8,10-triaza-benzo[e]azulene-1-carboxylic acid (3-isopropoxy-phenyl)-amide | H | H | H | H | 2 | 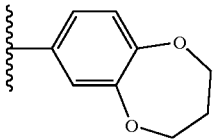 | LRMS m/z 363 |
| 24 | 3,4,5,6-Tetrahydro-3,8,10-triaza-benzo[e]azulene-1-carboxylic acid (3,4-dihydro-2H-benzo[b][1,4]dioxepin-7-yl)-amide | H | H | H | H | 2 | 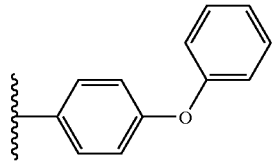 | LRMS m/z 377 |
| 25 | 3,4,5,6-Tetrahydro-3,8,10-triaza-benzo[e]azulene-1-carboxylic acid (4-phenoxy-phenyl)-amide | H | H | H | H | 2 | 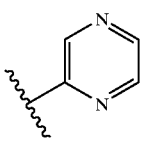 | LRMS m/z 397 |
| 26 | 3,4,5,6-Tetrahydro-3,8,10-triaza-benzo[e]azulene-1-carboxylic acid pyrazin-2-ylamide | H | H | H | H | 2 | 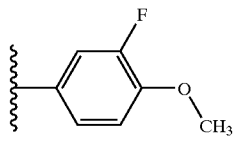 | LRMS calcd 306 found [M + 1] 307; ¹H NMR DMSO-d6, 2.14(m, 2H), 2.62(m, 2H), 2.80(m, 2H), 7.64(s, 1H), 8.30(1H, d), 8.38(m, 1H), 8.66(s, 1H), 9.04(s, 1H), 9.48(s, 1H), 11.94(bs, 1H), 13.57(s, 1H) |
| 27 | 3,4,5,6-Tetrahydro-3,8,10-triaza-benzo[e]azulene-1-carboxylic acid (3-fluoro-4-methoxy-phenyl)-amide | H | H | H | H | 2 | 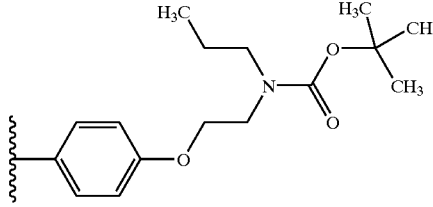 | Electrospray mass spectrum: m/z 351 [M − 1] |
| 28 | Propyl-(2-{4-[(3,4,5,6-tetrahydro-3,8,10-triaza-benzo[e]azulene-1-carbonyl)-amino]-phenoxy}-ethyl)-carbamic acid tert-butyl ester | | | | | | | LRMS calcd 505 found [M + 1] 506 |

TABLE 3-continued

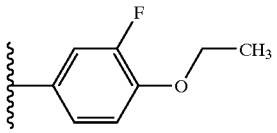

| Cmp # | Name | R³ | R⁴ | R⁵ | R⁶ | k | Ar | Spectral Data |
|---|---|---|---|---|---|---|---|---|
| 29 | 3,4,5,6-Tetrahydro-3,8,10-triaza-benzo[e]azulene-1-carboxylic acid (4-ethoxy-3-fluoro-phenyl)-amide | H | H | H | H | 2 | 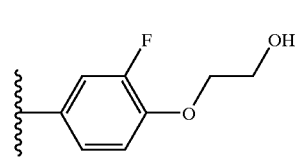 | LRMS 366.39 found (M + 1) 367.3 |
| 30 | 3,4,5,6-Tetrahydro-3,8,10-triaza-benzo[e]azulene-1-carboxylic acid [3-fluoro-4-(2-hydroxy-ethoxy)-phenyl]-amide | H | H | H | H | 2 | 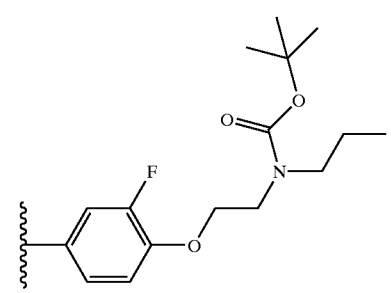 | LRMS calcd 382 found [M + 1] |
| 31 | Propyl-(2-{4-[(3,4,5,6-tetrahydro-3,8,10-triaza-benzo[e]azulene-1-carbonyl)-amino]-phenoxy}-ethyl)-carbamic acid tert-butyl ester | H | H | H | H | 2 | 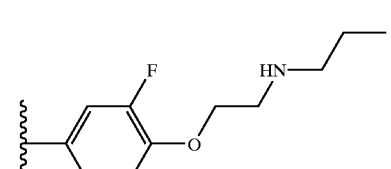 | LRMS calcd 505 found [M + 1] 506 |
| 32 | 3,4,5,6-Tetrahydro-3,8,10-triaza-benzo[e]azulene-1-carboxylic acid [3-fluoro-4-(2-propylamino-ethoxy)-phenyl]-amide | H | H | H | H | 2 | 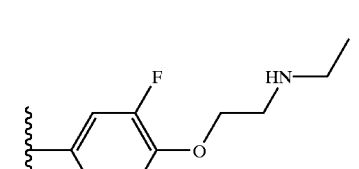 | LRMS calcd 423 found [M − 1] 422 |
| 33 | 3,4,5,6-Tetrahydro-3,8,10-triaza-benzo[e]azulene-1-carboxylic acid [4-(2-ethylamino-ethoxy)-3-fluoro-phenyl]-amide | H | H | H | H | 2 | 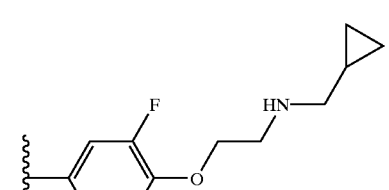 | LRMS calcd 409 found [M + 1] 410 |
| 34 | 3,4,5,6-Tetrahydro-3,8,10-triaza-benzo[e]azulene-1-carboxylic acid {4-[2-(cyclopropylmethyl-1-amino)-ethoxy]-3-fluoro-phenyl}-amide | H | H | H | H | 2 |  | LRMS calcd 435 found [M + 1] 436 |

TABLE 3-continued

| Cmp # | Name | R³ | R⁴ | R⁵ | R⁶ | k | Ar | Spectral Data |
|---|---|---|---|---|---|---|---|---|
| 35 | 3,4,5,6-Tetrahydro-3,8,10-triaza-benzo[e]azulene-1-carboxylic acid (1-ethyl-1H-pyrazol-4-yl)-amide | H | H | H | H | 2 | (1-ethyl-1H-pyrazol-4-yl) | ¹H NMR (DMSO) 1.33(t, 3H), 2.11–2.20(m, 2H), 2.55–2.62(m, 2H), 2.72–2.76(m, 2H), 4.01(q, 2H), 6.5(s, 1H), 7.5(s, 1H), 7.6(s, 1H), 8.6(s, 1H), 9.0(s, 1H), 11.8(brs, 1H), 12.7(brs, 1H) LCMS found (M + H) 323 |
| 36 | 3,4,5,6-Tetrahydro-3,8,10-triaza-benzo[e]azulene-1-carboxylic acid (1-propyl-1H-pyrazol-3-yl)-amide | H | H | H | H | 2 | (1-propyl-1H-pyrazol-3-yl) | LCMS found (M + H) 337 |
| 37 | 3,4,5,6-Tetrahydro-3,8,10-triaza-benzo[e]azulene-1-carboxylic acid [3-(2-ethoxy-ethoxy)-phenyl]-amide | H | H | H | H | 2 | [3-(2-ethoxy-ethoxy)-phenyl] | ¹H NMR (DMSO) 1.21–1.25(m, 3H), 2.25(t, 2H), 2.62(t, 2H), 2.76(t, 2H), 3.57–3.61(m, 2H), 3.78–3.80(m, 2H), 4.13–4.15(m, 2H), 6.66–6.69(m, 1H), 7.21–7.2(m., 2H), 7.54(brs, 1H), 7.66(m, 1H), 8.56(brs, 1H), 9.16(brs, 1H), 12.9(s, 1H) LCMS found (M + H) 393 |
| 38 | 3,4,5,6-Tetrahydro-3,8,10-triaza-benzo[e]azulene-1-carboxylic acid pyridazin-3-ylamide | H | H | H | H | 2 | pyridazin-3-yl | LRMS calcd 306 found [M + 1] 307 |
| 39 | 3,4,5,6-Tetrahydro-3,8,10-triaza-benzo[e]azulene-1-carboxylic acid (5-methyl-isoxazol-3-yl)-amide | H | H | H | H | 2 | (5-methyl-isoxazol-3-yl) | LCMS found (M + H) 310 |
| 40 | 3,4,5,6-Tetrahydro-3,8,10-triaza-benzo[e]azulene-1-carboxylic acid quinolin-3-ylamide | H | H | H | H | 2 | quinolin-3-yl | MS found [M + H] 356.2 |
| 41 | 3,4,5,6-Tetrahydro-3,8,10-triaza-benzo[e]azulene-1-carboxylic acid [6-(3-isopropoxy-propylamino)-pyridin-3-yl]-amide | H | H | H | H | 2 | [6-(3-isopropoxy-propylamino)-pyridin-3-yl] | MS found [M + H] 421.3 |

TABLE 3-continued

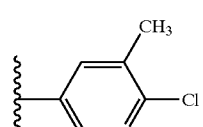

| Cmp # | Name | R³ | R⁴ | R⁵ | R⁶ | k | Ar | Spectral Data |
|---|---|---|---|---|---|---|---|---|
| 42 | 3,4,5,6-Tetrahydro-3,8,10-triaza-benzo[e]azulene-1-carboxylic acid (6-chloro-5-methyl-pyridin-3-yl)-amide | H | H | H | H | 2 | 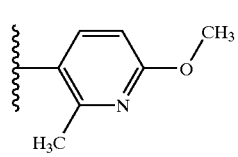 | MS found [M + H] 354.1 |
| 43 | 3,4,5,6-Tetrahydro-3,8,10-triaza-benzo[e]azulene-1-carboxylic acid (6-methoxy-2-methyl-pyridin-3-yl)-amide | H | H | H | H | 2 | 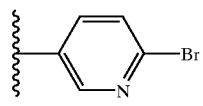 | MS found [M + H] 350.2 |
| 44 | 3,4,5,6-Tetrahydro-3,8,10-triaza-benzo[e]azulene-1-carboxylic acid (6-bromo-pyridin-3-yl)-amide | H | H | H | H | 2 | 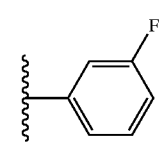 | MS found [M + H] 384.1 |
| 45 | 3,4,5,6-Tetrahydro-3,8,10-triaza-benzo[e]azulene-1-carboxylic acid (3-fluoro-phenyl)-amide | H | H | H | H | 2 | 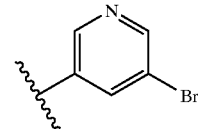 | LRMS calcd 322 found [M + 1] 323 |
| 46 | 3,4,5,6-Tetrahydro-3,8,10-triaza-benzo[e]azulene-1-carboxylic acid (5-bromo-pyridin-3-yl)-amide | H | H | H | H | 2 | 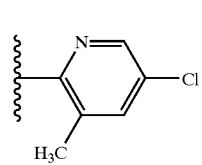 | MS found [M + H] 384.1 |
| 47 | 3,4,5,6-Tetrahydro-3,8,10-triaza-benzo[e]azulene-1-carboxylic acid (5-chloro-3-methyl-pyridin-2-yl)-amide | H | H | H | H | 2 | 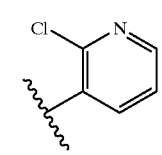 | MS found [M + H] 354.1 |
| 48 | 3,4,5,6-Tetrahydro-3,8,10-triaza-benzo[e]azulene-1-carboxylic acid (2-chloro-pyridin-3-yl)-amide | H | H | H | H | 2 | | MS found [M + H] 340.1 |

TABLE 3-continued

| Cmp # | Name | R³ | R⁴ | R⁵ | R⁶ | k | Ar | Spectral Data |
|---|---|---|---|---|---|---|---|---|
| 49 | 3,4,5,6-Tetrahydro-3,8,10-triaza-benzo[e]azulene-1-carboxylic acid (6-chloro-2-methyl-pyridin-3-yl)-amide | H | H | H | H | 2 | 2-methyl-6-chloro-pyridin-3-yl | MS found [M + H] 354.1 |
| 50 | 3,4,5,6-Tetrahydro-3,8,10-triaza-benzo[e]azulene-1-carboxylic acid (3-ethyl-6-methyl-pyridin-2-yl)-amide | H | H | H | H | 2 | 3-ethyl-6-methyl-pyridin-2-yl | MS found [M + H] 348.2 |
| 51 | 3,4,5,6-Tetrahydro-3,8,10-triaza-benzo[e]azulene-1-carboxylic acid (6-methyl-pyridin-3-yl)-amide | H | H | H | H | 2 | 6-methyl-pyridin-3-yl | MS found [M + H] 320.2 |
| 52 | 3,4,5,6-Tetrahydro-3,8,10-triaza-benzo[e]azulene-1-carboxylic acid (4-fluoro-phenyl)-amide | H | H | H | H | 2 | 4-fluoro-phenyl | MS found [M + H] 323.2 |
| 53 | 3,4,5,6-Tetrahydro-3,8,10-triaza-benzo[e]azulene-1-carboxylic acid pyrimidin-2-ylamide | H | H | H | H | 2 | pyrimidin-2-yl | MS found [M + H] 307.2 |
| 54 | 3,4,5,6-Tetrahydro-3,8,10-triaza-benzo[e]azulene-1-carboxylic acid (4-chloro-phenyl)-amide | H | H | H | H | 2 | 4-chloro-phenyl | MS found [M + H] 339.1 |
| 55 | 3,4,5,6-Tetrahydro-3,8,10-triaza-benzo[e]azulene-1-carboxylic acid (6-chloro-pyridin-3-yl)-amide | H | H | H | H | 2 | 6-chloro-pyridin-3-yl | MS found [M + H] 340.1 |

TABLE 3-continued

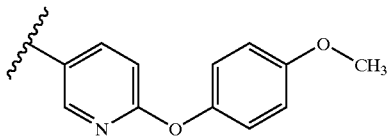

| Cmp # | Name | R³ | R⁴ | R⁵ | R⁶ | k | Ar | Spectral Data |
|---|---|---|---|---|---|---|---|---|
| 56 | 3,4,5,6-Tetrahydro-3,8,10-triaza-benzo[e]azulene-1-carboxylic acid [6-(4-methoxy-phenoxy)-pyridin-3-yl]-amide | H | H | H | H | 2 | 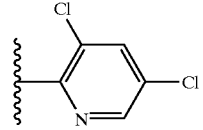 | MS found [M + H] 428.2 |
| 57 | 3,4,5,6-Tetrahydro-3,8,10-triaza-benzo[e]azulene-1-carboxylic acid (3,5-dichloro-pyridin-2-yl)-amide | H | H | H | H | 2 | 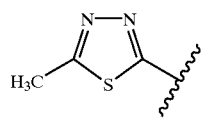 | MS found [M + H] 374.1 |
| 58 | 3,4,5,6-Tetrahydro-3,8,10-triaza-benzo[e]azulene-1-carboxylic acid (5-methyl-[1,3,4]thiadiazol-2-yl)-amide | H | H | H | H | 2 | 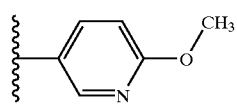 | MS found [M + H] 327.1 |
| 59 | 3,4,5,6-Tetrahydro-3,8,10-triaza-benzo[e]azulene-1-carboxylic acid (6-methoxy-pyridin-3-yl)-amide | H | H | H | H | 2 | 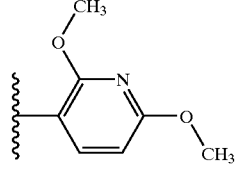 | MS found [M + H] 336.2 |
| 60 | 3,4,5,6-Tetrahydro-3,8,10-triaza-benzo[e]azulene-1-carboxylic acid (2,6-dimethoxy-pyridin-3-yl)-amide | H | H | H | H | 2 | 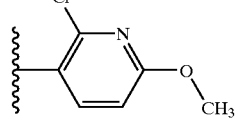 | MS found [M + H] 366.2 |
| 61 | 3,4,5,6-Tetrahydro-3,8,10-triaza-benzo[e]azulene-1-carboxylic acid (2-chloro-6-methoxy-pyridin-3-yl)-amide | H | H | H | H | 2 | 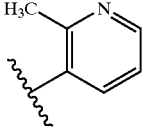 | LRMS calcd 369 found [M + 1] 370 |
| 62 | 3,4,5,6-Tetrahydro-3,8,10-triaza-benzo[e]azulene-1-carboxylic acid (2-methyl-pyridin-3-yl)-amide | H | H | H | H | 2 | | MS found [M + H] 320.2 |

TABLE 3-continued

| Cmp # | Name | R³ | R⁴ | R⁵ | R⁶ | k | Ar | Spectral Data |
|---|---|---|---|---|---|---|---|---|
| 63 | 3,4,5,6-Tetrahydro-3,8,10-triaza-benzo[e]azulene-1-carboxylic acid (3-methyl-pyridin-2-yl)-amide | H | H | H | H | 2 | 3-methylpyridin-2-yl | Electrospray mass spectrum: m/z 320 [M + 1] |
| 64 | 3,4,5,6-Tetrahydro-3,8,10-triaza-benzo[e]azulene-1-carboxylic acid [6-(2,4-dichloro-phenoxy)-pyridin-3-yl]-amide | H | H | H | H | 2 | 6-(2,4-dichlorophenoxy)pyridin-3-yl | MS found [M + H] 466.2 |
| 65 | 3,4,5,6-Tetrahydro-3,8,10-triaza-benzo[e]azulene-1-carboxylic acid (2,6-dimethyl-pyridin-3-yl)-amide | H | H | H | H | 2 | 2,6-dimethylpyridin-3-yl | MS found [M + H] 334.2 |
| 66 | 3,4,5,6-Tetrahydro-3,8,10-triaza-benzo[e]azulene-1-carboxylic acid [6-(4-trifluoromethyl-phenoxy)-pyridin-3-yl]-amide | H | H | H | H | 2 | 6-(4-trifluoromethylphenoxy)pyridin-3-yl | MS found [M + H] 466.2 |
| 67 | 3,4,5,6-Tetrahydro-3,8,10-triaza-benzo[e]azulene-1-carboxylic acid [4-(2-ethoxy-ethoxy)-phenyl]-amide | H | H | H | H | 2 | 4-(2-ethoxyethoxy)phenyl | ¹H NMR (DMSO) 1.09–1.13 (m, 3H), 2.15(t, 2H), 2.6(t, 2H), 2.74(t, 2H), 3.46–3.51(m, 2H), 3.65–3.67(m, 2H), 4.01–4.04(m, 2H), 6.66–6.69(m, 2H), 7.54(brs, 1H), 7.60–7.62(m, 2H), 8.56–8.57(brs, 1H), 11.7(brs, 1H), 12.1(s, 1H) LCMS found (M + H) 393 |
| 68 | 3,4,5,6-Tetrahydro-3,8,10-triaza-benzo[e]azulene-1-carboxylic acid [4-(2-isopropoxy-ethoxy)-phenyl]-amide | H | H | H | H | 2 | 4-(2-isopropoxyethoxy)phenyl | ¹H NMR (DMSO) 1.08–1.09 (m, 6H), 2.15(t, 2H), 2.6(t, 2H), 2.73(t, 2H), 3.58–3.61(m, 1H), 3.66(t, 2H), 4.0(t, 2H), 6.86–6.89(m, 2H), 7.54(brs, 1H), 7.60–7.62(m, 2H), 8.64(s, 1H), 9.16(brs, 1H), 12.1(s, 1H) LCMS found (M + H) 407 |

TABLE 3-continued

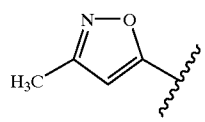

| Cmp # | Name | R³ | R⁴ | R⁵ | R⁶ | k | Ar | Spectral Data |
|---|---|---|---|---|---|---|---|---|
| 69 | 3,4,5,6-Tetrahydro-3,8,10-triaza-benzo[e]azulene-1-carboxylic acid (3-methyl-isoxazol-5-yl)-amide | H | H | H | H | 2 | 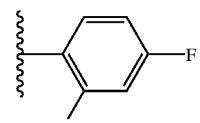 | LCMS found (M + H) 310 |
| 70 | 3,4,5,6-Tetrahydro-3,8,10-triaza-benzo[e]azulene-1-carboxylic acid (5-fluoro-2-methyl-phenyl)-amide | H | H | H | H | 2 | 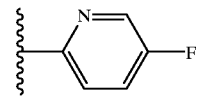 | Electrospray mass spectrum: m/z 335 [M − 1] |
| 71 | 3,4,5,6-Tetrahydro-3,8,10-triaza-benzo[e]azulene-1-carboxylic acid (5-fluoro-2-methyl-phenyl)-amide | H | H | H | H | 2 | 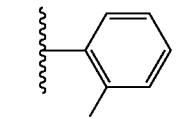 | Electrospray mass spectrum: m/z 324 [M + 1] |
| 72 | 3,4,5,6-Tetrahydro-3,8,10-triaza-benzo[e]azulene-1-carboxylic acid (2-methoxy-phenyl)-amide | H | H | H | H | 2 | 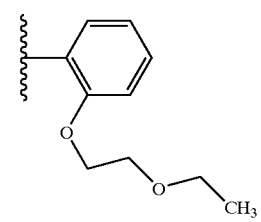 | LRMS 334.38 found (M + 1) 335.2 |
| 73 | 3,4,5,6-Tetrahydro-3,8,10-triaza-benzo[e]azulene-1-carboxylic acid [2-(2-ethoxy-ethoxy)-phenyl]-amide | H | H | H | H | 2 | 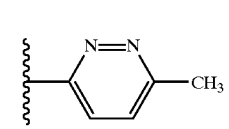 | LRMS 392.46 found (M + 1) 393.0 |
| 74 | 3,4,5,6-Tetrahydro-3,8,10-triaza-benzo[e]azulene-1-carboxylic acid 6-methyl-pyridazin-3-ylamide | H | H | H | H | 2 |  | LRMS 320.35 found (M + 1) 321.0 |

TABLE 3-continued

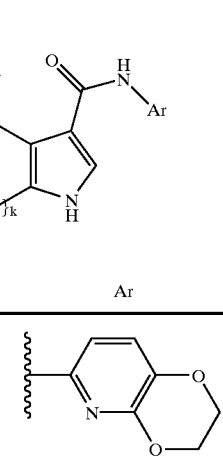

| Cmp # | Name | R³ | R⁴ | R⁵ | R⁶ | k | Ar | Spectral Data |
|---|---|---|---|---|---|---|---|---|
| 75 | 3,4,5,6-Tetrahydro-3,10-diaza-benzo[e]azulene-1-carboxylic acid (2,3-dihydro-[1,4]dioxino[2,3-b]pyridin-6-yl)-amide | H | H | H | H | 2 | 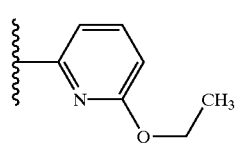 | LCMS found (M + H) 363 |
| 76 | 3,4,5,6-Tetrahydro-3,8,10-triaza-benzo[e]azulene-1-carboxylic acid (6-ethoxy-pyridin-2-yl)-amide | H | H | H | H | 2 | 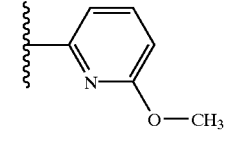 | LCMS found (M + H) 350 |
| 77 | 3,4,5,6-Tetrahydro-3,8,10-triaza-benzo[e]azulene-1-carboxylic acid (6-methoxy-pyridin-2-yl)-amide | H | H | H | H | 2 | 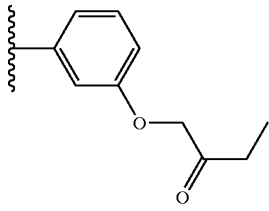 | LCMS found (M + H) 336 |
| 78 | 3,4,5,6-Tetrahydro-3,8,10-triaza-benzo[e]azulene-1-carboxylic acid [3-(2-oxo-butoxy)-phenyl]-amide | H | H | H | H | 2 | 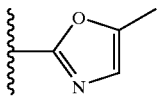 | LCMS found (M + H) 391 |
| 79 | 3,4,5,6-Tetrahydro-3,8,10-triaza-benzo[e]azulene-1-carboxylic acid (5-methyl-oxazol-2-yl)-amide | H | H | H | H | 2 | 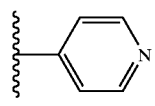 | LCMS found (M + H) 310 |
| 80 | 3,4,5,6-Tetrahydro-3,8,10-triaza-benzo[e]azulene-1-carboxylic acid pyridin-4-ylamide | H | CH₃ | H | H | 2 | 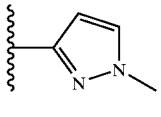 | LRMS 305 found (M + 1) 306 |
| 81 | 7-Methyl-3,4,5,6-tetrahydro-3,8,10-triaza-benzo[e]azulene-1-carboxylic acid (1-methyl-1H-pyrazol-3-yl)-amide | H | CH₃ | H | H | 2 |  | LRMS 322 found (M + 1) 323 |

TABLE 3-continued

| Cmp # | Name | R³ | R⁴ | R⁵ | R⁶ | k | Ar | Spectral Data |
|---|---|---|---|---|---|---|---|---|
| 82 | 3,4,5,6-Tetrahydro-3,8,10-triaza-benzo[e]azulene-1-carboxylic acid pyridin-2-ylamide | H | CH₃ | H | H | 2 | pyridin-2-yl | LRMS 305 found (M + 1) 306 |
| 83 | 7-Methyl-3,4,5,6-tetrahydro-3,8,10-triaza-benzo[e]azulene-1-carboxylic acid (3-methyl-isoxazol-5-yl)-amide | H | CH₃ | H | H | 2 | 3-methyl-isoxazol-5-yl | LRMS 323 found (M + 1) 324 |
| 84 | 7-Methyl-3,4,5,6-tetrahydro-3,8,10-triaza-benzo[e]azulene-1-carboxylic acid (5-methyl-isoxazol-3-yl)-amide | H | CH₃ | H | H | 2 | 5-methyl-isoxazol-3-yl | LRMS 323 found (M + 1) 324 |
| 85 | 3,4,5,6-Tetrahydro-3,8,10-triaza-benzo[e]azulene-1-carboxylic acid (6-methoxy-4-methyl-pyridin-3-yl)-amide | H | H | H | H | 2 | 6-methoxy-4-methyl-pyridin-3-yl | ¹H NMR (DMSO) 2.05–2.25(m, 5H), 2.6(t, 2H), 2.75(t, 2H), 3.80(s, 3H), 6.7(s, 1H), 7.45(d, 1H), 8.25(s, 1H), 8.6(s, 1H), 9.0(s, 1H), 11.35(s, 1H), 11.8(bs, 1H) |
| 86 | 3,4,5,6-Tetrahydro-3,8,10-triaza-benzo[e]azulene-1-carboxylic acid (2-chloro-6-methoxy-pyridin-3-yl)-amide | H | H | H | H | 2 | 2-chloro-6-methoxy-pyridin-3-yl | ¹H NMR (DMSO) 2.1–2.2(m, 2H), 2.6(t, 2H), 2.75(t, 2H), 3.80(s, 3H), 6.9(d, 1H), 7.6(s, 1H), 8.25(d, 1H), 8.65(s, 1H), 9.05(s, 1H), 11.9(bs, 1H), 12.4(bs, 1H) |
| 87 | 3,4,5,6-Tetrahydro-3,8,10-triaza-benzo[e]azulene-1-carboxylic acid (3-ethoxy-pyridin-2-yl)-amide | H | H | H | H | 2 | 3-ethoxy-pyridin-2-yl | LRMS 349 found (M − 1) 348 |
| 88 | 3,4,5,6-Tetrahydro-3,8,10-triaza-benzo[e]azulene-1-carboxylic acid (2-methyl-pyrimidin-4-yl)-amide | H | H | H | H | 2 | 2-methyl-pyrimidin-4-yl | LRMS 320 found (M − 1) 319 |

TABLE 3-continued

| Cmp # | Name | R³ | R⁴ | R⁵ | R⁶ | k | Ar | Spectral Data |
|---|---|---|---|---|---|---|---|---|
| 89 | 3,4,5,6-Tetrahydro-3,8,10-triaza-benzo[e]azulene-1-carboxylic acid (1-methyl-1H-pyrazol-3-yl)-amide | H | H | H | H | 2 | | LRMS 308 found (M − 1) 307 |
| 90 | 3,4,5,6-Tetrahydro-3,8,10-triaza-benzo[e]azulene-1-carboxylic acid (5-propyl-[1,3,4]oxadiazol-2-yl)-amide | H | H | H | H | 2 | | ¹H NMR [CDCl3 + CD3OD] 1.0(t, 3H), 1.8(qt, 2H), 2.25(m, 2H), 2.75–2.95(m, 6H), 7.7(s, 1H), 8.6(s, 1H), 9.1(s, 1H), LRMS 338 found (M − 1) 337 |
| 91 | 3,4,5,6-Tetrahydro-3,8,10-triaza-benzo[e]azulene-1-carboxylic acid [1-(3-cyclobutylamino-propyl)-1H-pyrazol-3-yl]-amide | H | H | H | H | 2 | | LRMS 405 found (M + 1) 406 |
| 92 | 3,4,5,6-Tetrahydro-3,8,10-triaza-benzo[e]azulene-1-carboxylic acid pyridin-2-ylamide | H | H | H | H | 2 | | ¹H NMR [CDCl3] 2.15–2.23(m, 2H), 2.63(t, 2H), 2.80(t, 2H), 6.98(dd, 1H), 7.63–7.70(m, 2H), 8.32(dd, 1H), 8.37(dd, 1H), 8.53(s, 1H0, 9.23(s, 1H), 10.73(s, 1H) |
| 93 | 3,4,5,6-Tetrahydro-3,8,10-triaza-benzo[e]azulene-1-carboxylic acid pyridin-4-ylamide | H | H | H | H | 2 | | ¹H NMR [DMSO-d6] 2.05–2.20(m, 2H), 2.62(t, 2H), 2.78(t, 2H), 7.53(s, 1H), 7.65(d, 2H), 8.42(d, 2H), 8.63(s, 1H), 9.20(s, 1H), 11.88(s, 1H) |
| 94 | 7-Methyl-3,4,5,6-tetrahydro-3,8,10-triaza-benzo[e]azulene-1-carboxylic acid (1-methyl-1H-pyrazol-3-yl)-amide | H | Me | H | H | 2 | | LRMS 322.4 found (M − 1) 321.3 |
| 95 | 3,4,5,6-Tetrahydro-3,8,10-triaza-benzo[e]azulene-1-carboxylic acid ]6-(3-diethylamino-propoxy)-pyridin-2-yl]-amide | H | H | H | H | 2 | | LCMS found (M + H) 435 |

Example 8

1-methyl-4,5,6,7-tetrahydro-1H-1,2,7-triaza-cyclopenta[e]azulene-9-carboxylic acid ethyl ester and 2-methyl-4,5,6,7-tetrahydro-2H-1,2,7-triaza-cyclopenta[e]azulene-9-carboxylic acid ethyl ester

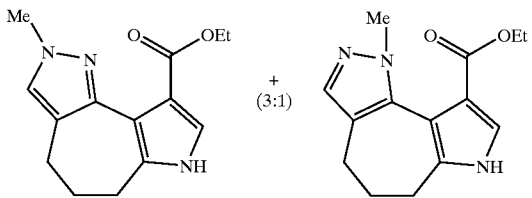
(3:1)

A mixture of ethyl 5-dimethylaminomethylene-4-oxo-1,4,5,6,7,8-hexahydro-cyclohepta[b]pyrrole-3-carboxylic acid ethyl ester (100 mg, 0.362 mmol) and methyl hydrazine (83 mg, 1.81 mmol) in EtOH (2 mL) is stirred at 100° C. for 3 h. After cooling, the reaction mixture is diluted with CH$_2$Cl$_2$ and washed with half saturated aq NaHCO$_3$ (10 mL), H$_2$O (10 mL), and brine (10 mL). The CH$_2$Cl$_2$ extract is dried over Na$_2$SO$_4$ and concentrated. The crude material is purified by flash chromatography on silica gel. Elution with 3:1 EtOAc-hexanes (+0.5% Et$_3$N) followed by 100% ethyl acetate (+0.5% Et$_3$N) separated the two regioisomers. Early fractions: 23 mg (25%) of 1-methyl-4,5,6,7-tetrahydro-1H-1,2,7-triaza-cyclopenta[e]azulene-9-carboxylic acid ethyl ester; electrospray mass spectrum: m/z 260 [M+1]; $^1$H NMR (CDCl$_3$, 400 MHz) δ9.32 (br s, 1H), 7.39 (d, J=2.8 Hz, 1H), 7.37 (s, 1H), 4.27 (q, J=7.2 Hz, 2H), 3.83 (s, 3H), 2.54 (m, 2H), 2.46 (m, 2H), 2.10 (m, 2H), 1.31 (t, J=7.2 Hz, 3H). Later fractions: 69 mg (74%) of 2-methyl-4,5,6,7-tetrahydro-2H-1,2,7-triaza-cyclopenta[e]azulene-9-carboxylic acid ethyl ester; electrospray mass spectrum: m/z 260 [M+1]; $^1$H NMR (CDCl$_3$, 300 MHz) δ8.42 (br s, 1H), 7.20 (d, J=3.0 Hz, 1H), 7.05 (s, 1H), 4.29 (q, J=7.2 Hz, 2H), 3.82 (s, 3H), 2.82 (m, 2H), 2.67 (m, 2H), 1.96 (m, 2H), 1.32 (t, J=7.2 Hz, 3H).

Example 9

2-Methyl-4,5,6,7-tetrahydro-2H-1,2,7-triaza-cyclopenta[e]azulene-9-carboxylic acid (2-fluoro-phenyl)-amide

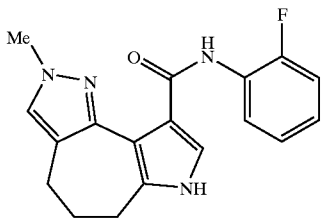

To a solution of 2-fluoroaniline (103 mg, 0.926 mmol) in CH$_2$Cl$_2$ (2.0 mL) at 0° C. under N$_2$ is slowly added AlMe$_3$ (0.46 mL, 2.0 M in toluene). The resulting solution is stirred at room temperature for 1 h. Next, 2-methyl-4,5,6,7-tetrahydro-2H-1,2,7-triaza-cyclopenta[e]azulene-9-carboxylic acid ethyl ester (60 mg, 0.231 mmol) is added in one portion. The resulting mixture is then stirred at reflux for 2 h. After cooling, the reaction mixture is carefully diluted with saturated aq NH$_4$Cl (~5 mL) and some H$_2$O. The mixture is stirred vigorously for 30 min. and then extracted three times with CH$_2$Cl$_2$(containing some (~5%) MeOH). The combined extracts are dried over K$_2$CO$_3$ and concentrated. The crude material is purified by flash chromatography on silica gel. Elution with 40:1 CHCl$_3$-MeOH followed by 30:1 CHCl$_3$-MeOH and finally 20:1 CHCl$_3$-MeOH afforded, after concentration of the fractions containing pure product, a residue, which is then granulated with Et$_2$O. The suspension is filtered, and the solid washed with Et$_2$O and dried, affording 45 mg (60%) of 2-methyl-4,5,6,7-tetrahydro-2H-1,2,7-triaza-cyclopenta[e]azulene-9-carboxylic acid (2-fluoro-phenyl)-amide as an off-white solid. Electrospray mass spectrum: m/z 325 [M+1].

Example 10

1-Methyl-4,5,6,7-tetrahydro-2H-1,2,7-triaza-cyclopenta[e]azulene-9-carboxylic acid (2-fluoro-phenyl)-amide

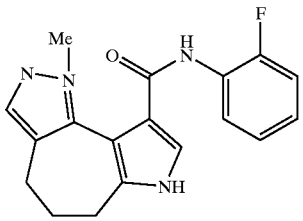

The title compound is prepared according to Example 9 using 2-fluoroaniline and 1-methyl-4,5,6,7-tetrahydro-1H-1,2,7-triaza-cyclopenta[e]azulene-9-carboxylic acid ethyl ester. Electrospray mass spectrum: m/z 325 [M+1].

Example 11

4,5,6,7-Tetrahydro-2H-1,2,7-triaza-cyclopenta[e]azulene-9-carboxylic acid ethyl ester

The title compound is prepared in analogous fashion to Example 8 using 5-dimethylaminomethylene-4-oxo-1,4,5,6,7,8-hexahydro-cyclohepta[b]pyrrole-3-carboxylic acid ethyl ester and hydrazine acetate. The crude product mixture is carried into the next step without purification. Electrospray mass spectrum: m/z 246 [M+1]; $^1$H NMR (DMSO-d$_6$, 300 MHz) δ>13.0 (br s, 1H), 11.65 (br s, 1H), 7.49 (s, 1H), 7.20 (s, 1H), 4.25 (q, J=7.2 Hz, 2H), 2.91 (m, 2H), 2.76 (m, 2H), 1.84 (m, 2H) 1.28 (t, J=7.2 Hz, 3H).

Example 12

Preparation of 4,5,6,7-Tetrahydro-2H-1,2,7-triaza-cyclopenta[e]azulene-9-carboxylic acid (2-fluorophenyl)-amide

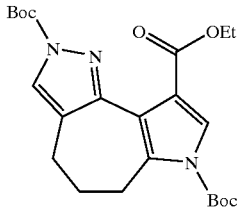

Step 1:

5,6-Dihydro-4H-1,2,7-triaza-cyclopenta[e]azulene-2,7,9-tricarboxylic acid 2,7-di-tert-butyl ester 9-ethyl ester is prepared by the procedure described in Example 8, using 4,5,6,7-tetrahydro-2H-1,2,7-triaza-cyclopenta[e]azulene-9-carboxylic acid ethyl ester, 2.3 eq of Boc$_2$O, and 2.5 eq of Et$_3$N. Electrospray mass spectrum: m/z 446 [M+1]; $^1$H NMR (CDCl$_3$, 300 MHz) δ7.77 (s, 1H), 7.62 (s, 1H), 4.35 (q, J=7.2 Hz, 2H), 3.26 (m, 2H), 2.68 (m, 2H), 1.99 (m, 2H), 1.61 (s, 9H), 1.59 (s, 9H), 1.33 (t, J=7.2 Hz, 3H).

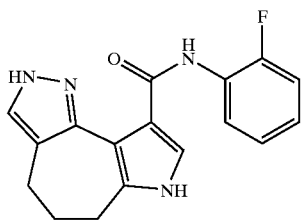

Step 2:

To a solution of 2-fluoroaniline (202 mg, 1.82 mmol) in CH$_2$Cl$_2$ (4.0 mL) at 0° C. under N$_2$ is slowly added AlMe$_3$ (0.91 mL, 2.0 M in toluene). The resulting solution is stirred at room temperature for 1 h. Next, 5,6-dihydro-4H-1,2,7-triaza-cyclopenta[e]azulene-2,7,9-tricarboxylic acid 2,7-di-tert-butyl ester 9-ethyl ester (162 mg, 0.364 mmol) is added in one portion. The resulting mixture is then stirred at reflux for 2 h. After cooling, the reaction mixture is carefully diluted with saturated aq NH$_4$Cl (~5 mL) and some H$_2$O. The mixture is stirred vigorously for 30 min. and then extracted three times with CH$_2$Cl$_2$(containing some (~5%) MeOH). The combined extracts are dried over K$_2$CO$_3$ and concentrated. The crude material is purified by flash chromatography on silica gel, affording 102 mg (68%) of an amide product containing only one Boc group. $^1$H NMR (CDCl$_3$, 300 MHz) δ8.52 (td, J=8.1, 1.4 Hz, 1H), 8.06 (s, 1H), 7.36 (s, 1H), 7.18–7.03 (m, 3H), 3.37 (m, 2H), 2.79 (m, 2H), 2.03 (m, 2H), 1.62 (s, 9H). This product is then dissolved in 4 mL of EtOH and 1 mL of conc. aq HCl. The solution is stirred at room temperature overnight and at 90° C. for 3 h. The reaction mixture is then concentrated under a stream of N$_2$ to afford a solid, which is then suspended in H$_2$O and filtered. The solid is thoroughly washed with H$_2$O and Et$_2$O to afford, after drying, 34 mg (44%) of 4,5,6,7-tetrahydro-2H-1,2,7-triaza-cyclopenta[e]azulene-9-carboxylic acid (2-fluoro-phenyl)-amide as a light yellow/off-white solid. Electrospray mass spectrum: m/z 311 [M+1].

Example 12a 2-(2-Diethylamino-ethyl)-4,5,6,7-tetrahydro-2H-1,2,7-triaza-cyclopenta[e]azulene-9-carboxylic acid [1,3,4]thiadiazol-2-ylamide

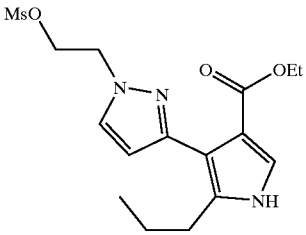

Step 1:

A solution of 2-(2-Hydroxy-ethyl)-4,5,6,7-tetrahydro-2H-1,2,7-triaza-cyclopenta[e]azulene-9-carboxylic acid ethyl ester (866 mg, 2.99 mmol) in CH$_2$Cl$_2$(6 mL) at 0° C. under N$_2$ is treated with pyridine (0.73 mL, 8.98 mmol) followed by methanesulfonyl chloride (0.28 mL, 3.59 mmol). The reaction mixture is stirred at 0° C. for 10 min. and at room temperature for 4 h. The reaction mixture is then concentrated in vacuo. The crude 2-(2-methanesulfonyloxy-ethyl)-4,5,6,7-tetrahydro-2H-1,2,7-triaza-cyclopenta[e]azulene-9-carboxylic acid ethyl ester is used without further purification. Electrospray mass spectrum: m/z 366 [M−1].

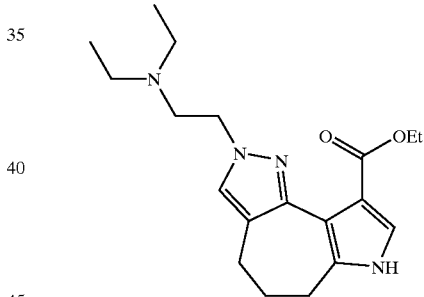

Step 2:

To a solution of 2-(2-methanesulfonyloxy-ethyl)-4,5,6,7-tetrahydro-2H-1,2,7-triaza-cyclopenta[e]azulene-9-carboxylic acid ethyl ester (158 mg, 0.43 mmol) in CH$_3$CN is added excess diethylamine (>3 eq) and excess K$_2$CO$_3$. The reaction mixture is stirred overnight at 83° C. in a sealed tube. The reaction mixture is then extracted with CH$_2$Cl$_2$ and washed with water. The aqueous wash is then extracted twice more with CH$_2$Cl$_2$. The combined extracts are dried over K$_2$CO$_3$ and concentrated. The crude material is purified by flash chromatography on silica gel, affording 107 mg (72%) of 2-(2-diethylamino-ethyl)-4,5,6,7-tetrahydro-2H-1,2,7-triaza-cyclopenta [e]azulene-9-carboxylic acid ethyl ester. Electrospray mass spectrum: m/z 343 [M−1]; $^1$H NMR (CDCl$_3$, 300 MHz) δ8.78 (br, 1H), 7.17 (d, J=2.7 Hz, 1H), 7.15 (s, 1H), 4.27 (q, J=7.2 Hz, 2H), 4.12 (t, J=7.2 Hz, 2H), 2.91 (m, 2H), 2.81 (m, 2H), 2.65 (m, 2H), 2.59 (q, J=7.2 Hz, 4H), 1.94 (m, 2H), 1.31 (t, J=7.2 Hz, 3H), 1.02 (t, J=7.2 Hz, 6H)

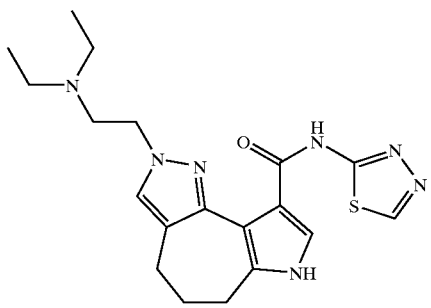

Step 3:

To a mixture of 2-amino-1,3,4-thiazole (81 mg, 0.798 mmol) in $CH_2Cl_2$ (2 mL) at 0° C. under $N_2$ is added 2.0 M trimethylaluminum in toluene (0.4 mL, 0.798 mmol). The mixture is then stirred at room temperature for 1 hr. To the resulting solution is added a solution of 2-(2-diethylamino-ethyl)-4,5,6,7-tetrahydro-2H-1,2,7-triaza-cyclopenta[e] azulene-9-carboxylic acid ethyl ester (55 mg, 0.16 mmol) in $CH_2Cl_2$(1.0 mL) via cannula, followed by a 0.5 mL rinse. The reaction mixture is then stirred at reflux for 4 h. After cooling, the reaction mixture is quenched by the addition of a small amount of 2.0 M aq NaOH and water. A small amount of MeOH is added, and the resulting mixture is stirred vigorously for 30 min. The mixture is filtered through a pad of Celite, washing with $CH_2Cl_2$ containing some (~5%) MeOH. The filtrate is concentrated, and the residue is purified by preparative thin-layer chromatography (silica gel). Two developments using 20:1 $CHCl_3$-MeOH (+1% triethylamine) affords 53 mg (83%) of 2-(2-diethylamino-ethyl)-4,5,6,7-tetrahydro-2H-1,2,7-triaza-cyclopenta[e] azulene-9-carboxylic acid [1,3,4]thiadiazol-2-ylamide as an off-white solid. Electrospray mass spectrum: m/z 398 [M−1]; $^1$H NMR (CDCl$_3$, 300 MHz) δ9.14 (br, 1H), 8.79 (s, 1H), 7.71 (d, J=3.0 Hz, 1H), 7.26 (d, J=0.6 Hz, 1H) 4.37 (m, 2H), 3.06 (m, 2H), 3.00 (m, 2H), 2.79 (m, 2H), 2.61 (q, J=7.2 Hz, 4H), 1.97 (m, 2H), 0.99 (t, J=7.2 Hz, 6H) The solid is dissolved in 3–4 mL of EtOH and treated with ~3 eq of 1.0 M HCl in $Et_2O$. The solution is stirred for 10 min. and then concentrated to remove most of the EtOH. Methyl tert-butyl ether is added, and the resulting precipitate is granulated and filtered. The solid is washed with $Et_2O$ and dried under a stream of $N_2$ to afford 54 mg (77%) of the hydrochloride salt of 2-(2-diethylamino-ethyl)-4,5,6,7-tetrahydro-2H-1,2,7-triaza-cyclopenta[e]azulene-9-carboxylic acid [1,3,4] thiadiazol-2-ylamide. Electrospray mass spectrum: m/z 398 [M−1]; $^1$H NMR (CD$_3$OD, 300 MHz) δ11.32 (br, 1H), 9.22 (s, 1H), 7.67 (d, J=3.0 Hz, 1H), 7.64 (s, 1H), 4.71 (m, 2H), 4.02 (m, 2H), 3.37 (q, J=7.2 Hz, 4H), 3.05 (m, 2H), 2.85 (m, 2H), 1.99 (m, 2H), 1.33 (t, J=7.2 Hz, 6H).

Example 12b

Using the method shown in Scheme 6 and further illustrated in Examples 8–12 the compounds shown in Table 4 were prepared.

TABLE 4

| Cpd # | Name | $R^A$ | $R^4$ | $R^5$ | $R^6$ | k | Ar | Spectral Data |
|---|---|---|---|---|---|---|---|---|
| 1 | 2-Methyl-4,5,6,7-tetrahydro-2H-1,2,7-triaza-cyclopenta[e]azulene-9-carboxylic acid (2-fluoro-phenyl)-amide | $CH_3$ | H | H | H | 2 | 2-fluorophenyl | MS m/z [M + 1] 325 |
| 2 | 2-Methyl-4,5,6,7-tetrahydro-2H-1,2,7-triaza-cyclopenta[e]azulene-9-carboxylic acid pyridin-3-ylamide | $CH_3$ | H | H | H | 2 | pyridin-3-yl | MS m/z [M + 1] 308 |
| 3 | 2-Methyl-4,5,6,7-tetrahydro-2H-1,2,7-triaza-cyclopenta[e]azulene-9-carboxylic acid pyrazin-2-ylamide | $CH_3$ | H | H | H | 2 | pyrazin-2-yl | MS m/z [M + 1] 309 |

TABLE 4-continued

| Cpd # | Name | R^A | R^4 | R^5 | R^6 | k | Ar | Spectral Data |
|---|---|---|---|---|---|---|---|---|
| 4 | 2-Methyl-4,5,6,7-tetrahydro-2H-1,2,7-triaza-cyclopenta[e]azulene-9-carboxylic acid(2,3-dihydro-benzo[1,4]dioxin-6-yl)-amide | $CH_3$ | H | H | H | 2 | 2,3-dihydro-benzo[1,4]dioxin-6-yl | MS m/z [M + 1] 365 |
| 5 | 2-Methyl-4,5,6,7-tetrahydro-2H-1,2,7-triaza-cyclopenta[e]azulene-9-carboxylic acid(4-ethoxy-phenyl)-amide | $CH_3$ | H | H | H | 2 | 4-ethoxy-phenyl | MS m/z [M − 1] 349 |
| 6 | 2-Methyl-4,5,6,7-tetrahydro-2H-1,2,7-triaza-cyclopenta[e]azulene-9-carboxylic acid(3-fluoro-4-methoxy-phenyl)-amide | $CH_3$ | H | H | H | 2 | 3-fluoro-4-methoxy-phenyl | MS m/z [M − 1] 353 |
| 7 | 2-Methyl-4,5,6,7-tetrahydro-2H-1,2,7-triaza-cyclopenta[e]azulene-9-carboxylic acid(5-methyl-pyridin-2-yl)-amide | $CH_3$ | H | H | H | 2 | 5-methyl-pyridin-2-yl | MS m/z [M − 1] 320 |
| 8 | 2-Methyl-4,5,6,7-tetrahydro-2H-1,2,7-triaza-cyclopenta[e]azulene-9-carboxylic acid(5-methyl-isoxazol-3-yl)-amide | $CH_3$ | H | H | H | 2 | 5-methyl-isoxazol-3-yl | MS m/z [M − 1] 310 |
| 9 | 2-Methyl-4,5,6,7-tetrahydro-2H-1,2,7-triaza-cyclopenta[e]azulene-9-carboxylic acid[3-(2-ethoxy-ethoxy)-phenyl]-amide | $CH_3$ | H | H | H | 2 | 3-(2-ethoxy-ethoxy)-phenyl | MS m/z [M + 1] 395 |
| 10 | 2-Methyl-4,5,6,7-tetrahydro-2H-1,2,7-triaza-cyclopenta[e]azulene-9-carboxylic acid[4-(2-ethoxy-ethoxy)-phenyl]-amide | $CH_3$ | H | H | H | 2 | 4-(2-ethoxy-ethoxy)-phenyl | MS m/z [M + 1] 395 |

TABLE 4-continued

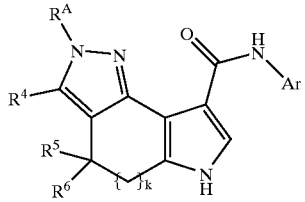

| Cpd # | Name | R^A | R^4 | R^5 | R^6 | k | Ar | Spectral Data |
|---|---|---|---|---|---|---|---|---|
| 11 | 2-Methyl-4,5,6,7-tetrahydro-2H-1,2,7-triaza-cyclopenta[e]azulene-9-carboxylic acid(2,3-dihydro-[1,4]dioxino[2,3-b]pyridin-6-yl)-amide | CH$_3$ | H | H | H | 2 | 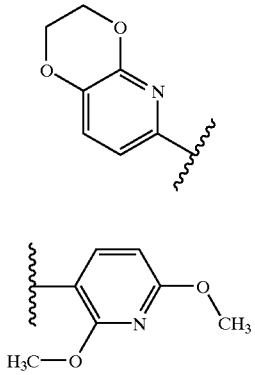 | MS m/z [M + 1] 366 |
| 12 | 2-Methyl-4,5,6,7-tetrahydro-2H-1,2,7-triaza-cyclopenta[e]azulene-9-carboxylic acid(2,6-dimethoxy-pyridin-3-yl)-amide | CH$_3$ | H | H | H | 2 | 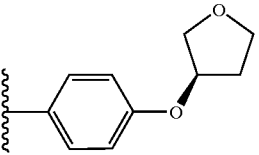 | MS m/z [M + 1] 368 |
| 13 | (R)-2-Methyl-4,5,6,7-tetrahydro-2H-1,2,7-triaza-cyclopenta[e]azulene-9-carboxylic acid[4-(tetrahydro-furan-3-yloxy)-phenyl]-amide | CH$_3$ | H | H | H | 2 | 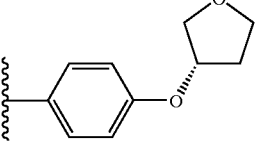 | MS m/z [M + 1] 393 |
| 14 | (S)-2-Methyl-4,5,6,7-tetrahydro-2H-1,2,7-triaza-cyclopenta[e]azulene-9-carboxylic acid[4-(tetrahydro-furan-3-yloxy)-phenyl]-amide | CH$_3$ | H | H | H | 2 | 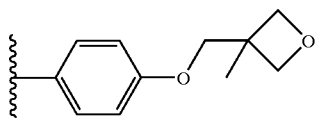 | MS m/z [M + 1] 393 |
| 15 | 2-Methyl-4,5,6,7-tetrahydro-2H-1,2,7-triaza-cyclopenta[e]azulene-9-carboxylic acid[4-(3-methyl-oxetan-3-ylmethoxy)-phenyl]-amide | CH$_3$ | H | H | H | 2 | 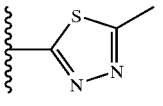 | MS m/z [M + 1] 409 |
| 16 | 2-Methyl-4,5,6,7-tetrahydro-2H-1,2,7-triaza-cyclopenta[e]azulene-9-carboxylic acid [1,3,4]thiadiazol-2-ylamide | CH$_3$ | H | H | H | 2 |  | MS m/z [M + 1] 329 |

TABLE 4-continued

| Cpd # | Name | R^A | R^4 | R^5 | R^6 | k | Ar | Spectral Data |
|---|---|---|---|---|---|---|---|---|
| 17 | 2-Methyl-4,5,6,7-tetrahydro-2H-1,2,7-triaza-cyclopenta[e]azulene-9-carboxylic acid(2-methoxy-pyridin-3-yl)-amide | $CH_3$ | H | H | H | 2 | 2-methoxy-pyridin-3-yl | MS m/z [M + 1] 338 |
| 18 | 2-Methyl-4,5,6,7-tetrahydro-2H-1,2,7-triaza-cyclopenta[e]azulene-9-carboxylic acid o-tolylamide | $CH_3$ | H | H | H | 2 | o-tolyl | MS m/z [M + 1] 321 |
| 19 | 2-Methyl-4,5,6,7-tetrahydro-2H-1,2,7-triaza-cyclopenta[e]azulene-9-carboxylic acid pyridin-2-ylamide | $CH_3$ | H | H | H | 2 | pyridin-2-yl | MS m/z [M + 1] 308 |
| 20 | 2-Methyl-4,5,6,7-tetrahydro-2H-1,2,7-triaza-cyclopenta[e]azulene-9-carboxylic acid(5-ethoxy-pyridin-2-yl)-amide | $CH_3$ | H | H | H | 2 | 5-ethoxy-pyridin-2-yl | MS m/z [M + 1] 352 |
| 21 | 2-Methyl-4,5,6,7-tetrahydro-2H-1,2,7-triaza-cyclopenta[e]azulene-9-carboxylic acid(5-methoxy-pyridin-2-yl)-amide | $CH_3$ | H | H | H | 2 | 5-methoxy-pyridin-2-yl | MS m/z [M + 1] 338 |
| 22 | 2-(2-Hydroxy-ethyl)-4,5,6,7-tetrahydro-2H-1,2,7-triaza-cyclopenta[e]azulene-9-carboxylic acid pyridin-3-ylamide | -CH$_2$CH$_2$OH | H | H | H | 2 | pyridin-3-yl | MS m/z [M − 1] 336 |
| 23 | 2-Ethyl-4,5,6,7-tetrahydro-2H-1,2,7-triaza-cyclopenta[e]azulene-9-carboxylic acid pyridin-3-ylamide | -CH$_2$CH$_3$ | H | H | H | 2 | pyridin-3-yl | MS m/z [M − 1] 320 |

TABLE 4-continued

| Cpd # | Name | R^A | R^4 | R^5 | R^6 | k | Ar | Spectral Data |
|---|---|---|---|---|---|---|---|---|
| 24 | 2,3-Dimethyl-4,5,6,7-tetrahydro-2H-1,2,7-triaza-cyclopenta[e]azulene-9-carboxylic acid(1-methyl-1H-pyrazol-3-yl)-amide | CH$_3$ | CH$_3$ | H | H | 2 | 1-methyl-pyrazol-3-yl | MS m/z [M − 1] 323.3 |
| 25 | 2,3-Dimethyl-4,5,6,7-tetrahydro-2H-1,2,7-triaza-cyclopenta[e]azulene-9-carboxylic acid pyrazin-2-ylamide | CH$_3$ | CH$_3$ | H | H | 2 | pyrazin-2-yl | MS m/z [M + 1] 321.3 |
| 26 | 2-(2-Ethylamino-ethyl)-4,5,6,7-tetrahydro-2H-1,2,7-triaza-cyclopenta[e]azulene-9-carboxylic acid pyridin-3-ylamide | CH$_2$CH$_2$NHCH$_2$CH$_3$ | H | H | H | 2 | pyridin-3-yl | MS m/z [M − 1] 363 |
| 27 | 2-(2-Ethylamino-ethyl)-4,5,6,7-tetrahydro-2H-1,2,7-triaza-cyclopenta[e]azulene-9-carboxylic acid(1-methyl-1H-pyrazol-3-yl)-amide | CH$_2$CH$_2$NHCH$_2$CH$_3$ | H | H | H | 2 | 1-methyl-pyrazol-3-yl | MS m/z [M − 1] 366 |
| 28 | 2-(2-Ethylamino-ethyl)-4,5,6,7-tetrahydro-2H-1,2,7-triaza-cyclopenta[e]azulene-9-carboxylic acid[1,3,4]thiadiazol-2-ylamide | CH$_2$CH$_2$NHCH$_2$CH$_3$ | H | H | H | 2 | [1,3,4]thiadiazol-2-yl | MS m/z [M − 1] 370 |

TABLE 4-continued

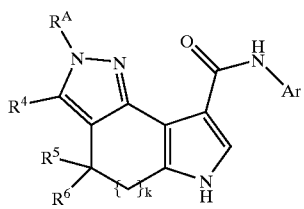

| Cpd # | Name | R^A | R^4 | R^5 | R^6 | k | Ar | Spectral Data |
|---|---|---|---|---|---|---|---|---|
| 29 | 2-(2-Diethylamino-ethyl)-4,5,6,7-tetrahydro-2H-1,2,7-triaza-cyclopenta[e]azulene-9-carboxylic acid(1-methyl-1H-pyrazol-3-yl)-amide | (diethylaminoethyl) | H | H | H | 2 | 1-methyl-1H-pyrazol-3-yl | MS m/z [M − 1] 394 |
| 30 | 2-(2-Diethylamino-ethyl)-4,5,6,7-tetrahydro-2H-1,2,7-triaza-cyclopenta[e]azulene-9-carboxylic acid[1,3,4]thiadi-azol-2-ylamide | (diethylaminoethyl) | H | H | H | 2 | [1,3,4]thiadiazol-2-yl | MS m/z [M − 1] 398 |

Example 13

4,5,6,7-Tetrahydro-1-oxa-2,7-diaza-cyclopenta[e]azulene-9-carboxylic acid ethyl ester

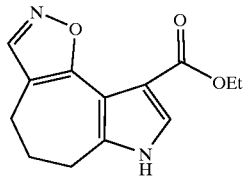

In a sealed tube, 4-oxo-5,6,7,8-tetrahydro-4H-cyclohepta[b]pyrrole-1,3-dicarboxylic acid 1-tert-butyl ester 3-ethyl ester (2.6 mmol) and tris(dimethylamino)methane (5.2 mmol) are combined and heated at 60° C. for 3 hours. After cooling to RT the volatile material is removed in vacuo. To the residue were added hydroxylamine hydrochloride (7.8 mmol) and 7 mL EtOH. The mixture is heated at 100° C. for 16 hours. The solvent is evaporated in vacuo and the residue is taken up in CH$_2$Cl$_2$ and washed two times with NaHCO$_3$ (aq). The organic layer is dried over Na$_2$SO$_4$ and evaporated in vacuo and the residue chromatographed using 10% MeOH in CH$_2$Cl$_2$ as mobile phase to yield 4,5,6,7-tetrahydro-1-oxa-2,7-diaza-cyclopenta[e]azulene-9-carboxylic acid ethyl ester as a white solid (76%). $^1$H NMR (CDCl$_3$) 1.19 (t, 3H), 1.95–2.07 (m, 2H), 2.78 (t, 2H), 2.95 (t, 2H), 4.38 (q, 2H), 7.26 (s, 1H), 8.03 (s, 1H), 8.77 (s, 1H).

Example 14

3-Methyl-4,5,6,7-tetrahydro-1-oxa-2,7-diaza-cyclopenta[e]azulene-9-carboxylic acid ethyl ester

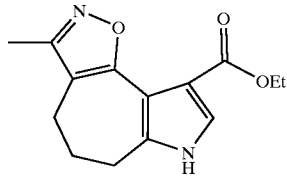

In a sealed tube were 5-acetyl-4-oxo-5,6,7,8-tetrahydro-4H-cyclohepta[b]pyrrole-1,3-dicarboxylic acid 1-tert-butyl ester 3-ethyl ester (1.1 mmol) and hydroxylamine hydrochloride (2.2 mmol) and 10 mL EtOH. The mixture is heated at 100° C. for 16 hours. The solvent is evaporated in vacuo and the residue is taken up in CH$_2$Cl$_2$ and washed two times with NaHCO$_3$ (aq). The organic layer is dried over Na$_2$SO$_4$ and evaporated in vacuo and the residue chromatographed using 10% MeOH in CH$_2$Cl$_2$ as mobile phase to yield 3-methyl-4,5,6,7-tetrahydro-1-oxa-2,7-diaza-cyclopenta[e]azulene-9-carboxylic acid ethyl ester as a white solid (76%). $^1$H NMR (CDCl$_3$+CD$_3$OD) 1.3 (t, 3H), 1.90–1.98 (m, 2H), 2.10 (s, 3H), 2.35 (t, 2H), 2.75–2.82 (m, 2H), 4.21 (q, 2H), 7.15 (s, 1H)

Example 14a

Using the method shown in Scheme 7 and further illustrated in Examples 13–14 the compounds shown in Table 5 were prepared.

TABLE 5

| Cpd# | Name | R4 | R5 | R6 | k | Ar | Spectral Data |
|---|---|---|---|---|---|---|---|
| 1 | 4,5,6,7-Tetrahydro-1-oxa-2,7-diaza-cyclopenta[e]azulene-9-carboxylic acid phenyl-amide | H | H | H | 2 | phenyl | LRMS calcd 293.32 found (M + 1) 294 |
| 2 | 4,5,6,7-Tetrahydro-1-oxa-2,7-diaza-cyclopenta[e]azulene-9-carboxylic acid (3-methoxy-phenyl)-amide | H | H | H | 2 | 3-methoxyphenyl | LRMS calcd 323.3 found (M + 1) 324 |
| 3 | 4,5,6,7-Tetrahydro-1-oxa-2,7-diaza-cyclopenta[e]azulene-9-carboxylic acid (2,3-dihydro-benzo[1,4]dioxin-6-yl)amide | H | H | H | 2 | 2,3-dihydrobenzo[1,4]dioxin-6-yl | LRMS calcd 351.3 found (M + 1) 352.3 |
| 4 | 4,5,6,7-Tetrahydro-1-oxa-2,7-diaza-cyclopenta[e]azulene-9-carboxylic acid (4-methoxy-phenyl)-amide | H | H | H | 2 | 4-methoxyphenyl | LRMS calcd 323.3 found (M − 1) 322 |
| 5 | 4,5,6,7-Tetrahydro-1-oxa-2,7-diaza-cyclopenta[e]azulene-9-carboxylic acid [4-(2-propylamino-ethoxy)-phenyl]-amide | H | H | H | 2 | 4-(2-propylamino-ethoxy)phenyl | LRMS calcd 394.4 found (M + 1) 395 |
| 6 | Propyl-(2-{4-[(4,5,6,7-tetrahydro-1-oxa-2,7-diaza-cyclopenta[e]-azulene-9-carbonyl)-amino]-phenoxy}-ethyl)-carbamic acid tert-butyl ester | H | H | H | 2 | 4-{2-[N-Boc-N-propyl-amino]ethoxy}phenyl | LRMS calcd 494.59 found (M − 1) 493.3 |
| 7 | 4,5,6,7-Tetrahydro-1-oxa-2,7-diaza-cyclopenta[e]-azulene-9-carboxylic acid (5-ethoxy-pyridin-2-yl)amide | H | H | H | 2 | 5-ethoxy-pyridin-2-yl | LRMS calcd 338.36 found (M + 1) 339 |
| 8 | 4,5,6,7-Tetrahydro-1-oxa-2,7-diaza-cyclopenta[e]azulene-9-carboxylic acid pyridin-3-ylamide | H | H | H | 2 | pyridin-3-yl | LRMS calcd 294.3 found (M + 1) 295.3 |

TABLE 5-continued

| Cpd# | Name | R4 | R5 | R6 | k | Ar | Spectral Data |
|---|---|---|---|---|---|---|---|
| 9 | 3-Methyl-4,5,6,7-tetrahydro-1-oxa-2,7-diaza-cyclopenta[e]azulene-9-carboxylic acid (4-methoxy-phenyl)-amide | CH$_3$ | H | H | 2 | 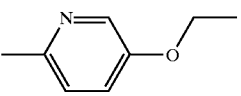 | LRMS calcd 337.4 found (M + 1) 338 |
| 10 | 3-Methyl-4,5,6,7-tetrahydro-1-oxa-2,7-diaza-cyclopenta[e]azulene-9-carboxylic acid (5-ethoxy-pyridin-2-yl)-amide | CH$_3$ | H | H | 2 | 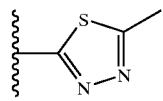 | LRMS calcd 352.4 found (M + 1) 353 |
| 11 | 3-Methyl-4,5,6,7-tetrahydro-1-oxa-2,7-diaza-cyclopenta[e]azulene-9-carboxylic acid 2-(5-methyl-[1,3,4]thiadiazol-2-yl)-amide | CH$_3$ | H | H | 2 | 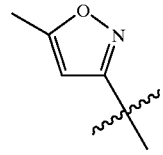 | LRMS calcd 329.4 found (M + 1) 330 |
| 12 | 3-Methyl-4,5,6,7-tetrahydro-1-oxa-2,7-diaza-cyclopenta[e]azulene-9-carboxylic acid (5-methyl-isoxazol-3-yl)-amide | CH$_3$ | H | H | 2 | 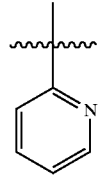 | LRMS calcd 312.3 found (M + 1) 313 |
| 13 | 3-Methyl-4,5,6,7-tetrahydro-1-oxa-2,7-diaza-cyclopenta[e]azulene-9-carboxylic acid pyridin-2-ylamide | CH3 | H | H | 2 | 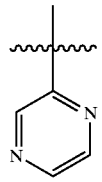 | LRMS calcd 308.3 found (M + 1) 309 |
| 14 | 3-Methyl-4,5,6,7-tetrahydro-1-oxa-2,7-diaza-cyclopenta[e]azulene-9-carboxylic acid pyrazin-2-ylamide | CH3 | H | H | 2 | 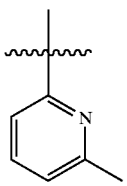 | LRMS calcd 309.3 found (M + 1) 310 |
| 15 | 3-Methyl-4,5,6,7-tetrahydro-1-oxa-2,7-diaza-cyclopenta[e]azulene-9-carboxylic acid (6-methyl-pyridin-2-yl)-amide | CH3 | H | H | 2 | | LRMS calcd 322.3 found (M + 1) 323 |

Example 15

2-methyl-5,6-dihydro-4H-thiazolo[4,5-e]indole-8-carboxylic acid ethyl ester

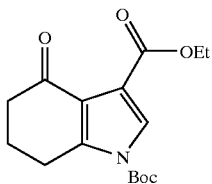

Step 1:

To a mixture of 4-Oxo-4,5,6,7-tetrahydro-1H-indole-3-carboxylic acid ethyl ester (2.4 mmol) in 10 mL 1,4-dioxane is added di-tert-butyl dicarbonate (2.9 mmol), followed by a solution of $K_2CO_3$ (2.9 mmol) in 5 mL $H_2O$. After stirring at RT for 16 hours 50 mL ethyl acetate and 50 mL $H_2O$ are added to the mixture. The organic layer is separated and the aqueous layer is extracted several times with EtOAc. The organic layers are combined, dried over $Na_2SO_4$ and evaporated in vacuo yielding 4-Oxo-4,5,6,7-tetrahydro-indole-1,3-dicarboxylic acid 1-tert-butyl ester 3-ethyl ester, 700 mg, as a dark yellow/brown oil (95%). $^1$H NMR (CDCl$_3$) 1.38 (t, 3H), 1.62 (s, 9H), 2.11–2.19 (m, 2H), 2.50–2.58 (m, 2H), 3.17 (t, 2H), 4.37 (q, 2H), 7.70 (s, 1H).

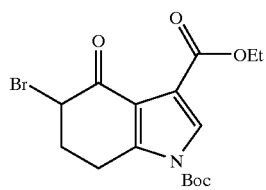

Step 2:

To the solution of 4-oxo-4,5,6,7-tetrahydro-indole-1,3-dicarboxylic acid 1-tert-butyl ester 3-ethyl ester (33 mmol) in 140 mL THF is added dropwise a solution of phenyltrimethylammonium bromide (33 mmol) in 56 mL THF. After stirring at RT for an additional 1½ hours the mixture is poured onto 200 mL 5% NaHCO$_3$ solution, and is then extracted several times with EtOAc. The organic layers are combined, dried over Na$_2$SO$_4$ and evaporated in vacuo. The dark brown oil is chromatographed using ethyl acetate 1:hexanes 10 as a mobile phase to yield 5-bromo-4-oxo-4,5,6,7-tetrahydro-indole-1,3-dicarboxylic acid 1-tert-butyl ester 3-ethyl ester, 5 g, as a white solid (40%). $^1$H NMR (CDCl$_3$)1.39 (t, 3H), 1.62 (s, 9H), 2.42–2.51 (m, 2H), 3.20–3.38 (m, 2H), 4.35 (q, 2H), 4.58 (t, 1H), 7.79 (s, 1H)

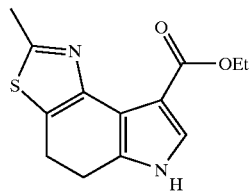

Step 3:

To a solution of 5-bromo-4-oxo-4,5,6,7-tetrahydro-indole 1,3-dicarboxylic acid 1-tert-butyl ester 3-ethyl ester (0.78 mmol) in 10 mL CH$_3$OH is added thioacetamide (1.55 mmol). After stirring under refluxing for 16 hours the solvent is removed in vacuo. The brown oil is chromatographed using EtOAc 1: hexane 1, followed by 5% MeOH in CH$_2$Cl$_2$ as mobile phases to yield 2-methyl-5,6-dihydro-4H-thiazolo[4,5-e]indole-8-carboxylic acid ethyl ester as a white solid (34%). $^1$H NMR (DMSO-d$_6$) 1.27 (t, 3H), 2.60 (s, 3H), 2.78(t, 2H), 2.96 (t, 2H), 4.19 (q, 2H), 7.21 (s, 1H), 11.44 (s, 1H).

Example 16

2-Ethyl-5,6-dihydro-4H-thiazolo[4,5-e]indole-8-carboxylic acid ethyl ester

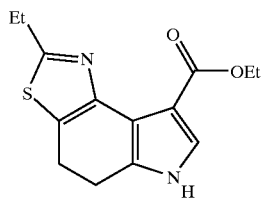

The title compound is prepared by reacting 5-bromo-4-oxo-4,5,6,7-tetrahydro-indole 1,3-dicarboxylic acid 1-tert-butyl ester 3-ethyl ester with thiopropionamide essentially according to the procedures described in Example 15, Step 3. $^1$H NMR (CDCl$_3$) 1.33–1.42 (m, 6H), 2.80–2.90 (m, 2H), 2.98–3.10 (m, 4H), 2.37 (q, 2H), 7.24 (s, 1H), 8.60 (s, 1H).

Example 17

2-Methyl-3,4,5,6-tetrahydro-imidazo[4,5-e]indole-8-carboxylic acid ethyl ester

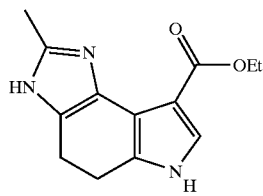

To a solution of 5-bromo-4-oxo-4,5,6,7-tetrahydro-indole 1,3-dicarboxylic acid 1-tert-butyl ester 3-ethyl ester (1.66 mmol) in 15 mL 1,4-dioxane is added acetamidine hydrochloride (3.32 mmol). After stirring under refluxing for 16 hours the solvent is removed in vacuo. To the residue is added 14 mL CHCl$_3$ and 2 mL MeOH and the mixture is stirred for 10 min. The solid is filtered off. The mother liquid is concentrated and is chromatographed using 10% MeOH in CH$_2$Cl$_2$ as mobile phase to yield 2-methyl-3,4,5,6-tetrahydro-imidazo[4,5-e]indole-8-carboxylic acid ethyl ester as a white solid (30%). $^1$H NMR (DMSO-d$_6$) 1.30 (t, 3H), 2.28 (s, 3H), 2.70 (t, 2H), 2.79 (t, 2H), 4.22 (q, 2H), 7.20 (s, 1H), 10.58 (s, 1H), 11.43 (s, 1H).

Example 18

2-Pyridin-4-yl-4,5,6,7-tetrahydro-3H-1,3,7-triaza-cyclopenta-[e]azulene-9-carboxylic acid methyl ester

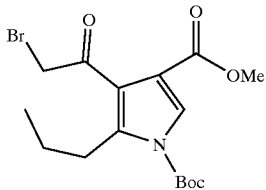

Step 1:

To a solution of 4-Oxo-5,6,7,8-tetrahydro-4H-cyclohepta[b]pyrrole1,3-dicarboxylic acid 3-methyl ester 1-tert-butyl ester(1.1 g, 3.6 mmol) in DMSO(20 mL) is added 1,3-dibromo-5,5-dimethylhydantoin(1.5 g, 5.4 mmol) portion wise with the aid of a cooling bath and the resulting mixture is stirred for 18 h at RT. Water is added and the reaction mixture is extracted with ether. The combined ether layers are washed with saturated brine, dried over $Na_2SO_4$, and concentrated in vacuo. The residue is purified by flash chromatography on silica gel (10% EtOAc/Hex to 25% EtOAc/Hex) to yield 915 mg of 5-Bromo-4-oxo-5,6,7,8-tetrahydro-4H-cyclohepta[b]pyrrole-1,3-dicarboxylic acid 1-tert-butyl ester 3-methyl ester as a bright yellow oil (66%). $^1$H NMR(CDCl$_3$) 1.59 (s, 9H), 1.72–1.84 (m, 1H), 2.12–2.25 (m, 2H), 2.43–2.58 (m, 1H), 3.05–3.14 (m, 1H), 3.40–3.49 (m, 1H), 3.80 (s, 3H), 4.75 (m, 1H), 7.79 (s, 1H)

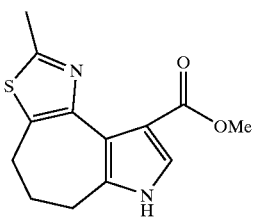

Step 2:

A mixture of 5-Bromo-4-oxo-5,6,7,8-tetrahydro-4H-cyclohepta[b]pyrrole-1,3-dicarboxylic acid 1-tert-butyl ester 3-methyl ester(467 mg, 1.2 mmol), 4-Amidinopyridine hydrochloride(953 mg, 6.1 mmol), and NaHCO$_3$(813 mg, 9.7 mmol) in dioxane(20 mL) is refluxed for 20 h. After cooling to RT, MeOH(5 mL) is added and the mixture is filtered. The filtrate is concentrated in vacuo and the brown residue is purified by flash chromatography on silica gel (10% MeOH/CH$_2$Cl$_2$) to yield 197 mg of 2-Pyridin-4-yl-4,5,6,7-tetrahydro-3H-1,3,7-triaza-cyclopenta[e]azulene-9-carboxylic acid methyl ester as a yellow solid (53%). $^1$H NMR (CDCl$_3$) 2.06 (quint, 2H), 2.98 (t, 2H), 3.04 (t, 2H), 3.91 (s, 1H), 7.46 (s, 1H), 7.76 (d, 2H) 8.28 (br s, 1H) 8.56 (d, 2H)

Example 19

2-Pyridin-4-yl-4,5,6,7-tetrahydrdo-3H-1,3,7-triaza-cyclopenta[e]-azulene-9-carboxylic acid phenyl amide

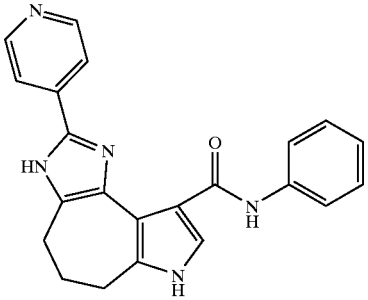

To a solution of Aniline(155 L, 1.7 mmol) in CH$_2$Cl$_2$(5 mL) at RT is added Trimethylaluminum(0.85 mL of 2M solution in toluene, 1.7 mmol) and the mixture is stirred for 30 min. To this is added a solution of 2-Pyridin-4-yl-4,5,6,7-tetrahydro-3H-1,3,7-triaza-cyclopenta[e]azulene-9-carboxylic acid methyl ester(51 mg, 0.17 mmol) in CH$_2$Cl$_2$(2 mL) and the mixture is refluxed for 18 h and diluted with CH$_2$Cl$_2$. MeOH(5 mL) is added slowly with vigorous stirring. The mixture is filtered through celite, concentrated in vacuo, and purified by flash chromatography on silica gel to yield 20 mg of 2-Pyridin-4-yl-4,5,6,7-tetrahydrdo-3H-1,3,7-triaza-cyclopenta[e]azulene-9-carboxylic acid phenyl amide as a yellow solid(32%). LRMS calcd 369.43 found (M+H) 370.07

Example 20

2-Methyl-4,5,6,7-tetrahydro-3-thia-1,7-diaza-cyclopenta[e]azulene-9-carboxylic acid methyl ester A mixture of 5-Bromo-4-oxo-5,6,7,8-tetrahydro-4-H-cyclohepta[b]pyrrole-1,3-dicarboxylic acid 1-tert-butyl ester 3-methyl ester(880 mg, 2.27 mmol) and Thioacetamide(426 mg, 4.54 mmol) in MeOH(20 mL) is refluxed for 20 h and concentrated in vacuo. The residue is purified by flash chromatography on silica gel (50% EtOAc/Hex to 10% MeOH/CH$_2$Cl$_2$) to yield 382 mg of 2-Methyl-4,5,6,7-tetrahydro-3-thia-1,7-diaza-cyclopenta[e]azulene-9-carboxylic acid methyl ester as a yellow foam(64%). $^1$H NMR (CD$_3$OD) 2.18 (quint, 2H), 2.61 (s, 3H), 2.70 (t, 2H) 2.78 (t, 2H), 3.73 (s, 3H), 7.29 (s, 1H)

Example 21

Using the method shown in Scheme 8 and further illustrated in Examples 15–20 the compounds shown in Table 6 were prepared.

TABLE 6

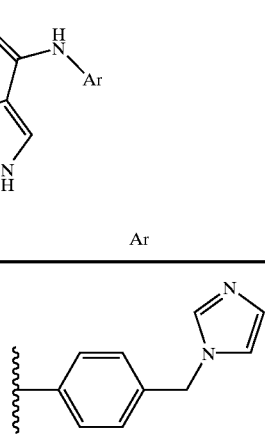

| Cpd# | Name | X | R4 | R5 | R6 | k | Ar | Spectral Data |
|---|---|---|---|---|---|---|---|---|
| 1 | 2-Methyl-4,5,6,7-tetrahydro-3-thia-1,7-diaza-cyclopenta[e]azulene-9-carboxylic acid(4-imidazol-1-ylmethyl-phenyl)-amide | S | CH$_3$ | H | H | 2 | 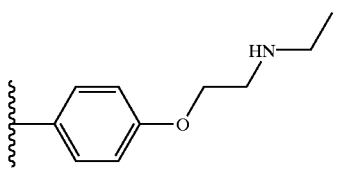 | LRMS calcd 403.5 found (M + 1) 404.1 |
| 2 | 2-Methyl-4,5,6,7-tetrahydro-3-thia-1,7-diaza-cyclopenta[e]azulene-9-carboxylic acid[4-(2-ethylamino-ethoxy)-phenyl]-amide | S | CH$_3$ | H | H | 2 | 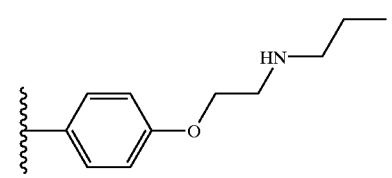 | LRMS calcd 410.54 found (M + 1) 411.3 |
| 3 | 2-Methyl-4,5,6,7-tetrahydro-3-thia-1,7-diaza-cyclopenta[e]azulene-9-carboxylic acid[4-(2-propylamino-ethoxy)-phenyl]-amide | S | CH$_3$ | H | H | 2 | 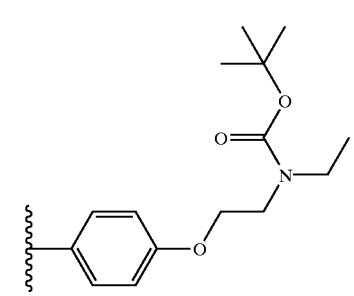 | LRMS calcd 424.57 found (M − 1) 423.2 |
| 4 | Ethyl-(2-{4-[(2-methyl-4,5,6,7-tetrahydro-3-thia-1,7-diaza-cyclopenta[e]azulene-9-carbonyl)-amino]phenoxy}-ethyl)-carbamic acid tert-butyl ester | S | CH$_3$ | H | H | 2 | 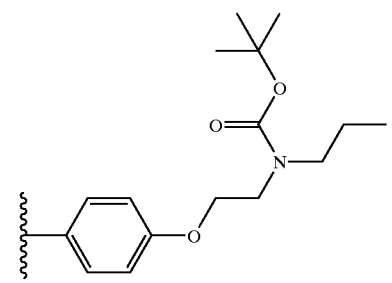 | LRMS calcd 510.66 found (M − 1) 509.4 |
| 5 | (2-{4-[(2-Methyl-4,5,6,7-tetrahydro-3-thia-1,7-diaza-cyclopenta[e]azulene-9-carbonyl)-amino]-phenoxy}-ethyl)-propyl-carbamic acid tert-butyl ester | S | CH$_3$ | H | H | 2 | 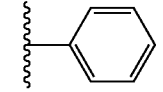 | LRMS calcd 524.68 found (M − 1) 523.2 |
| 6 | 2-Methyl-5,6-dihydro-4H-thiazolo[4,5-e]indole-8-carboxylic acid phenylamide | S | CH$_3$ | H | H | 1 |  | LRMS calcd 309.39 found (M + 1) 310.88 |

TABLE 6-continued

| Cpd# | Name | X | R4 | R5 | R6 | k | Ar | Spectral Data |
|---|---|---|---|---|---|---|---|---|
| 7 | 2-Methyl-5,6-dihydro-4H-thiazolo[4,5-e]indole-8-carboxylic acid [4-(3-imidazol-1-yl-propoxy)-phenyl]-amide | S | CH₃ | H | H | 1 | 4-(3-imidazol-1-yl-propoxy)phenyl | LRMS calcd 433.53 found (M + 1) 434.03 |
| 8 | 2-Methyl-5,6-dihydro-4H-thiazolo[4,5-e]indole-8-carboxylic acid [4-(2-imidazol-1-yl-ethyl)-phenyl]-amide | S | CH₃ | H | H | 1 | 4-(2-imidazol-1-yl-ethyl)phenyl | LRMS calcd 403.51 found (M + 1) 404.0 |
| 9 | 2-Methyl-5,6-dihydro-4H-thiazolo[4,5-e]indole-8-carboxylic acid [4-(2-imidazol-1-yl-ethoxy)-phenyl]-amide | S | CH₃ | H | H | 1 | 4-(2-imidazol-1-yl-ethoxy)phenyl | LRMS calcd 419.51 found (M + 1) 420.0 |
| 10 | 2-Methyl-5,6-dihydro-4H-thiazolo[4,5-e]indole-8-carboxylic acid (4-[1,2,4]triazol-1-ylmethyl-phenyl)-amide | S | CH₃ | H | H | 1 | 4-[1,2,4]triazol-4-ylmethyl-phenyl | LRMS calcd 390.47 found (M + 1) 391.1 |
| 11 | 2-Methyl-5,6-dihydro-4H-thiazolo[4,5-e]indole-8-carboxylic acid (4-imidazol-1-ylmethyl-phenyl)-amide | S | CH₃ | H | H | 1 | 4-imidazol-1-ylmethyl-phenyl | LRMS calcd 389.48 found (M + 1) 390.1 |
| 12 | 2-Methyl-5,6-dihydro-4H-thiazolo[4,5-e]indole-8-carboxylic acid (1H-benzoimidazol-5-yl)-amide | S | CH₃ | H | H | 1 | 1H-benzoimidazol-5-yl | LRMS 349.42 found (M + 1) 350.2 |
| 13 | 2-Methyl-5,6-dihydro-4H-thiazolo[4,5-e]indole-8-carboxylic acid [3-fluoro-4-(2-morpholin-4-yl-ethoxy)-phenyl]-amide | S | CH₃ | H | H | 1 | 3-fluoro-4-(2-morpholin-4-yl-ethoxy)phenyl | LRMS calcd 456.54 found 456.85 |

TABLE 6-continued

| Cpd# | Name | X | R4 | R5 | R6 | k | Ar | Spectral Data |
|---|---|---|---|---|---|---|---|---|
| 14 | 2-Methyl-5,6-dihydro-4H-thiazolo[4,5-e]indole-8-carboxylic acid {4-[2-(4-benzyl-piperidin-1-yl)-ethoxy]-phenyl}-amide | S | CH$_3$ | H | H | 1 | 4-[2-(4-benzylpiperidin-1-yl)ethoxy]phenyl | LRMS calcd 526.70 found 527.1 |
| 15 | 2-Methyl-5,6-dihydro-4H-thiazolo[4,5-e]indole-8-carboxylic acid [3-fluoro-4-(2-pyrrolidin-1-yl-ethoxy)-phenyl]-amide | S | CH$_3$ | H | H | 1 | 3-fluoro-4-(2-pyrrolidin-1-yl-ethoxy)phenyl | LRMS calcd 440.54 found 440.9 |
| 16 | 2-Methyl-5,6-dihydro-4H-thiazolo[4,5-e]indole-8-carboxylic acid [4-(2-propylamino-ethoxy)-phenyl]-amide | S | CH$_3$ | H | H | 1 | 4-(2-propylamino-ethoxy)phenyl | LRMS calcd 410.54 found (M + 1) 411.0 |
| 17 | 2-Methyl-5,6-dihydro-4H-thiazolo[4,5-e]indole-8-carboxylic acid [4-(1-benzyl-1H-imidazol-2-ylmethoxy)-phenyl]-amide | S | CH$_3$ | H | H | 1 | 4-(1-benzyl-1H-imidazol-2-ylmethoxy)phenyl | LRMS calcd 496.59 found 497.03 |
| 18 | 2-Ethyl-5,6-dihydro-4H-thiazolo[4,5-e]indole-8-carboxylic acid phenylamide | S | Et | H | H | 1 | phenyl | LRMS calcd 323.42 found 323.93 |
| 19 | 2-Methyl-3,4,5,6-tetrahydro-imidazo[4,5-e]indole-8-carboxylic acid phenylamide | NH | CH$_3$ | H | H | 1 | phenyl | LRMS calcd 292.34 found (M − 1) 291.0 |
| 20 | 2-Methyl-4,5,6,7-tetrahydro-3H-1,3,7-triaza-cyclopenta[e]azulene-9-carboxylic acid phenylamide | NH | CH$_3$ | H | H | 2 | phenyl | LRMS calcd 306.37 found (M + H) 307.30 |

TABLE 6-continued

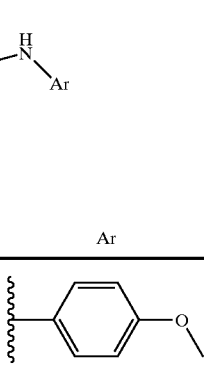

| Cpd# | Name | X | R4 | R5 | R6 | k | Ar | Spectral Data |
|---|---|---|---|---|---|---|---|---|
| 21 | 2-Methyl-4,5,6,7-tetrahydro-3H-1,3,7-triaza-cyclopenta[e]azulene-9-carboxylic acid(4-methoxy-phenyl)amide | NH | CH₃ | H | H | 2 | 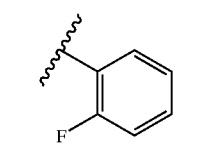 | LRMS calcd 336.39 found (M + H) 337.07 |
| 22 | 2-Methyl-4,5,6,7-tetrahydro-3H-1,3,7-triaza-cyclopenta[e]azulene-9-carboxylic acid(2-fluoro-phenyl)-amide | NH | CH₃ | H | H | 2 | 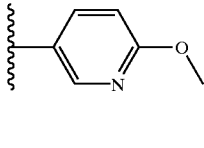 | LRMS calcd 324.35 found (M + H) 325.40 |
| 23 | 2-Methyl-4,5,6,7-tetrahydro-3H-1,3,7-triaza-cyclopenta[e]azulene-9-carboxylic acid(6-methoxy-pyridin-3-yl)-amide | NH | CH₃ | H | H | 2 |  | LRMS calcd 337.38 found (M + H) 338.07 |
| 24 | 2-Cyclopropyl-4,5,6,7-tetrahydro-3H-1,3,7-triaza-cyclopenta[e]azulene-9-carboxylic acid phenylamide | NH | 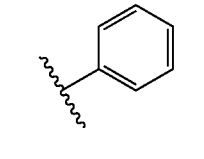 | H | H | 2 | 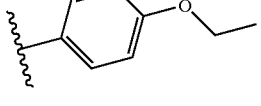 | LRMS calcd 332.41 found (M + H) 333.06 |
| 25 | 2-Methyl-4,5,6,7-tetrahydro-3H-1,3,7-triaza-cyclopenta[e]azulene-9-carboxylic acid(4-ethoxy-phenyl)-amide | NH | CH₃ | H | H | 2 |  | LRMS calcd 350.41 found (M + H) 351.08 |
| 26 | 2-Pyridin-4-yl-4,5,6,7-tetrahydro-3H-1,3,7-triaza-cyclopenta[e]azulene-9-carboxylic acid (4-methoxy-phenyl)-amide | NH | 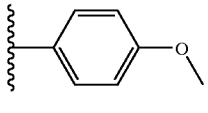 | H | H | 2 | 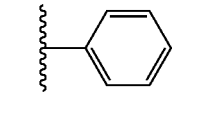 | LRMS calcd 399.39 found (M + H) 400.09 |
| 27 | 2-Methyl-4,5,6,7-tetrahydro-3-thia-1,7-diaza-cyclopenta[e]azulene-9-carboxylic acid phenylamide | S | CH₃ | H | H | 2 | 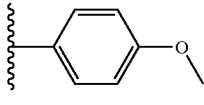 | LRMS calcd 323.42 found (M + H) 324.30 |
| 28 | 2-Methyl-4,5,6,7-tetrahydro-3-thia-1,7-diaza-cyclopenta[e]azulene-9-carboxylic acid(4-methoxy-phenyl)-amide | S | CH₃ | H | H | 2 | | LRMS calcd 353.44, found (M + H) 354.02 |

TABLE 6-continued

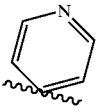

| Cpd# | Name | X | R4 | R5 | R6 | k | Ar | Spectral Data |
|---|---|---|---|---|---|---|---|---|
| 29 | 2-Pyridin-4-yl-4,5,6,7-tetrahydro-3-thia-1,7-diaza-cyclopenta[e]azulene-9-carboxylic acid phenylamide | S | 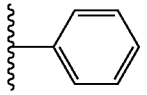 | H | H | 2 | 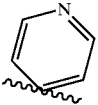 | LRMS calcd 386.48 found (M + H) 387.03 |
| 30 | 2-Pyridin-4-yl-4,5,6,7-tetrahydro-3-thia-1,7-diaza-cyclopenta[e]azulene-9-carboxylic acid (4-methoxy-phenyl)-amide | S | 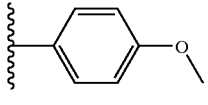 | H | H | 2 | 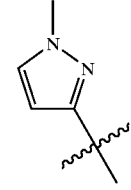 | LRMS calcd 416.50 found (M + H) 417.03 |
| 31 | 2-Methyl-4,5,6,7-tetrahydro-3-thia-1,7-diaza-cyclopenta[e]azulene-9-carboxylic acid(1-methyl-1H-pyrazol-3-yl)-amide | S | $CH_3$ | H | H | 2 | 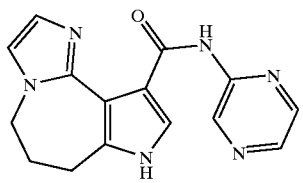 | LRMS calcd 327 found (M + H) 328 |

Example 21a

Preparation of 4,5,6,7-tetrahydro-1,3a,7-triaza-cyclopenta[e]azulene-9-carboxylic acid pyrazin-2-ylamide Step 1:

A mixture of 4-oxo-4,5,6,7-tetrahydro-1H-indole-3-carboxylic acid propyl ester (2.0 g) and $NaN_3$ (2.0 g) in 50 mL of trifluoroacetic acid is stirred at 60–80° C. for a period of 3 days during which additional 2.5 g $NaN_3$ of is added on first, second and third day. After diluted with water, the mixture is extracted with Ethyl acetate. The extract is washed with $NaHCO_3$, brine and concentrated under reduced pressure. The residue is subject to a silica gel chromatography eluting with 10% MeOH in $CH_2Cl_2$ to give 500 mg of 4-oxo-1,4,5,6,7,8-hexahydro-pyrrolo[3,2-c]azepine-3-carboxylic acid propyl ester as a foam.

Step 2:

A mixture of compound (500 mg) from Step 1 and $P_4S_{10}$ (2.0 g) in 20 mL of pyridine is heated at 80° C. with stirring overnight. It is cooled and evaporated under vacuum, then diluted with water and stirred. The insoluble material is filtered and the mother liquid is extracted with $CH_2Cl_2$/EtOAc (1:4). The combined extract is washed with brine, dried and concentrated to give 120 mg of 4-thioxo-1,4,5,6,7,8-hexahydro-pyrrolo[3,2-c]azepine-3-carboxylic acid propyl ester.

Step 3:

A mixture of compound (120 mg) from Step 2, Hg(OAc)$_2$(160 mg) and 2,2-dimethoxy-ethylamine (0.5 mL) in 5 mL of THF is stirred at room temperature for 2 hours. The volatiles are removed under vacuum. The residue is dissolved in 15 mL of MeOH and 1 mL of 37% HCl. The resultant mixture is heated at 50° C. overnight. It is cooled and evaporated under vacuum, then diluted with MeOH and $CH_2Cl_2$(2:1). The mixture is filtered through celite. The mother liquid is concentrated to a residue to which are added ethyl acetate, water and $K_2CO_3$. The organic layer is separated and concentrated to a solid (57 mg) as 4,5,6,7-tetrahydro-1,3a,7-triaza-cyclopenta[e]azulene-9-carboxylic acid propyl ester.

Step 4:

To a stirred solution of aminopyrazine (100 mg) in 5 mL of dichloroethane is added a solution of $AlMe_3$ in toluene (2 M, 0.5 mL) under nitrogen. The mixture is stirred at room temperature for 1 hour. 25 mg of compound from Step 3 is added once. The resultant mixture is heated at 60° C. overnight. It is cooled and quenched with water, and diluted with $CH_2Cl_2$. The organic layer is separated and washed with brine, dried and concentrated. The residue is subject to a silica gel plate chromatography eluting with 10% MeOH in CH$_2$Cl$_2$ yields 5 mg of 4,5,6,7-tetrahydro-1,3a,7-triaza-cyclopenta[e]azulene-9-carboxylic acid pyrazin-2-ylamide.

Example 21b

Preparation of 2-methoxy-7H-pyrrolo [2,3-c][1,5] naphthyridine 9-carboxylic acid-pyridin-2-ylamide Step 1:

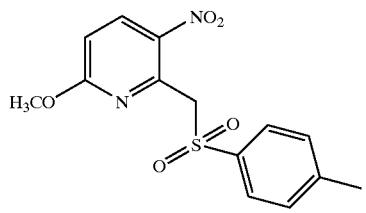

A mixture of 15.4 g (0.1 mol) of 6-methoxy-3-nitropyridine and 20.4 g (0.1 mol) of 1-chloromethane-sulfonyl-4-methyl-benzene is dissolved in 100 mL of DMF and cooled to 5 C. To this solution is added, dropwise, 100 mL (0.1 mol) of a 1M solution of potassium t-butoxide in THF, keeping the temperature≦10 C. The dark reaction mixture is stirred for 18 hours at room temperature. The reaction mixture is evaporated to remove the THF, and to the remaining solution is added 100 mL of water. A dark brown precipitate formed which is collected by filtration. This solid is triturated with isopropyl ether for 1 hour and refiltered to yield 12 grams of 6-methoxy-3-nitro-2-(toluene-4-sulfonylmethyl)-pyridine. $^1$H NMR (CDCl$_3$) δ8.25 (d, 1H), 7.60 (m, 2H), 7.30 (m, 2H), 6.80 (d, 1H), 5.10 (s, 1H), 3.75 (s, 3H), 2.40 (s, 3H). Mass Spectrum: m/e=323.1 (p+1), TLC (CDCl$_3$) Rf=0.45

Step 2:

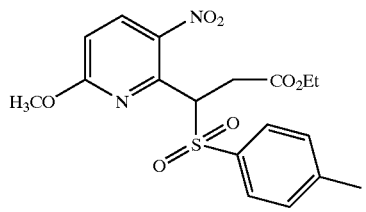

A mixture of 5.0 g (15.5 mmol) of 6-methoxy-3-nitro-2-(toluene-4-sulfonyl methyl)-pyridine and 1.8 mL (16 mmol) of ethyl bromoacetate is dissolved in 20 mL of DMF. To this solution is added 4.4 g (32 mmol) of K$_2$CO$_3$ and the reaction mixture is heated to 50° C. for 18 hours. The reaction mixture is cooled to room temperature and diluted with 300 mL of water. The mixture is extracted with ethyl acetate. The ethyl acetate extracts are dried (Na$_2$SO$_4$) and evaporated to yield 7.2 grams of 6-methoxy-3-nitro-pyridin-2-yl]-[toluene-4-sulfonyl]-acetic acid ethyl ester. $\underline{H}$ NMR (CDCl$_3$) δ8.30 (d, 1H), 7.60 (d, 2H), 7.30 (d, 2H), 6.80 (d, 1H), 6.30 (m, 1H), 4.0 (q, 2H), 3.80 (s, 3H), 3.60 (m, 1H), 3.10 (m, 1H), 2.40 (s, 3H), 1.10 (t, 3H). Mass spectrum: m/e=409.0 (p+1). TLC (7/3: hexanes/ethyl acetate) Rf=0.5.

Step 3:

To a solution of 10.2 grams (0.0259 mol) in 500 mL of ethanol is added approximately 1 gram of Raney Nickel. The mixture is hydrogenated at 40 psi for 18 hours. The mixture is filtered and the solvent evaporated to yield 9.45 grams of [3-amino-6-methoxy-pyridin-2-yl]-[toluene-4-sulfonyl-acetic acid ethyl ester. $\underline{H}$ NMR (CDCl$_3$) δ7.4–7.8 (m, 5H), 7.10 (m, 1H), 6.5 (m, 1H), 5.2 (m, 1H), 4.0 (q, 2H), 3.25 (s, 3H) 3.0–3.2 (m, 2H), 1.1 (s, 3H). Mass spectrum: m/e=365.3 (p+1) TLC (7/3: hexanes/ethyl acetate) Rf–0.4.

Step 4:

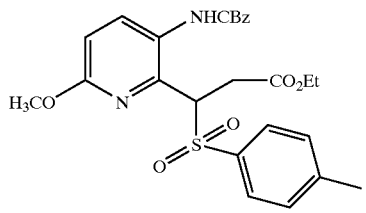

To a solution of 9.45 g (0.026 m) of [3-amino-6-methoxy-pyridin-2-yl]-[toluene-4-sulfonyl]-acetic acid ethyl ester dissolved in 150 mL of methylene chloride is added 150 mL of saturated sodium bicarbonate followed by 5.56 mL (0.038 m) of carbo-benzyloxy chloride. The reaction mixture is stirred for 20 hours at room temperature. The water layer is separated from the organic layer and the organic layer is dried (Na$_2$SO$_4$) and evaporated to yield 15.73 grams of [3-benzyloxycarbonylamino-6-methoxy-pyridin-2-yl]-[toluene-4-sulfonyl]-acetic acid ethyl ester as a yellow solid. $\underline{H}$ NMR (CDCl$_3$) δ7.8 (m, 1H), 7.6 (m, 1H), 7.3 (m,10H), 6.7 (m, 1H), 5.2 (m, 3H), 4.0 (m, 2H), 3.3 (s, 3H), 3.1 (m, 2H), 1.1 (m, 3H) TLC (7/3 hexanes/ethyl acetate) Rf=0.6.

Step 5:

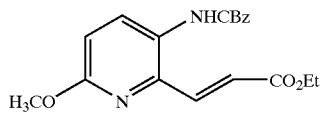

To a cooled (5° C.) solution of 15.7 g (0.031 mol) of (3-benzyloxycarbonylamino-6-methoxy-pyridin-2-yl)-(toluene-4-sulfonyl)-acetic acid ethyl ester dissolved in 160 mL of THF is added, dropwise, 31 mL of a 1N solution of potassium-t-butoxide dissolved in THF. The reaction mixture is warmed to room temperature and stirred for 2 hours.

The reaction is quenched with 5 mL of water and evaporated. The residue is dissolved in 200 mL of ethyl acetate and 200 mL of water. The ethyl acetate layers are dried (Na$_2$SO$_4$) and evaporated. The residue is chromatographed on 375 grams of silica gel using 7/3 hexanes/ethyl acetate as the eluant. Appropriate fractions are combined and evaporated to yield 5.57 grams of 3-[3-benzyloxycarbonylamino-6-methoxy-pyridin-2-yl]-acrylic acid ethyl ester. H NMR (CDCl$_3$) δ7.8 (m, 2H), 7.4 (m, 2H), 7.0 (m, 1H), 6.8 (m, 1H), 6.7 (m, 1H), 5.2 (s, 2H), 4.2 (q, 2H) 3.9 (s, 3H), 1.3 (t, 3H). Mass spectrum: m/e=357 (p+1).

Step 6:

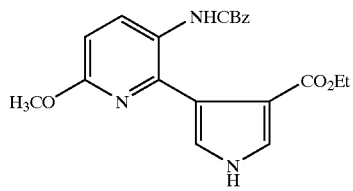

A solution of 3.96 g (0.02 mol) of tosylmethyl isocyamide in 50 mL of THF is cooled to −70° C. To this solution is added, dropwise 40.6 mL of potassium bis (trimethylsilyl)-amide (0.5M solution in toluene). After the addition is complete the mixture is stirred for 45 minutes at −70° C. To this mixture is added, dropwise, a solution of 5.5 g (0.015 mol) of 3-(3-benzyloxycarbonylamino-6-methoxy pyridin-2-yl)-acetic acid ethyl ester dissolved in 50 mL of THF. The reaction mixture is warmed to room temperature and stirred for 20 hours. The reaction mixture is quenched with water and extracted with ethyl acetate. The organic extracts are dried (Na$_2$SO$_4$) and evaporated. The residue is chromatographed on 150 g of silica gel using 50/50 ethyl acetate/hexanes as the eluant. Appropriate fractions are combined and evaporated to yield 3.2 g of 4-(benzyloxycarbonylamino-6-methoxy-pyridin-2-yl)-1H-pyrrole-3-carboxylic acid ethyl ester. H NMR (CDCl$_3$) δ9.20 (m, 1H), 8.10 (m, 1H), 7.60 (m, 1H), 7.30 (m, 5H), 6.90 (m, 1H), 6.70 (m, 1H), 5.10 (s, 2H), 4.10 (q, 2H), 3.90 (s, 3H), 1.90 (s, 1H), 1.10 (t, 3H). TLC (ethyl acetate) Rf=0.9.

Step 7:

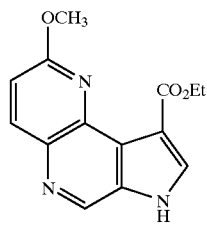

A 10 mL aliquot DMF is cooled to 5° C. To this is added 2.26 mL (0.024 mol) of phosphorous oxychloride. The mixture is warmed to room temperature, stirred for 15 minutes and cooked to 5° C. To this solution is added dropwise a solution 3.2 g (0.08 mol) of 4-(benzyloxycarbonylamino-6-methoxy-pyridin-2-yl)-1H-pyrrole-3-carboxylic acid ethyl ester dissolved in 15 mL of DMF. The reaction mixture is warmed to room temperature and stirred for 3 hours. The reaction mixture is carefully poured into 100 mL of saturated sodium bicarbonate. The pH is adjusted to 8 with solid K$_2$CO$_3$ and the mixture extracted with ethyl acetate. The organic extracts are dried (Na$_2$SO$_4$) and evaporated. The residue is chromatographed on 150 g of silica gel using ethyl acetate followed by 10/1 chloroform/methanol as the eluant. Appropriate fractions are combined to yield 1.46 grams of 8-methoxy-3H-pyrrolo[2,3-c]quinoline-1-carboxylic acid ethyl ester. H NMR (CDCl$_3$) δ9.10 (s, 1H), 8.35 (d, 1H), 8.10 (s, 1H, 7.2 (s, 1H), 7.05 (d, 1H), 4.4 (q, 2H), 4.10 (s, 3H), 1.40 (t, 3H). Mass spectrum: m/e=260 (p+1). TLC (ethyl acetate) Rf=0.3.

Step 8:

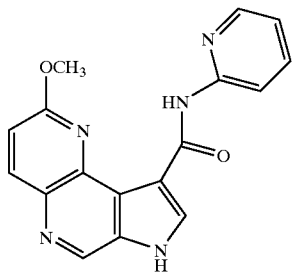

A solution of 0.56 grams (6.0 mmol) of 2-amino pyridine in 5 mL of methylene chloride is cooled to 5° C. To this is added 2.25 mL (4.5 mmol) of trimethyl aluminum (2M solution in toluene). This mixture is then stirred for 45 minutes at room temperature. This solution is then added dropwise to a solution of 0.4 g (1.5 mmol) of 8-methoxy-3H-pyrrolo[2,3-c]quinoline-1-carboxylic acid ethyl ester dissolved in 15 mL of methylene chloride. This mixture is heated to 35° C. for 18 hours. The reaction mixture is cooled to 5° C. and quenched with 20 mL of saturated sodium chloride. After 30 minutes the reaction mixture is filtered. The collected solids are stirred in water and the pH is adjusted to 1.8 with 1N HCl. The mixture is filtered. The filtrate is then adjusted to pH=9.0 with 1N NaOH. A tan solid precipitate is collected, washed with acetone and dried. This solid is triturated with 50 mL of 1/1 methanol/chloroform and filtered to afforded 300 mg of 2-methoxy-7H-pyrrolo[2,3-c]-[1,5]napthyridine-9-carboxylic acid-pyridin-2-yl amide. H NMR (CDCIl$_3$) δ12.3 (s, 1H), 9.1 (s, 1H), 8.5 (m, 2H), 8.4 (s, 1H), 8.3 (m, 1H), 7.85 (m, 1H), 7.2 (m, 2H), 7.1 (m, 1H), 4.2 (s, 3H). Mass spectrum: m/e=320 (p+1).

Example 21c

Using the method shown in Scheme 10 and further illustrated in Example 21b the compounds shown in Table 7 were prepared.

TABLE 7

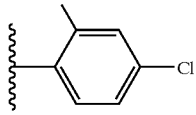

| Cpd# | Name | R3a | R3 | R4 | Ar | Spectral Data |
|------|------|-----|----|----|----|---------------|
| 1 | 2-Methoxy-7H-pyrrolo[2,3-c][1,5]naphthyridine-9-carboxylic acid (2,4-dichloro-phenyl)-amide | CH$_3$O | H | H | 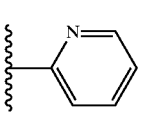 | m/e = 308, 310 |
| 2 | 2-Methoxy-7H-pyrrolo[2,3-c][1,5]naphthyridine-9-carboxylic acid pyridin-2-ylamide | CH$_3$O | H | H | 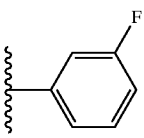 | m/e = 320.1 (P + 1) |
| 3 | 2-Methoxy-7H-pyrrolo[2,3-c][1,5]naphthyridine-9-carboxylic acid (3-fluoro-phenyl)-amide | CH$_3$O | H | H | 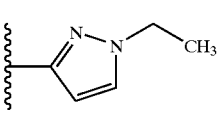 | m/e = 337 (P + 1) |
| 4 | 2-Methoxy-7H-pyrrolo[2,3-c][1,5]naphthyridine-9-carboxylic acid (1-ethyl-1H-pyrazol-3-yl)-amide | CH$_3$O | H | H |  | m/e = 337 (p + 1) |
| 5 | 2-Methoxy-7H-pyrrolo[2,3-c][1,5]naphthyridine-9-carboxylic acid (4-chloro-phenyl)-amide | CH$_3$O | H | H | 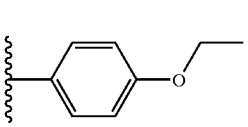 | m/e = 352, 354 |
| 6 | 2-Methoxy-7H-pyrrolo[2,3-c][1,5]naphthyridine-9-carboxylic acid (4-ethoxy-phenyl)-amide | CH$_3$O | H | H | 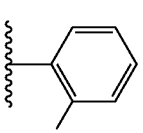 | m/e = 363 (p + 1) |
| 7 | 2-Methoxy-7H-pyrrolo[2,3-c][1,5]naphthyridine-9-carboxylic acid o-tolylamide | CH$_3$O | H | H | 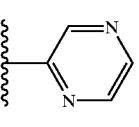 | m/e = 333 (p + 1) |
| 8 | 2-Methoxy-7H-pyrrolo[2,3-c][1,5]naphthyridine-9-carboxylic acid pyrazin-2-ylamide | CH$_3$O | H | H | 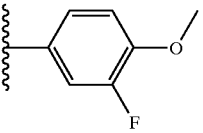 | m/e = 435 (p + 1) |
| 9 | 2-Methoxy-7H-pyrrolo[2,3-c][1,5]naphthyridine-9-carboxylic acid (3-fluoro-4-methoxy-phenyl)-amide | CH$_3$O | H | H | | m/e = 367 (p + 1) |

TABLE 7-continued

| Cpd# | Name | R3a | R3 | R4 | Ar | Spectral Data |
|---|---|---|---|---|---|---|
| 10 | 2-Methoxy-7H-pyrrolo[2,3-c][1,5]naphthyridine-9-carboxylic acid (6-methoxy-2-methyl-pyridin-3-yl)-amide | CH₃O | H | H | 6-methoxy-2-methyl-pyridin-3-yl | Mm/e = 364 (p + 1) |
| 11 | 2-Methoxy-7H-pyrrolo[2,3-c][1,5]naphthyridine-9-carboxylic acid (3-methoxy-phenyl)amide | CH₃O | H | H | 3-methoxy-phenyl | m/e = 349 (p + 1) |
| 12 | 2-Methoxy-7H-pyrrolo[2,3-c][1,5]naphthyridine-9-carboxylic acid (5-methyl-pyridin-2-yl)-amide | CH₃O | H | H | 5-methyl-pyridin-2-yl | m/e = 448 (p + 1) |
| 13 | 2-Methoxy-7H-pyrrolo[2,3-c][1,5]naphthyridine-9-carboxylic acid (2,4-difluoro-phenyl)-amide | CH₃O | H | H | 2,4-difluoro-phenyl | m/e = 355 (p + 1) |
| 14 | 2-Methoxy-7H-pyrrolo[2,3-c][1,5]naphthyridine-9-carboxylic acid (4-fluoro-phenyl)-amide | CH₃O | H | H | 4-fluoro-phenyl | m/e = 337 (p + 1) |
| 15 | 2-Methoxy-7H-pyrrolo[2,3-c][1,5]naphthyridine-9-carboxylic acid p-tolylamide | CH₃O | H | H | p-tolyl | m/e = 333 (p + 1) |
| 16 | 2-Methoxy-7H-pyrrolo[2,3-c][1,5]naphthyridine-9-carboxylic acid (6-methoxy-pyridin-3-yl)-amide | CH₃O | H | H | 6-methoxy-pyridin-3-yl | m/e = 350 (p + 1) |
| 17 | 2-Methoxy-7H-pyrrolo[2,3-c][1,5]naphthyridine-9-carboxylic acid (1H-pyrazol-3-yl)-amide | CH₃O | H | H | 1H-pyrazol-3-yl | m/e = 309 (P + 1) |
| 18 | 2-Methoxy-7H-pyrrolo[2,3-c][1,5]naphthyridine-9-carboxylic acid isoxazol-3-ylamide | CH₃O | H | H | isoxazol-3-yl | m/e = 310 (p + 1) |

Example 21d

Preparation of 3,4,5,6-tetrahydro-3,5,10-triaza-benzo(e)azulene-1-carboxylic acid (3-fluro-phenyl)-amide Step 1:

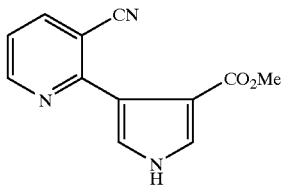

A solution of 13.55 g (0.069 mol) of tosylmethyl isocyamide dissolved in 200 mL of dry THF is cooled to −70° C. under an atmosphere of nitrogen. To this solution is added dropwise 138 mL (0.069 mol) of potassium bis(trimethylsilyl) amide (0.5M solution in toluene) maintaining the temperature<−65° C. After the addition is complete the mixture is stirred 1 hour at −70° C. To this solution 8.68 g (0.048 mol) of 3-(3-cyano-pyridyl-2-yl) acrylic acid methyl ester (A. N. Kost, L. N. Zhukauskaite, *Chem. Heterocycic Compds. English Trans.*, 1971, 7, 469–473) dissolved in 150 mL of dry THF is added dropwise maintaining the temperature at −65° C. The reaction mixture is stirred at −65° C. for 45 minutes and then warmed to −10° C. and stirred an additional 2 hours. The reaction is quenched with 75 mL of water and extracted with ethyl acetate. The organic extracts are dried ($Na_2SO_4$) and evaporated. The residue is chromatographed on 400 g of silica gel using ethyl acetate as the eluant. Appropriate fractions are combined and evaporated to yield 5.4 grams of 4-cyano-pyindin-2-yl-1H-pyrrole-3-carboxylic acid methyl ester. H NMR ($CDCl_3$) δ9.5 (s, 1H), 8.8 (m, 1H), 8.0 (m, 1H), 7.45 (m, 1H), 7.35 (m, 1H), 7.05 (m, 1H), 3.7 (s, 3H). Mass spectrum: m/e=228 (p+1). TLC (ethyl acetate) Rf=0.5.

Step 2:

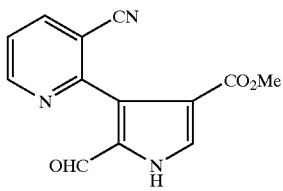

A solution of 30 mL (360 mmol) of DMF in 200 mL of methylene chloride is cooled to 5° C. under a nitrogen atmosphere. To this is added 16 mL (180 mmol) of phosphorus oxychloride, maintaining the temperature<10° C. After addition is complete the reaction is stirred for a ½ hour. To this is added dropwise a solution of 4.0 g (18 mmol) of 4-cyano-pyridin-2-yl-1H-pyrrole-3-carboxylic acid methyl ester dissolved in 100 mL of methylene chloride. The reaction mixture is then heated to 40° C. for 48 hours. The reaction mixture is cooled to room temperature and slowly poured in 300 mL of saturated sodium bicarbonate. The organic layer is then extracted from the aqueous layer, dried ($Na_2SO_4$) and evaporated. The residue is chromatographed on 150 grams of silica gel using 1/1 ethyl acetate/hexanes as the eluant. Appropriate fractions are combined to yield 0.75 g of 4-(3-cyano-pyridin-2-yl)-5-formyl-1H-pyrrole-3-carboxylic acid methyl ester. H NMR ($CDCl_3$) δ10.1 (s, 1H), 9.4 (s, 1H), 8.8 (m, 1H), 8.1 (m, 1H), 7.75 (m, 1H), 7.5 (m, 1H), 3.75 (s, 3H) Mass spectrum: m/e=256.2 (p+1). TLC (10/1 ethyl acetate/chloroform) Rf=0.7. Continued elution of the column afforded 2.5 grams of the starting pyrrole methyl ester.

Step 3:

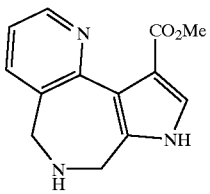

A mixture of 0.75 g (2.9 mmol) of 4-(3cyano-pyridin-2-yl-5-formyl-1H-pyrrole-3-carboxylic acid methyl ester dissolved in 40 mL of methanol containing 2 mL of concentrated HCl and 500 mg of 10% Pd/C catalyst is hydrogenated at 50 PSI for 24 hours. The reaction mixture is filtered and evaporated. The residue is dissolved in a mixture of 50 mL water and ethyl acetate. The ethyl acetate extracts are dried ($Na_2SO_4$) and evaporated to yield 0.35 grams of recovered starting material. The pH of the water layer is adjusted to 9.0 with 1N NaOH and evaporated. The residue is triturated with chloroform. The chloroform extracts are combined, dried ($Na_2SO_4$) and evaporated. The residue is chromatographed on 9 grams of silica gel using 5/1 chloroform/methanol as the eluant. Appropriate fractions are combined and evaporated to yield 180 mg of 3,4,5,6-tetrahydro-3,5,10-triaza-benzo(e)azulene-1-carboxylic acid methyl ester. H NMR ($CDCl_3$) δ10.1 (s, 1H), 8.50 (m, 1H), 7.50 (m, 1H), 7.20 (s, 1H), 7.05 (m, 1H), 3.90 (s, 2H), 3.75 (s, 2H), 3.80 (s, 3H). Mass spectrum: m/e=244.3 (p+1). TLC (5/1/0.1 chloroform/methanol/ammonium hydroxide) Rf=0.2.

Step 4:

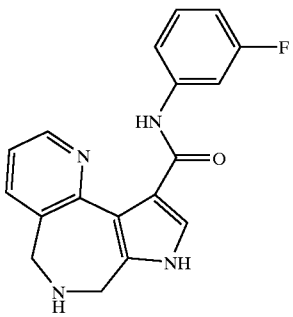

To a solution of 0.38 mL (4 mmol) of 3-fluoroaniline in 2 mL of methylene chloride under a nitrogen atmosphere is added dropwise 1.5 mL (3 mmol) of trimethyl aluminum (2M solution of toluene). This mixture is stirred at room temperature for 30 minutes. To this mixture is added a solution of 0.12 g (0.5 mmol) of 3,4,5,6-tetrahydro-3,5,10-triaza-benzo(e)azulene-1-carboxylic acid methyl ester dissolved in 8 mL of methylene chloride. The reaction mixture is heated to 40° C. for 24 hours; cooled to room temperature and quenched with 0.5 mL of saturated NaCl. After stirring for 30 minutes an additional 5 mL of methylene chloride and 2 grams of anhydrous sodium sulfate is added. The reaction mixture is filtered. The filtrate is evaporated and chromatographed on 10 grams of silica gel using 10/1/0.5 chloroform/methanol/ammonium hydroxide as the eluant. Appropriate fractions are combined and evaporated to 23 mg of 3,4,5,6-tetrahydro-3,5,10-triaza-benzo(e)azulene-1-carboxylic acid (3-fluoro-phenyl)-amide. H NMR ($CD_3OD$) δ8.70 (m, 1H), 7.90 (m, 1H), 7.80 (m, 1H), 7.60 (s, 1H), 7.30 (m, 3H), 6.90 (m, 1H), 3.87 (s, 2H), 3.70 (s, 2H). Mass spectrum: m/e=323.2 (p+1). TLC (10/1/0.1 chloroform/methanol/ammonium hydroxide) Rf=0.3.

Example 21e

Preparation of 5-benzyl-3,4,5,6-tetrahydro-3,5,10-triaza-benzo[e]azulene-1-carboxylic acid pyridin-2-ylamide Step 1 (Step 4' Scheme 11):

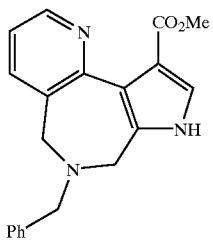

A mixture of 130 mg (0.53 mmol) of 3,4,5,6-Tetrahydro-3,5,10-triaza-benzo[e]azulene-1-carboxylic acid methyl ester and 0.6 mL (0.6 mmol of benzaldehyde is dissolved in 10 mL of dichloroethane. To this solution is added 270 mg (1.3 mmol) of sodium triacetoxyborohydride and the resulting mixture is stirred for 18 hours at room temperature. A 10 mL solution of saturated Na$_2$HCO$_3$ is added, and the reaction stirred for 60 minutes. The organic layer is separated from the aqueous layer, dried (Na$_2$SO$_4$) and evaporated. The residue is chromatographed on 10 grams of silica gel using 50/1 chloroform/methanol as the eluant. Appropriate fractions are combined to yield 118 mg of 5-benzyl-3,4,5,6-tetrahydro-3,5,10-triaza-benzo[e]azulene-1-carboxylic acid methyl ester. $\underline{H}$ NMR (CDCl$_3$) δ10.1 (s, 1H), 8.6 (d, 1H), 7.55 (d, 1H), 7.3 (m, 6H), 7.1 (m, 1H), 3.70 (s, 3H), 3.60 (s, 2H), 3.55 (s, 2H), 3.35 (s, 2H). Mass spectrum: m/e 334.3 (p+1). TLC (10/1 chloroform/methanol) Rf=0.15.

Step 2 (Step 5' in Scheme 11):

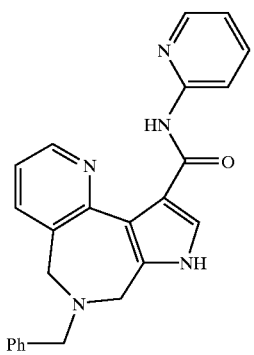

To a solution of 110 mg (1.2 mmol) of 2-aminopyridine in 2 mL of methylene chloride is added dropwise 0.5 mL (1.0 mmol) of trimethyl aluminum (2M solution in toluene). This mixture is stirred at room temperature for ½ hour. The resulting solution is then added dropwise to a 68 mg (0.2 mmol) solution of 5-Benzyl-3,4,5,6-tetrahydro-3,5,10-triaza-benzo[e]azulene-1-carboxylic acid methyl ester dissolved in 8 mL of methylene chloride and the mixture heated to 40° C. for 4 hours. The reaction mixture is quenched with the dropwise addition of 0.75 mL of 1N NaOH and then dried with anhydrous Na$_2$SO$_4$ The reaction mixture is filtered, and the filtrate evaporated. The residue is chromatographed on 9 grams of silica gel using 50/1 chloroform/methanol as the eluant. Appropriate fractions are combined and evaporated to yield 65 mg of 5-benzyl-3,4,5,6-tetrahydro-3,5,10-triaza-benzo[e]azulene-1-carboxylic acid pyridin-2-ylamide. $\underline{H}$ NMR (CDCl$_3$) δ14.1 (s, 1H), 11.0 (s, 1H), 8.8 (m, 1H), 8.4 (m, 2H), 7.7 (s, 1H), 7.6 (m, 2H), 7.4 (m, 6H), 6.95 (m, 1H), 3.7 (s, 2H), 3.55 (s, 2H), 3.50 (s, 2H). Mass spectrum: m/e=396.3 (p+1). TLC (10/1 chloroform/methanol) Rf=0.6

Example 21f

Preparation of 5-methyl-3,4,5,6-tetrahydro-3,5,10-triaza-benzo(e)azulene-1-carboxylic acid pyridin-2-yl-amide.

Step 1:

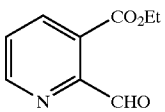

A mixture of 11.3 g (0.069 mol) of 2-methyl-nicotinic acid ethyl ester and 8.4 g (0.076 mol) of selenium dioxide in 150 mL of dioxane is refluxed under nitrogen for 4 hours. The reaction mixture is cooled to room temperature and filtered. The filtrate is evaporated and the residue is chromatographed on 400 grams of silica gel using 50/50 ethyl acetate/hexanes as the eluant. Appropriate fractions are combined to yield 5 g of 2-formyl-nicotinic acid ethyl ester. $\underline{H}$ NMR (CDCl$_3$) δ10.3 (s, 1H), 8.8 (m, 1H), 8.0 (m, 1H), 7.5 (m, 1H), 4.30 (q, 2H), 1.4 (t, 3H). TLC (7/3 hexanes/ethyl acetate) Rf=0.2.

Step 2:

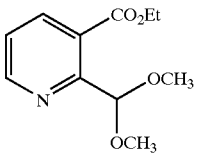

A mixture of 15.4 g (0.086 mol) of 2-formyl-nicotinic acid ethyl ester and 17.9 g (0.094 mol) of p-toluene-sulfonic-acid-monohydrate dissolved in 150 mL of methanol is refluxed for 8 hours. The reaction mixture is cooled to room temperature and the solvent evaporated. The residue is added to water and the pH adjusted to 9.0 with 1N NaOH. The water is extracted with ethyl acetate. The ethyl acetate extracts are dried (Na$_2$SO$_4$) and evaporated. The residue is chromatographed on 400 g of silica gel using 1/1 ethyl acetate/hexanes as the eluant. Appropriate fractions are combine and evaporated to yield 11.25 grams of 2-dimethoxymethyl-nicotinic acid ethyl ester. $\underline{H}$ NMR (CDCl$_3$) δ8.70 (d, 1H), 8.0 (d, 1H), 7.2 (m, 1H), 6.0 (s, 1H), 4.3 (q, 2H), 3.4 (s, 6H), 1.3 (t, 3H).

Step 3:

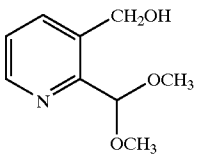

A mixture of 11.3 g (0.05 mol) of 2-dimethoxymethyl-nicotinic acid ethyl ester dissolved in 150 mL of ether and 2.09 g (0.055 mol) of lithium aluminum hydride is stirred at room temperature for 18 hours. An additional 530 mg of lithium aluminum hydride is added and the reaction mixture stirred for another 3 hours. The reaction mixture is cooled using an ice bath and quenched with 6 mL of 1N NaOH and 8 g of sodium sulfate decahydrate. After a ½ hour the reaction mixture is filtered and the filtrate evaporated. The residue is chromatographed on 180 g of silica gel using ethyl acetate as the eluant. Appropriate fractions are combined and evaporated to yield 4.45 g of (2-dimethoxymethyl-pyridin-3-yl) methanol. H NMR (CDCl$_3$) δ8.40 (d, 1H), 7.70 (d, 1H), 7.20 (m, 1H), 5.35 (s, 1H), 4.75 (s, 2H), 3.40 (s, 3H).

Step 4:

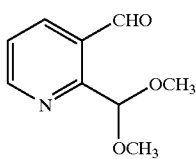

A mixture of 321 mg (1.75 mmol) of (2-dimethoxymethyl-pyridin-3-yl)-methanol and 763 mg (8.77 mmol) of MnO$_2$ in 10 mL of toluene is refluxed for 1.5 hours. The reaction mixture is cooled to room temperature and filtered. The filtrate is evaporated to yield 271 mg of 2-dimethoxymethyl-pyridine-3-carbaldehyde. H NMR (CDCl$_3$) δ10.30 (s, 1H), 8.30 (d, 1H), 8.10 (d, 1H), 7.30 (m, 1H), 5.40 (s, 2H), 4.40 (s, 6H).

Step 5:

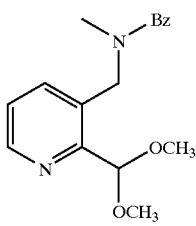

To a mixture of 2.0 g (11 mmol) of 2-dimethoxymethyl-pyridin-3-carbaldehyde and 1.6 mL (12 mmol) of N-benzyl methyl amine in 30 mL of dichloroethane is added 4.7 g (22 mmol) of sodium triacetoxyborohydride. The reaction is stirred for 18 hours at room temperature. To this mixture is added 20 mL of water. After 1 hour of stirring the pH of the reaction mixture is adjusted to 8.0 with 1N NaOH. The organic layer is separated from the water layer, dried and evaporated to yield 1.9 grams of benzyl-(2-dimethoxymethyl-pyridin-3-ylmethyl)-methyl-amine. H NMR (CDCl$_3$) δ8.5 (d, 1H), 7.9 (d, 1H), 7.3 (m, 6H), 5.6 (s, 1H), 3.7 (s, 2H), 3.5 (s, 2H), 3.3 (s, 6H) 2.1 (s, 3H). Mass spectrum: m/e=287.8 (p+1). TLC (1/1 ethyl acetate/hexanes) Rf=0.2.

Step 6:

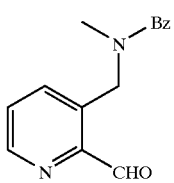

A mixture of 1.9 g (6.6 mmol) of benzyl-(2-dimethoxymethyl-pyridin-3-yl-methyl)-methyl-amine dissolved in 20 mL of acetone and 20 mL of 1N HCl is heated to 65° C. for 6 hours. The reaction mixture is cooled to room temperature and evaporated to remove the acetone. To the resulting residue is added 40 mL of ethyl acetate and the pH of the mixture adjusted to 9.0 with 5N NaOH. The organic layer is separated from the water layer, dried (Na$_2$SO$_4$) and evaporated to afford 1.5 grams of 3-(benzyl-methyl-amino)-methyl-pyridine-2-carbaldehyde. H NMR (CDCl$_3$) δ10.1 (s, 1H), 8.7 (m, 1H), 8.15 (m, 1H), 7.45 (m, 1H), 7.25 (m, 5H), 4.0 (s, 2H), 3.6 (s, 3H) 2.1 (S, 3H). TLC (1/1 ethyl acetate/hexanes) Rf=0.4.

Step 7:

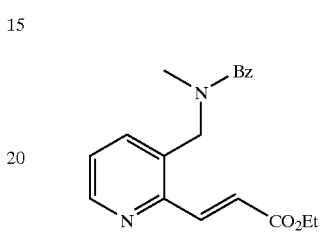

A solution of 1.9 mL (9.4 mmol) of triethylphosphoroacetate in 25 mL of anhydrous THF is cooled to −50° C. under a nitrogen atmosphere. To this is added dropwise 19 mL (9.5 mmol) of potassium bis(trimethylsilyl) amide (0.5M in toluene). After 10 minutes, a solution of 1.5 g (6.2 mmol) of 3-(benzyl-methyl-amino)-methyl-pyridine-2-carbaldehyde dissolved in 10 mL of anhydrous THF is added dropwise. After the addition is complete the reaction mixture is warmed to room temperature and stirred for 2 hours. The reaction is quenched with 20 mL of water and extracted with ethyl acetate. The ethyl acetate extracts are dried (Na$_2$SO$_4$) and evaporated. The residue is chromatographed on 40 g of silica gel using 3/1 hexanes/ethyl acetate as the eluant. Appropriate fractions are combined and evaporated to yield 1.8 g of 3-{3-[[benzyl-methyl-amino]-methyl]-pyridin-2-yl}-acrylic acid ethyl ester. H NMR (CDCl$_3$) δ8.5 (d, 1H), 8.2 (d, 1H), 7.7 (m, 1H), 7.3 (m, 5H), 7.1 (d, 1H), 4.3 (q, 2H), 3.65 (s, 2H), 3.55 (s, 2H), 2.10 (s, 3H), 1.30 (t, 3H). Mass spectrum: m/e=311.3 (p+1). TLC (2/1 hexanes/ethyl acetate) Rf=0.7.

Step 8:

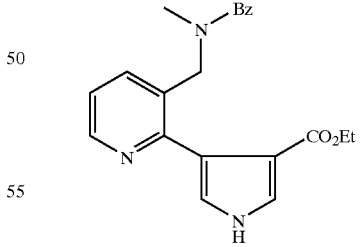

A solution of 2.3 g (11.6 mmol) of tosylmethyl isocyanide in 25 mL of anhydrous THF is cooled to −50° C. under a nitrogen atmosphere. To this solution is added dropwise 23 mL (11.6 mmol) of potassium bis(trimethylsilyl) amide (0.5M solution in toluene) keeping the temperature<−50° C. After addition is complete this mixture is stirred for a 0.5 hour. To this mixture a solution of 1.8 g (5.8 mmol) of 3-{3-[[benzyl-methyl-amino]-methyl]-pyridin-2-yl}-acrylic acid ethyl ester dissolved in 10 mL of anhydrous THF is added dropwise maintaining a temperature<−50° C. After addition is complete the reaction mixture is quenched with 10 mL of water and extracted with ethyl acetate. The organic extracts are dried (Na₂SO₄) and evaporated. The residue is redissolved in approximately 100 mL of ethyl acetate and 100 mL of water. The pH of the mixture is adjusted to 2.0 with 1N HCL. The ethyl acetate layer is separated from the water layer. An additional 100 mL of ethyl acetate is added to the water layer and the pH adjusted to 9.0 with 1N NaOH. The ethyl acetate layer is separated from the water layer, dried (Na₂SO₄) and 2 evaporated to yield 1.9 grams of 4-{3-[[benzyl-methyl-amino]-methyl]-pyridin-2-yl}-1H-pyrrole-3-carboxylic acid ethyl ester. H NMR (CDCl₃) δ8.5 (m, 1H), 8.0 (m, 1H), 7.35 (s, 6H), 7.30 (m, 5H), 7.20 (m, 1H), 6.60 (s, 1H), 4.0 (q, 2H), 3.42 (s, 2H), 3.38 (s, 2H), 2.0 (s, 3H), 1.0 (t, 3H). Mass spectrum: m/e=350.3 (p+1). TLC (10/1 chloroform/methanol) Rf=0.35.

Step 9:

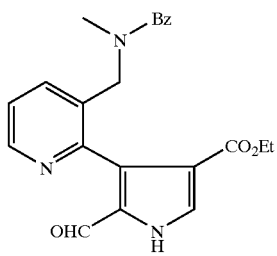

A solution of 6 mL of DMF dissolved in 20 mL of methylene chloride is cooled to 5° C. under a nitrogen atmosphere. To this is added dropwise 2 mL (22 mmol) of phosphorous oxychloride. The reaction is stirred at room temperature for 30 minutes and this solution is added to a cooled (5° C.) solution of 3-{[[benzyl-methyl-amino]-methyl]-pyridin-2-yl}-acrylic acid ethyl ester dissolved in 20 mL of methylene chloride. This mixture is then stirred for 18 hours at room temperature. The reaction mixture is quenched with 20 mL of saturated NaHCO₃ and extracted with ethyl acetate. The organic extracts are dried (Na₂SO₄) and evaporated. The residue is chromatographed on 100 g of silica gel using 4/1 ethyl acetate/chloroform as the eluant. Appropriate fractions are combined and evaporated to yield 1.5 g of 4-{3-[[benzyl-methyl-amino]-methyl]-pyridin-2-yl}-5-formyl-1H-pyrrole-3-carboxylic acid ethyl ester. H NMR (CDCl₃) δ11.1 (s, 1H), 9.2 (s, 1H), 8.6 (d, 1H), 8.0 (s, 1H), 7.6 (d, 1H), 7.4 (m, 1H) 7.2 (m, 5H), 4.0 (q, 2H), 2.95 (s, 2H), 2.85 (s, 2H), 2.0 (s, 3H), 1.0 (t, 3H). Mass spectrum: m/e=378.3 (p+1). TLC (10/1 ethyl acetate/chloroform) Rf=0.6.

Step 10:

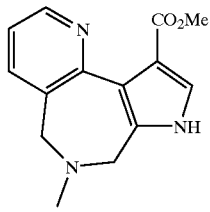

To a solution of 1.5 grams (4 mmol) of 4-{3-[[benzyl-methyl-amino]-methyl]-pyridin-2-yl}-5-formyl-1H-pyrrole-3-carboxylic acid ethyl ester in 50 mL of ethanol containing 2 mL of concentrated HCL is added 500 mg of 10% Pd/C and this mixture is hydrogenated at 50 PSI for 48 hours. The reaction mixture is filtered and the filtrate evaporated. The residue is chromatographed on 100 g of silica gel using 10/1 chloroform/methanol as the eluant. Appropriate fractions are combined to yield 495 mg of 5-methyl-3,4,5,6-tetrahydro-3,5,10-triaza-benza(e)azulene-1-carboxylic acid ethyl ester. H NMR (CDCl₃) δ8.65 (d, 1H), 7.65 (d, 1H), 7.35 (s, 1H), 7.15 (m, 1H), 4.10 (q, 2H), 3.50 (s, 2H), 3.40 (s, 2H), 2.40 (s, 2H), 1.20 (t, 3H). Mass spectrum: m/e=378.3 (p+1). TLC (10/1 chloroform/methanol) Rf=0.15.

Step 11:

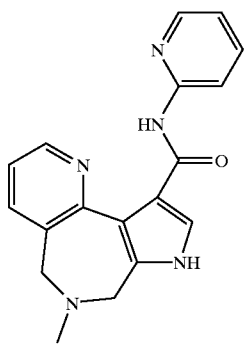

To a solution of 0.17 g (1.8 mmol) of 2-aminopyridine in 2 mL of methylene chloride is added 0.75 mL (1.5 mmol) of trimethyl aluminum (2M solution in toluene) under a nitrogen atmosphere. This mixture is stirred for 0.5 hour at room temperature. This mixture is then added dropwise to a solution of 84 mg (0.3 mmol) of 5-methyl-3,4,5,6-tetrahydro-3,5,10-triaza-benzo(e)azulene-1-carboxylic acid ethyl ester dissolved in 8 mL of methylene chloride. The reaction mixture is heated to 40° C. for 18 hours. The reaction mixture is cooled to room temperature and quenched with 0.2 mL of 1N NaOH. To this is added anhydrous Na₂SO₄ and the reaction filtered. The filtrate is evaporated and the residue chromatographed on 20 g silica gel using 5/1 chloroform/methanol as the eluant. Appropriate fractions are combined and evaporated to yield 60 mg of 5-methyl-3,4,5,6-tetrahydro-3,5,10-triaza-benza(e)azulene-1-carboxylic acid pyridin-2-yl-amide. H NMR (CDCl₃) δ13.9 (s, 1H), 11.1 (s, 1H), 8.8 (m, 1H), 8.4 (m, 2H), 7.7 (m, 3H), 7.2 (m, 1H), 6.9 (m, 1H), 3.6 (s, 2H), 3.4 (s, 2H), 2.4 (s, 3H). Mass spectrum: m/e=320.2 (p+1). TLC (5/1 chloroform/methanol) Rf=0.5.

Example 21g

Using the method shown in Schemes 11 and 12 and further illustrated in Examples 21d–21f the compounds shown in Table 8 were prepared.

TABLE 8

| Cpd# | Name | R3a | R3 | R4 | R5 | Ar | Spectral Data |
|---|---|---|---|---|---|---|---|
| 1 | 5-Methyl-3,4,5,6-tetrahydro-3,5,10-triaza-benzo[e]azulene-1-carboxylic acid(1H-pyrazol-3-yl)-amide | H | H | H | CH$_3$ | 1H-pyrazol-3-yl | m/e = 309(P + 1) |
| 2 | 3,4,5,6-Tetrahydro-3,5,10-triaza-benzo[e]azulene-1-carboxylic acid pyridin-2-ylamide | H | H | H | H | pyridin-2-yl | m/e = 306(p + 1) |
| 3 | 5-Methyl-3,4,5,6-tetrahydro-3,5,10-triaza-benzo[e]azulene-1-carboxylic acid | H | H | H | CH$_3$ | pyridin-2-yl | m/e = 320(p + 1) |
| 4 | 5-Benzyl-3,4,5,6-tetrahydro-3,5,10-triaza-benzo[e]azulene-1-carboxylic acid pyridin-2-ylamide | H | H | H | benzyl | pyridin-2-yl | m/e = 396(p + 1) |
| 5 | 5-Pyridin-2-ylmethyl-3,4,5,6-tetrahydro-3,5,10-triaza-benzo[e]azulene-1-carboxylic acid pyridin-2-ylamide | H | H | H | pyridin-2-ylmethyl | pyridin-2-yl | m/e = 397(p + 1) |
| 6 | 5-Methyl-3,4,5,6 tetrahydro-3,5,10-triaza-benzo[e]azulene-1-carboxylic acid pyridin-3-ylamide | H | H | H | CH$_3$ | pyridin-3-yl | m/e = 320(p + 1) |
| 7 | 5-Methyl-3,4,5,6-tetrahydro-3,5,10-triaza-benzo[e]azulene-1-carboxylic acid(3-fluoro-phenyl)-amide | H | H | H | CH$_3$ | 3-fluoro-phenyl | m/e = 337(p + 1) |
| 8 | 3,4,5,6-Tetrahydro-3,5,10-triaza-benzo[e]azulene-1-carboxylic acid(3-fluoro-phenyl)-amide | H | H | H | H | 3-fluoro-phenyl | m/e = 323(P + 1) |
| 9 | 5-Methyl-3,4,5,6-tetrahydro-3,5,10-triaza-benzo[e]azulene-1-carboxylic acid isoxazol-3-ylamide | H | H | H | CH$_3$ | isoxazol-3-yl | m/e = 310(p + 1) |

Example 22

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SR[1] International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 23

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 24

Binding Assay

This assay is a standard assay for $GABA_A$ binding affinity. The high affinity and high selectivity of compounds of this invention for the benzodiazepine site of the $GABA_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containing 100 μl of tissue homogenate, 100 μl of radioligand, (0.5 nM $^{3}H$-RO15-1788 [$^{3}H$-Flumazenil], specific activity 80 Ci/mmol), and test compound or control (see below), are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 μM Diazepam (Research Biochemicals International, Natick, Mass.). Data were collected in triplicate, averaged, and percent inhibition of total specific binding (Total Specific Binding=Total−Nonspecific) is calculated for each compound.

A competition binding curve is obtained with up to 11 points spanning the compound concentration range from $10^{-12}M$ to $10^{-5}M$ obtained per curve by the method described above for determining percent inhibition. $K_i$ values are calculated according the Cheng-Prussof equation. When tested in this assay, preferred compounds of Formulas I exhibit $K_i$ values of less than 1 uM, more preferred compounds of the invention have $K_i$ values of less than 500 nM and highly preferred compounds have $K_i$ values of less than 100 nM.

Example 25

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 AM RO$^{15}$-1788+ test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

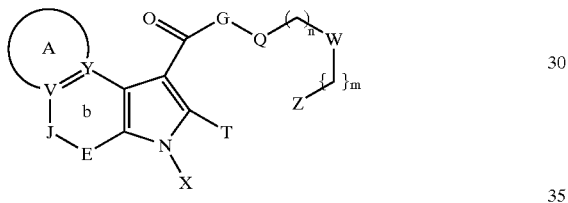

or a pharmaceutically acceptable salt thereof wherein:
the b-ring is a 7 membered ring with one nitrogen;
E represents $(CR^1R^2)_k$, —$CR^1$=$CR^2$—, —N=$CR^1$—, —$CR^1$=N—, —NR'—$(CR^1R^2)$—, or —$(CR^1R^2)$—NR'—, wherein
$R^1$ and $R^2$ independently represent
hydrogen, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, or mono- or di($C_1$–$C_6$)alkylamino($C_1$–$C_6$)alkyl, or
phenyl, pyridyl, phenyl($C_1$–$C_6$)alkyl, or pyridyl ($C_1$–$C_6$) alkyl, where each phenyl or pyridyl is optionally substituted with $C_1$–$C_6$ alkyl, $C_1$–$C_6$ alkoxy, halogen, hydroxy, cyano, nitro, amino, and mono- or di($C_1$–$C_6$)alkylamino;
k is 2;
R' represents
hydrogen, $C_1$–$C_6$ alkyl, $C_1$–$C_6$ alkanoyl, $C_1$–$C_6$ alkoxy($C_1$–$C_6$)alkyl, $C_2$–$C_6$ alkenyl, $C_2$–$C_6$ alkynyl, $C_1$–$C_6$ haloalkyl, amino($C_1$–$C_6$)alkyl, or mono- or di($C_1$–$C_6$)alkylamino($C_1$–$C_6$) alkyl, or
aryl, heteroaryl, aryl($C_1$–$C_6$)alkyl, or heteroaryl ($C_1$–$C_6$)alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$)alkylamino;
G is oxygen or NH;

J represents $(CR^5R^6)_d$ where
d is 1; and
$R^5$ and $R^6$ together form a carbonyl group; or
$R^5$ and $R^6$ are independently hydrogen or $R^{100}$,
where each $R^{100}$ is independently selected from halogen, hydroxy, nitro, cyano, $R_{10}$, amino, —NH ($R_{10}$), —N($R_{10}$)($R_{10}$), —COOH, —O($R_{10}$), —$SO_2NH_2$, —$SO_2NH(R_{10})$, —$SO_2N(R_{10})(R_{10})$, —NHCO($R_{10}$), —N($R_{10}$)CO($R_{10}$), —NHCO$_2$($R_{10}$), —N($R_{10}$)CO$_2$($R_{10}$), —NNSO$_2$($R_{10}$), —N($R_{10}$)SO$_2$ ($R_{10}$), —$SO_2NHCO(R_{10})$, —$SO_2N(R_{10})CO(R_{10})$, —CONHSO$_2$($R_{10}$), —CON($R_{10}$)SO$_2$($R_{10}$), —CONH$_2$, —CONH($R_{10}$), —CON($R_{10}$)($R_{10}$), —CO$_2$($R_{10}$), —CO($R_{10}$), —SR$_{10}$, SO($R^{10}$), —SO$_2$ ($R_{10}$), aryl having from 1 to 3 rings, and heteroaryl, said heteroaryl having from 1 to 3 rings, 5 to 7 ring members in each ring, and in at least one of said rings from 1 to about 3 heteroatoms selected from nitrogen, oxygen and sulfur, and where each aryl and heteroaryl is optionally substituted with 1, 2, or 3 groups independently selected from $C_1$–$C_6$ alkyl, $C_1$–$C_6$ alkoxy, halogen, hydroxy, cyano, nitro, amino, and mono- or di($C_1$–$C_6$)alkylamino;
each $R_{10}$ is independently a straight, branched, or cyclic alkyl group having up to 8 carbon atoms, contains zero or one or more double or triple bonds, and is optionally substituted with one or more substituents independently selected from hydroxy, oxo, halogen, amino, mono- or di-($C_2$–$C_6$)alkylamino, cyano, nitro, $C_1$–$C_6$alkoxy, —COOH, —$SO_2NH_2$, —$SO_2NH(C_1$–$C_6$ alkyl), —$SO_2N(C_1$–$C_6$alkyl)($C_1$–$C_6$alkyl), —NHCO ($C_1$–$C_6$alkyl), —N($C_1$–$C_6$alkyl)CO($C_1$–$C_6$alkyl), NHCO$_2$($C_1$–$C_6$alkyl), —N($C_1$–$C_6$alkyl)CO$_2$ ($C_1$–$C_6$alkyl), —NHSO$_2$($C_1$–$C_6$alkyl), —N($C_1$–$C_6$alkyl)SO$_2$($C_1$–$C_6$alkyl), —SO$_2$N ($C_1$–$C_6$alkyl)CO($C_1$–$C_6$alkyl), —SO$_2$NHCO ($C_1$–$C_6$alkyl), —CON($C_1$–$C_6$alkyl)SO$_2$ ($C_1$∝$C_6$alkyl), —CONHSO$_2$($C_1$–$C_6$alkyl), —CONH$_2$, —CONH(alkyl), —CON(alkyl) (alkyl), —CO$_2$(alkyl), —CO(alkyl), —SO$_{0-2}$ ($C_1$–$C_6$alkyl), and $C_3$–$C_7$cycloalkyl;
the group

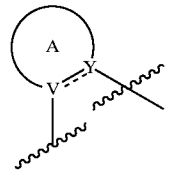

is the A ring and represents an optionally substituted saturated, partially unsaturated, or aromatic heterocyclic ring containing at least one nitrogen, oxygen, or sulfur atom,
where the A ring is optionally substituted with up to three groups independently selected from $R^{100}$;
V is nitrogen, carbon, or CH;
Y is carbon or CH;
X is hydrogen, hydroxy, amino, mono- or di($C_1$–$C_6$) alkylamino, $C_1$–$C_6$alkyl, or $C_1$–$C_6$ alkoxy;
T is hydrogen, halogen, hydroxy, amino, mono- or di($C_1$–$C_6$) alkylamino, $C_1$–$C_6$ alkyl, or $C_1$–$C_6$ alkoxy;
Q is a saturated carbocyclic or heterocyclic group, partially unsaturated carbocyclic or heterocyclic group, an aryl group, or heteroaryl group, where each group has from 1 to 3 rings where each ring contains from 3 to 8 ring members, and where each heterocyclic and heteroaryl group contains at least one ring having from 1 to 3 heteroatoms selected from nitrogen, oxygen and sulfur; and where each carbocyclic, heterocyclic, aryl, or heteroaryl group is optionally substituted with 1, 2, or 3 groups independently selected from $C_1$–$C_6$ alkyl, $C_1$–$C_6$ alkoxy, halogen, hydroxy, oxo, cyano, nitro, amino, $C_1$–$C_6$ haloalkyl, $C_1$–$C_6$ haloalkoxy, and mono- or di($C_1$–$C_6$) alkylamino;

W is a bond, oxygen, NH, sulfur, —CH=CH—, —C≡C—, or $CR^7R^8$ where $R^7$ and $R^8$ are the same or different and represent hydrogen, $C_1$–$C_6$ alkyl, halo($C_1$–$C_6$)alkyl, amino($C_1$–$C_6$)alkyl, hydroxy ($C_1$–$C_6$)alkyl, or $C_1$–$C_6$ alkoxy($C_1$–$C_6$)alkyl, or $CR^7R^8$ represents $C_3$–$C_7$ cycloalkyl;

Z is hydrogen, hydroxy, hydroxy($C_1$–$C_6$)alkyl, $C_1$–$C_6$ alkoxy, —CO($C_1$–$C_6$)alkyl, $C_3$–$C_7$ cycloalkyl, $C_3$–$C_7$ cycloalkyl ($C_1$–$C_6$)alkyl, $C_3$–$C_7$ cycloalkyl ($C_1$–$C_6$)alkoxy, amino, mono- or di($C_1$–$C_6$) alkylamino, or $NR_{11}COR_{12}$ where $R_{11}$ and $R_{12}$ are the same or different and represent hydrogen or $C_1$–$C_6$ alkyl, or $NCOR_{11}R_{12}$ represents a heterocycloalkanone ring, or Z is a saturated carbocyclic or heterocyclic group, a partially unsaturated carbocyclic or heterocyclic group, an aryl group, or a heteroaryl group, where each group has from 1 to 3 rings where each saturated ring contains from 3 to 8 ring members and each aromatic or partially unsaturated ring contains from 5–8 ring members, and where each heterocyclic and heteroaryl group contains at least one ring having from 1 to 3 heteroatoms selected from nitrogen, oxygen and sulfur; and where each carbocyclic, heterocyclic, aryl, and heteroaryl group is optionally substituted with 1, 2, or 3 groups independently selected from $C_1$–$C_6$ alkyl, $C_1$–$C_6$ alkoxy, halogen, hydroxy, cyano, nitro, amino, $C_1$–$C_6$ haloalkyl, $C_1$–$C_6$ haloalkoxy, and mono- or di($C_1$–$C_6$)alkylamino;

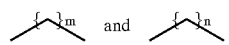

independently represent saturated carbon chains optionally substituted with one or more substituents independently selected from halogen, cyano, nitro, amino, mono- or di($C_1$–$C_6$)alkylamino, $C_2$–$C_6$ alkenyl, $C_2$–$C_6$ alkynyl, $C_1$–$C_6$ alkoxy, $C_1$–$C_6$ haloalkyl, $C_1$–$C_6$ haloalkoxy, $C_1$–$C_6$ alkyl, and $C_3$–$C_7$ cycloalkyl;

m is 0, 1, 2, or 3; and n is 0, 1, 2, or 3;

provided that when V is nitrogen, E does not contain nitrogen.

2. A compound or salt according to claim 1, wherein

G is NH;

E represents $(CR^1R^2)_k$;

the A ring represents a group of the formula:

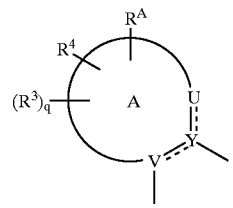

which represents a saturated, partially unsaturated, or aromatic heterocyclic ring selected from thienyl, thiazolyl, pyridyl, pyridonyl, pyrimidinyl, pyrimidinyl, imidazolyl, pyrazolyl, pyrazinyl, pyridizinyl, piperidinyl, oxazolyl, isoxazolyl, triazolyl, pyrrolyl, furanyl, diazenyl, triazenyl, 1,2,4-triazolone, 4,5-dihydroimidazolyl, and 1,4,5,6-tetrahydropyrimidinyl, where any amino-hydrogen is optionally replaced by $R^A$ where:

U is nitrogen, $NR^A$, S, or O;

V is nitrogen, carbon or CH;

Y is carbon, or CH;

$R^A$ is selected from ($C_1$–$C_6$)alkyl, $C_1$–$C_6$ haloalkyl, amino($C_1$–$C_6$)alkyl, or mono- or di($C_1$–$C_6$) alkylamino($C_1$–$C_6$)alkyl, hydroxy($C_1$–$C_6$)alkyl, $C_1$–$C_6$ alkoxy($C_1$–$C_6$)alkyl, aryl, heteroaryl, aryl ($C_1$–$C_6$)alkyl, or heteroaryl($C_1$–$C_6$)alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di ($C_1$–$C_6$) alkylamino;

$R^3$ and $R^4$ are substituents on carbon atoms and independently carry the same definitions as $R^5$ and $R^6$; and q is 1 or 2;

$R^5$ and $R^6$ are independently hydrogen or $R_{100}$ where each $R_{200}$ is independently selected from the group consisting of halogen, hydroxy, nitro, cyano, ($C_1$–$C_6$)alkyl, amino, $C_1$–$C_6$ haloalkyl, —COOH, —$SO_2NH_2$, —NH (($C_1$–$C_6$)$alkyl_1$), —N(($C_1$–$C_6$)$alkyl_1$)(($C_1$–$C_6$)$alkyl_1$), —O(($C_1$–$C_6$)$alkyl_1$), —$SO_2$N(($C_1$–$C_6$)$alkyl_1$)(($C_1$–$C_6$) $alkyl_1$), —$SO_2$NH(($C_1$–$C_6$)$alkyl_1$), —NHCO(($C_1$–$C_6$) $alkyl_1$), —N(($C_1$–$C_6$)$alkyl_1$)CO(($C_1$–$C_6$)$alkyl_1$), —$NHCO_2$(($C_1$–$C_6$)$alkyl_1$), —N(($C_1$–$C_6$)$alkyl_1$)$CO_2$ (($C_1$–$C_6$)$alkyl_1$), —$NHSO_2$(($C_1$–$C_6$)$alkyl_1$), —N(($C_1$–$C_6$)$alkyl_1$) $SO_2$(($C_1$–$C_6$)$alkyl_1$), —$SO_2$NHCO(($C_1$–$C_6$)$alkyl_1$), —$CONH_2$, —$SO_2$N (($C_1$–$C_6$)$alkyl_1$)CO(($C_1$–$C_6$)$alkyl_1$), —$CO_2$(($C_1$–$C_6$) $alkyl_1$), —$CONHSO_2$(($C_1$–$C_6$)$alkyl_1$), —CON (($C_1$–$C_6$)$alkyl_1$)$SO_2$(($C_1$–$C_6$)$alkyl_1$), —CONH (($C_1$–$C_6$)$alkyl_1$), —CON(($C_1$–$C_6$)$alkyl_1$)(($C_1$–$C_6$) $alkyl_1$), —CO(($C_1$–$C_6$)$alkyl_1$), and —$SO_{0-2}$(($C_1$–$C_6$) $alkyl_1$);

wherein each $alkyl_1$ group is $C_1$–$C_6$ alkyl optionally substituted with up to three substituents independently selected from hydroxy, oxo, halogen, amino, mono- or di-($C_1$–$C_6$)alkylamino, cyano, nitro, $C_1$–$C_6$alkoxy, —$SO_2$NH(($C_1$–$C_4$)alkyl), —NHCO (($C_1$–$C_4$)alkyl), —COOH, —$SO_2$N(($C_1$–$C_4$)alkyl) (($C_1$–$C_4$)alkyl), —$SO_2NH_2$, —$CONH_2$, —N(($C_1$–$C_4$)alkyl)CO($C_1$–$C_4$)alkyl), —$NHSO_2$ (($C_1$–$C_4$)alkyl), —N(($C_1$–$C_4$)alkyl)$CO_2$(($C_1$–$C_4$) alkyl), —CONH(($C_1$–$C_4$)alkyl), —$NHCO_2$(($C_1$–$C_4$) alkyl), —$CONHSO_2$(($C_1$–$C_4$)alkyl), —CO(($C_1$–$C_4$) alkyl), —N(($C_1$–$C_4$)alkyl)$SO_2$(($C_1$–$C_4$)alkyl), —SO$_2$NHCO((C$_1$–C$_4$)alkyl), —SO$_2$N((C$_1$–C$_4$)alkyl)CO((C$_1$–C$_4$)alkyl), —CON((C$_1$–C$_4$)alkyl)SO$_2$((C$_1$–C$_4$)alkyl), —CON((C$_1$–C$_4$)alkyl)((C$_1$–C$_4$)alkyl), —CO$_2$((C$_1$–C$_4$)alkyl), —SO$_{0-2}$((C$_1$–C$_4$)alkyl), and (C$_3$–C$_7$) cycloalkyl;

Q is phenyl, naphthyl, quinolinyl, thienyl, pyridyl, pyridonyl, pyrimidinyl, pyrimdinonyl, piperazinyl, pyrazinyl, oxazolyl, isoxazolyl, oxadiazolyl, thiadiazolyl, triazolyl, pyrazolyl, furanyl, diazenyl, triazenyl, or triazolopyrazinyl group, each of which is unsubstituted or substituted with up to three substituents independently selected from R$_1$ and R$_{11}$ wherein R$_1$ represents hydroxy, cyano, halogen, nitro, amino, mono- or di(C$_1$–C$_6$)alkylamino, (C$_2$–C$_6$)alkenyl, (C$_2$–C$_6$)alkynyl, (C$_1$–C$_6$)alkoxy, C$_1$–C$_6$ haloalkyl, or C$_1$–C$_6$ haloalkoxy; and R$_{11}$ represents (C$_1$–C$_6$)alkyl which optionally contains 1–2 heteroatoms selected from nitrogen, sulfur and oxygen and is optionally substituted with one or more carbocyclic or heterocyclic groups;

Z is hydrogen, hydroxy, straight or branched chain (C$_1$–C$_6$)alkoxy, (C$_3$–C$_7$) cycloalkyl, (C$_3$–C$_7$) cycloalkyl(C$_1$–C$_3$)alkoxy, amino, mono or di(C$_1$–C$_6$)alkylamino, or NR$_{11}$COR$_{12}$ where R$_{11}$ and R$_{12}$ are the same or different and represent hydrogen or straight or branched chain (C$_1$–C$_6$)alkyl, or NR$_{11}$COR$_{12}$ represents a C$_3$–C$_7$ heterocycloalkanone ring, or Z is phenyl, napthyl, quinolinyl, thienyl, thiazolyl, pyridyl, piperidinyl, piperazinyl, pyrrolidinyl, azetidinyl, pyrimidinyl, imidazolyl, pyrazolyl, pyrazinyl, pyridizinyl, piperidinyl, oxazolyl, isoxazolyl, thiadiazolyl, triazolyl, oxadiazolyl, pyrrolyl, furanyl, pyrimidinyl, diazenyl, triazenyl, 1,2,4-triazolone, 4,5-dihydroimidazolyl, or 1,4,5,6-tetrahydropyrimidinyl, each of which is optionally substituted with one, two or three groups independently selected from C$_1$–C$_6$ alkyl, C$_1$–C$_6$ alkoxy, halogen, hydroxy, cyano, nitro, amino, C$_1$–C$_6$ haloalkyl, C$_1$–C$_6$ haloalkoxy, and mono- or di(C$_1$–C$_6$)alkylamino;

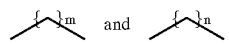

independently represent saturated carbon chains optionally substituted with one, two or three substituents.

3. A compound or salt according to claim 2, wherein U is nitrogen, NR$^A$, S, or O; V is nitrogen, carbon or CH; and Y is carbon, or CH.

4. A compound according to claim 1, which has the formula:

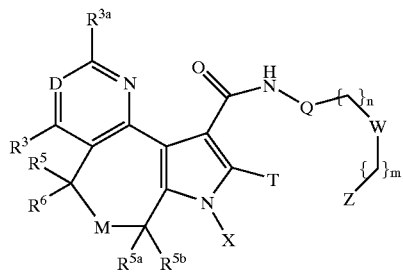

wherein
M is NR';

D is nitrogen or CR$^3$ where
R$^{3a}$ and, each R$^3$ independently represents hydrogen, halogen, hydroxy, cyano, nitro, amino, mono- or di(C$_1$–C$_6$)alkylamino, C$_1$–C$_6$ alkyl, C$_1$–C$_6$ alkoxy, amino(C$_1$–C$_6$) alkyl, mono- or di(C$_1$–C$_6$)alkylamino (C$_1$–C$_6$)alkyl, aryl, heteroaryl, hydroxy(C$_1$–C$_6$)alkyl, halo(C$_1$–C$_6$)alkyl, cyano(C$_1$–C$_6$)alkyl, nitro (C$_1$–C$_6$)alkyl, or C$_1$–C$_6$ alkyl substituted with aryl or heteroaryl; and R$^{5a}$ and R$^{5b}$ are independently
hydrogen, hydroxy, halogen, cyano, nitro, C$_1$–C$_6$ alkyl, C$_1$–C$_6$ alkoxy, amino, or mono- or di(C$_1$–C$_6$)alkylamino, or
phenyl, pyridyl, phenyl(C$_1$–C$_6$)alkyl, or pyridyl (C$_1$–C$_6$)alkyl where each phenyl and pyridyl is optionally substituted with C$_1$–C$_6$ alkyl, C$_1$–C$_6$ alkoxy, halogen, hydroxy, cyano, nitro, amino, and mono- or di(C$_1$–C$_6$)alkylamino;

R' is
hydrogen, C$_1$–C$_6$ alkyl, , C$_1$–C$_6$ alkoxy(C$_1$–C$_6$)alkyl, C$_2$–C$_6$ alkenyl, C$_2$–C$_6$ alkynyl, C$_1$–C$_6$ haloalkyl, amino(C$_1$–C$_6$)alkyl, or mono- or di(C$_1$–C$_6$)alkylamino(C$_1$–C$_6$)alkyl, or
aryl, heteroaryl, aryl(C$_1$–C$_6$) alkyl, or heteroaryl (C$_1$–C$_6$)alkyl, where each aryl and heteroaryl is optionally substituted with up to 3 groups independently selected from C$_1$–C$_6$ alkyl, C$_1$–C$_6$ alkoxy, halogen, hydroxy, cyano, nitro, amino, and mono- and di(C$_1$–C$_6$)alkylamino.

5. A compound according to claim 4, wherein D is CR$^3$.

6. A compound according to claim 4, wherein D is nitrogen.

7. A compound according to claim 5 or 6, where
R$^5$ and R$^6$ are independently hydrogen or C$_1$–C$_6$ alkyl;
M is NR' where R' is
hydrogen, C$_1$–C$_6$ alkyl, , C$_1$–C$_6$ alkoxy(C$_1$–C$_6$)alkyl, C$_2$–C$_6$ alkenyl, C$_2$–C$_6$ alkynyl, C$_1$–C$_6$ haloalkyl, amino(C$_1$–C$_6$)alkyl, or mono- or di(C$_1$–C$_6$)alkylamino(C$_1$–C$_6$)alkyl, or
aryl, heteroaryl, aryl(C$_1$–C$_6$)alkyl, or heteroaryl (C$_1$–C$_6$)alkyl, where each aryl and heteroaryl is optionally substituted with up to 3 groups independently selected from C$_1$–C$_6$ alkyl, C$_1$–C$_6$ alkoxy, halogen, hydroxy, cyano, nitro, amino, and mono- and di(C$_1$–C$_6$)alkylamino;

R$^{5a}$ and R$^{5b}$ are hydrogen.

8. A compound according to claim 7, wherein
X and T are hydrogen; and
R$^{3a}$ and each R$^3$ independently represent
hydrogen, halogen, hydroxy, cyano, nitro, amino, mono- or di(C$_1$–C$_6$)alkylamino, C$_1$–C$_6$ alkyl, C$_1$–C$_6$ alkoxy, amino(C$_1$–C$_6$)alkyl, hydroxy(C$_1$–C$_6$)alkyl, halo(C$_1$–C$_6$)alkyl, or
phenyl, pyridyl, pyrimidinyl, imidazolyl, or C$_1$–C$_6$ alkyl substituted with phenyl, pyridyl, or pyrimidinyl, or imidazolyl, where each phenyl, pyridyl, pyrimidinyl, and imidazolyl is optionally substituted with one or two groups independently selected from C$_1$–C$_6$ alkyl, C$_1$–C$_6$ alkoxy, halogen, hydroxy, and amino.

9. A compound according to claim 8, wherein each each R$^3$ is hydrogen and R$^{3a}$ is hydrogen, C$_1$–C$_6$ alkyl, halogen, hydroxy, C$_1$–C$_6$ alkoxy, amino or mono- or di(C$_1$–C$_6$) alkylamino.

10. A compound according to claim 9, where R$^{3a}$ is hydrogen, C$_1$–C$_6$ alkyl, hydroxy, or C$_1$–C$_6$ alkoxy.

11. A compound according to claim 10, where R' is hydrogen, $C_1$–$C_6$ alkyl, or $C_1$–$C_6$ alkyl substituted with phenyl or pyridyl, where each phenyl or pyridyl is optionally substituted with halogen, hydroxy, amino, $C_1$–$C_6$ alkyl or $C_1$–$C_6$ alkoxy.

12. A compound according to claim 5 or 6, wherein X and T are hydrogen; and
$R^{3a}$ and each $R^3$ independently represent
hydrogen, halogen, hydroxy, cyano, nitro, amino, mono- or di($C_1$–$C_6$)alkylamino, $C_1$–$C_6$ alkyl, $C_1$–$C_6$ alkoxy, amino($C_1$–$C_6$)alkyl, hydroxy($C_1$–$C_6$)alkyl, halo($C_1$–$C_6$)alkyl, cyano($C_1$–$C_6$)alkyl, or nitro ($C_1$–$C_6$)alkyl, or
phenyl, pyridyl, pyrimidinyl, imidazolyl, or $C_1$–$C_6$ alkyl substituted with phenyl, pyridyl, or pyrimidinyl, or imidazolyl, where each phenyl, pyridyl, pyrimidinyl, and imidazolyl is optionally substituted with one or two groups independently selected from $C_1$–$C_6$ alkyl, $C_1$–$C_6$ alkoxy, halogen, hydroxy, and amino.

13. A compound according to claim 12, wherein each each $R^3$ is hydrogen and $R^{3a}$ is hydrogen, $C_1$–$C_6$ alkyl, halogen, hydroxy, $C_1$–$C_6$ alkoxy, amino or mono- or di($C_1$–$C_6$) alkylamino.

14. A compound according to claim 13, where $R^{3a}$ is hydrogen, $C_1$–$C_6$ alkoxy, hydroxy, or $C_1$–$C_6$ alkoxy.

15. A compound according to any one of claim 2, wherein the b ring has the formula:

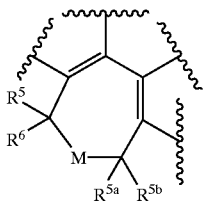

wherein
M is NR' or oxygen; and
$R^{5a}$ and $R^{5b}$ are independently
hydrogen, hydroxy, halogen, cyano, nitro, $C_1$–$C_6$ alkyl, $C_1$–$C_6$ alkoxy, amino, or mono- or di($C_1$–$C_6$) alkylamino, or
phenyl, pyridyl, phenyl($C_1$–$C_6$)alkyl, or pyridyl ($C_1$–$C_6$)alkyl, where each phenyl and pyridyl is optionally substituted with $C_1$–$C_6$ alkyl, $C_1$–$C_6$ alkoxy, halogen, hydroxy, cyano, nitro, amino, and mono- or di($C_1$–$C_6$)alkylamino; and
R' is hydrogen or $C_1$–$C_6$ alkyl.

16. A compound according to claim 15, where
$R^5$ and $R^6$ are independently hydrogen or $C_1$–$C_6$ alkyl;
M is NR' where R' is hydrogen, $C_1$–$C_6$ alkyl, $C_1$–$C_6$ alkoxy($C_1$–$C_6$)alkyl, $C_2$–$C_6$ alkenyl, $C_2$–$C_6$ alkynyl, $c_1$–$C_6$ haloalkyl, amino($C_1$–$C_6$)alkyl, or mono- or di($C_1$–$C_6$)alkylamino($C_1$–$C_6$)alkyl, or aryl, heteroaryl, aryl($C_1$–$C_6$)alkyl, or heteroaryl ($C_1$–$C_6$)alkyl, where each aryl and heteroaryl is optionally substituted with up to 3 groups independently selected from $C_1$–$C_6$ alkyl, $C_1$–$C_6$ alkoxy, halogen, hydroxy, cyano, nitro, amino, and mono- and di($C_1$–$C_6$)alkylamino; and
$R^{5a}$ and $R^{5b}$ are hydrogen.

17. A compound according to claim 16, wherein X and T are hydrogen.

18. A compound according to claim 17, where R' is hydrogen, $C_1$–$C_6$ alkyl, or $C_1$–$C_6$ alkyl substituted with phenyl or pyridyl, where each phenyl or pyridyl is optionally substituted with halogen, hydroxy, amino, $C_1$–$C_6$ alkyl or $C_1$–$C_6$ alkoxy.

19. A compound according to claim 15, wherein $R^5$ and $R^6$ are both hydrogen, X is hydrogen or methyl, $R^{5a}$ and $R^{5b}$ are independently hydrogen or $C_1$–$C_2$ alkyl, M is NR' where R' is methyl, and

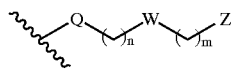

represents pyridyl or pyrazolyl, each of which is optionally substituted with $C_1$–$C_3$ alkyl.

20. A compound of the formula:

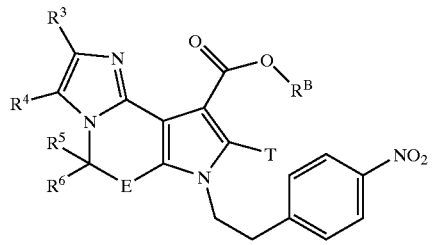

wherein
E represents $(CR^1R^2)_k$, wherein
$R^1$ and $R^2$ are the same or different and independently represent hydrogen, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$) alkyl, or mono- or di($C_1$–$C_6$)alkylamino($C_1$–$C_6$)alkyl; and k is 2;
$R^3$ and $R^4$ independently carry the same definitions as $R^5$ and $R^6$;
$R^5$ and $R^6$ together form a carbonyl group; or
$R^5$ and $R^6$ are independently chosen from hydrogen, halogen, hydroxy, nitro, cyano, $R_{10}$, amino, $C_1$–$C_6$ haloalkyl, —NH($R_{10}$), —N($R_{10}$)($R_{10}$), —COOH, —O($R_{10}$), —SO$_2$NH$_2$, —SO$_2$NH($R_{10}$), —SO$_2$N($R_{10}$) ($R_{10}$), —NHCO($R_{10}$), —N($R_{10}$)CO($R_{10}$), —NHCO$_2$ ($R_{10}$), —N($R_{10}$)CO$_2$($R_{10}$), —NHSO$_2$($R_{10}$), —N($R_{10}$) SO$_2$($R_{10}$), —SO$_2$NHCO($R_{10}$), —SO$_2$N($R_{10}$)CO($R_{10}$), —CONHSO$_2$($R_{10}$), —CON($R_{10}$) SO$_2$($R_{10}$), —CONH$_2$, —CONH($R_{10}$), —CON($R_{10}$)($R_{10}$), —CO$_2$ ($R_{10}$), —CO($R_{10}$), —SO$_{0-2}$($R_{10}$), carbocyclic aryl having from 1 to 3 rings, and heteroaryl, said heteroaryl having from 1 to 3 rings, 5 to 7 ring members in each ring, and in at least one of said rings from 1 to about 3 heteroatoms selected from nitrogen, oxygen and sulfur, and where each said carbocyclic aryl or heteroaryl is optionally substituted with 1, 2, or 3 groups independently selected from $C_1$–$C_6$ alkyl, $C_1$–$C_6$ alkoxy, halogen, hydroxy, cyano, nitro, amino, and mono- or di($C_1$–$C_6$)alkylamino;
$R_{10}$ is independently straight, branched, or cyclic alkyl, containing zero or 1 or more double or triple bonds, and is optionally substituted with one or more substituents independently chosen from hydroxy, oxo, halogen, amino, mono- or di-($C_1$–$C_6$)alkylamino, cyano, nitro, $C_1$–$C_6$alkoxy, —COOH, —SO$_2$NH$_2$, —SO$_2$NH ($C_1$–$C_6$alkyl), —SO$_2$N($C_1$–$C_6$alkyl)($C_1$–$C_6$alkyl), —NHCO($C_1$–$C_6$alkyl), —N($C_1$–$C_6$alkyl)CO ($C_1$–$C_6$alkyl), NHCO$_2$($C_1$–$C_6$alkyl), —N($C_1$–$C_6$alkyl)
CO$_2$($C_1$–$C_6$alkyl), —NHSO$_2$($C_1$–$C_6$alkyl),
—N($C_1$–$C_6$alkyl)SO$_2$($C_1$–$C_6$alkyl), —SO$_2$N
($C_1$–$C_6$alkyl)CO($C_1$–$C_6$alkyl), —SO$_2$NHCO
($C_1$–$C_6$alkyl), —CON($C_1$–$C_6$alkyl) SO$_2$($C_1$–$C_6$alkyl),
—CONHSO$_2$($C_1$–$C_6$alkyl), —CONH$_2$, —CONH
(alkyl), —CON(alkyl)(alkyl), —CO$_2$(alkyl), —CO
(alkyl), —SO$_{0-2}$($C_1$–$C_6$alkyl), and $C_3$–$C_7$cycloalkyl;

T is chosen from hydrogen, halogen, hydroxy, amino, ($C_1$–$C_6$)alkyl, and ($C_1$–$C_6$)alkoxy; and $R^B$ is chosen from hydrogen, methyl, ethyl and benzyl.

21. A compound according to claim 1, which is selected from the group consisting of:

5-Methyl-3,4,5,6-tetrahydro-3,5,10-triaza-benzo[e] azulene-1-carboxylic acid (1H-pyrazol-3-yl)-amide;

3,4,5,6-Tetrahydro-3,5,10-triaza-benzo[e]azulene-1-carboxylic acid pyridin-2-ylamide;

5-Methyl-3,4,5,6-tetrahydro-3,5,10-triaza-benzo[e] azulene-1-carboxylic acid pyridin-2-ylamide;

5-Benzyl-3,4,5,6-tetrahydro-3,5,10-triaza-benzo[e] azulene-1-carboxylic acid pyridin-2-ylamide;

5-Pyridin-2-ylmethyl-3,4,5,6-tetrahydro-3,5,10-triaza-benzo[e]azulene-1-carboxylic acid pyridin-2-ylamide;

5-Methyl-3,4,5,6-tetrahydro-3,5,10-triaza-benzo[e] azulene-1-carboxylic acid pyridin-3-ylamide;

5-Methyl-3,4,5,6-tetrahydro-3,5,10-triaza-benzo[e] azulene-1-carboxylic acid (3-fluoro-phenyl)-amide;

3,4,5,6-Tetrahydro-3,5,10-triaza-benzo[e]azulene-1-carboxylic acid (3-fluoro-phenyl)-amide;

5-Methyl-3,4,5,6-tetrahydro-3,5,10-triaza-benzo[e] azulene-1-carboxylic acid isoxazol-3-ylamide.

22. A compound according to claim 1 where Q is phenyl, pyridyl, pyrimidinyl, triazolyl, thiazolyl, thiadiazolyl, quinolinyl, pyrazolyl, isoxazolyl, pyrazinyl, triazolyl ($C_1$–$C_6$)alkyl, pyridazinyl, 2-oxo-3-hydropyridyl, oxazole, oxadiazolyl, benzimidazol-5-yl, each of which is optionally substituted with 1, 2 or 3 groups independently selected from halogen, $C_1$–$C_6$ alkoxy, $C_1$–$C_6$ alkyl, $C_3$–$C_7$ cycloalkyl, $C_3$–$C_7$ cycloalkyl($C_1$–$C_3$)alkyl, $C_1$–$C_6$ alkylthio, $C_1$–$C_6$ alkylamino, $C_3$–$C_7$ cycloalkylamino, $C_3$–$C_7$ cycloalkyl($C_1$–$C_3$)alkylamino, $C_1$–$C_6$ alkoxycarbonylamino($C_1$–$C_6$)alkyl), $C_1$–$C_6$ alkoxycarbonyl(($C_1$–$C_6$)alkyl)amino($C_1$–$C_6$)alkyl), $C_1$–$C_6$ alkylamino($C_1$–$C_6$)alkoxy, furanyl, (4-benzylpiperidinyl)($C_1$–$C_6$)alkoxy, (4-benzylpiperazinyl)($C_1$–$C_6$)alkoxy, $C_1$–$C_6$ alkoxy ($C_1$–$C_6$)alkyl, $C_1$–$C_6$ alkoxy($C_1$–$C_6$)alkoxy, $C_1$–$C_6$ alkoxy($C_1$–$C_6$)alkylamino, morpholinyl($C_1$–$C_6$) alkoxy, trifluoromethyl, $C_1$–$C_6$ haloalkoxy, 1,3-dioxolanyl, ethyl-methanesulfonylamino($C_1$–$C_6$) alkoxy, 1,4-dioxepinyl, 1,4-dioxanyl, phenyoxy, pyrrolidinyl($C_1$–$C_6$)alkoxy, hydroxy($C_1$–$C_6$alkyl, hydroxy($C_1$–$C_6$)alkoxy, $C_1$–$C_4$ alkylamino($C_1$–$C_4$) alkyl, imidazolyl, imidazolyl($C_1$–$C_6$)alkyl, imidazolyl ($C_1$–$C_6$)alkoxy, triazolyl($C_1$–$C_6$)alkyl, benzyloxy ($C_1$–$C_6$)alkoxy, piperidinyl($C_1$–$C_6$)alkyl, piperazinyl ($C_1$–$C_6$)alkyl, morpholinyl($C_1$–$C_6$)alkyl, pyrrolidinyl ($C_1$–$C_6$)alkyl, azetidinyl($C_1$–$C_6$)alkoxy, azetidinyl ($C_1$–$C_6$)alkyl, $C_1$–$C_4$ alkoxy($C_1$–$C_4$)alkylamino ($C_1$–$C_4$)alkyl, $C_1$–$C_6$ alkanoyl($C_1$–$C_6$)alkoxy, $C_1$–$C_6$ alkoxyphenoxy, phenoxy substituted with halo($C_1$–$C_6$) alkyl, tetrahydrofuranyloxy, oxetanyl($C_1$–$C_6$)alkoxy, oxetanyl($C_1$–$C_6$)alkyl, and 1-benzylimidazolyl($C_1$–$C_6$) alkoxy.

23. A compound according to claim 20, wherein

E is —CH$_2$CH$_2$—;

$R^3$, $R^4$, $R^5$, and $R^6$, are independently hydrogen, halogen, amino, hydroxy, methyl, ethyl, methoxy, or ethoxy; and X and T are independently hydrogen, methyl, or ethyl.

24. A compound according to claim 20, where Q is phenyl, pyridyl, pyrimidinyl, 2-oxo-3-hydropyridyl, each of which is optionally substituted with 1 or 2 groups independently selected from halogen, $C_1$–$C_6$ alkoxy, $C_1$–$C_6$ alkyl, $C_3$–$C_7$ cycloalkyl, $C_3$–$C_7$ cycloalkyl($C_1$–$C_3$)alkyl, $C_1$–$C_6$ alkylthio, $C_1$–$C_6$ alkylamino, $C_3$–$C_7$ cycloalkylamino, $C_3$–$C_7$ cycloalkyl($C_1$–$C_3$)alkylamino, $C_1$–$C_6$ alkoxycarbonylamino($C_1$–$C_6$)alkyl), $C_1$–$C_6$ alkoxycarbonyl(($C_1$–$C_6$)alkyl)amino($C_1$–$C_6$)alkyl), $C_1$–$C_6$ alkylamino($C_1$–$C_6$)alkoxy, furanyl, (4-benzylpiperidinyl)($C_1$–$C_6$)alkoxy, (4-benzylpiperazinyl)($C_1$–$C_6$)alkoxy, $C_1$–$C_6$ alkoxy ($C_1$–$C_6$)alkyl, $C_1$–$C_6$ alkoxy($C_1$–$C_6$)alkoxy, $C_1$–$C_6$ alkoxy($C_1$–$C_6$)alkylamino, morpholinyl($C_1$–$C_6$) alkoxy, trifluoromethyl, $C_1$–$C_6$ haloalkoxy, 1,3-dioxolanyl, ethyl-methanesulfonylamino($C_1$–$C_6$) alkoxy, 1,4-dioxepinyl, 1,4-dioxanyl, phenyoxy, pyrrolidinyl($C_1$–$C_6$)alkoxy, hydroxy($C_1$–$C_6$alkyl, hydroxy($C_1$–$C_6$)alkoxy, $C_1$–$C_4$ alkylamino($C_1$–$C_4$) alkyl, imidazolyl, imidazolyl($C_1$–$C_6$)alkyl, imidazolyl ($C_1$–$C_6$)alkoxy, triazolyl($C_1$–$C_6$)alkyl, benzyloxy ($C_1$–$C_6$)alkoxy, piperinidyl($C_1$–$C_6$)alkyl, piperazinyl ($C_1$–$C_6$)alkyl, morpholinyl($C_1$–$C_6$)alkyl, pyrrolidinyl ($C_1$–$C_6$)alkyl, azetidinyl($C_1$–$C_6$)alkoxy, azetidinyl ($C_1$–$C_6$)alkyl, $C_1$–$C_4$ alkoxy($C_1$–$C_4$)alkylamino ($C_1$–$C_4$)alkyl, $C_1$–$C_6$ alkanoyl($C_1$–$C_6$)alkoxy, $C_1$–$C_6$ alkoxyphenoxy, phenoxy substituted with halo($C_1$–$C_6$) alkyl, tetrahydrofuranyloxy, oxetanyl($C_1$–$C_6$) alkoxy, oxetanyl($C_1$–$C_6$)alkyl, and 1-benzylimidazolyl($C_1$–$C_6$) alkoxy.

25. A compound according to claim 20, wherein $R^3$, $R^4$, $R^5$, and $R^6$, are independently hydrogen, halogen, amino, hydroxy, methyl, ethyl, methoxy, or ethoxy; and X and T are independently hydrogen, methyl, or ethyl.

26. A compound or salt according to claim 25, wherein $R^1$, $R_3$, $R_4$, $R_5$, and $R_6$ are hydrogen.

27. A compound or salt according to claim 25, wherein $R^1$, $R^2$, $R_3$, $R_4$, $R_5$, and $R_6$ are hydrogen.

* * * * *